United States Patent
Ali et al.

(10) Patent No.: US 10,568,949 B2
(45) Date of Patent: *Feb. 25, 2020

(54) METHOD OF ELICITING AN ANTI-TUMOR IMMUNE RESPONSE WITH CONTROLLED DELIVERY OF TLR AGONISTS IN POROUS POLYMERLC DEVICES

(71) Applicants: President and Fellows of Harvard College, Cambridge, MA (US); Dana-Farber Cancer Institute, Inc., Boston, MA (US)

(72) Inventors: Omar Abdel-Rahman Ali, Cambridge, MA (US); Glenn Dranoff, Sudbury, MA (US); David J. Mooney, Sudbury, MA (US)

(73) Assignees: President and Fellows of Harvard College, Cambridge, MA (US); Dana-Farber Cancer Institute, inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/818,509

(22) Filed: Nov. 20, 2017

(65) Prior Publication Data

US 2018/0289789 A1 Oct. 11, 2018

Related U.S. Application Data

(60) Continuation of application No. 15/135,216, filed on Apr. 21, 2016, now Pat. No. 9,821,045, which is a division of application No. 13/741,271, filed on Jan. 14, 2013, now Pat. No. 9,370,558, which is a continuation-in-part of application No. 12/867,426, filed as application No. PCT/US2009/000914 on Feb. 13, 2009, now Pat. No. 10,328,133, which is a continuation-in-part of application No. 13/510,356, filed as application No. PCT/US2010/057630 on Nov. 22, 2010, now abandoned.

(60) Provisional application No. 61/143,630, filed on Jan. 9, 2009, provisional application No. 61/065,672, filed on Feb. 13, 2008, provisional application No. 61/586,624, filed on Jan. 13, 2012, provisional application No. 61/281,663, filed on Nov. 20, 2009.

(51) Int. Cl.
| | | |
|---|---|---|
| *A61K 39/00* | (2006.01) | |
| *A61K 39/39* | (2006.01) | |
| *A61K 45/06* | (2006.01) | |
| *A61K 31/4745* | (2006.01) | |
| *A61K 31/708* | (2006.01) | |
| *A61K 31/7088* | (2006.01) | |
| *A61K 38/19* | (2006.01) | |

(52) U.S. Cl.
CPC ...... *A61K 39/0011* (2013.01); *A61K 31/4745* (2013.01); *A61K 31/708* (2013.01); *A61K 31/7088* (2013.01); *A61K 38/193* (2013.01); *A61K 39/39* (2013.01); *A61K 45/06* (2013.01); *A61K 2039/54* (2013.01); *A61K 2039/55516* (2013.01); *A61K 2039/55522* (2013.01); *A61K 2039/55561* (2013.01); *A61K 2039/55588* (2013.01); *A61K 2039/6093* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |

(Continued)

FOREIGN PATENT DOCUMENTS

| | | |
|---|---|---|
| CN | 1757662 A | 4/2006 |
| CN | 101655611 A | 2/2010 |

(Continued)

OTHER PUBLICATIONS

Abrahams et al., Expression and secretion of antiviral factors by trophoblast cells following stimulation by the TLR-3 agonist, Poly(I : C). Hum Reprod. Sep. 2006;21(9):2432-9.

(Continued)

Primary Examiner — Elly-Gerald Stoica
(74) Attorney, Agent, or Firm — McCarter & English, LLP; Maria Laccotripe Zacharakis; Maneesh Gulati

(57) ABSTRACT

The present invention comprises compositions, methods, and devices for creating an stimulating an antigen-specific dendritic cell immune response. Devices and methods provide prophylactic and therapeutic immunity to subjects against cancer and infectious agents.

27 Claims, 35 Drawing Sheets

Specification includes a Sequence Listing.

(56) References Cited

U.S. PATENT DOCUMENTS

| | | |
|---|---|---|
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson et al. |
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,427,602 B1 | 9/2008 | Shea et al. |
| 7,575,759 B2 | 8/2009 | Murphy et al. |
| 7,687,241 B2 | 3/2010 | Chen |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,709,464 B2 | 4/2014 | Ma et al. |
| 8,728,456 B2 | 5/2014 | Sands et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,675,561 B2 | 6/2017 | Bencherif et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,149,897 B2 | 12/2018 | Mooney et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1 | 10/2004 | Collins et al. |
| 2004/0220111 A1 | 11/2004 | Kleinman et al. |
| 2004/0228858 A1 | 11/2004 | Hanson et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0206308 A1 | 8/2008 | Jabbari et al. |
| 2008/0233181 A1 | 9/2008 | Nagy et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0223255 A1 | 9/2011 | Thiesen et al. |
| 2011/0300186 A1 | 12/2011 | Hellstrom et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0072547 A1 | 3/2013 | Hackam et al. |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |
| 2015/0024026 A1 | 1/2015 | Mooney et al. |
| 2015/0072009 A1 | 3/2015 | Kim et al. |
| 2015/0366956 A1 | 12/2015 | Mooney et al. |
| 2016/0220667 A1 | 8/2016 | Mooney et al. |
| 2016/0220668 A1 | 8/2016 | Mooney et al. |
| 2016/0228543 A1 | 8/2016 | Mooney et al. |
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0182138 A1 | 6/2017 | Kim et al. |
| 2017/0246281 A1 | 8/2017 | Super et al. |
| 2018/0021253 A1 | 1/2018 | Sandeep et al. |
| 2018/0117171 A1 | 5/2018 | Mooney et al. |
| 2018/0164298 A1 | 6/2018 | Ali et al. |
| 2018/0243231 A1 | 8/2018 | Bencherif et al. |
| 2018/0344821 A1 | 12/2018 | Kim et al. |

FOREIGN PATENT DOCUMENTS

| | | |
|---|---|---|
| EP | 0562862 A1 | 9/1993 |
| EP | 1452191 A2 | 9/2004 |
| EP | 1561481 A2 | 8/2005 |
| EP | 1712238 A1 | 10/2006 |
| EP | 1975230 A1 | 10/2008 |

(56) References Cited

FOREIGN PATENT DOCUMENTS

| | | |
|---|---|---|
| JP | 2000-503884 A | 4/2000 |
| JP | 2001-524136 A | 11/2001 |
| JP | 2003-506401 A | 2/2003 |
| JP | 2003-180815 A | 7/2003 |
| JP | 2004-520043 A | 7/2004 |
| JP | 2005-160669 A | 6/2005 |
| JP | 2005-170816 A | 6/2005 |
| JP | 2005-528401 A | 9/2005 |
| JP | 2007-500673 A | 1/2007 |
| JP | 2007-503881 A | 3/2007 |
| JP | 2007-505827 A | 3/2007 |
| JP | 2007-528848 A | 10/2007 |
| JP | 2008-515503 A | 5/2008 |
| JP | 2008-528114 A | 7/2008 |
| JP | 2009-519042 A | 5/2009 |
| JP | 2009-521406 A | 6/2009 |
| JP | 2009-540921 A | 11/2009 |
| JP | 2010-502824 A | 1/2010 |
| JP | 2010-508976 A | 3/2010 |
| JP | 2010-227012 A | 10/2010 |
| JP | 2011-511684 A | 4/2011 |
| JP | 2011-511834 A | 4/2011 |
| JP | 2013-531043 A | 8/2013 |
| WO | WO-1996/02555 A1 | 2/1996 |
| WO | WO-1996/16086 A1 | 5/1996 |
| WO | WO-1998/12228 A1 | 3/1998 |
| WO | WO-1998/16266 A1 | 4/1998 |
| WO | WO-1999/44583 A2 | 9/1999 |
| WO | WO-1999/51259 A2 | 10/1999 |
| WO | WO-2000/50006 A2 | 8/2000 |
| WO | WO-2001/10421 A1 | 2/2001 |
| WO | WO-2001/35932 A2 | 5/2001 |
| WO | WO-2001/37810 A2 | 5/2001 |
| WO | WO-2002/16557 A2 | 2/2002 |
| WO | WO-2002/40071 A1 | 5/2002 |
| WO | WO-2002/058723 A2 | 8/2002 |
| WO | WO-2002/092054 A2 | 11/2002 |
| WO | WO-2003/020161 A2 | 3/2003 |
| WO | WO-2003/020884 A2 | 3/2003 |
| WO | WO-2003/088905 A2 | 10/2003 |
| WO | WO-2004/006990 A2 | 1/2004 |
| WO | WO-2004/029230 A2 | 4/2004 |
| WO | WO-2004/030706 A2 | 4/2004 |
| WO | WO-2004/031371 A2 | 4/2004 |
| WO | WO-2004/089413 A1 | 10/2004 |
| WO | WO-2005/013896 A2 | 2/2005 |
| WO | WO-2005/013933 A1 | 2/2005 |
| WO | WO-2005/020849 A2 | 3/2005 |
| WO | WO-2005/025614 A2 | 3/2005 |
| WO | WO-2005/026318 A2 | 3/2005 |
| WO | WO-2005/037190 A2 | 4/2005 |
| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/030901 A1 | 3/2007 |
| WO | WO-2007/039150 A2 | 4/2007 |
| WO | WO-2007/042554 A2 | 4/2007 |
| WO | WO-2007/063075 A1 | 6/2007 |
| WO | WO-2007/064152 A1 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/106852 A1 | 7/2013 |
| WO | WO-2013/158673 A1 | 10/2013 |
| WO | WO-2013/172967 A1 | 11/2013 |
| WO | WO-2014/063128 A1 | 4/2014 |
| WO | WO-2015/168379 A2 | 11/2015 |
| WO | WO-2016/123573 A1 | 8/2016 |
| WO | WO-2016/161372 A1 | 10/2016 |

OTHER PUBLICATIONS

Agache et al., Mechanical properties and Young's modulus of human skin in vivo. Arch Dermatol Res. 1980;269(3):221-32.

Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.

Aguado et al., Improving viability of stem cells during syringe needle flow through the design of hydrogel cell carriers. Tissue Eng Part A. Apr. 2012;18(7-8):806-15.

Akira et al., Pathogen recognition and innate immunity. Cell. Feb. 24, 2006;124(4):783-801.

Akira et al., Toll-like receptors: critical proteins linking innate and acquired immunity. Nat Immunol. Aug. 2001;2(8):675-80.

Akpalo et al., Fibrin-polyethylene oxide interpenetrating polymer networks: new self-supported biomaterials combining the properties of both protein gel and synthetic polymer. Acta Biomater. Jun. 2011;7(6):2418-27.

Aldhous, Print Me a Heart and a Set of Arteries. New Scientist. 2006;2547:19.

Ali et al., Biomaterial-based vaccine induces regression of established intracranial glioma in rats. Pharm Res. May 2011;28(5):1074-80.

Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.

Ali et al., Converging Cell Therapy with Biomaterials. Cell Transplantation from Laboratory to Clinic. 2006:591-609.

Ali et al., Identification of immune factors regulating antitumor immunity using polymeric vaccines with multiple adjuvants. Cancer Res. Mar. 15, 2014;74(6):1670-81.

Ali et al., In situ regulation of DC subsets and T cells mediates tumor regression in mice. Sci Transl Med. Nov. 25, 2009;1(8):1-10.

(56) References Cited

OTHER PUBLICATIONS

Ali et al., Infection-mimicking materials to program dendritic cells in situ. Nat Mater. Feb. 2009;8(2):151-8.

Ali et al., Sustained GM-CSF and PEI condensed pDNA presentation increases the level and duration of gene expression in dendritic cells. J Control Release. Dec. 18, 2008;132(3):273-8.

Ali et al., The efficacy of intracranial PLG-based vaccines is dependent on direct implantation into brain tissue. J Control Release. Sep. 25, 2011;154(3):249-57.

Allen et al., Regulation of satellite cells during skeletal muscle growth and development. Proc Soc Exp Biol Med. Jun. 1990;194(2):81-6.

Allen et al., Regulation of skeletal muscle satellite cell proliferation by bovine pituitary fibroblast growth factor. Exp Cell Res. May 1984;152(1):154-60.

Almarza et al., Evaluation of three growth factors in combinations of two for temporomandibular joint disc tissue engineering. Arch Oral Biol. Mar. 2006;51(3):215-21.

Alsberg et al., Cell-interactive alginate hydrogels for bone tissue engineering. J Dent Res. Nov. 2001;80(11):2025-9.

Alsberg et al., Engineering growing tissues. Proc Natl Acad Sci U S A. Sep. 17, 2002;99(19):12025-30.

Alsberg et al., Regulating bone formation via controlled scaffold degradation. J Dent Res. Nov. 2003;82(11):903-8.

Ambrosini et al., Astrocytes produce dendritic cell-attracting chemokines in vitro and in multiple sclerosis lesions. J Neuropathol Exp Neurol. Aug. 2005;64(8):706-15.

American Diabetes Association, Standards of Medical Care in Diabetes—2013. Diabetes Care. 2013;36(S1):S11-S66.

Anderson et al., Biomaterial microarrays: rapid, microscale screening of polymer-cell interaction. Biomaterials. Aug. 2005;26(23):4892-7.

Anderson et al., Nanoliter-scale synthesis of arrayed biomaterials and application to human embryonic stem cells. Nat Biotechnol. Jul. 2004;22(7):863-6.

Anderson et al., The NOD mouse: a model of immune dysregulation. Annu Rev Immunol. 2005;23:447-85.

Anderson, A role for nitric oxide in muscle repair: nitric oxide-mediated activation of muscle satellite cells. Mol Biol Cell. May 2000;11(5):1859-74.

Annual Review. 2008:122-131.

Arany et al., At the edge of translation—materials to program cells for directed differentiation. Oral Dis. Apr. 2011;17(3):241-51.

Aschner et al., Metabolic memory for vascular disease in diabetes. Diabetes Technol Ther. Jun. 2012;14 Suppl 1:S68-74.

Atala et al., Endoscopic treatment of vesicoureteral reflux with a chondrocyte-alginate suspension. J Urol. Aug. 1994;152(2 Pt 2):641-3.

Aubin et al., Directed 3D cell alignment and elongation in microengineered hydrogels. Biomaterials. Sep. 2010;31(27):6941-6951.

Augst et al., Alginate hydrogels as biomaterials. Macromol Biosci. Aug. 7, 2006;6(8):623-33.

Babensee et al., Host response to tissue engineered devices. Advanced Drug Delivery Reviews. Aug. 3, 1998;33(1-2):111-139.

Bachelder et al., Acid-degradable polyurethane particles for protein-based vaccines: biological evaluation and in vitro analysis of particle degradation products. Mol Pharm. Sep.-Oct. 2008;5(5):876-84.

Bachem et al., Superior antigen cross-presentation and XCR1 expression define human CD11c+CD141+ cells as homologues of mouse CD8+ dendritic cells. J Exp Med. Jun. 7, 2010;207(6):1273-81.

Badovinac et al., Regulation of CD8+ T cells undergoing primary and secondary responses to infection in the same host. J Immunol. May 15, 2003;170(10):4933-42.

Bakri et al., Pharmacokinetics of intravitreal bevacizumab (Avastin). Ophthalmology. May 2007;114(5):855-9.

Balakrishna et al., Structural correlates of antibacterial and membrane-permeabilizing activities in acylpolyamines. Antimicrob Agents Chemother. Mar. 2006;50(3):852-61.

Banchereau et al., Dendritic cells and the control of immunity. Nature. Mar. 19, 1998;392(6673):245-52.

Bar-Cohen et al., Electroactive Polymer Actuators and Sensors. MRS Bullet. 2008;33(3):173-181.

Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.

Barbero et al., Growth factor supplemented matrigel improves ectopic skeletal muscle formation—a cell therapy approach. J Cell Physiol. Feb. 2001;186(2):183-92.

Barbucci et al., Hyaluronic acid hydrogel in the treatment of osteoarthritis. Biomaterials. Dec. 2002;23(23):4503-13.

Barrio et al., A two-dimensional numerical study of spatial pattern formation in interacting Turing systems. Bull Math Biol. May 1999;61(3):483-505.

Bates, Improved muscle regeneration by combining VEGF with IGF1. Regen Med. Nov. 2010;5(6):853-4.

Beaucage et al., The Functionalization of Oligonucleotides Via Phosphoramidite Derivatives. Tetrahedron. Mar. 5, 1993;49(10):1925-1963.

Beauchamp et al., Dynamics of myoblast transplantation reveal a discrete minority of precursors with stem cell-like properties as the myogenic source. J Cell Biol. Mar. 22, 1999;144(6):1113-22.

Becker et al., Cytological demonstration of the clonal nature of spleen colonies derived from transplanted mouse marrow cells. Nature. Feb. 2, 1963;197:452-4.

Beebe et al., Functional hydrogel structures for autonomous flow control inside microfluidic channels. Nature. Apr. 6, 2000;404(6778):588-90.

Bekiari et al., Study of poly(N,N-dimethylacrylamide)/CdS nanocomposite organic/inorganic gels. Langmuir. Sep. 14, 2004;20(19):7972-5.

Bell, Models for the specific adhesion of cells to cells. Science. May 12, 1978;200(4342):618-27.

Bencherif et al., End-group effects on the properties of PEG-co-PGA hydrogels. Acta Biomater. Jul. 2009;5(6):1872-83.

Bencherif et al., Influence of cross-linker chemistry on release kinetics of PEG-co-PGA hydrogels. J Biomed Mater Res A. Jul. 2009;90(1):142-53.

Bencherif et al., Influence of the degree of methacrylation on hyaluronic acid hydrogels properties. Biomaterials. Apr. 2008;29(12):1739-49.

Bencherif et al., Injectable preformed scaffolds with shape-memory properties. Proc Natl Acad Sci U S A. Nov. 27, 2012;109(48):19590-5.

Bencherif et al., Nanostructured hybrid hydrogels prepared by a combination of atom transfer radical polymerization and free radical polymerization. Biomaterials. Oct. 2009;30(29):5270-8.

Bencherif et al., Synthesis by AGET ATRP of degradable nanogel precursors for in situ formation of nanostructured hyaluronic acid hydrogel. Biomacromolecules. Sep. 14, 2009;10(9):2499-507.

Benton et al., Photocrosslinking of gelatin macromers to synthesize porous hydrogels that promote valvular interstitial cell function. Tissue Eng Part A. Nov. 2009;15(11):3221-30.

Berg et al., Il-10 is a central regulator of cyclooxygenase-2 expression and prostaglandin production. J Immunol. Feb. 15, 2001;166(4):2674-80.

Bergstraesser et al., Stimulation and inhibition of human mammary epithelial cell duct morphogenesis in vitro. Proc Assoc Am Physicians. Mar. 1996;108(2):140-54.

Bianco et al., The meaning, the sense and the significance: translating the science of mesenchymal stem cells into medicine. Nat Med. Jan. 2013;19(1):35-42.

Bilodeau et al., Regular Pyramid Punch Problem. J Appl Mech. 1992;59(3):519-523.

Bischoff, Proliferation of muscle satellite cells on intact myofibers in culture. Dev Biol. May 1986;115(1):129-39.

Blanas et al., Induction of autoimmune diabetes by oral administration of autoantigen. Science. Dec. 6, 1996;274(5293):1707-9.

(56) References Cited

OTHER PUBLICATIONS

Blumenthal et al., Polyurethane scaffolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomaterials. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnol Prog. Sep.-Oct. 2001;17(5):945-50.
Bouhadir et al., Synthesis of Cross-Linked Poly(aldehyde guluronate) Hydrogels. Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromolecules. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;165(11):6278-86.
Bryant et al., Photo-patterning of porous hydrogels for tissue engineering. Biomaterials. Jul. 2007;28(19):2978-86.
Buckwalter et al., Form of Antigen Dictates Immunity: Irradiated Cell vs. Whole Cell Lysate Vaccination. J Immunol. Apr. 1, 2007;178(1 Suppl):S77.
Bullard et al., Fetal wound healing: current biology. World J Surg. Jan. 2003;27(1):54-61.
Buonaguro et al., Translating tumor antigens into cancer vaccines. Clin Vaccine Immunol. Jan. 2011;18(1):23-34.
Burdick et al., Controlled degradation and mechanical behavior of photopolymerized hyaluronic acid networks. Biomacromolecules. Jan.-Feb. 2005;6(1):386-91.
Burdick et al., Photoencapsulation of osteoblasts in injectable RGD-modified PEG hydrogels for bone tissue engineering. Biomaterials. Nov. 2002;23(22):4315-23.
Burdick et al., Stimulation of neurite outgrowth by neurotrophins delivered from degradable hydrogels. Biomaterials. Jan. 2006;27(3):452-9.
Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.
Bégué et al., Vaccination against human papillomavirus. Implementation and efficacy against cervical cancer control. Bull Acad Natl Med. Dec. 2007;191(9):1805-16.
Callahan et al., At the bedside: CTLA-4- and PD-1-blocking antibodies in cancer immunotherapy. J Leukoc Biol. Jul. 2013;94(1):41-53.
Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).
Calvert, Gel Sensors and Actuators. MRS Bullet. 2008;33(3):207-212.
Cameron et al., The influence of substrate creep on mesenchymal stem cell behaviour and phenotype. Biomaterials. Sep. 2011;32(26):5979-93.
Cao et al., Promoting angiogenesis via manipulation of VEGF responsiveness with notch signaling. Biomaterials. Sep. 2009;30(25):4085-93.
Carlson et al., Notch signaling pathway and tissue engineering. Front Biosci. Sep. 1, 2007;12:5143-56.
Carmeliet et al., Angiogenesis in cancer and other diseases. Nature. Sep. 14, 2000;407(6801):249-57.
Carmeliet, Mechanisms of angiogenesis and arteriogenesis. Nat Med. Apr. 2000;6(4):389-95.
Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.
Ceriello et al., Clinical review 2: The "metabolic memory": is more than just tight glucose control necessary to prevent diabetic complications? J Clin Endocrinol Metab. Feb. 2009;94(2):410-5.
Ceriello et al., The emerging challenge in diabetes: the "metabolic memory". Vascul Pharmacol. Nov.-Dec. 2012;57(5-6):133-8.
Champion et al., Shape induced inhibition of phagocytosis of polymer particles. Pharm Res. Jan. 2009;26(1):244-9.
Chan et al., Antifibrotic effects of suramin in injured skeletal muscle after laceration. J Appl Physiol. Sep. 2003;95(2):771-80.
Chan et al., Helix induction in antimicrobial peptides by alginate in biofilms. J Biol Chem. Sep. 10, 2004;279(37):38749-54.
Chan et al., Traction dynamics of filopodia on compliant substrates. Science. Dec. 12, 2008;322(5908):1687-91.
Chang, Mouse models for studies of retinal degeneration and diseases. Methods Mol Biol. 2013;935:27-39.
Chen et al., Adipogenic differentiation of adipose tissue-derived human mesenchymal stem cells: effect of gastric bypass surgery. Surg Endosc. Dec. 2012;26(12):3449-56.
Chen et al., Functional Human Vascular Network Generated in Photocrosslinkable Gelatin Methacrylate Hydrogels. Adv Funct Mater. May 23, 2012;22(10):2027-2039.
Chen et al., Integrated approach to designing growth factor delivery systems. FASEB J. Dec. 2007;21(14):3896-903.
Chen et al., Polymeric growth factor delivery strategies for tissue engineering. Pharm Res. Aug. 2003;20(8):1103-12.
Chen et al., Skeletal muscle stem cells. Reprod Biol Endocrinol. Nov. 13, 2003;1:101. 7 pages.
Chen et al., Spatio-temporal VEGF and PDGF delivery patterns blood vessel formation and maturation. Pharm Res. Feb. 2007;24(2):258-64.
Chiang et al., Whole tumor antigen vaccines. Semin Immunol. Jun. 2010;22(3):132-43.
Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.
Choi et al., Three-dimensional scaffolds for tissue engineering: the importance of uniformity in pore size and structure. Langmuir. Dec. 21, 2010;26(24):19001-6.

(56) References Cited

OTHER PUBLICATIONS

Choi, Replacement Organs, Hot Off the Press. New Scientist. 2003;177(2379):16.
Chou et al., Characterization of Photocross Linked Alginate Hydrogels for Nucleus Pulposus Cell Encapsulation. J Biomed Mater Res A. 2009;91A(1):187-194.
Chromiak et al., Bioreactor perfusion system for the long-term maintenance of tissue-engineered skeletal muscle organoids. In Vitro Cell Dev Biol Anim. Oct. 1998;34(9):694-703.
Clark et al., Myosin II and mechanotransduction: a balancing act. Trends Cell Biol. Apr. 2007;17(4):178-86.
Clauss et al., Interstitial transport of rabbit and sheep antibodies in normal and neoplastic tissues. Cancer Res. Jun. 15, 1990;50(12):3487-92.
ClinicalTrials.gov, NCT00729664, Multiple Ascending Dose (MDX1105-01) (Anti-PDL1). 4 pages, Sep. 3, 2015.
ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.gov, NCT01352884, Study to Assess the Safety, and Pharmacokinetics of AMP-224 in Patients with Advanced Cancer. 3 pages, Sep. 2, 2016.
ClinicalTrials.gov, NCT01391143, Safety Study of MGA271 in Refractory Cancer. 4 pages, Sep. 28, 2016.
Cohen et al., Controlled delivery systems for proteins based on poly(lactic/glycolic acid) microspheres. Pharm Res. Jun. 1991;8(6):713-20.
Comisar et al., Engineering RGD nanopatterned hydrogels to control preosteoblast behavior: a combined computational and experimental approach. Biomaterials. Oct. 2007;28(30):4409-17.
Conboy et al., The regulation of Notch signaling controls satellite cell activation and cell fate determination in postnatal myogenesis. Dev Cell. Sep. 2002;3(3):397-409.
Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.
Conn et al., Purification of a glycoprotein vascular endothelial cell mitogen from a rat glioma-derived cell line. Proc Natl Acad Sci U S A. Feb. 1990;87(4):1323-7.
Cook et al., A sialomucopeptide liberated by trypsin from the human erythrocyte. Nature. Dec. 17, 1960;188:1011-2.
Cooper et al., Extended amplification in vitro and replicative senescence: key factors implicated in the success of human myoblast transplantation. Hum Gene Ther. Aug. 10, 2003;14(12):1169-79.
Cooper, Metabolic memory: implications for diabetic vascular complications. Pediatr Diabetes. Aug. 2009;10(5):343-6.
Corcione et al., CCL19 and CXCL12 trigger in vitro chemotaxis of human mantle cell lymphoma B cells. Clin Cancer Res. Feb. 1, 2004;10(3):964-71.
Cornelison et al., Single-cell analysis of regulatory gene expression in quiescent and activated mouse skeletal muscle satellite cells. Dev Biol. Nov. 15, 1997;191(2):270-83.
Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Crameri et al., Improved green fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inching toward the finish line. J Clin Invest. Feb. 2002;109(3):311-2.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Flt3. J Exp Med. Jul. 21, 2003;198(2):293-303.
Dainiak et al., Gelatin-fibrinogen cryogel dermal matrices for wound repair: preparation, optimisation and in vitro study. Biomaterials. Jan. 2010;31(1):67-76.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.
David et al., The in vitro Desensitization of Sensitive Cells by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor cells. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts. Biophys J. Apr. 1999;76(4):2307-16.
Den Haan et al., CD8(+) but not CD8(−) dendritic cells cross-prime cytotoxic T cells in vivo. J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Cell Dev Biol Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Di Nicola et al., Human bone marrow stromal cells suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.
Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.

(56) References Cited

OTHER PUBLICATIONS

Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
DuFort et al., Balancing forces: architectural control of mechanotransduction. Nat Rev Mol Cell Biol. May 2011;12(5):308-19.
DuPont et al., Role of YAP/TAZ in mechanotransduction. Nature. Jun. 8, 2011;474(7350):179-83.
Duraiswamy et al., Dual blockade of PD-1 and CTLA-4 combined with tumor vaccine effectively restores T-cell rejection function in tumors-response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
Edwards et al., Evaluation of biomechanical properties of human skin. Clin Dermatol. Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.
Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus ligand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.

Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-cell-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyostelium. FEBS Lett. Nov. 5, 2004;577(1-2):227-32.
Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Clin Cancer Res. Mar. 15, 2008;14(6):1603-8.
Fontaine et al., Surgical treatment of peripheral circulation disorders. Helv Chir Acta. Dec. 1954;21(5-6):499-533.
Fox, Management of worsening multiple sclerosis with mitoxantrone: a review. Clin Ther. Apr. 2006;28(4):461-74.
Fransen et al., Local immunomodulation for cancer therapy: Providing treatment where needed. Oncoimmunology. Nov. 1, 2013;2(11):e26493.
Friedenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Furqan et al., STAT inhibitors for cancer therapy. J Hematol Oncol. Dec. 5, 2013;6:90. 11 pages.
Gamvrellis et al., Vaccines that facilitate antigen entry into dendritic cells. Immunol Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Gasic et al., Removal and regeneration of the cell coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.

(56) References Cited

OTHER PUBLICATIONS

GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3. May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. P49771.1, Jan. 9, 2013.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Godbey et al., Size matters: molecular weight affects theefficiency of poly(ethylenimine) as a gene delivery vehicle. J Biomed Mater Res. Jun. 5, 1999;45(3):268-75.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.

(56) References Cited

OTHER PUBLICATIONS

Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harris et al., Open pore biodegradable matrices formed with gas foaming. J Biomed Mater Res. Dec. 5, 1998;42(3):396-402.
Harris, Classification, Diagnostic Criteria, and Screening for Diabetes. Diabetes in America. NIH Publication No. 95-1468. Chapter 2. (1995):15-36.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomaterials. Mar.-Apr. 2004;25(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro through a gradient amplification mechanism. Proc Natl Acad Sci U S A. Nov. 1, 2005;102(44):15779-84.
Henry et al., The VIVA trial: Vascular endothelial growth factor in Ischemia for Vascular Angiogenesis. Circulation. Mar. 18, 2003;107(10):1359-65.
Hermanson, Bioconjugate Techniques. Academic Press, New York. pp. 152-186, (1996).
Heslop et al., Transplanted primary neonatal myoblasts can give rise to functional satellite cells as identified using the Myf5nlacZl+ mouse. Gene Ther. May 2001;8(10):778-83.
Hildner et al., Batf3 deficiency reveals a critical role for CD8alpha+ dendritic cells in cytotoxic T cell immunity. Science. Nov. 14, 2008;322(5904):1097-100.
Hill et al., Designing scaffolds to enhance transplanted myoblast survival and migration. Tissue Eng. May 2006;12(5):1295-304.
Hill et al., Muscle satellite (stem) cell activation during local tissue injury and repair. J Anat. Jul. 2003;203(1):89-99.
Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.
Hirano et al., Peptide and Protein Presenting Materials for Tissue Engineering. Adv Mat. Jan. 16, 2004;16(1):17-25.
Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.
Hodi et al., Immunologic and clinical effects of antibody blockade of cytotoxic T lymphocyte-associated antigen 4 in previously vaccinated cancer patients. Proc Natl Acad Sci USA. Feb. 26, 2008;105(8):3005-10.
Hodi et al., Improved survival with ipilimumab in patients with metastatic melanoma. N Engl J Med. Aug. 19, 2010;363(8):711-23.
Holland et al., Dual growth factor delivery from degradable oligo(poly(ethylene glycol) fumarate) hydrogel scaffolds for cartilage tissue engineering. Journal of Controlled Release. 2005;101:111-125.
Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.
Horsley et al., IL-4 acts as a myoblast recruitment factor during mammalian muscle growth. Cell. May 16, 2003;113(4):483-94.
Hsiong et al., Differentiation stage alters matrix control of stem cells. J Biomed Mater Res A. Apr. 2008;85A(1):145-56.
Huang et al., Fabrication and in vitro Testing of Polymeric Delivery Systems for Condensed DNA. J Biomed Mater Res. 2003;67:1384-1392.
Huang et al., Long-Term In Vivo Gene Expression via Delivery of PEI-DNA Condensates From Porous Polymer Scaffolds. Hum Gene Ther. 2005;16(5):609-617.
Hubbell et al., Materials Engineering for Immunomodulation. Nature. 2009;462:449-460.
Hubbell, Biomaterials in tissue engineering. Biotechnology (N Y). Jun. 1995;13(6):565-76.
Huebsch et al., Harnessing traction-mediated manipulation of the cell/matrix interface to control stem-cell fate. Nat Mater. Jun. 2010;9(6):518-26.
Humphries et al., Integrin ligands at a glance. J Cell Sci. Oct. 1, 2006;119(Pt 19):3901-3.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Hutson et al., Synthesis and characterization of tunable poly(ethylene glycol): gelatin methacrylate composite hydrogels. Tissue Eng Part A. Jul. 2011;17(13-14):1713-23.
Hwang et al., Fabrication of three-dimensional porous cell-laden hydrogel for tissue engineering. Biofabrication. Sep. 2010;2(3):035003. 12 pages.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unique chemotactic response profile and specific expression of chemokine receptors CCR4 and CCR8 by CD4(+)CD25(+) regulatory T cells. J Exp Med. Sep. 17, 2001;194(6):847-53.
Ihnat et al., Hypothesis: the 'metabolic memory', the new challenge of diabetes. Diabet Med. Jun. 2007;24(6):582-6.
Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Isern et al., Self-renewing human bone marrow mesenspheres promote hematopoietic stem cell expansion. Cell Rep. May 30, 2013;3(5):1714-24.

(56) References Cited

OTHER PUBLICATIONS

Ishihara et al., Roles of bradykinin in vascular permeability and angiogenesis in solid tumor. Int Immunopharmacol. Mar. 2002;2(4):499-509.
Iwamoto et al., Preparation of an Ionic Polymer Gel Microactuator and Measurement of its Periodic Motions. Nippon Kagaku Kaishi. 1997;9:609-614.
Jain, Molecular Regeneration of Vessel Maturation. Nat Med. Jun. 1, 2003;9:685-693.
Jain, The manufacturing techniques of various drug loaded biodegradable poly(lactide-co-glycolide) (PLGA) devices. Biomaterials. Dec. 2000;21(23):2475-90.
Jankovic et al., In the absence of IL-12, CD4(+) T cell responses to intracellular pathogens fail to default to a Th2 pattern and are host protective in an IL-10(−/−) setting. Immunity. Mar. 2002;16(3):429-39.
Janmey et al., From tissue mechanics to transcription factors. Differentiation. Oct. 2013;86(3):112-20.
Jego et al., Plasmacytoid dendritic cells induce plasma cell differentiation through type I interferon and interleukin 6. Immunity. Aug. 2003;19(2):225-34.
Jiang et al. Two-piconewton slip bond between fibronectin and the cytoskeleton depends on talin. Nature. Jul. 17, 2003;424(6946):334-7.
Jiang et al., Click hydrogels, microgels and nanogels: emerging platforms for drug delivery and tissue engineering. Biomaterials. Jun. 2014;35(18):4969-85.
Jiang et al., Self-organization of periodic patterns by dissociated feather mesenchymal cells and the regulation of size, number and spacing of primordia. Development. Nov. 1999;126(22):4997-5009.
Jinushi et al., Enhancing the clinical activity of granulocyte-macrophage colony-stimulating factor-secreting tumor cell vaccines. Immunol Rev. Apr. 2008;222:287-98.
Jinushi et al., MFG-E8-mediated uptake of apoptotic cells by APCs links the pro- and antiinflammatory activities of GM-CSF. J Clin Invest. Jul. 2007;1 17(7):1902-13.
Johnson et al., Activation of skeletal muscle satellite cells and the role of fibroblast growth factor receptors. Exp Cell Res. Aug. 1995;219(2):449-53.
Jokinen et al., Integrin-mediated cell adhesion to type I collagen fibrils. J Biol Chem. Jul. 23, 2004;279(30):31956-63.
Jugdutt et al., Aging and defective healing, adverse remodeling, and blunted post-conditioning in the reperfused wounded heart. J Am Coll Cardiol. Apr. 8, 2008;51(14):1399-403.
Juntanon et al., Electrically controlled release of sulfosalicylic acid from crosslinked poly(vinyl alcohol) hydrogel. Int J Pharm. May 22, 2008;356(1-2):1-11.
Kang et al., Effect of Porous Structure on the Degradation of Freeze-Dried Gelatin Hydrogels. J Bioact Compat Poly. Jul. 1, 1999;14(4):331-343.
Kanzler et al., Therapeutic targeting of innate immunity with Toll-like receptor agonists and antagonists. Nat Med. May 2007;13(5):552-9.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Katayama et al., Integrated analysis of the genome and the transcriptome by FANTOM. Brief Bioinform. Sep. 2004;5(3):249-58.
Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthalaldehyde-bis-guanylhydrazone scaffolds. Bioorg Med Chem Lett. Mar. 1, 2006;16(5):1305-8.
Kim et al., An overview of cartilage tissue engineering. Yonsei Med J. Dec. 2000;41(6):766-73.
Kim et al., Injectable, spontaneously assembling, inorganic scaffolds modulate immune cells in vivo and increase vaccine efficacy. Nat Biotechnol. Jan. 2015;33(1):64-72.
Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem cells within thermosensitive hydrogel matrices. Biomaterials. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a multicompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and In Viivo Tissue Stiffening. Curr Biol. Sep. 29, 2009;19:1511-1518.
Klinman, Immunotherapeutic uses of CpG oligodeoxynucleotides. Nat Rev Immunol. Apr. 2004;4(4):249-58.
Kohane, Microparticles and nanoparticles for drug delivery. Biotechnol Bioeng. Feb. 1, 2007;96(2):203-9.
Kondo et al., A reaction-diffusion wave on the skin of the marine angelfish Pomacanthus. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromolecules. Sep.-Oct. 2004;5(5):1720-7.
Kong et al., Decoupling the Dependence of Rheological/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nanoscale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Kratky et al., Direct activation of antigen-presenting cells is required for CD8+ T-cell priming and tumor vaccination. Proc Natl Acad Sci U S A. Oct. 18, 2011;108(42):17414-9.
Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 11, 2009. 1 page.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kurts et al., CD8 T cell ignorance or tolerance to islet antigens depends on antigen dose. Proc Natl Acad Sci U S A. Oct. 26, 1999;96(22):12703-7.

(56) References Cited

OTHER PUBLICATIONS

Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.
Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Kyi et al., Checkpoint blocking antibodies in cancer immunotherapy. FEBS Lett. Jan. 21, 2014;588(2):368-76.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticles in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomaterials. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomaterials. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun. May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.
Levental et al., Soft biological materials and their impact on cell function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., pH sensitive Laponite/alginate hybrid hydrogels: swelling behaviour and release mechanism. Soft Matter. 2011;7:6231-6238.
Li et al., Purified hybrid cells from dendritic cell and tumor cell fusions are superior activators of antitumor immunity. Cancer Immunol Immunother. Nov. 2001;50(9):456-62.
Li, TNF-alpha is a mitogen in skeletal muscle. Am J Physiol Cell Physiol. Aug. 2003;285(2):C370-6.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology. 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu et al., Selective inhibition of IDO1 effectively regulates mediators of antitumor immunity. Blood. Apr. 29, 2010;115(17):3520-30.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Urology. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease. J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.

(56) References Cited

OTHER PUBLICATIONS

Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.
Manavski et al., Vascular niche controls organ regeneration. Circ Res. Mar. 28, 2014;114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci USA. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomaterials. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci USA. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McWhorter et al., Modulation of macrophage phenotype by cell shape. Proc Natl Acad Sci U S A. Oct. 22, 2013;110(43):17253-8.
Meier et al., Peptide Nucleic Acids(PNAs)-Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008;103(2):194-202. Includes supplementary materials.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
MGI, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acylhomospermines. J Med Chem. Apr. 7, 2005;48(7):2589-99.
Miller et al., Melanoma. N Engl J Med. Jul. 6, 2006;355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005;18(2):219-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell regulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.
Nair et al., Polymers as biomaterials for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBI Accession No. 001020539, Jan. 30, 2011.
NCBI Accession No. 001020540, Jan. 30, 2011.

(56) References Cited

OTHER PUBLICATIONS

NCBI Accession No. 001028928, Jan. 30, 2011.
NCBI Accession No. 001193, May 3, 2014.
NCBI Accession No. 001552.2, Mar. 16, 2014.
NCBI Accession No. 001561.5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBI Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBI Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic cells. Nature Medicine. Mar. 1, 1998;4(3):328-32.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomaterials. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., The alpha 6 beta 4 integrin is a receptor for both laminin and kalinin. Exp Cell Res. Apr. 1994;211(2):360-7.
Noguera-Troise et al., Blockade of Dll4 inhibits tumour growth by promoting non-productive angiogenesis. Nature. Dec. 21, 2006;444(7122):1032-7.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000 ;1(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistance-forming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Orner et al., Arrays for the combinatorial exploration of cell adhesion. J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.
Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin Invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Mattei et al., In vivo measurements of the elastic mechanical properties of human skin by indentation tests. Med Eng Phys. Jun. 2008;30(5):599-606.
Pajonk et al., From sol-gel to aerogels and cryogels. J Non Cryst Solids. May 1990;121(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for alginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomaterials. Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute lymphoblastic leukaemia (ALL R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Patterson et al., Differential binding of chemokines to macrophages and neutrophils in the human inflamed synovium. Arthritis Res. 2002;4(3):209-14.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1alpha,25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomaterials. Jan. 2010;31(3);385-91.
Pelinkovic et al., Tissue engineering and gene therapy of the musculoskeletal system with muscle cells. Z Orthop Ihre Grenzgeb. Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., The use of poly(ethylene glycol) hydrogels to investigate the impact of ECM chemistry and mechanics on smooth muscle cells. Biomaterials. Oct. 2006;27(28):4881-93.
Phillippi, Patterning of Multiple Cell Lineages from a Single Stem Cell Population. Annual Meeting of the American Society for Cell Biology. Dec. 10, 2006.
Pinho et al., PDGFRa and CD51 mark human nestin+ sphere-forming mesenchymal stem cells capable of hematopoietic progenitor cell expansion. J Exp Med. Jul. 1, 2013;210(7):1351-67.
Platten et al., Cancer Immunotherapy by Targeting IDO1/TDO and Their Downstream Effectors. Front Immunol. Jan. 12, 2015;5:673. 7 pages.
Pluen et al., Role of tumor-host interactions in interstitial diffusion of macromolecules: cranial vs. subcutaneous tumors. Proc Natl Acad Sci U S A. Apr. 10, 2001;98(8):4628-33.
Pooyan et al., Conjugates bearing multiple formyl-methionyl peptides display enhanced binding to but not activation of phagocytic cells. Bioconjug Chem. Mar.-Apr. 2002;13(2):216-23.

(56) References Cited

OTHER PUBLICATIONS

Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
PRNewsWire, GlaxoSmithKline and Amplimmune Form Global Strategic Collaboration. Alliance to Focus on AMP-224 for Cancer and Other Diseases. 3 pages, Aug. 4, 2010.
Pulendran et al., Flt3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscale patterning. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006;116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-Azcón et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al., Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines. Nat Biotechnol. Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National Institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.

Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticles. Science. Feb. 22, 2013;339(6122):971-5.
Rosenberg et al., Cancer immunotherapy: moving beyond current vaccines. Nat Med. Sep. 2004;10(9):909-15.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al., Alginate hydrogels as synthetic extracellular matrix materials. Biomaterials. Jan. 1999;20(1):45-53.
Rowley et al., Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002;158(2):345-55.
Ryu et al., The construction of three-dimensional micro-fluidic scaffolds of biodegradable polymers by solvent vapor based bonding of micro-molded layers. Biomaterials. Feb. 2007;28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-glycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001;194(2):173-9.
Sansonetti, The innate signaling of dangers and the dangers of innate signaling. Nat Immunol. Dec. 2006;7(12):1237-42.
Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.

(56) References Cited

OTHER PUBLICATIONS

Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Smidsrød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Stachowiak et al., Inverse opal hydrogel-collagen composite scaffolds as a supportive microenvironment for immune cell migration. J Biomed Mater Res A. Jun. 1, 2008;85(3):815-28.
Steinman et al., Taking dendritic cells into medicine. Nature. Sep. 27, 2007;449(7161):419-26.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. Oct. 20, 1997;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor Impregnated in Gelatin Hydrogels. Journal of Controlled Release. Sep. 1994;31(2):189-199.
Takahashi et al., Induction of pluripotent stem cells from adult human fibroblasts by defined factors. Cell. Nov. 30, 2007;131(5):861-72.

(56) References Cited

OTHER PUBLICATIONS

Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 2, 1997;278(5335):117-20.
Tanaka et al., Collapse of gels in an electric field. Science. Oct. 29, 1982;218(4571):467-9.
Tang et al., Combining radiation and immunotherapy: a new systemic therapy for solid tumors? Cancer Immunol Res. Sep. 2014;2(9):831-8.
Tannous, Gaussia luciferase reporter assay for monitoring biological processes in culture and in vivo. Nat Protoc. 2009;4(4):582-91.
Tatsumi et al., HGF/SF is present in normal adult skeletal muscle and is capable of activating satellite cells. Dev Biol. Feb. 1, 1998;194(1):114-28.
Ten Dijke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatory cell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995;33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagen-agarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1)49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.

(56) References Cited

OTHER PUBLICATIONS

W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Waldron-Lynch et al., Advances in Type 1 diabetes therapeutics: immunomodulation and beta-cell salvage. Endocrinol Metab Clin North Am. Jun. 2009;38(2):303-17.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(I-lactic acid). Cytotherapy. Oct. 2012;14(9):1080-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2001;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.
Xie et al., Preparation and Application of Surface-Coated Superparamagnetic Nanobeads in the Isolation of Genomic DNA. J Magn Magnetic Mater. Jun. 2004;277(1-2):16-23.
Xiong et al., Transcription Factor STAT3 as a Novel Molecular Target for Cancer Prevention. Cancers (Basel). Apr. 16, 2014;6(2):926-57.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomaterials. Oct. 2005;26(30):5991-8.
Yeung et al., Effects of substrate stiffness on cell morphology, cytoskeletal structure, and adhesion. Cell Motil Cytoskeleton. Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science. Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010;107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010;6(6):468-473.
Zhang et al., A comparative study of the antigen-specific immune response induced by co-delivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Generation of a syngeneic mouse model to study the effects of vascular endothelial growth factor in ovarian carcinoma. Am J Pathol. Dec. 2002;161(6):2295-309.
Zhang et al., Talin depletion reveals independence of initial cell spreading from integrin activation and traction. Nat Cell Biol. Sep. 2008;10(9):1062-8.
Zhao et al., A cell-permeable Stat3 SH2 domain mimetic inhibits Stat3 activation and induces antitumor cell effects in vitro. J Biol Chem. Nov. 12, 2010;285(46):35855-65.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.

(56) References Cited

OTHER PUBLICATIONS

Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.
Zhou et al., Microstructure and Mechanical Properties of Poly(L-lactide) Scaffolds Fabricated by Gelatin Particle Leaching Method. J Appl Polymer Sci. Nov. 5, 2005:98(3):1373-1379.
Zizzari et al., The Macrophage Galactose-Type C-Type Lectin (MGL) Modulates Regulatory T Cell Functions. PLoS One. Jul. 6, 2015;10(7):e0132617. 12 pages.

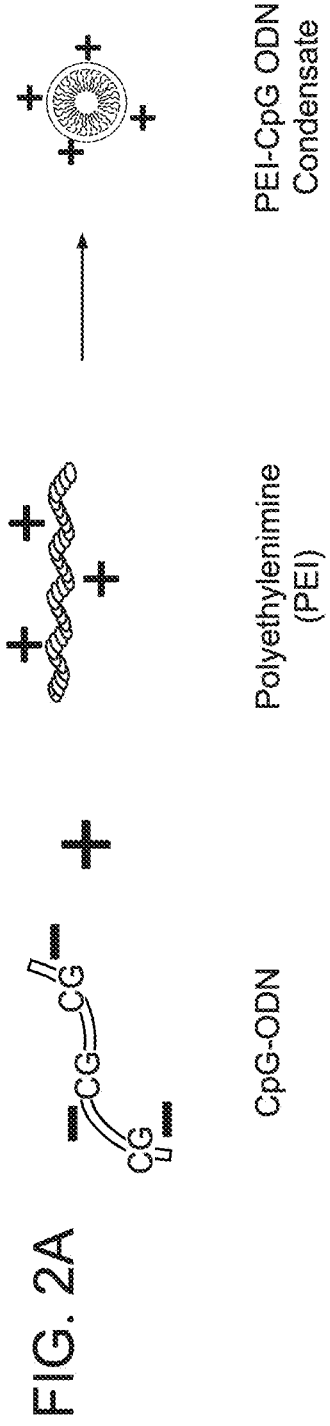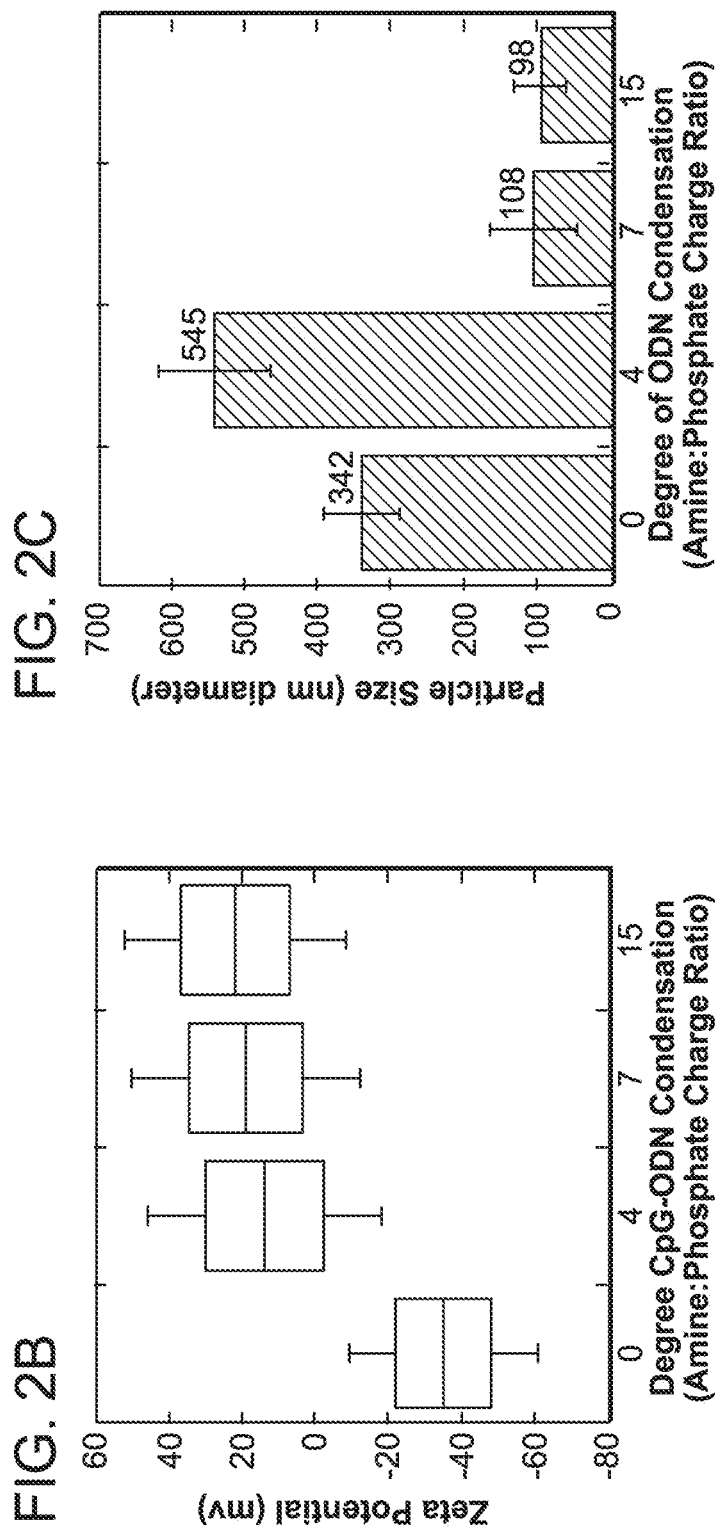

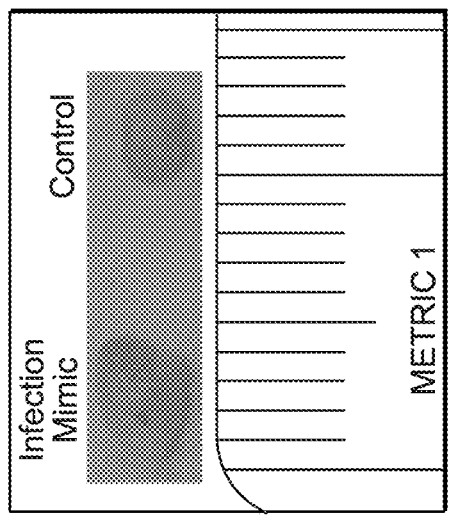
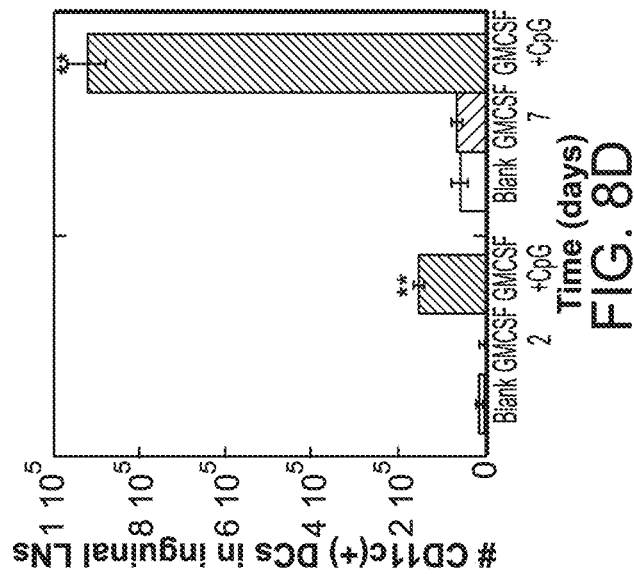
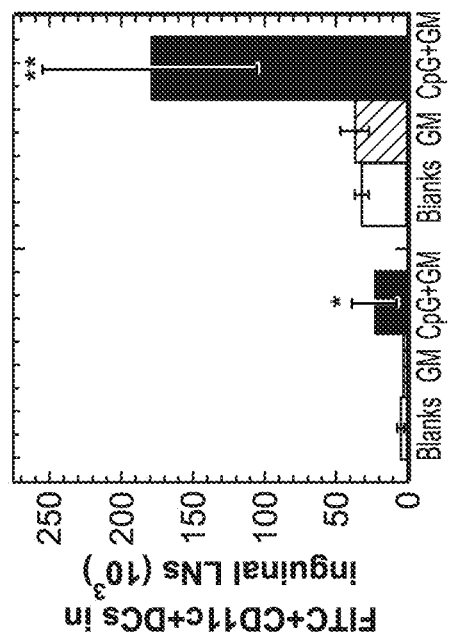
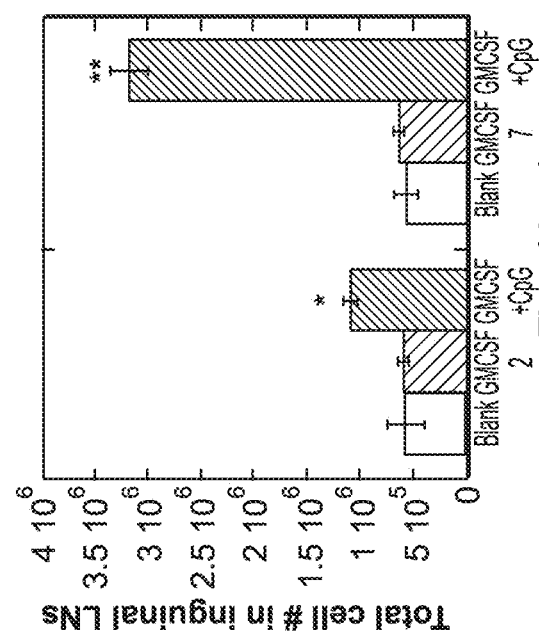
FIG. 8A
FIG. 8B
FIG. 8C
FIG. 8D

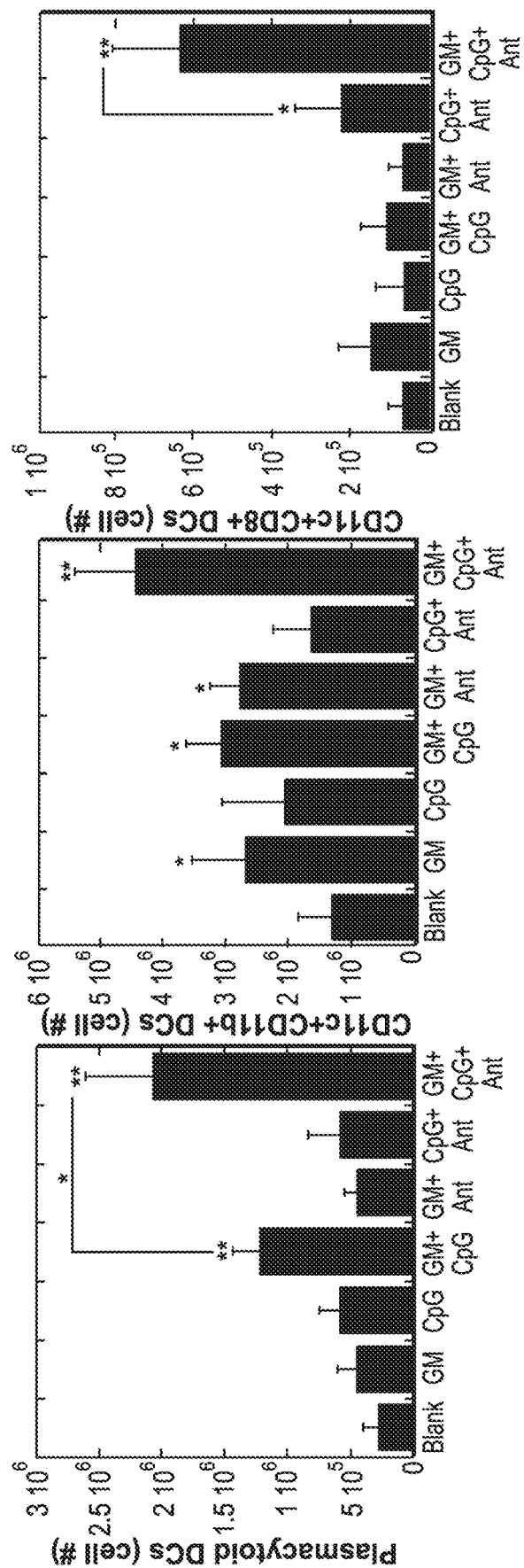

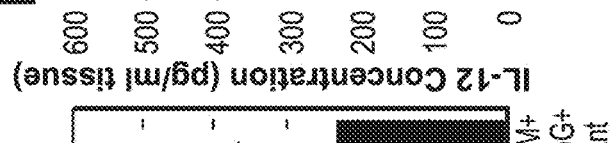
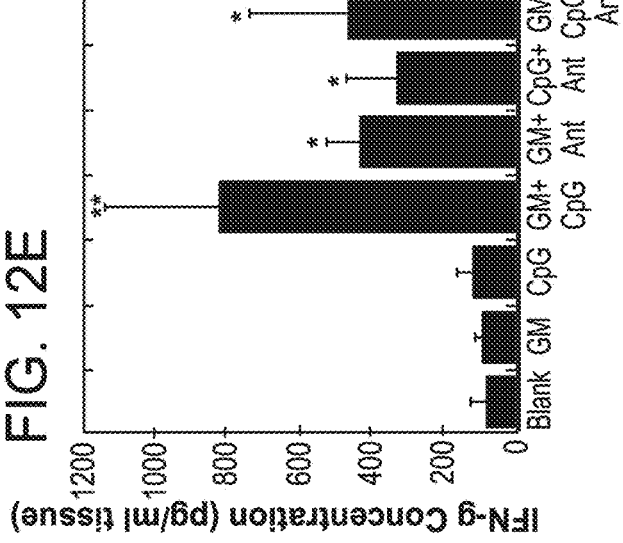
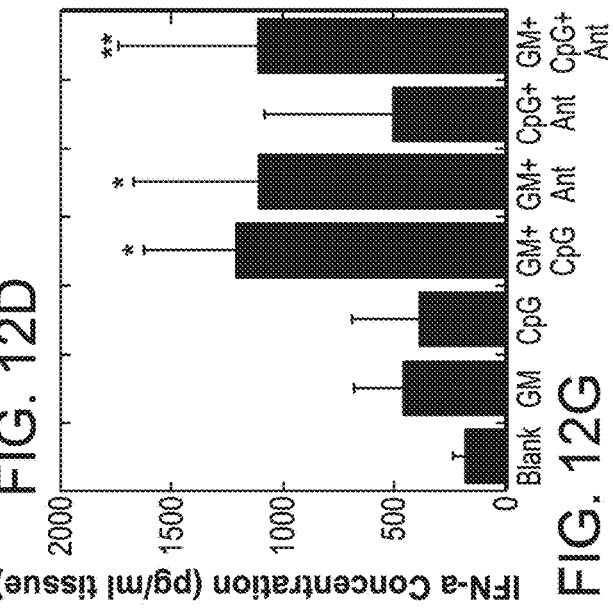
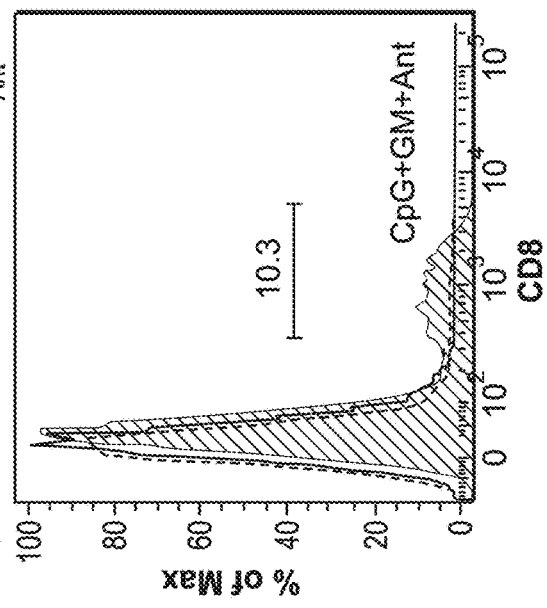

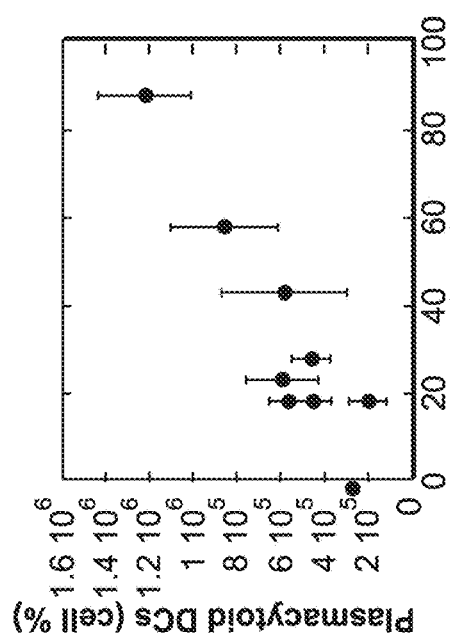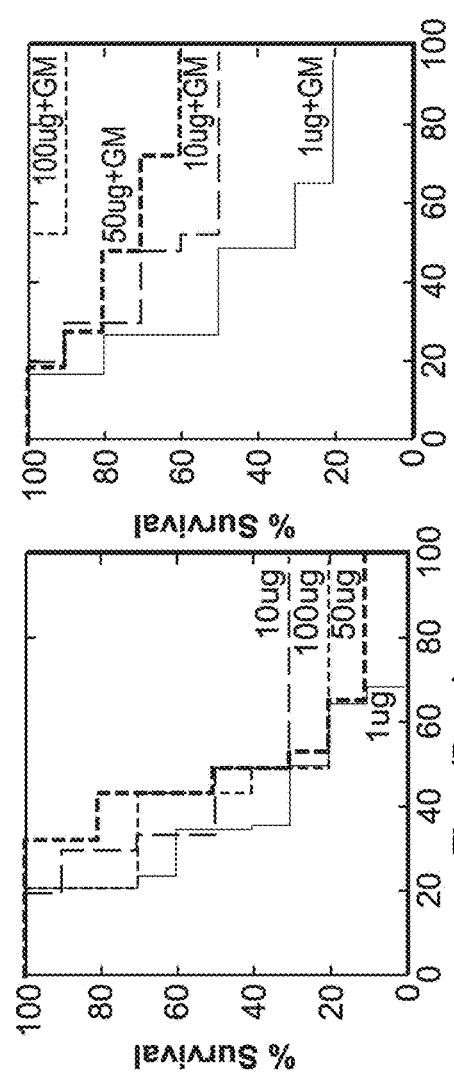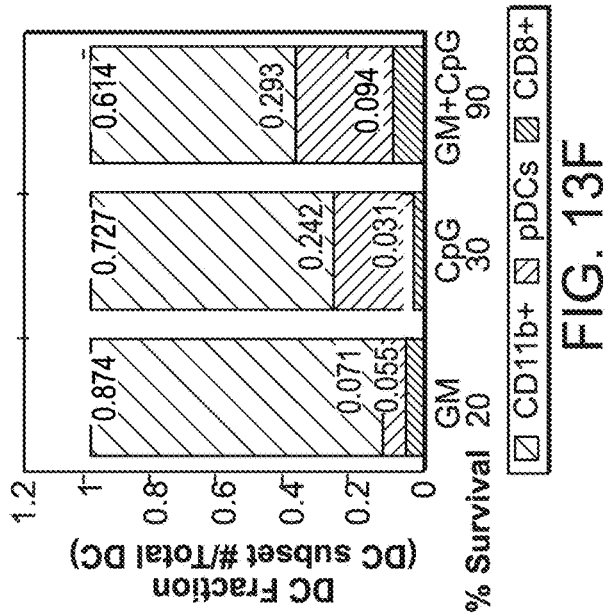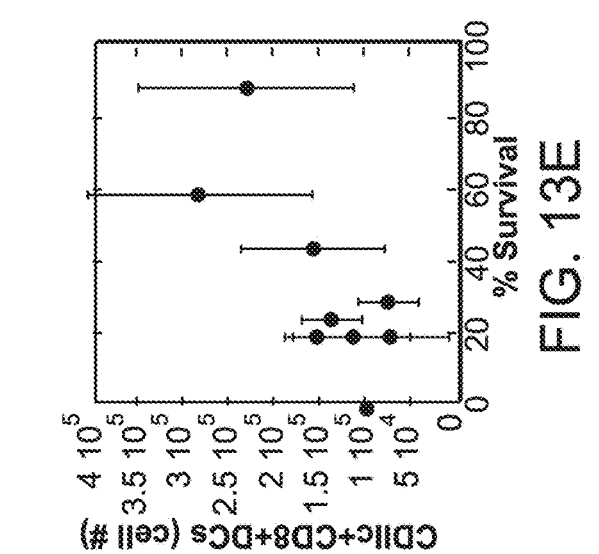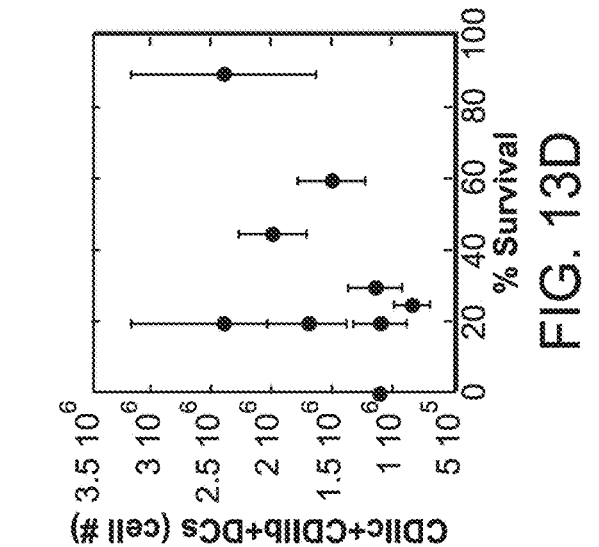
FIG. 13A, FIG. 13B, FIG. 13C, FIG. 13D, FIG. 13E, FIG. 13F

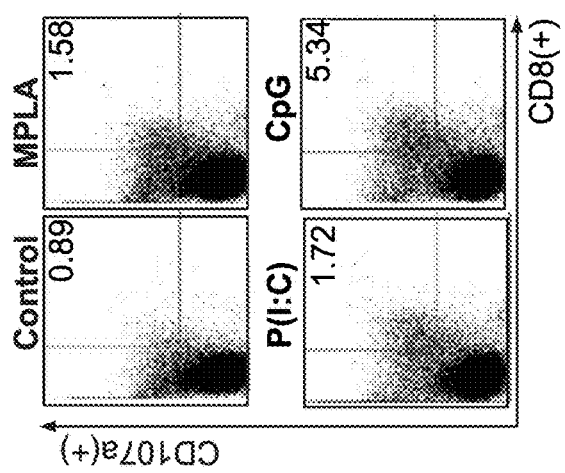
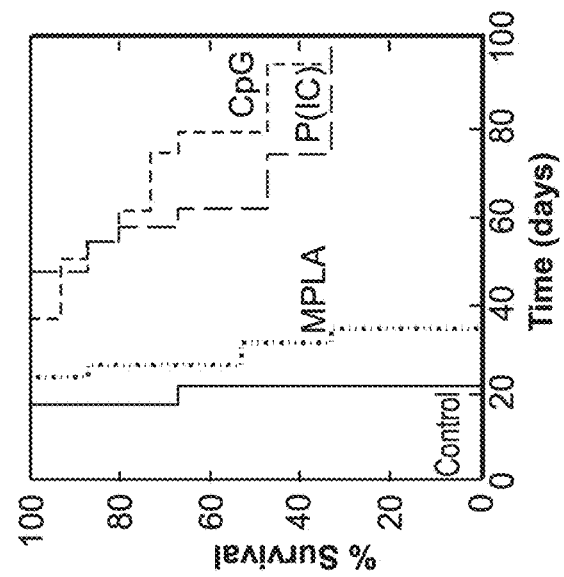
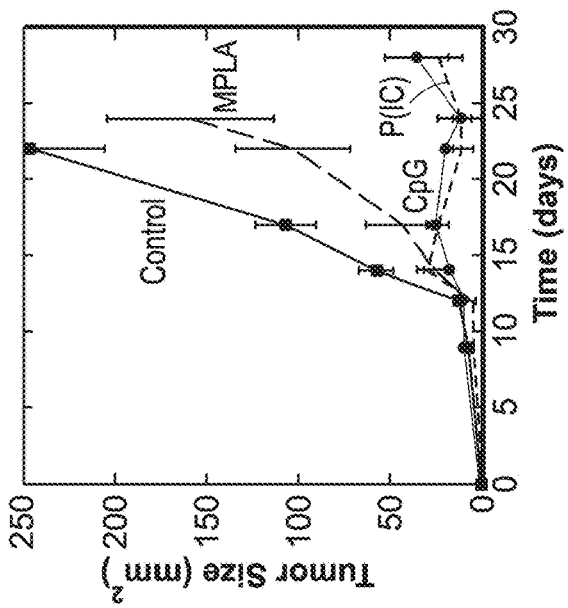
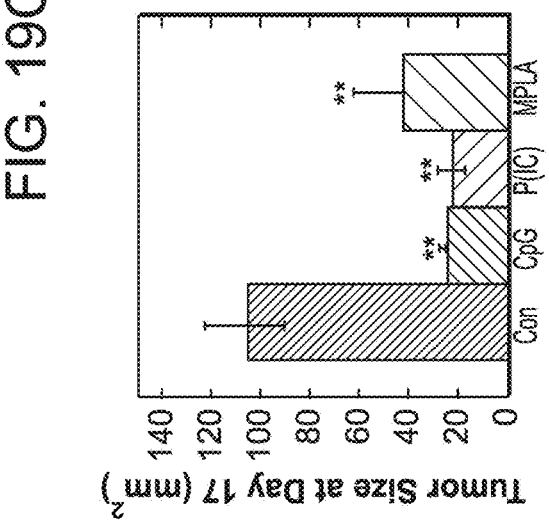
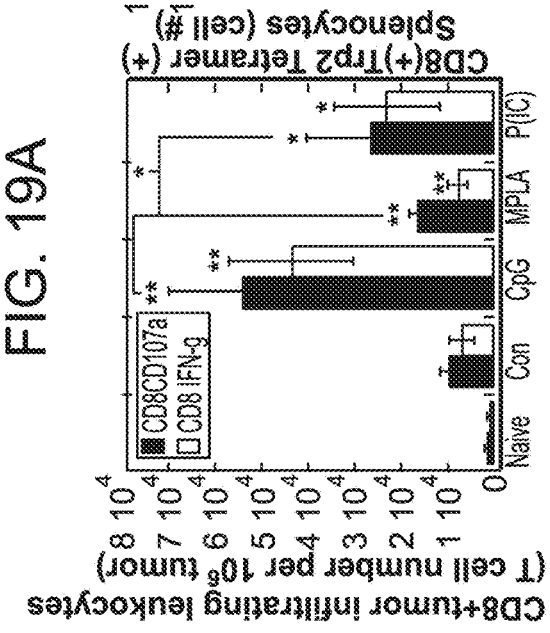
FIG. 19A
FIG. 19B
FIG. 19C
FIG. 19D
FIG. 19E
FIG. 19F

… (1)

SEQUENCE LISTING

```
<160> NUMBER OF SEQ ID NOS: 13

<210> SEQ ID NO 1
<211> LENGTH: 3868
<212> TYPE: DNA
<213> ORGANISM: Homo sapiens
```

-continued

<400> SEQUENCE: 1

```
ggaggtcttg tttccggaag atgttgcaag gctgtggtga aggcaggtgc agcctagcct      60
cctgctcaag ctacaccctg gccctccacg catgaggccc tgcagaactc tggagatggt     120
gcctacaagg gcagaaaagg acaagtcggc agccgctgtc ctgagggcac agctgtggt     180
gcaggagcca agacctgagg gtggaagtgt cctcttagaa tggggagtgc ccagcaaggt     240
gtaccccgcta ctggtgctat ccagaattcc catctctccc tgctctctgc ctgagctctg     300
ggccttagct cctccctggg cttggtagag acaggtgtg aggccctcat gggatgtagg      360
ctgtctgaga ggggagtgga agaggaagg ggtgaaggag ctgtctgcca tttgactatg      420
caaatggcct ttgactcatg ggaccctgtc ctcctcactg ggggcagggt ggagtggagg     480
gggagctact aggctggtat aaaaatctta cttcctctat tctctgagcc gctgctgccc     540
ctgtgggaag ggacctcgag tgtgaagcat ccttccctgt agctgctgtc cagtctgccc     600
gccagaccct ctggagaagc ccctgccccc cagcatgggt ttctgccgca gcgccctgca     660
cccgctgtct ctcctggtgc aggccatcat gctggccatg accctggccc tgggtacctt     720
gcctgccttc ctaccctgtg agctccagcc ccacggcctg gtgaactgca actggctgtt     780
cctgaagtct gtgccccact tctccatggc agcaccccgt ggcaatgtca ccagcctttc     840
cttgtcctcc aaccgcatcc accacctcca tgattctgac tttgcccacc tgcccagcct     900
gcggcatctc aacctcaagt ggaactgccc gccggttggc ctcagcccca tgcacttccc     960
ctgccacatg accatcgagc ccagcacctt cttggctgtg cccaccctgg aagagctaaa    1020
cctgagctac aacaacatca tgactgtgcc tgcgctgccc aaatccctca tatccctgtc    1080
cctcagccat accaacatcc tgatgctaga ctctgccagc ctcgccggcc tgcatgccct    1140
gcgcttccta ttcatggacg gcaactgtta ttacaagaac ccctgcaggc aggcactgga    1200
ggtggccccg ggtgcctcc ttggcctggg caacctcacc cacctgtcac tcaagtacaa     1260
caacctcact gtggtgccc gcaacctgcc ttccagcctg gagtatctgc tgttgtccta     1320
caaccgcatc gtcaaactgg cgcctgagga cctggccaat ctgaccgccc tgcgtgtgct    1380
cgatgtgggc ggaaattgcc gccgctgcga ccacgctccc aaccccctgca tggagtgccc    1440
tcgtcacttc ccccagctac atcccgatac cttcagccac ctgagccgtc ttgaaggcct    1500
ggtgttgaag gacagttctc tctcctggct gaatgccagt tggttccgtg ggctgggaaa    1560
cctccgagtg ctggacctga gtgagaactt cctctacaaa tgcatcacta aaaccaaggc    1620
cttccagggc ctaacacagc tgcgcaagct taacctgtcc ttcaattacc aaaagaggggt    1680
gtcctttgcc cacctgtctc tggcccttc cttcgggagc ctggtcgccc tgaaggagct    1740
ggacatgcac ggcatcttct tccgctcact cgatgagacc acgctccggc cactggcccg    1800
cctgcccatg ctccagactc tgcgtctgca gatgaacttc atcaaccagg cccagctcgg    1860
catcttcagg gccttccctg gcctgcgcta cgtggacctg tcgacaaacc gcatcagcgg    1920
agcttcggag ctgacagcca ccatgggggga ggcagatgga ggggagaagg tctggctgca    1980
gcctggggac cttgctccgg ccccagtgga cactcccagc tctgaagact tcaggcccaa    2040
ctgcagcacc ctcaacttca ccttggatct gtcacgaac aacctggtga ccgtgcagcc    2100
ggagatgttt gcccagctct cgcacctgca gtgcctgcgc ctgagccaca actgcatctc    2160
gcaggcagtc aatggctccc agttcctgcc gctgaccggt ctgcaggtgc tagacctgtc    2220
ccacaataag ctggaccttct accacgagca ctcattcacg gagctaccac gactggaggc    2280
```

```
cctggacctc agctacaaca gccagcccTT tggcatgcag ggcgtgggcc acaacttcag    2340
cttcgtggct cacctgcgca ccctgcgcca cctcagcctg gcccacaaca acatccacag    2400
ccaagtgtcc cagcagctct gcagtacgtc gctgcgggcc ctggacttca gcggcaatgc    2460
actgggccat atgtgggccg agggagacct ctatctgcac ttcttccaag gcctgagcgg    2520
tttgatctgg ctggacttgt cccagaaccg cctgcacacc ctcctgcccc aaaccctgcg    2580
caacctcccc aagagcctac aggtgctgcg ctctccgtga caattacctgg ccttctttaa    2640 gtggtggagc ctccacttcc tgcccaaact ggaagtcctc gacctggcag gaaaccagct    2700
gaaggccctg accaatggca gcctgcctgc tggcacccgg ctccggaggc tggatgtcag    2760
ctgcaacagc atcagcttcg tggcccccgg cttcttttcc aaggccaagg agctgcgaga    2820
gctcaacctt agcgccaacg ccctcaagac agtggaccac tcctggtttg gcccctggc    2880 gagtgccctg caaatactag atgtaagcgc caaccctctg cactgcgcct gtggggcggc    2940
ctttatggac ttcctgctgg aggtgcaggc tgccgtgccc ggtctgccca gccgggtgaa    3000
gtgtggcagt ccgggccagc tccagggcct cagcatcttt gcacaggacc tgcgcctctg    3060
cctggatgag gccctctcct gggactgttt cgccctctcg ctgctggctg tggctctggg    3120
cctgggtgtg cccatgctgc atcacctctg tggctgggac ctctggtact gcttccacct    3180
gtgcctggcc tggcttccct ggcgggggcg gcaaagtggg cgagatgagg atgccctgcc    3240
ctacgatgcc ttcgtggtct tcgacaaaac gcagagcgca gtggcagact gggtgtacaa    3300
cgagcttcgg gggcagctgg aggagtgccg tgggcgctgg gcactccgcc tgtgcctgga    3360
ggaacgcgac tggctgcctg caaaaccct ctttgagaac ctgtgggcct cggtctatgg    3420
cagccgcaag acgctgtttg tgctggccca cacggaccgg gtcagtggtc tcttgcgcgc    3480
cagcttcctg ctggcccagc agcgcctgct ggaggaccgc aaggacgtcg tggtgctggt    3540
gatcctgagc cctgacggcc gccgctcccg ctatgtgcgg ctgcgccagc gcctctgccg    3600
ccagagtgtc ctcctctggc cccaccagcc cagtggtcag cgcagcttct gggcccagct    3660
gggcatggcc ctgaccaggg acaaccacca cttctataac cggaacttct gccagggacc    3720
cacggccgaa tagccgtgag ccggaatcct gcacggtgcc acctccacac tcacctcacc    3780
tctgcctgcc tggtctgacc ctcccctgct cgcctccctc accccacacc tgacacagag    3840
caggcactca ataaatgcta ccgaaggc                                       3868
```

<210> SEQ ID NO 2
<211> LENGTH: 1032
<212> TYPE: PRT
<213> ORGANISM: Homo sapiens

<400> SEQUENCE: 2

```
Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95
```

```
Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
            115                 120                 125

Asn Leu Ser Tyr Asn Asn Ile Met Thr Val Pro Ala Leu Pro Lys Ser
            130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
                195                 200                 205

Asn Asn Leu Thr Val Val Pro Arg Asn Leu Pro Ser Ser Leu Glu Tyr
            210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
            245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
            290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
            355                 360                 365

Leu Asp Met His Gly Ile Phe Phe Arg Ser Leu Asp Glu Thr Thr Leu
            370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
            405                 410                 415

Leu Arg Tyr Val Asp Leu Ser Asp Asn Arg Ile Ser Gly Ala Ser Glu
            420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
            450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
            485                 490                 495

His Leu Gln Cys Leu Arg Leu Ser His Asn Cys Ile Ser Gln Ala Val
            500                 505                 510
```

```
Asn Gly Ser Gln Phe Leu Pro Leu Thr Gly Leu Gln Val Leu Asp Leu
            515                 520                 525

Ser His Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Gln
        675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
        835                 840                 845

Leu Cys Leu Ala Trp Leu Pro Trp Arg Gly Arg Gln Ser Gly Arg Asp
    850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
```

```
                930             935              940
Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
                965                 970                 975

Arg Ser Arg Tyr Val Arg Leu Arg Gln Arg Leu Cys Arg Gln Ser Val
                980                 985                 990

Leu Leu Trp Pro His Gln Pro Ser Gly Gln Arg Ser Phe Trp Ala Gln
                995                 1000                1005

Leu Gly Met Ala Leu Thr Arg Asp Asn His His Phe Tyr Asn Arg
        1010                1015                1020

Asn Phe Cys Gln Gly Pro Thr Ala Glu
        1025                1030

<210> SEQ ID NO 3
<211> LENGTH: 128
<212> TYPE: PRT
<213> ORGANISM: Homo sapiens

<400> SEQUENCE: 3

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
                20                  25                  30

Thr Ala Ala Glu Met Asn Glu Thr Val Glu Val Ile Ser Glu Met Phe
            35                  40                  45

Asp Leu Gln Glu Pro Thr Cys Leu Gln Thr Arg Leu Glu Leu Tyr Lys
        50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
                100                 105                 110

Asp Phe Leu Leu Val Ile Pro Phe Asp Cys Trp Glu Pro Val Gln Glu
            115                 120                 125

<210> SEQ ID NO 4
<211> LENGTH: 904
<212> TYPE: PRT
<213> ORGANISM: Homo sapiens

<400> SEQUENCE: 4

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
                20                  25                  30

Glu Val Ala Asp Cys Ser His Leu Lys Leu Thr Gln Val Pro Asp Asp
            35                  40                  45

Leu Pro Thr Asn Ile Thr Val Leu Asn Leu Thr His Asn Gln Leu Arg
        50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
```

```
            100                 105                 110
Gln Leu Ser Asp Lys Thr Phe Ala Phe Cys Thr Asn Leu Thr Glu Leu
            115                 120                 125
His Leu Met Ser Asn Ser Ile Gln Lys Ile Lys Asn Asn Pro Phe Val
        130                 135                 140
Lys Gln Lys Asn Leu Ile Thr Leu Asp Leu Ser His Asn Gly Leu Ser
145                 150                 155                 160
Ser Thr Lys Leu Gly Thr Gln Val Gln Leu Glu Asn Leu Gln Glu Leu
                165                 170                 175
Leu Leu Ser Asn Asn Lys Ile Gln Ala Leu Lys Ser Glu Glu Leu Asp
            180                 185                 190
Ile Phe Ala Asn Ser Ser Leu Lys Lys Leu Glu Leu Ser Ser Asn Gln
        195                 200                 205
Ile Lys Glu Phe Ser Pro Gly Cys Phe His Ala Ile Gly Arg Leu Phe
    210                 215                 220
Gly Leu Phe Leu Asn Asn Val Gln Leu Gly Pro Ser Leu Thr Glu Lys
225                 230                 235                 240
Leu Cys Leu Glu Leu Ala Asn Thr Ser Ile Arg Asn Leu Ser Leu Ser
                245                 250                 255
Asn Ser Gln Leu Ser Thr Thr Ser Asn Thr Thr Phe Leu Gly Leu Lys
            260                 265                 270
Trp Thr Asn Leu Thr Met Leu Asp Leu Ser Tyr Asn Asn Leu Asn Val
        275                 280                 285
Val Gly Asn Asp Ser Phe Ala Trp Leu Pro Gln Leu Glu Tyr Phe Phe
    290                 295                 300
Leu Glu Tyr Asn Asn Ile Gln His Leu Phe Ser His Ser Leu His Gly
305                 310                 315                 320
Leu Phe Asn Val Arg Tyr Leu Asn Leu Lys Arg Ser Phe Thr Lys Gln
                325                 330                 335
Ser Ile Ser Leu Ala Ser Leu Pro Lys Ile Asp Asp Phe Ser Phe Gln
            340                 345                 350
Trp Leu Lys Cys Leu Glu His Leu Asn Met Glu Asp Asn Asp Ile Pro
        355                 360                 365
Gly Ile Lys Ser Asn Met Phe Thr Gly Leu Ile Asn Leu Lys Tyr Leu
    370                 375                 380
Ser Leu Ser Asn Ser Phe Thr Ser Leu Arg Thr Leu Thr Asn Glu Thr
385                 390                 395                 400
Phe Val Ser Leu Ala His Ser Pro Leu His Ile Leu Asn Leu Thr Lys
                405                 410                 415
Asn Lys Ile Ser Lys Ile Glu Ser Asp Ala Phe Ser Trp Leu Gly His
            420                 425                 430
Leu Glu Val Leu Asp Leu Gly Leu Asn Glu Ile Gly Gln Glu Leu Thr
        435                 440                 445
Gly Gln Glu Trp Arg Gly Leu Glu Asn Ile Phe Glu Ile Tyr Leu Ser
    450                 455                 460
Tyr Asn Lys Tyr Leu Gln Leu Thr Arg Asn Ser Phe Ala Leu Val Pro
465                 470                 475                 480
Ser Leu Gln Arg Leu Met Leu Arg Arg Val Ala Leu Lys Asn Val Asp
                485                 490                 495
Ser Ser Pro Ser Pro Phe Gln Pro Leu Arg Asn Leu Thr Ile Leu Asp
            500                 505                 510
Leu Ser Asn Asn Asn Ile Ala Asn Ile Asn Asp Asp Met Leu Glu Gly
        515                 520                 525
```

```
Leu Glu Lys Leu Glu Ile Leu Asp Leu Gln His Asn Leu Ala Arg
        530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
    690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
    850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
            900

<210> SEQ ID NO 5
<211> LENGTH: 3057
<212> TYPE: DNA
<213> ORGANISM: Homo sapiens
```

```
<400> SEQUENCE: 5
cactttcgag agtgccgtct atttgccaca cacttccctg atgaaatgtc tggatttgga      60
ctaaagaaaa aaggaaaggc tagcagtcat ccaacagaat catgagacag actttgcctt     120
gtatctactt ttggggggc cttttgccct ttgggatgct gtgtgcatcc tccaccacca     180
agtgcactgt tagccatgaa gttgctgact gcagccacct gaagttgact caggtacccg     240
atgatctacc cacaaacata acagtgttga accttaccca taatcaactc agaagattac     300
cagccgccaa cttcacaagg tatagccagc taactagctt ggatgtagga tttaacacca     360
tctcaaaact ggagccagaa ttgtgccaga aacttcccat gttaaaagtt ttgaacctcc     420
agcacaatga gctatctcaa ctttctgata aaacctttgc cttctgcacg aatttgactg     480
aactccatct catgtccaac tcaatccaga aaattaaaaa taatcccttt gtcaagcaga     540
agaatttaat cacattagat ctgtctcata atggcttgtc atctacaaaa ttaggaactc     600
aggttcagct ggaaaatctc caagagcttc tattatcaaa caataaaatt caagcgctaa     660
aaagtgaaga actggatatc tttgccaatt catctttaaa aaaattagag ttgtcatcga     720
atcaaattaa agagttttct ccagggtgtt tcacgcaat tggaagatta tttggcctct     780
ttctgaacaa tgtccagctg ggtcccagcc ttacagaaa gctatgtttg gaattagcaa     840
acacaagcat tcggaatctg tctctgagta acagccagct gtccaccacc agcaatacaa     900 cttcttggg actaaagtgg acaaatctca ctatgctcga tctttcctac aacaacttaa     960
atgtggttgg taacgattcc tttgcttggc ttccacaact agaatatttc ttcctagagt    1020
ataataatat acagcatttg ttttctcact ctttgcacgg gcttttcaat gtgaggtacc    1080
tgaatttgaa acggtctttt actaaacaaa gtatttccct tgcctcactc cccaagattg    1140
atgatttttc ttttcagtgg ctaaaatgtt tggagcacct taacatggaa gataatgata    1200
ttccaggcat aaaaagcaat atgttcacag gattgataaa cctgaaatac ttaagtctat    1260
ccaactcctt tacaagtttg cgaactttga caaatgaaac atttgtatca cttgctcatt    1320
ctcccttaca catactcaac ctaaccaaga ataaaatctc aaaaatagag agtgatgctt    1380
tctcttggtt gggccaccta gaagtacttg acctgggcct taatgaaatt gggcaagaac    1440
tcacaggcca ggaatggaga ggtctagaaa atattttcga aatctatctt tcctacaaca    1500
agtacctgca gctgactagg aactcctttg ccttggtccc aagccttcaa cgactgatgc    1560
tccgaagggt ggcccttaaa aatgtggata gctctccttc accattccag cctcttcgta    1620
acttgaccat tctggatcta agcaacaaca acatagccaa cataaatgat gacatgttgg    1680
agggtcttga gaaactagaa attctcgatt tgcagcataa caacttagca cggctctgga    1740
aacacgcaaa ccctggtggt cccatttatt tcctaaaggg tctgtctcac ctccacatcc    1800
ttaacttgga gtccaacggc tttgacgaga tcccagttga ggtcttcaag gatttatttg    1860
aactaaagat catcgattta ggattgaata atttaaacac acttccagca tctgtcttta    1920
ataatcaggt gtctctaaag tcattgaacc ttcagaagaa tctcataaca tccgttgaga    1980
agaaggtttt cgggccagct ttcaggaacc tgactgagtt agatatgcgc tttaatccct    2040
ttgattgcac gtgtgaaagt attgcctggt tgttaattg gattaacgag acccatacca    2100
acatccctga gctgtcaagc cactaccttt gcaacactcc acctcactat catgggttcc    2160
cagtgagact ttttgataca tcatcttgca aagacagtgc ccccttttgaa ctcttttca    2220 tgatcaaatac cagtatcctg ttgattttta tctttattgt acttctcatc cactttgagg    2280
gctggaggat atcttttat tggaatgttt cagtacatcg agttcttggt ttcaaagaaa    2340
```

```
tagacagaca gacagaacag tttgaatatg cagcatatat aattcatgcc tataaagata    2400
aggattgggt ctgggaacat ttctcttcaa tggaaaagga agaccaatct ctcaaatttt    2460
gtctggaaga aagggacttt gaggcgggtg tttttgaact agaagcaatt gttaacagca    2520
tcaaaagaag cagaaaaatt atttttgtta acacacca tctattaaaa gacccattat     2580
gcaaaagatt caaggtacat catgcagttc aacaagctat tgaacaaaat ctggattcca    2640
ttatattggt tttccttgag gagattccag attataaact gaaccatgca ctctgtttgc    2700
gaagaggaat gtttaaatct cactgcatct tgaactggcc agttcagaaa gaacggatag    2760
gtgcctttcg tcataaattg caagtagcac ttggatccaa aaactctgta cattaaattt    2820
atttaaatat tcaattagca aaggagaaac tttctcaatt taaaaagttc tatggcaaat    2880
ttaagttttc cataaaggtg ttataatttg tttattcata tttgtaaatg attatattct    2940
atcacaatta catctcttct aggaaaatgt gtctccttat ttcaggccta ttttgacaa     3000 ttgacttaat tttacccaaa ataaaacata taagcacgta aaaaaaaaaa aaaaaaa      3057
```

<210> SEQ ID NO 6
<211> LENGTH: 20
<212> TYPE: DNA
<213> ORGANISM: Artificial Sequence
<220> FEATURE:
<223> OTHER INFORMATION: Chemically synthesized oligonucleotide.

<400> SEQUENCE: 6
tccatgagct tcctgagctt                                                 20

<210> SEQ ID NO 7
<211> LENGTH: 125
<212> TYPE: PRT
<213> ORGANISM: Mus musculus

<400> SEQUENCE: 7

Met Ala Pro Thr Arg Ser Pro Ile Thr Val Thr Arg Pro Trp Lys His
1               5                   10                  15

Val Glu Ala Ile Lys Glu Ala Leu Asn Leu Leu Asp Asp Met Pro Val
            20                  25                  30

Thr Leu Asn Glu Glu Val Glu Val Ser Asn Glu Phe Ser Phe Lys
        35                  40                  45

Lys Leu Thr Cys Val Gln Thr Arg Leu Lys Ile Phe Glu Gln Gly Leu
    50                  55                  60

Arg Gly Asn Phe Thr Lys Leu Lys Gly Ala Leu Asn Met Thr Ala Ser
65                  70                  75                  80

Tyr Tyr Gln Thr Tyr Cys Pro Pro Thr Pro Glu Thr Asp Cys Glu Thr
                85                  90                  95

Gln Val Thr Thr Tyr Ala Asp Phe Ile Asp Ser Leu Lys Thr Phe Leu
            100                 105                 110

Thr Asp Ile Pro Phe Glu Cys Lys Lys Pro Val Gln Lys
        115                 120                 125

<210> SEQ ID NO 8
<211> LENGTH: 781
<212> TYPE: DNA
<213> ORGANISM: Homo sapiens

<400> SEQUENCE: 8
acacagagag aaaggctaaa gttctctgga ggatgtggct gcagagcctg ctgctcttgg    60

```
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg gagctgtaca gcagggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caagagaaac ctgaaggact    420
ttctgcttgt catccccttt gactgctggg agccagtcca ggagtgagac cggccagatg    480
aggctggcca gccgggggag ctgctctctc atgaaacaag agctagaaac tcaggatggt    540
catcttggag ggaccaaggg gtgggccaca gccatggtgg gagtggcctg gacctgccct    600
gggccacact gacctgata caggcatggc agaagaatgg gaatatttta tactgacaga    660
aatcagtaat atttatatat tttatttttt aaaatattta tttatttatt tatttaagtt    720
catattccat atttattcaa gatgttttac cgtaataatt attattaaaa atatgcttct    780
a                                                                   781
```

\<210\> SEQ ID NO 9
\<211\> LENGTH: 144
\<212\> TYPE: PRT
\<213\> ORGANISM: Homo sapiens

\<400\> SEQUENCE: 9

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

\<210\> SEQ ID NO 10
\<211\> LENGTH: 20
\<212\> TYPE: DNA
\<213\> ORGANISM: Artificial Sequence
\<220\> FEATURE:
\<223\> OTHER INFORMATION: Chemically synthesized oligonucleotide.

\<400\> SEQUENCE: 10

```
tccatgacgt tcctgacgtt                                                20
```

\<210\> SEQ ID NO 11
\<211\> LENGTH: 95
\<212\> TYPE: PRT
\<213\> ORGANISM: Homo sapiens -continued

```
<400> SEQUENCE: 11

Met Cys Cys Thr Lys Ser Leu Leu Ala Ala Leu Met Ser Val Leu
1               5                   10                  15

Leu Leu His Leu Cys Gly Glu Ser Glu Ala Ser Asn Phe Asp Cys Cys
            20                  25                  30

Leu Gly Tyr Thr Asp Arg Ile Leu His Pro Lys Phe Ile Val Gly Phe
            35                  40                  45

Thr Arg Gln Leu Ala Asn Glu Gly Cys Asp Ile Asn Ala Ile Ile Phe
    50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 12
<211> LENGTH: 235
<212> TYPE: PRT
<213> ORGANISM: Homo sapiens

<400> SEQUENCE: 12

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235

<210> SEQ ID NO 13
<211> LENGTH: 10
<212> TYPE: DNA
<213> ORGANISM: Artificial Sequence
<220> FEATURE:
```

```
<223> OTHER INFORMATION: Bacterial ribosomal RNA sequence

<400> SEQUENCE: 13
cggaaagacc                                                              10
```

METHOD OF ELICITING AN ANTI-TUMOR IMMUNE RESPONSE WITH CONTROLLED DELIVERY OF TLR AGONISTS IN POROUS POLYMERLC DEVICES

RELATED APPLICATIONS

This application is a continuation of U.S. Ser. No. 15/135,216, filed Apr. 21, 2016, which is a divisional of U.S. Ser. No. 13/741,271, filed Jan. 14, 2013, which (i) claims the benefit of priority under 35 U.S.C. § 119(e) to U.S. Provisional Application No. 61/586,624, filed Jan. 13, 2012; (ii) is a continuation-in-part of U.S. Ser. No. 12/867,426, filed Jan. 13, 2012, which is a national stage application, filed under 35 U.S.C. § 371, of International Application No. PCT/US2009/000914, filed Feb. 13, 2009, which claims the benefit of priority under 35 U.S.C. § 119(e) to U.S. Provisional Application No. 61/143,630, filed Jan. 9, 2009 and U.S. Provisional Application No. 61/065,672, filed Feb. 13, 2008; and (iii) is a continuation-in-part of U.S. Ser. No. 13/510,356, filed Nov. 22, 2010, which is a national stage application, filed under 35 U.S.C. § 371, of International Application No. PCT/US2010/057630, filed Nov. 22, 2010, which claims the benefit of priority under 35 U.S.C. § 119(e) to U.S. Provisional Application No. 61/281,663, filed Nov. 20, 2009. Each of these applications is incorporated herein by reference in its entirety.

GOVERNMENT SUPPORT

This invention was made with government support under R37 DE013033 awarded by the National Institutes of Health. The Government has certain rights in the invention.

SEQUENCE LISTING

The instant application contains a Sequence Listing which has been submitted via EFS-Web. The contents of the text file named "29297_091C01US_ST25.txt", which was created on Nov. 20, 2017 and is 35 KB in size, are hereby incorporated by reference in their entirety.

BACKGROUND OF THE INVENTION

Dendritic cells (DCs) collect and process antigens for presentation to T cells. DCs are the most potent activators of the immune system among antigen presenting cells. Research focused on using dendritic cells for a therapeutic benefit has been slow because dendritic cells are rare and difficult to isolate.

SUMMARY OF THE INVENTION

The invention features a device and method for stimulating immune cells such as dendritic cells, in situ. For example, presentation of Toll-like receptor (TLR) agonists in the context of the device is used for cancer vaccination. Incorporation and presentation of the TLR agonists embedded in structural polymeric devices specifically stimulates CD8(+) dendritic cells (DCs) (corresponding to CD141+ DCs in humans) and plasmacytoid DCs, which subsets of DCs are critical for cancer vaccination.

Accordingly, the invention provides a device comprising a porous polymeric structure composition, a tumor antigen, and a toll-like receptor (TLR) agonist. For example, the device comprises a polymeric structure composition, a tumor antigen, and a combination of toll-like receptor (TLR) agonists, wherein the TLR agonist is selected from the group consisting of TLR1, TLR2, TLR3, TLR4, TLR5, TLR6, TLR7, TLR8, TLR9, TLR10, TLR11, TLR12, and TLR13. For example, the polymeric structure comprises poly (D,L-lactide-co-glycolide) (PLG). Exemplary TLR agonists include pathogen associated molecular patterns (PAMPs), e.g., an infection-mimicking composition such as a bacterially-derived immunomodulator. TLR agonists include nucleic acid or lipid compositions [e.g., monophosphoryl lipid A (MPLA)].

Certain nucleic acids function as TLR agonists, e.g., TLR1 agonists, TLR2 agonists, TLR3 agonists, TLR4 agonists, TLR5 agonists, TLR6 agonists, TLR7 agonists, TLR8 agonists, TLR9 agonists, TLR10 agonists, TLR11 agonists, TLR12 agonists, or TLR13 agonists. In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). TLR9 agonists are useful to stimulate plasmacytoid DCs. For example, the device comprises 5 µg, 10 µg, 25 µg, 50 µg, 100 µg, 250 µg, or 500 µg of CpG-ODN.

In another example, the TLR agonist comprises a TLR3 agonist such as polyinosine-polycytidylic acid (poly I:C), PEI-poly (I:C), polyadenylic-polyuridylic acid (poly (A:U)), PEI-poly (A:U), or double stranded ribonucleic acid (RNA). TLR3 agonists are useful to stimulate CD8+ DCs in mice and CD141+ DCs in humans. A plurality of TLR agonists, e.g., a TLR3 agonist such as poly I:C and a TLR9 agonist such as CpG act in synergy to activate an anti-tumor immune response. For example, the device comprises a TLR3 agonist such as poly (I:C) and the TLR9 agonist (CpG-ODN) or a PEI-CpG-ODN. Preferably, the TLR agonist comprises the TLR3 agonist, poly (I:C) and the TLR9 agonist, CpG-ODN. The combination of poly (I:C) and CpG-ODN act synergistically as compared to the vaccines incorporating CpG-ODN or P(I:C) alone.

In some cases, the TLR agonist comprises a TLR4 agonist selected from the group consisting of lipopolysaccharide (LPS), monophosphoryl lipid A (MPLA), a heat shock protein, fibrinogen, heparin sulfate or a fragment thereof, hyaluronic acid or a fragment thereof, nickel, an opoid, α1-acid glycoprotein (AGP), RC-529, murine β-defensin 2, and complete Freund's adjuvant (CFA). In other cases, the TLR agonist comprises a TLR5 agonist, wherein the TLR5 agonist is flagellin. Other suitable TLR agonists include TRL7 agonists selected from the group consisting of single-stranded RNA, guanosine anologs, imidazoqinolines, and loxorbine.

Preferably, the TLR agonist is present at a concentration effective to induce the local production of interleukin-12 (IL-12) by dendritic cells.

The invention also provides a device comprising a porous polymeric structure composition, a disease-associated antigen, and a toll-like receptor (TLR) agonist, wherein the TLR agonist preferentially binds to TLR3. In some cases, the polymeric structure composition comprises poly-lactide-co-glycolide (PLG). The TLR3 agonist is present in an amount to preferentially stimulate CD8+ dendritic cells or CD141+ dendritic cells.

Preferably, the TLR agonist comprises a TLR3 agonist. In some cases, the TLR3 agonist comprises polyinosine-polycytidylic acid (poly I:C) or PEI-poly (I:C). For example, the TLR agonist comprises a nucleic acid. In other cases, the TLR agonist further comprises a TLR9 agonist. For example, the TLR9 agonist comprises a cytosine-guanosine oligonucleotide (CpG-ODN) or a PEI-CpG-ODN. Optionally, the device comprises a combination of TLR agonists, the combination comprising a TLR3 agonist and a TLR9 agonist. For example, the TLR3 agonist comprises poly (I:C) and the TLR9 agonist comprises CpG-ODN.

Alternatively, the device comprises a combination of TLR agonists, the combination comprising a TLR3 agonist and a TLR4 agonist. For example, the TLR3 agonist comprises poly (I:C) and the TLR4 agonist comprises MPLA.

Optionally, the device further comprises a recruitment composition. Exemplary recruitment compositions include granulocyte macrophage colony stimulating factor (GM-CSF), Flt3L, and CCL20. For example, the recruitment composition comprises encapsulated GM-CSF.

In some cases, the disease-associated antigen comprises a tumor antigen. For example, the tumor antigen comprises a tumor lysate, purified protein tumor antigen, or synthesized tumor antigen.

Optionally, the TLR agonist further comprises pathogen associated molecular patterns (PAMPs). For example, the PAMP comprises a monophosphoryl lipid A (MPLA).

Also provided is a device comprising a polymeric structure composition, a tumor antigen, and a combination of TLR agonists, wherein the TLR agonist is selected from the group consisting of TLR1, TLR2, TLR3, TLR4, TLR5, TLR6, TLR7, TLR5, TLR9, TLR10, TLR11, TLR12, and TLR13.

A method for eliciting an anti-tumor immune response is carried out by contacting or implanting into a subject a device comprising a polymeric structure composition, a tumor antigen, and a TLR agonist, wherein the TLR agonist preferentially binds to TLR3. For example, the TLR agonist comprises a TLR3 agonist. Alternatively, the TLR agonist comprises a TLR3 agonist and a TLR9 agonist.

Preferably, the anti-tumor immune response comprises activation of a CD8+ dendritic cell or a CD141+ dendritic cell. In some cases, the anti-tumor immune response comprises activation of a plasmacytoid dendritic cell or a CD141+ dendritic cell. Alternatively, the anti-tumor immune response comprises a reduction in tumor burden.

Preferably, the TLR agonist is present at a concentration effective to induce production of interleukin-12 (IL-12) by dendritic cells.

Optionally, the device further comprises granulocyte macrophage colony stimulating factor (GM-CSF). In some examples, the GM-CSF is encapsulated. Another optional recruitment composition is a cytokine. For example, the device comprises 1 μg, 3 μg, 5 μg, 10 μg, 25 μg, or 50 μg of GM-CSF.

The device also contains a tumor antigen, e.g., in the form of a tumor lysate (cultured cells or patient-derived primary cells) or purified tumor antigen such as a synthesized/synthetic recombinant protein or biochemically-purified antigen from a tumor cell.

Also with in the invention is a method for eliciting an anti-tumor immune response by contacting a subject, e.g., implanting into a subject, a device comprising a porous polymeric structure composition, a tumor antigen, and a TLR agonist. For example, the TLR agonist is selected from the group consisting of TLR1, TLR2, TLR3, TLR4, TLR5, TLR6, TLR7, TLR8, TLR9, TLR10, TLR11, TLR12, and TLR13. The device described above is associated with advantages over earlier vaccines. The most significant advantage is its ability to stimulate critical subsets of DCs that mediate potent anti-tumor activity. The method involves administering to a subject a device that contains a TLR3 agonist and/or a TLR9 agonist, which leads to elicitation of an anti-tumor immune response characterized by activation of plasmacytoid DCs and/or CD141+ DCs in the subject to which the vaccine was administered. The vaccine is useful for prophylaxis as well as therapy.

The device is administered, e.g., topically applied or implanted, and is present over a period of time, e.g., indwelling, while constantly recruiting, educating, and dispersing or sending cells forth to lymph nodes or sites of disease or infection in the body. Improvements over existing devices include long term, ongoing activation of cells that enter the device and concomitant long term, ongoing egress of immunologically activated, e.g., antigen primed cells. The device includes a scaffold composition, a recruitment composition, and a deployment composition. The deployment composition that mediates prolonged and continuous egress of primed cells is an infection-mimicking composition such as a bacterially-derived immunomodulator. In preferred embodiments, the bacterially-derived immunomodulator is a nucleic acid such as a cytosine-guanosine oligonucleotide (CpG-ODN).

The methods are used to treat a wide variety of diseases and to develop vaccines against a wide variety of antigens. In a preferred embodiment, the present invention is used to develop a cancer vaccine. Another preferred embodiment of the present invention comprises an infection-mimicking microenvironment with means to activate the host immune system and subsequently induce an immune response. The use of a synthetic cytosine-guanosine oligodeoxynucleotide (CpG-ODN) sequence with exogenous granulocyte macrophage colony stimulating factor (GM-CSF) provides a method for precisely controlling dendritic cell migration and modulating antigen-specific immune responses. In fact, the approach of using of this synthetic cytosine-guanosine oligonucleotide (CpG-ODN) sequence and/or poly (I:C) demonstrates significant improvements over earlier immune therapies.

Various components of the device are tabulated and described below.

TABLE 1

| EXEMPLARY DEVICE | FUNCTION | | |
|---|---|---|---|
| | Attract a DC to Device | Present an Immunogenic Factor | Induce DC Migration from Device |
| 1 | Scaffold Composition | Scaffold Composition | Scaffold Composition |
| 2 | Bioactive Composition | Bioactive Composition | Bioactive Composition |
| 3 | Scaffold Composition | Bioactive Composition | Bioactive Composition |
| 4 | Scaffold Composition | Scaffold Composition | Bioactive Composition |
| 5 | Bioactive Composition | Scaffold Composition | Scaffold Composition |
| 6 | Bioactive Composition | Bioactive Composition | Scaffold Composition |
| 7 | Bioactive Composition | Scaffold Composition | Bioactive Composition |
| 8 | Scaffold Composition | Bioactive Composition | Scaffold Composition |

Devices perform three primary functions, e.g. attracting cells to the device, presenting an immunogenic factor, and inducing cell migration away from the device. Each of these primary functions are performed by the scaffold (bold font) and/or biological (standard font) composition(s). Table 1 provides exemplary combinations of either the scaffold or biological composition paired with at least one primary function in exemplary devices (1-8). For example, the scaffold composition performs all three primary functions (device 1). In an alternative example, the scaffold composition performs one primary function, e.g. attracts cells to the device (preferably, dendritic cells), whereas the biological composition performs two primary functions, e.g. presents an immunogenic factor and induces cells (preferably, dendritic cells) to migrate away from the device (device 3). Device 5, for instance, is the inverse combination of device 3. Exemplary secondary functions of the scaffold and/or biological compositions include, but are not limited to, targeting the device to a particular cell or tissue type, adhering/releasing the device to/from the surface of one or more cells or tissues, and modulating the stability/degradation of the device.

The invention comprises a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition. Alternatively the bioactive composition incorporated into or coated onto the scaffold composition attracts a dendritic cell, introduces an immunogenic factor into the dendritic cell thereby activating the dendritic cell, and induces the dendritic cell to migrate away from the scaffold composition. In other preferred embodiments, the scaffold composition or bioactive composition separately attract a dendritic cell to the device, introduce an immunogenic factor into the dendritic cell, and induce the dendritic cell to migrate away from the device.

DCs include conventional DCs as well as specific subsets of DCs. The TLR agonists, e.g., TLR3 agonists, preferentially attract and stimulate CD141+ DCs in the human (CD8+ DCs in the mouse). The TLR9 agonist, e.g., CpG, preferentially attract and stimulate plasmacytoid DCs.

In preferred embodiments, the recruitment composition is GM-CSF, e.g., encapsulated GM-CSF. The device temporally controls local GM-CSF concentration, thereby controlling recruitment, residence, and subsequent dispersement/deployment of immune cells to lymph nodes or tissue sites distant from location of the device, e.g., sites of infection or tumor location. The concentration of GM-CSF determines whether if functions as a recruitment element or a deployment element. Accordingly, a method of programming dendritic cells in situ is carried out by introducing to a subject a device comprising scaffold composition and encapsulated recruitment composition. A pulse of recruitment composition is released from the device within 1-7 days of introduction of the device, leaving a residual amount of the recruitment composition in or on the device. The pulse is followed by slow release of the residual amount over several weeks. The local concentration of the recruitment composition and the temporal pattern of release mediates recruitment, retention, and subsequent release of dendritic cells from the device. For example, the pulse comprises at least 50, 60, 75, 90 or 95% of the amount of the recruitment composition associated with the device. An exemplary temporal release profile comprises a pulse characterized by release of at least 60% of the amount of the recruitment composition associated with the device in 1-5 days following the introduction of the device to a subject. Following the pulse, the residual amount is slowly released over an extended period of time (e.g., 1, 2, 3, 4, 5, 6, 7, 8, 9, 10, 12 days or 2, 3, 4, 5 or more weeks) following the pulse period.

Other recruitment compositions include Flt3L and/or CCL20. The recruitment compounds are used individually or in combination.

The method of making a scaffold is carried out by providing a scaffold composition, incorporating into or coating onto the scaffold composition a first bioactive composition comprising polypeptides with means for attracting or repelling a dendritic cell, and contacting the scaffold composition with a second bioactive composition, wherein the second bioactive composition is covalently or non-covalently associated with the scaffold composition wherein the second bioactive composition comprises a immunogenic factor. In an alternate embodiment of this method, the linking and contacting steps are repeated to yield a plurality of layers, wherein the second bioactive composition comprises a combination of compounds with means to activate a dendritic cell.

Methods comprise continuous in situ dendritic cell programming, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition. The devices recruit and stimulate a heterogeneous population of dendritic cells. Each subset is specialized and contributes significantly to the generation of an immune response. For example, the device mediates CpG-ODN presentation and enrichment of a subset of dendritic cells, plasmacytoid DC (pDC), or CD141+ DCs, which are particularly important in development of anti-tumor immunity.

Methods comprise increasing vaccine efficacy, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition, thereby increasing the effectiveness of a vaccination procedure.

Methods comprise vaccinating a subject against cancer, comprising administering to a subject, a device comprising a scaffold composition and bioactive composition, the bioactive composition being incorporated into or conjugated onto the scaffold composition, wherein the scaffold composition attracts a dendritic cell, introduces a immunogenic factor into the dendritic cell thereby activating the dendritic cell, and induces the dendritic cell to migrate away from the scaffold composition, thereby conferring upon a subject anti-tumor immunity, e.g., IL-12 production, and reduced tumor burden. In the case of a localized or solid tumor, the device is administered or implanted at or near the tumor site or site from which the tumor was excised or surgically removed. For example, the device is implanted at a distance of 1, 3, 5, 10, 15, 20, 25, 40 mm from a tumor site or site of excision, e.g., the PLG vaccine device is administered 16-21 mm away from a tumor mass.

Immunogenic factors include TLR ligands. For example, the immunogenic factor used is a modified TLR-9 ligand sequence, PEI-CpG-ODN. Preferably, the TLR ligand is a TLR3 agonist such as poly (I:C) or condensed PEI-poly (I:C).

Scaffold compositions comprise a non-biodegradable material. Exemplary non-biodegradable materials include, but are not limited to, metal, plastic polymer, or silk polymer. Moreover, scaffold compositions are composed of a biocompatible material. This biocompatible material is non-toxic or non-immunogenic.

Bioactive compositions are covalently or non-covalently linked to the scaffold composition. Bioactive compositions comprise an element, either covalently or non-covalently bonded to the surface of the scaffold composition, with means to attract a dendritic cell. Alternatively, or in addition, bioactive compositions comprise an element, either covalently or non-covalently bonded to the surface of the scaffold composition, with means to introduce an immunogenic factor into a dendritic cell. Alternatively, or further in addition, bioactive compositions comprises an element, either covalently or non-covalently bonded to the surface of the scaffold composition, with means to induce a dendritic cell to migrate away from the scaffold composition.

The element of the bioactive composition with means to manipulate a dendritic cell is a secreted or membrane-bound amino acid, peptide, polypeptide, protein, nucleotide, dinucleotide, oligonucleotide, polynucleotide, polymer, small molecule or compound. In a preferred embodiment, this element is granulocyte macrophage colony stimulating factor (GM-CSF), because this element attracts dendritic cells to the scaffold composition. In another preferred embodiment, this element is a PEI-CpG-ODN sequence because this element has means to introduce CpG-ODN sequences into a dendritic cell thereby activating the cell. In some embodiments, this element is a polynucleotide or polypeptide encoding for CCR7, a chemokine receptor that mediates dendritic cell migration towards lymph nodes and away from the scaffold composition. The CCR7 element is introduced into a dendritic cell simultaneously or sequentially with PEI-CpG-ODN sequences to enhance dendritic cell migration away from the scaffold composition.

Scaffold compositions of the present invention contain an external surface. Scaffold compositions of the present invention alternatively, or in addition, contain an internal surface. External or internal surfaces of the scaffold compositions are solid or porous. Pore size is less than about 10 nm, in the range of about 100 nm-20 μm in diameter, or greater than about 20 μm. In preferred embodiments, the size of the pores allows the migration into and subsequent exit of cells such as DCs from the device. For example, the pores are nanoporous, microporous, or macroporous. For example, the diameter of nanopores are less than about 10 nm; micropore are in the range of about 100 μm-20 μm in diameter; and, macropores are greater than about 20 μm (preferably greater than about 100 μm and even more preferably greater than about 400 μm). In one example, the scaffold is macroporous with open, interconnected pores of about 100-500 μm in diameter, e.g., 100-200, 200-400, or 400-500 μm. The size of the pores and the interconnected architecture allows the cells to enter, traverse within the volume of the device via the interconnected pores, and then leave the device via the pores to go to locations in the body outside of the device, e.g. to a tumor site, where an immune response is mounted against tumor cells. The activated DCs migrate away from the device and mount an immune response to solid tumors at discrete locations or throughout the body in the case of metastatic tumor cells or blood tumors such as leukemias.

Scaffold compositions of the present invention comprise one or more compartments.

Devices of the present invention are administered or implanted orally, systemically, sub- or trans-cutaneously, as an arterial stent, or surgically.

The devices and methods of the invention provide a solution to several problems associated with protocols for continuous cell programming in situ. In situ cell programming systems that stimulate immune responses of the cells and induce their outward migration to populate infected or diseased bodily tissues enhance the success of recovery, e.g., the specific elimination of diseased tissue. Such a device that controls cell function and/or behavior, e.g., locomotion, contains a scaffold composition and one or more bioactive compositions. The bioactive composition is incorporated into or coated onto the scaffold composition. The scaffold composition and/or bioactive composition temporally and spatially (directionally) controls dendritic cell attraction, programming, and migration.

The devices mediate active recruitment, modification, and release of host cells from the material in vivo, thereby improving the function of cells that have contacted the scaffold. For example, the device attracts or recruits cells already resident in the body to the scaffold material, and programs or reprograms the resident cells to a desired fate (e.g., immune activation).

This device includes a scaffold composition which incorporates or is coated with a bioactive composition; the device regulates attraction, activation, and migration of dendritic cells. Depending on the application for which the device is designed, the device regulates attraction, activation, and/or migration of dendritic cells through the physical or chemical characteristics of the scaffold itself. For example, the scaffold composition is differentially permeable, allowing cell migration only in certain physical areas of the scaffold. The permeability of the scaffold composition is regulated, for example, by selecting or engineering a material for greater or smaller pore size, density, polymer cross-linking, stiffness, toughness, ductility, or viscoelascticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or re-hydration, oxygenation, chemical or pH alteration, or ongoing self-assembly of the scaffold composition.

Attraction, activation, and/or migration are regulated by a bioactive composition. The device controls and directs the activation and migration of cells through its structure. Chemical affinities are used to channel cells towards a specific area of egress. For example, cytokines are used to attract or retard the migration of cells. By varying the density and mixture of those bioactive substances, the device controls the timing of the migration. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold also regulates the diffusion of bioactive agents through the device.

The bioactive composition includes one or more compounds that regulate cell function and/or behavior. The bioactive composition is covalently linked to the scaffold composition or non-covalently associated with the scaffold.

Signal transduction events that participate in the process of cell migration are initiated in response to immune mediators. Thus, the device optionally contains a second bioactive composition that comprises GM-CSF, a CpG-ODN or poly (I:C) sequence, a cancer antigen, and/or an immunomodulator.

In some cases, the second bioactive composition is covalently linked to the scaffold composition, keeping the composition relatively immobilized in or on the scaffold composition. In other cases, the second bioactive composition is noncovalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, π aromatic, and hydrophobic.

The scaffold composition is biocompatible. The composition is bio-degradable/erodable or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. One preferred scaffold composition includes an RGD-modified alginate.

Another preferred scaffold composition a macroporous poly-lactide-co-glycolide (PLG). For example, the PLG matrix includes GM-CSF, danger signals, and a target antigen, e.g., a cancer antigen and serves as a residence for recruited DCs as they are programmed. The recruitment element, GM-CSF, is encapsulated into the PLG scaffolds. PLG matrices that comprise the encapsulated GM-CSF provide a pulse of the dendritic cell recruitment composition and then a gradual slower rate of release. The pulse comprises at least 40, 50, 60, 75, 80% or more of the initial amount of bioactive composition with the remaining percent being released gradually over the next days or weeks after administration to the site in or on the subject to be treated. For example, release is approximately 60% of bioactive GM-CSF load within the first 5 days, followed by slow and sustained release of bioactive GM-CSF over the next 10 days. This release profile mediates a rate of diffusion of the factor through the surrounding tissue to effectively recruit resident DCs.

Porosity of the scaffold composition influences migration of the cells through the device. Pores are nanoporous, microporous, or macroporous. For example, the diameter of nanopores are less than about 10 nm; micropore are in the range of about 100 nm-20 μm in diameter; and, macropores are greater than about 20 μm (preferably greater than about 100 μm and even more preferably greater than about 400 μm). In one example, the scaffold is macroporous with aligned pores of about 400-500 μm in diameter.

The device is manufactured in one stage in which one layer or compartment is made and infused or coated with one or more bioactive compositions. Exemplary bioactive compositions comprise polypeptides or polynucleotides. Alternatively, the device is manufactured in two or more (3, 4, 5, 6, . . . 10 or more) stages in which one layer or compartment is made and infused or coated with one or more bioactive compositions followed by the construction of a second, third, fourth or more layers, which are in turn infused or coated with one or more bioactive compositions in sequence. Each layer or compartment is identical to the others or distinguished from one another by the number or mixture of bioactive compositions as well as distinct chemical, physical and biological properties.

A method of making a scaffold is carried out by providing a scaffold composition and covalently linking or noncovalently associating the scaffold composition with a first bioactive composition. Exemplary devices and methods of making them are described in U.S. Ser. No. 12/867,426, U.S. Ser. No. 13/510,356, and PCT/US2012/35505, each of which is hereby incorporated by reference. The first bioactive composition preferably contains granulocyte macrophage colony stimulating factor. The scaffold composition is also contacted with a second bioactive composition, preferably one or more cytosine-guanosine oligonucleotide (CpG-ODN) sequences. The second bioactive composition is associated with the scaffold composition to yield a doped scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components to one another and/or insertion of semi-permeable, permeable, or nonpermeable membranes within or at one or more boundaries of the device to further control/regulate locomotion of cells or bioactive compositions.

Therapeutic applications of the device include the instruction of immune cells. For example, the method includes the steps of providing a device that includes scaffold composition with a bioactive composition incorporated therein or thereon and a mammalian cell bound to the scaffold and contacting a mammalian tissue with the device, e.g., by implanting or affixing the device into or onto a mammalian tissue. At the time of administering or implanting the device, exemplary relative amounts of each component, recruiting composition (e.g., GM-CSF, Flt3L, or CCL20), danger signal (e.g., CpG-ODN), and antigen (e.g., purified tumor antigen or tumor cell lysate) are as follows: GM-CSF: 0.5 μg-500 μg; CpG-ODN: 50 μg-3,000 μg; and Tumor antigen/lysate: 100 μg-10,000 μg.

A method of modulating an activity of a cell, e.g., a host cell, is carried out by administering to a mammal a device containing a scaffold composition and a recruitment composition incorporated therein or thereon, and then contacting the cell with a deployment signal. The cells leave the device after encountering antigen (and other factors) and thus being activated to seek out tumor cells in the body to which an immune response is mounted. The activity of the cell at egress differs from that prior to entering the device. Cells are recruited into the device and remain resident in the device for a period of time, e.g., minutes; 0.2. 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to a change in the activity or level of activity of the cells. Encountering the antigen and other compounds in the device induces egress of the altered (re-educated or reprogrammed) cells, and the cells migrate out of the device and into surrounding tissues or remote target locations to seek out and mediate immunity against diseased cells such as tumor cells.

The deployment signal is a composition such as protein, peptide, or nucleic acid or a state of activation of the cell. For example, having ingested antigen, DCs become activated and migrate to lymph nodes, the spleen, and other anatomical locations, where they meet up with T cells to further propagate an antigen-specific immune response, e.g., anti-cancer response. For example, cells migrating into the device only encounter the deployment signal once they have entered the device. In some cases, the deployment signal is a nucleic acid molecule, e.g., a plasmid containing sequence encoding a protein that induces migration of the cell out of the device and into surrounding tissues. The deployment signal occurs when the cell encounters the plasmid in the device, the DNA becomes internalized in the cell (i.e., the cell is transfected), and the cell manufactures the gene product encoded by the DNA. In some cases, the molecule that signals deployment is an element of the device and is released from the device in delayed manner (e.g., temporally or spatially) relative to exposure of the cell to the recruitment composition. Alternatively, the deployment signal is a reduction in or absence of the recruitment composition. For example, a recruitment composition induces migration of cells into the device, and a reduction in the concentration or depletion, dissipation, or diffusion of the recruitment composition from the device results in egress of cells out of the device. In this manner, immune cells such as T cells, B cells, or dendritic cells (DCs) of an individual are recruited into the device, primed and activated to mount an immune response against an antigen-specific target. Optionally, an antigen corresponding to a target to which an immune response is desired is incorporated into or onto the scaffold structure. Cytokines, such as granulocyte macrophage colony stimulating factor (GM-CSF) are also a component of the device to amplify immune activation and/or induce migration of the primed cells to lymph nodes. Other cell specific recruitment compositions are described below.

The device recruit cells in vivo, modifies these cells, and then promotes their migration to another site in the body. This approach is exemplified herein in the context of dendritic cells and cancer vaccine development but is also useful to other vaccines such as those against microbial pathogens as well as cell therapies in general. Cells educated using the devices described herein promote regeneration of a tissue or organ immediately adjacent to the material, or at some distant site. Alternatively, the cells are educated to promote destruction of a tissue (locally or at a distant site). The methods are also useful for disease prevention, e.g., to promote cell-based maintenance of tissue structure and function to stop or retard disease progression or age-related tissue changes. The education of cells within the device, "programming" and "reprogramming" permits modification of the function or activity of any cell in the body to become a multipotent stem cell again and exert therapeutic effects.

The inability of traditional and ex vivo DC-based vaccination strategies to coordinate and sustain an immune response mediated by the heterogeneous DC network in cancer patients has led to limited clinical effectiveness of these approaches. The devices and methods described herein have distinct advantages, because preferential recruitment and expansion of pDCs dramatically improves immune responses to cancer antigens and reduces tumor progression compared to previous vaccine approaches.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 1 is a diagram showing the mechanisms by which bacterial invasion and bacterial toxins damage resident skin cells promoting the production of inflammatory cytokines, including GM-CSF, and activation of dermal endothelium. Cytokine stimulation induces extravasation of leukocytes and recruits skin resident DCs (langerhans cells) and monocytes/preDCs. DCs, recruited to the site of inflammation encounter and ingest bacterium and bacterial products including antigenic molecules and CpG-rich DNA, which stimulates TLR9 activation. As a result of TLR ligation and the inflammatory conditions, the DC rapidly matures to upregulate its expression of MHC-antigen complexes, costimulatory molecules, and CCR7 and begins to home to the lymph nodes where it initiates and propagates antigen specific T-cell responses.

FIGS. 2A-C. FIG. 2A is a schematic representation of PEI condensation of CpG-rich oligonucleotide sequences. The PEI polycation with positively charged amine groups is mixed with CpG-ODNs consisting of negatively charged phosphate groups at charge ratios (NH3+:PO4-) resulting in positively charged PEI-CpG-ODN condensates. FIG. 2B is a bar graph showing the zeta potential (my) of CpG-ODN 1826 and its PEI condensates at charge ratios of 4, 7 and 15. Box plots represent the mean and standard deviation (n=4) FIG. 2C is a bar graph showing the particle size of CpG-ODN 1826 and its PEI condensates at charge ratios of 4, 7 and 15. Values represent the average particle size and the standard deviation (n=4).

FIGS. 3A-C show in vitro uptake of CpG-ODN by JAWSII DCs. FIGS. 3A-B are bright field images of cells and their corresponding fluorescent images displaying the uptake of TAMRA labeled CpG-ODN molecules (A) or PEI-CpG-ODN condensates (B). FIG. 3C is a bar graph showing quantification of uptake of naked (-o-) and PEI-CpG-ODN (-●-) condensates over a period of 110 hours. FIG. 3D is a line graph showing quantification of uptake of PEI-CpG-ODN condensates and subsequent decondensation within JAWSII DCs. The number of PEI-CpG-ODN condensates in the cells (-■-), and the amount of uncondensed CpG-ODN (-□-) was monitored and quantified over a period of 70 hours. Scale bar-20 μm. Values in C (n>10 cells) and D (n>7 cells) represent the mean and standard deviation.

FIG. 4A is a series of brightfield images of activated DC morphology in correlation with fluorescent images displaying the uptake of TAMRA labeled CpG-ODN molecules condensed with PEI (charge ratio—7). FIG. 4B is a series of FACS histograms of JawsII DCs positive for the activation markers CD86, MHCII and CCR7 following no stimulation (tinted line), CpG-ODN (---), and PEI-CpG-ODN condensates (-). FIG. 4C is a chart showing tabulated data displaying the percentage of DCs positive for the activation markers CD86, MHCII, and CCR7 following no stimulation, and stimulation with TNF-α/LPS or CpG-ODN or PEI-CpG-ODN. FIG. 4D is a bar graph showing CpG-ODN and DC emigration toward CCL19. The effects of no stimulation (■), and PEI (■) or CpG-ODN (■) or PEI-CpG-ODN (■) stimulation on DC emigration from the top wells of transwell systems toward media supplemented with 300 ng/ml CCL19. Migration counts taken at 24 hours. Scale bar-20 μm. Values in C and D (n=4) represent the mean and standard deviation. CpG-ODN activation media (5 μg/ml). * P<0.05** P<0.01.

FIG. 5A is a series of bar graphs showing the percentage of JawsII DCs positive for MHCII and CCR7 expression after PEI-CpG-ODN (5 μg/ml) stimulation in media supplemented with 0 (□), 50 (■) and 500 ng/ml GM-CSF (■). FIG. 5B is a line graph showing CpG-ODN and DC emigration toward CCL19 in the presence of GM-CSF. The effects of no stimulation (-■-), and stimulation with PEI (---) or CpG-ODN (-●-) or PEI-CpG-ODN (-●-) on DC emigration from the top wells of transwell systems toward media supplemented with 300 ng/ml CCL19. Migration counts taken at 24 hours. Values represent the mean and standard deviation (n=4).

FIG. 6A is a line graph showing the fraction of PEI-CpG-ODN condensates retained in PLG matrices over time with incubation in PBS in vitro. FIGS. 6B-C are bar graphs showing emigration of JAWS II DCs from CpG-ODN loaded scaffolds. (B) The total number of DCs that migrated from scaffolds loaded with 5, 50, 500 μg of CpG-ODN toward media supplemented with 300 ng/ml CCL19. (C) The total number of DCs that migrated from scaffolds loaded with 25 μg of CpG-ODN in the presence of 500 ng/ml GM-CSF toward media supplemented with 300 ng/ml CCL19. Migration counts taken at 48 hours. Values represent mean and standard deviation (n=4 or 5).

FIG. 7A is a chart showing the tabulated data of host DC recruitment (cell #) and DC activation (% expressing MHC or CCR7) in response to various dosages of PEI-CpG-ODN and GM-CSF loaded into PLG matrices. Matrices were implanted into the backs of C57/BL6J mice for 7 days. FIG. 7B is a bar graph showing the number of CD11c(+)MHCII(+) and CD11c(+)CCR7(+) host DCs isolated from matrices loaded with PEI-ODN control, 10 μg PEI-CpG-ODN, 400 and 3000 ng GM-CSF, and 400 and 3000 ng GM-CSF in combination with 10 μg PEI-CpG-ODN at Day 7 after implantation into the backs of C57/BL6J mice. Values represent the mean and standard deviation (n=3-5). * P<0.05** P<0.01.

FIGS. 8A-D. Infection mimics continuously disperse programmed DCs in situ. FIG. 8A is a bar graph showing the number of FITC(+) DCs that have homed to the inguinal lymph nodes as a function of time subsequent to their residence at FITC painted blank matrices (-□-), FITC painted GM-CSF loaded matrices (-■-), and FITC painted GM-CSF and CpG-ODN matrices (-■-). GM-CSF dose was 3000 ng and CPG-ODN dose was 10 µg. FIG. 8B is a digital photograph of inguinal lymph nodes extracted from C57BL/6J mice (control) and at 10 days after the implantation of matrices incorporating 10 µg CpG-ODN+3000 ng GM-CSF (infection-mimic). FIGS. 8C-D are bar graphs showing the total number of cells (C) and CD11c+ DCs (D) isolated from inguinal lymph nodes extracted from C57BL/6J mice at 2 and 7 days after the implantation of blank matrices (□) and matrices incorporating 3000 ng GM-CSF (■) or 10 µg CpG-ODN+3000 ng GM-CSF (□). Values in A, C and D represent the mean and standard deviation (n=4 or 5). * P<0.05** P<0.01.

FIG. 10A is a series of representative photomicrographs of tumor sections from mice vaccinated with PLG cancer vaccines that appropriately control the presentation of tumor lysates, 3000 ng GM-CSF and CpG-ODN and blank (blank) scaffold controls. Sections were stained to detect for CD4(+) and CD8(+) T cell infiltrates into tumor tissue that was explanted from mice that had developed tumors at days 20-25. FIG. 10B is a bar graph showing T-cell infiltrates into B16-FI0 melanoma tumors of vaccinated animals. Tumors were explanted from C57BL/6J mice treated with blank PLG scaffolds (□), or PLG scaffolds incorporating B16-F10 melanoma tumor lysates, 3000 ng GM-CSF and 10 µg PEI-CpG-ODN (■) at days 20-25. T-cell infiltrates were examined in randomized sections of tumors (n=4, 1 mm³). Scale bar-50 µm. Values in A, D and E represent the mean and standard deviation (n=3 or 4). * P<0.05**P<0.01.

FIGS. 11 A-F. In vivo control of DC recruitment and programming.

FIGS. 12 A-G. Antigen co-presentation with CpG-ODN to DCs infiltrating PLG matrices enhances local CD8+ cDC numbers, IL-12 production and total CD8(+) cell numbers. The number of (FIG. 12A) plasmacytoid DCs, (B) CD11c (+)CD11b(+) cDCs, and (FIG. 12C) CD11c(+)CD8(+) cDCs at day 10 post-implantation in blank matrices (Blanks) and in response to doses of 3000 ng GM-CSF (GM) or 100 µg CpG-ODN (CpG) alone or in combination (CpG+GM) or co-presented with tumor lysates (GM+Ant, CpG+Ant and CpG+GM+Ant). The in vivo concentration of (FIG. 12D) IFN-α (E) IFN-γ and (FIG. 12F) IL-12 at day 10 post-implantation in blank matrices (Blanks) and in response to doses of 3000 ng GM-CSF (GM) or 100 µg CpG-ODN (CpG) alone or in combination (CpG+GM) or co-presented with tumor lysates (GM+Ant, CpG+Ant and CpG+GM+Ant). (FIG. 12G). FACS histograms of CD8(+) cells infiltrating Blank PLG matrices(——) and matrices loaded with 3000 ng GM-CSF and 100 µg CpG-ODN alone (---) or with tumor antigens (tinted line). Values in A-F represent mean and standard deviation (n=4 or 5). * P<0.05 ** P<0.01.

FIGS. 13A-F. Tumor protection regulated by CpG-ODN presentation and plasmacytoid DC enrichment. Survival times of mice vaccinated with PLG vaccines 14 days prior to B16-F10 melanoma tumor challenge. (FIG. 13A) shows a comparison of survival times in mice vaccinated with PLG matrices loaded with tumor lysates and 1, 10, 50 or 100 µg of CpG-ODN. FIG. 13B shows a comparison of survival times in mice vaccinated with PLG matrices loaded with tumor lysates, 3000 ng GM-CSF and 1, 10, 50 or 100 µg of CpG-ODN. A correlation between the number of (FIG. 13C) CD11c(+)PDCA-1(+) DCs, (FIG. 13D) CD11c(+)CD11b(+) DCs, and (FIG. 13E) CD11c(+)CD8(+) cDCs at the PLG vaccine site at day 10 and the percent of animals surviving B16-F10 melanoma tumor challenge at Day 100. FIG. 13F shows the fraction of total DC population consisting of CD11c(+)CD11b(+) cDCs, CD11c(+)PDCA-1(+) pDCs, and CD11c(+)CD8(+) cDCs generated at the PLG vaccine site at day 10. Survival percentage is taken at Day 100 after challenge with B16-F10 melanoma cells.

FIG. 14A shows a comparison of the survival time in C57BL/6 mice treated with blank PLG scaffolds, and PLG vaccines (3 µg GM-CSF+100 µg CpG-ODN+ tumor lysates). FIG. 14B shows a comparison of tumor growth in C57BL/6 mice treated with blank PLG scaffolds, and PLG vaccines (3 µg GM-CSF+100 µg CpG-ODN+ tumor lysates). Mice were inoculated with $5 \times 10^5$ B16-F10 melanoma tumor cells at Day 0 and tumors were allowed to grow for 7 days when mice were either implanted with blank PLG matrices or PLG vaccine. The average tumor size was expressed as one-half the product of the smallest and largest diameter.

FIG. 16G shows the total numbers of CD11c(+)CD8(+) DCs and pDCs at scaffold site at day 7, and (H) the local IL-12 concentration after implantation of GM-CSF loaded scaffolds (Con) and scaffolds loaded with GM-CSF in combination with CpG-ODN (CpG), MPLA (MPLA), and P(I:C) (P(IC)). Values represent mean and standard deviations (n=6). ** P<0.01, as compared to GM-CSF loaded matrices (Con).

FIG. 17A shows a comparison of survival times in untreated mice (Control) and mice treated with GMCSF loaded PLG scaffolds (GM-CSF) or with PLG scaffolds loaded with GM-CSF in combination with CpG-ODN (CpG), P(I:C), or MPLA. Plots of the normalized magnitude of (B) CD11c(+)CD8(+) DC infiltration, (C) pDC infiltration at the vaccine site, and (D) local IL-12 concentration versus the percent of animals surviving B16-F10 melanoma tumor challenge at Day 100 (survival data taken from experimental conditions in (A; red data points) and previously reported data with this system). r values in B-C represent the linear correlation coefficient between x-axis variable and survival percentage.

FIGS. 19A-F are graphs showing therapeutic vaccination and anti-tumor T cell activity. A comparison of the (A) tumor size and (B) overall survival in mice bearing established melanoma tumors (inoculated with $5 \times 10^5$ B16-F10 cells and allowed to develop for 9 days) and treated with either GM-CSF loaded matrices (Con) or matrices loaded with GM-CSF in combination with CpG-ODN (CpG), MPLA (MPLA), and P(I:C) (P(IC)). (C) FACS plots representing tumor infiltrating leukocytes isolated from explanted tumors at Day 18 after tumor challenge. Mice were treated with GM-CSF loaded matrices (Control) or matrices loaded with GM-CSF in combination with CpG-ODN (CpG), MPLA (MPLA), and P(I:C) (P(IC)) at Day 9 after tumor inoculation and cell isolations from tumors were prepared at Day 18 and stained for activated, cytotoxic T cell markers, CD8(+) and CD107a. Numbers in FACS plots indicate the percentage of the cell population positive for both markers. (D) The numbers of CD8(+), tumor-infiltrating T cells positive for both IFNγ and CD107a in untreated mice (nave) or mice vaccinated with various treatments. (E) The total numbers of Trp2-specific cytotoxic T cells in splenocytes of vaccinated mice. FIG. 19F is a bar chart showing a comparison of the tumor size at Day 17. * P<0.05 ** P<0.01, as compared to control matrices (loaded with GM-CSF), unless otherwise noted.

FIG. 21A shows the local TNF-α concentration after implantation of GM-CSF loaded matrices (Con) and scaffolds loaded with GM-CSF in combination with CpG-ODN (CpG), MPLA (MPLA), and P(I:C) (P(IC)). Values represent mean and standard deviations (n=5).  P<0.01, as compared to GM-CSF loaded matrices (Con). FIG. 21B shows the local IFN-α concentration after implantation of GM-CSF loaded scaffolds (Con) and scaffolds loaded with GM-CSF in combination with CpG-ODN (CpG), MPLA (MPLA), and P(I:C) (P(IC)). Values represent mean and standard deviations (n=5). P<0.01, as compared to GM-CSF loaded matrices (Con). FIG. 21C shows the local IL-12p70 concentration after implantation of GM-CSF loaded scaffolds (Con) and vaccine scaffolds (loaded with tumor lysate, GM-CSF and CpG-ODN)(CpG), in wildtype (vax) and Cd8atm1Mak/J mice (CD8 Tc KO). FIG. 21D shows the local IFN-γ concentration after implantation of GM-CSF loaded scaffolds (Con) and vaccine scaffolds (loaded with tumor lysate, GM-CSF and CpG-ODN)(CpG), in wildtype (vax) and B6.129S2-Cd8atm1Mak/J mice (CD8 Tc KO).

FIG. 24A shows the cumulative release of GM-CSF, Flt3L, or CCL20 from PLG scaffolds. FIG. 24B shows a representative photograph of scaffold histological sections stained for CD11(+) DC infiltrates (pink) into macroporous blank (left) and GM-CSF loaded scaffolds (right) at Day 10 after implantation. Scale bar—100 μm. FIG. 24C shows the total numbers of CD11c (+) DCs at scaffold site at day 7 after implantation of Blank PLG matrices (Con) and matrices loaded with GM-CSF (GM), Flt3L (FL3) and CCL20 (CCL20). Values represent mean and standard deviations (n=6). * P<0.05 ** P<0.01, as compared to GM-CSF loaded matrices.

FIG. 25A shows FACS histograms and plots representing scaffold infiltrating dendritic cells in CpG-ODN loaded PLG scaffolds (Con) or scaffolds loaded with GM-CSF (GM), Flt3L(F13L) or CCL20(CCL20) in combination with CpG-ODN at day 7 post-implantation in mice. Histograms indicate the relative frequency of MHCII and CD86 expression in CD11c(+) DCs infiltrating the indicated scaffold formulation. Dot plots indicate cells stained for CD11c (+) in combination with activated, plasmacytoid DC marker, PDCA-1. Numbers in the upper right quadrant of FACS plots indicate the percentage of CD11c(+)PDCA-1(+) pDCs. FIG. 25B shows the total numbers of activated CD11c(+) DCs positive for MHCII and CD86 expression, and FIG. 25C shows CD11c(+)PDCA-1(+) pDCs present in scaffold at day 7 after implantation of CpG-ODN loaded PLG scaffolds (Con) or scaffolds loaded with GM-CSF (GM), Flt3L(F13L) or CCL20(CCL20) in combination with CpG-ODN. Values represent mean and standard deviations (n=5). * P<0.05 ** P<0.01, as compared to controls (Con) unless otherwise indicated.

(FIG. 26D shows the overall survival of mice bearing melanoma tumors, and treated with either CpG-ODN loaded matrices (Blank) or matrices loaded with CpG-ODN in combination with GMCSF, Flt3L and CCL20 (n=8). Values represent mean and standard deviations (n=5). * P<0.05, as compared to CCL20 loaded matrices (CC20).

DETAILED DESCRIPTION OF THE INVENTION

Figure 1:
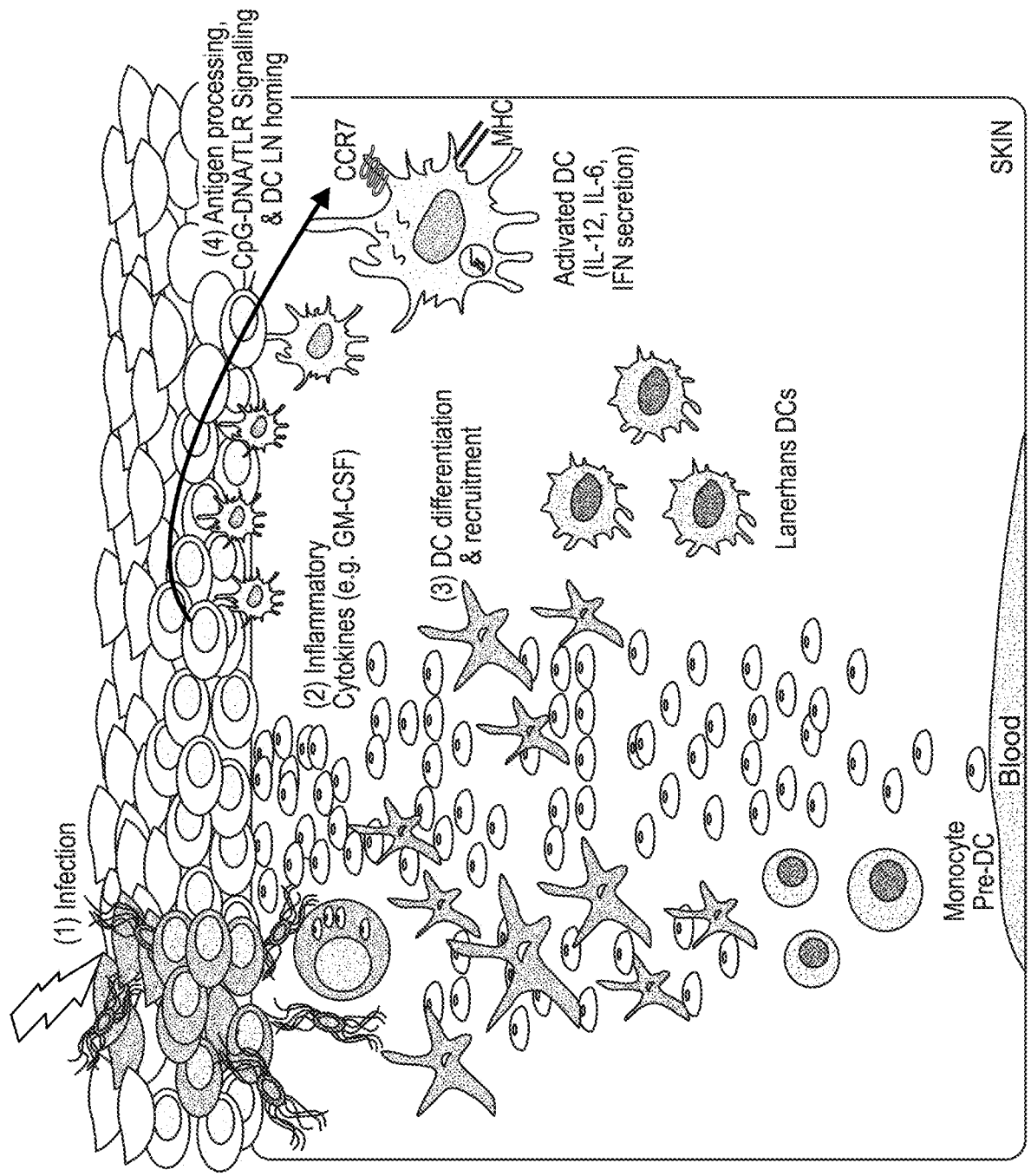
FIG. 1 is a diagram of the immune response to infection.

Prior to the invention, cancer vaccines typically depended on cumbersome and expensive manipulation of cells in the laboratory, and subsequent cell transplantation resulted in poor lymph node homing and limited efficacy. The invention solves these problems by using materials that mimic key aspects of bacterial infection to directly control immune cell trafficking and activation in the body. Presentation of TLR agonists for cancer vaccination leads to improved activation of immune cells. The vaccines and methods comprise incorporation and presentation of TLR agonists embedded in structural polymeric devices. The data described herein demonstrate the critical role of CD8(+) Dendritic cells (DCs) and plasmacytoid DCs (as well as conventional DCs) for cancer vaccination, which are preferentially recruited and activated using the TLR-agonist containing structural polymeric device. The device is manufactured as a tiny bioengineered porous disc filled with tumor-specific antigens and TLR agonists. The disc is implanted into the body, e.g., inserted under the skin, where it activates the immune system to destroy tumor cells. While typical earlier methods involved growing cells outside the body, this approach reprograms cells that are already in the body.

In some examples, the device includes a recruitment component. Thus, the device optionally includes a recruitment molecule such as a cytokine. In those situations, polymers were designed to first release a cytokine to recruit and house host dendritic cells (DCs), and subsequently present cancer antigens and danger signals to activate the resident DCs and dramatically enhance their homing to lymph nodes. Specific and protective anti-tumor immunity was generated with these materials, as 90% survival was achieved in animals that otherwise die from cancer within 25 days. These materials are useful in cancer and other vaccines to program and control the trafficking of a variety of cell types in the body.

A polymer system was designed to not only serve as a drug delivery device, but also as a physical, antigen-presenting structure to which the DCs are recruited, and where DCs reside while they are activated using a material (poly [lactide-co-glycolide]) and bioactive molecules (GM-CSF and CpG-ODN). These bioactive molecules have excellent safety profiles. The material system serves as an effective cancer vaccine, eliminating the time, expense and regulatory burden inherent to existing cell therapies and reducing or eliminating the need for multiple, systemic injections and high total drug loading. The devices described herein utilize infection-mimicking materials to program DCs in situ.

A quantitative understanding of the ability of GM-CSF to impact DC recruitment, activation and emigration in vitro was developed in order to appropriately design a material system for vaccination. GM-CSF enhanced DC recruitment and proliferation in a dose dependent manner. However, high concentrations (>100 ng/ml) of GM-CSF inhibited DC migration toward a lymph node derived chemoattractant (CCL19). Immunohistochemical staining revealed that the high concentrations of GM-CSF (500 ng/ml) also downregulated DC expression of the CCL19 receptor CCR7 and MHCII. These results indicated that control over GM-CSF exposure was needed to both recruit and program DCs in vivo. If GM-CSF alone is to be used for both purposes, its local concentration is designed to decrease over time in order to release DCs that become trapped in the material. Alternatively, provision of a danger signal (e.g., CpG-ODN) in the local environment is used to release DCs from GM-CSF inhibition once they reside at the infection-mimicking site.

Based on this understanding, a macroporous poly-lactide-co-glycolide (PLG) matrix was designed to present GM-CSF, danger signals, and cancer antigens in a defined spatiotemporal manner in vivo, and serve as a residence for recruited DCs as they are programmed. GM-CSF was encapsulated (54% efficiency) into PLG scaffolds using a high pressure $CO_2$ foaming process. These matrices released approximately 60% of their bioactive GM-CSF load within the first 5 days, followed by slow and sustained release of bioactive GM-CSF over the next 10 days. This release profile allows diffusion of the factor through the surrounding tissue to effectively recruit resident DCs.

As described herein, in situ dendritic cell targeting systems are utilized to therapeutically manipulate the immune system with TLR agonists. As described in detail below, macroporous polymeric scaffolds were designed that deliver three different classes of TLR agonists in vivo: CpG-ODN, MPLA, and P(I:C) in combination with GM-CSF, Flt3L, or CCL20 to augment DC recruitment and activation. The ability of in situ TLR presentation from macroporous matrices to modulate DC subset generation, and cancer vaccine efficacy in a B16-F10 melanoma model was also characterized. The ability of these systems to effect immune protection and tumor regression required CD8(+) DCs and correlated strongly with plasmacytoid DCs(pDCs) and IL-12 production, regardless of the TLR agonist type or dose. Thus, the results presented herein demonstrate that 3D polymer matrices are utilized to regulate DC subsets in situ for immunotherapy and indicate that CD8(+) DCs, pDCs and IL-12 signaling are critical components of successful material-based vaccination protocols.

The generation of immunity requires collaboration between dendritic cells (DCs) and T cells, as the priming of cytotoxic T lymphocyte (CTL) by DCs is a crucial event in the fight against infection and tumors (Lanzavecchia A. and Sallusto F., 2001 Cell, 106: 263-266). DCs regulate immune responses by recognizing, processing, and decoding pathogen associated molecular patterns (PAMPs) and antigenic molecules (Banchereau J, and Steinman R M., 1998 Nature, 392: 245-252; Mellman I. and Steinman R. M., 2001 Cell, 106: 255-258; Sansonetti P. J., 2006 Nat. Immunol., 7: 1237-1242; Meylan et al., 2006 Nature, 442: 39-44; Akira et al., 2006 Cell, 124: 783-801). PAMP recognition by pattern recognition receptors (PRRs) present intercellularly or at the DC surface signal the presence of infection and triggers signal transduction pathways ultimately resulting in DC activation (Sansonetti P. J., 2006 Nat. Immunol., 7: 1237-1242; Meylan et al., 2006 Nature, 442: 39-44; Akira et al., 2006 Cell, 124: 783-801). Generally, activated DCs are characterized by enhanced expression of MHC and co-stimulatory molecules and proinflammatory cytokines, which enables DCs to translate pathogenic signals to naïve T cells and trigger adaptive immune responses (Banchereau J, and Steinman R M., 1998 Nature, 392: 245-252; Mellman I. and Steinman R. M., 2001 Cell, 106: 255-258; Sansonetti P. J., 2006 Nat. Immunol., 7: 1237-1242; Meylan et al., 2006 Nature, 442: 39-44; Akira et al., 2006 Cell, 124: 783-801; Gilboa, E., 2007 J Clin Invest., 117: 1195-1203; Banchereau J. and Steinman R. M., 2007 Nature, 49: 419-426). DCs act as a network of distinct subsets that perform specialized functions to stimulate and polarize T cell responses in order to coordinate immune regulation (Naik et al., 2007 Nat Immunol, 8: 1217-1226; O'Garral A. and Trinchieri G. 2004 Nat Immunol, 5: 1206-1208; D'Amico A and Wu L., 2003 J Exp Med, 2: 293-303; Villadangos J A and Schnorrer P, 2007 Nat Rev Immunol, 7: 543-555; Liu Y J, 2001 Cell, 106: 259-262; Jego et al., 2003 Immunity, 19: 225-234; Randolph et al., 2008 Annu. Rev. Immunol., 26: 293-316). Antigen processing and presentation to T cells is predominantly attributed to the conventional DC subset (cDCs), consisting of both CD8(−) DCs and CD8(+) DCs. CD8(+) DCs are especially adept at cross-presentation of exogenous antigen, IL-12 production and induction of cytotoxic T cell responses (Schnorrer P, 2006 PNAS 28: 10729-34; Skokos D. and Nussenzweig M. C., J Exp Med, 204: 1525-1531; Den Haana et al., 2000 J Exp Med, 12: 1685-1696; Moser M. and Murphy K. M., 2000 Nat. Immunol., 1: 199-205; Hildner et al., 2008 Science, 322:1097-1100). The plasmacytoid DC (pDC) subset has the capacity to produce significant amounts of type-1 interferons (IFNs) in response to microbial nucleic acids, particularly during viral infection, to facilitate T cell activation, growth and survival for disease clearance (Liu Y J, 2001 Cell, 106: 259-262; Jego et al., 2003 Immunity, 19: 225-234; Randolph et al., 2008 Annu. Rev. Immunol., 26: 293-316; Kanzler et al., 2007 Nat. Med., 13: 552-559). Moreover, the processes mediated by pDC and CD8(+) DC subsets have been associated with priming t-helper 1 (Th1) effector cells for the control of infection and tumors. A balanced distribution of activated DC subsets is associated with the control of autoimmune disease and tumors, indicating that these cells may cooperate during the generation of protective immunity.

Prior to the invention described herein, cancer vaccines are designed to introduce antigen in combination with immunostimulatory signals to activate DCs either ex vivo prior to administration, or in situ (Gilboa E., 2007 J Clin Invest., 117: 1195-1203; Banchereau J. and Steinman R. M., 2007 Nature, 49: 419-426; Kanzler et al., 2007 Nat. Med., 13: 552-559; Hansen et al., 2013 Vaccine, 31(4), 639-46; Schuler et al., 2003 Curr Opin Immunol, 15: 138-147; Curiel T. J, 2002 J Clin Invest, 109: 311-312). A range of stimuli are used to trigger DC maturation and differentiation including proinflammatory cytokines, PAMPs recognized by the toll-like receptor (TLR) family, and feedback signals from innate and adaptive immune cells. As described in detail below, discrete combinations of these stimuli and DC subsets differentially control T cell activation and polarization, and these components are optimized and exploited to generate effective immune responses that eradicate tumors or infectious agents. However, it is currently unclear what components and DC subsets should be included in cancer vaccines, partly because current techniques limit the cell types that can be cultured or targeted (Kanzler et al., 2007 Nat. Med., 13: 552-559; Hansen et al., 2013 Vaccine, 31(4), 639-46; Schuler et al., 2003 Curr Opin Immunol, 15: 138-147; Curiel T. J, 2002 J Clin Invest, 109: 311-312). Standard DC-based protocols widely used in the clinic utilize monocyte-derived conventional DCs that are unable to cross-present antigens, or efficiently produce IL-12 or type-1 IFNs that can prime CTL-mediated immune responses and tumor cell death (Hansen et al., 2013 Vaccine, 31(4), 639-46; Schuler et al., 2003 Curr Opin Immunol, 15: 138-147; Curiel T. J, 2002 J Clin Invest, 109: 311-312). Prior to the invention described herein, there were attempts to utilize type 1 differentiated DCs in combination with TLR agonists to boost CTL priming capacity, but this maturation is accompanied by decreased migratory and stimulatory function upon implantation (Hansen et al., 2013 Vaccine, 31(4), 639-46). Described herein are macroporous polymer matrices that regulate the trafficking and activation of DCs in vivo by precisely controlling the presentation of GMCSF and CpG-oligonucleotide (CpG-ODN) adjuvants (Ali et al., 2009 Nat Mater, 2: 151-8; Ali et al., 2009 Sci Transl Med, 1:8-19). When applied as cancer vaccines, these matrices led to induce CTL-mediated eradication of melanoma tumors (Ali et al., 2009 Sci Transl Med, 1:8-19).

As described herein, matrices were modified to present 3 different classes of TLR agonists, CpG-ODN, monophosphoryl lipid A (MPLA), and polyinosinic:polycytidylic acid (P(I:C)), all in combination with GM-CSF. The ability of each vaccine to recruit and generate activated DC subsets, in vivo was first quantified. The impact of DC induction on T cell-mediated immunity and cancer vaccine efficacy in vaccine models of B16-F10 melanoma was next assessed. These studies demonstrate that anti-tumor efficacy requires CD8(+) DCs and is strongly correlated with pDC numbers and local IL-12 production. Survival outcomes were also correlated to an array of inflammatory cytokines, which revealed a strong relationship between IL-12 production and antitumor efficacy. Altogether, the results presented herein demonstrate that various DC subsets are recruited and utilized for in situ vaccination, and provide important cellular and molecular insights into cancer vaccine design.

Inflammatory Mediators

Dendritic Cell (DC) proliferation, migration and maturation are sensitive to inflammatory mediators, and granulocyte macrophage colony stimulating factor (GM-CSF) has been identified as a potent stimulator of immune responses, specifically against cancer antigens. GM-CSF also has the ability to recruit and program these antigen-presenting immune cells. Additionally, Cytosine-guanosine (CpG) oligonucleotide (CpG-ODN) sequences found in bacterial DNA are potent immunomodulators that stimulate DC activation, leading to specific T-cell responses. Creating an infection mimicking microenvironment by the presentation of exogenous GM-CSF and CpG-ODN provides an avenue to precisely control the number and timing of DC migration and modulate antigen specific immune responses.

The vertebrate immune system employs various mechanisms for pathogen recognition making it adept at generating antigen-specific responses and clearing infection. Immunity is controlled by antigen presenting cells (APCs), especially dendritic cells (DCs), which capture antigens and are activated by stimuli, unique 'danger signals' of the invading pathogen, such as CpG dinucleotide sequences in bacterial DNA (Banchereau J, and Steinman R M. Nature. 392, 245-252. (1998); Klinman D M. Nat. Rev. Immunol. 4, 249-58 (2004); each herein incorporated by reference).

However, cancerous cells, derived from self-tissues, are void of the danger signals required to signal DC maturation and instead promote an immunosuppressive microenvironment that allows cells to escape immunity. Key elements of infection are inflammatory cytokines and danger signals (FIG. 1). A polymeric material system is ideal to present these factors in the required spatiotemporal manner to provide an infection-mimicking microenvironment in situ that useful as a vaccine. These infection mimics provide the continuous programming of host DCs, providing for efficient DC activation and dispersement in situ. These infection-mimicking devices are used for numerous vaccine applications including melanoma cancer vaccines.

In many infections, inflammatory cytokines and danger signals stimulate specific DC responses that mediate immune recognition and pathogen clearance (FIG. 1). For example, upon bacterial invasion and release of toxins, skin cells such as fibroblasts, keratinocytes and melanocytes are damaged resulting in the release of inflammatory cytokines, such as GM-CSF (Hamilton J. Trends in Immunol. 23, 403-408. (2002); Hamilton J., and Anderson G. Growth Factors. 22(4), 225-231. (2004); each herein incorporated by reference), that act to recruit Langerhans D C (skin) and DC precursors (monocytes; blood) (Hamilton J. Trends in Immunol. 23, 403-408. (2002); Hamilton J., and Anderson G. Growth Factors. 22(4), 225-231. (2004); Bowne W. B., et al. Cytokines Cell Mol Ther. 5(4), 217-25. (1999); Dranoff, G. Nat. Rev. Cancer 4, 11-22 (2004); each herein incorporated by reference). As DCs arrive to the site of infection they begin to differentiate, and increase in phagocytic ability in response to the inflammation (Mellman I., and Steinman R. M. Cell. 106, 255-258. (2001), herein incorporated by reference), and DCs that ingest bacteria or their products begin to process antigens and DC maturation proceeds via endosomal TLR9 signaling stimulated by CpG dinucleotide sequences in bacterial DNA (Krieg A. M., Hartmann G., and Weiner G. J. CpG DNA: A potent signal for growth, activation, and maturation of human dendritic cells. Proc Natl Acad Sci USA. 16, 9305-9310 (1999), herein incorporated by reference). Mature DCs then home to the lymph nodes where they prime antigen specific T-cell responses that clear infection.

CpG-ODNs are potent "danger signals" that upregulate DC expression of CCR7, CD80/86 costimulatory molecules, and MHC-antigen complexes. Importantly, TLR9 signaling induces DCs into promoting Th1-like, cytotoxic-T cell responses, by cytokine production (e.g. type 1 IFN) and cross-presentation of antigen onto MHCI molecules. The presentation of these signals concurrently with tumor antigens provides the danger signal needed to promote immune responses that effectively fight cancerous cells.

Different classes of CPG-ODNs promote different immune responses depending on the ODN's specific structure and sequence. The ODN utilized in the present invention, CpG-ODN 1826, has been successfully tested in various mouse vaccination models, including melanoma. CpG-ODN 1826 has shown a beneficial effect alone or when used as adjuvant for peptide vaccines and whole cell vaccines. Moreover, ODN 1826 has been shown to directly promote DC maturation and cytokine production. This particular CpG ODN sequence also indirectly activates Th1 cells and NK cells and, thus, enhances adaptive cellular immune responses.

Vector systems that promote CpG internalization into DCs to enhance delivery and its localization to TLR9 have been developed. The amine-rich polycation, polyethylimine (PEI) has been extensively used to condense plasmid DNA, via association with DNA phosphate groups, resulting in small, positively charge condensates facilitating cell membrane association and DNA uptake into cells (Godbey W. T., Wu K. K., and Mikos, A. G. J. of Biomed Mater Res, 1999, 45, 268-275; Godbey W. T., Wu K. K., and Mikos, A. G. Proc Natl Acad Sci USA. 96(9), 5177-81. (1999); each herein incorporated by reference). Consequently, PEI has been utilized as a non-viral vector to enhance gene transfection and to fabricate PEI-DNA loaded PLG matrices that promoted long-term gene expression in host cells in situ (Huang Y C, Riddle F, Rice K G, and Mooney D J. Hum Gene Ther. 5, 609-17. (2005), herein incorporated by reference). Therefore, CpG-ODNs were condensed with PEI molecules, and the size and charge of these PEI-CpG-ODN condensates, as dependent on the amine-phosphate charge ratio, was characterized. The ability of PEI condensation to enhance DC internalization of CpG-ODN was assessed, and the subsequent decondensation of PEI-CpG-ODN within DCs and its promotion of DC activation was analyzed in vitro. To determine whether PEI-CpG-ODNs had the potential to improve upon the vaccination effects of the GM-CSF based system described in chapter 3, its stimulatory effects on DCs maturation and mobilization in the presence of GM-CSF was also examined.

To appropriately mimic infection and program cells in situ a PLG system was designed to not only serve as a drug delivery device, that releases inflammatory cytokines (e.g. GM-CSF) but also as a physical structure to which the DCs are recruited and reside while they are activated by danger signals (e.g. CpG-ODNs). The ability to control DC recruitment to and DC residence within porous PLG matrices is achieved using temporal control over the delivery of GM-CSF in situ, which results in batches of programmed DCs being dispersed only when GM-CSF levels were designed to subside in situ. This system dispersed 6% of programmed DCs to the lymph nodes and induced protective anti-tumor immunity in 23% of mice when applied as a cancer vaccine. The cell programming and dispersement efficiency is improved using an overriding secondary signal (CpG-ODN) that continuously releases DCs from GM-CSF inhibition and promotes DC maturation and dispersement in the presence of high GM-CSF levels in situ. Specifically, PLG matrices were fabricated to locally present synthetic CpG-ODN with exogenous GM-CSF allowing for DCs recruited by GM-CSF to be stimulated by CpG-ODN in situ.

Dendritic Cells

Dendritic cells (DCs) are immune cells within the mammalian immune system and are derived from hematopoietic bone marrow progenitor cells. More specifically, dendritic cells can be categorized into lymphoid (or plasmacytoid) dendritic cell (pDC) and myeloid dendritic cell (mDC) subdivisions having arisen from a lymphoid (or plasmacytoid) or myeloid precursor cell, respectively. From the progenitor cell, regardless of the progenitor cell type, an immature dendritic cell is born. Immature dendritic cells are characterized by high endocytic activity and low T-cell activation potential. Thus, immature dendritic cells constitutively sample their immediate surrounding environment for pathogens. Exemplary pathogens include, but are not limited to, a virus or a bacteria. Sampling is accomplished by pattern recognition receptors (PRRs) such as the toll-like receptors (TLRs). Dendritic cells activate and mature once a pathogen is recognized by a pattern recognition receptor, such as a toll-like receptor.

Mature dendritic cells not only phagocytose pathogens and break them down, but also, degrade their proteins, and present pieces of these proteins, also referred to as antigens, on their cell surfaces using MHC (Major Histocompatibility Complex) molecules (Classes I, II, and III). Mature dendritic cells also upregulate cell-surface receptors that serve as co-receptors for T-cell activation. Exemplary co-receptors include, but are not limited to, CD80, CD86, and CD40. Simultaneously, mature dendritic cells upregulate chemotactic receptors, such as CCR7, that allows the cell to migrate through the blood stream or the lymphatic system to the spleen or lymph node, respectively.

Dendritic cells are present in external tissues that are in contact with the external environment such as the skin (dendritic cells residing in skin are also referred to as Langerhans cells). Alternatively, dendritic cells are present in internal tissues that are in contact with the external environment such as linings of the nose, lungs, stomach, and intestines. Finally, immature dendritic cells reside in the blood stream. Once activated, dendritic cells from all off these tissues migrate to lymphoid tissues where they present antigens and interact with T cells and B cells to initiate an immune response. One signaling system of particular importance for the present invention involves the chemokine receptor CCR7 expressed on the surface of dendritic cells and the chemokine receptor ligand CCL19 secreted by lymph node structures to attract migrating mature dendritic cells toward high concentrations of immune cells. Exemplary immune cells activated by contact with mature dendritic cells include, but are not limited to, helper T cells, killer T cells, and B cells. Although multiple cell types within the immune system present antigens, including macrophages and B lymphocytes, dendritic cells are the most potent activators of all antigen-presenting cells.

Dendritic cells earned their name from the characteristic cell shape comprising multiple dendrites extending from the cell body. The functional benefit of this cell shape is a significantly increased cell surface and contact area to the surroundings compared to the cell volume. Immature dendritic cells sometimes lack the characteristic dendrite formations and are referred to as veiled cells. Veiled cells possess large cytoplasmic veils rather than dendrites.

Plasmacytoid dendritic cells (pDCs) are innate immune cells that circulate in the blood and are found in peripheral lymphoid organs. They constitute <0.4% of peripheral blood mononuclear cells (PBMC). In humans these cells express the surface markers CD123, BDCA-2(CD303) and BDCA-4(CD304), but do not express high levels of CD11c or CD14, which distinguishes them from conventional dendritic cells or monocytes, respectively. Mouse pDC express CD11c, B220, BST-2 (mPDCA) and Siglec-H and are negative for CD11b. As components of the innate immune system, these cells express intracellular Toll-like receptors 7 and 9 which detect ssRNA and CpG DNA motifs, respectively. Upon stimulation and subsequent activation, these cells produce large amounts of type I interferon (mainly IFN-α (alpha) and IFN-β (beta)), which are critical pleiotropic anti-viral compounds mediating a wide range of effects. The CD8−subset presents antigen using the class II pathway to CD4+ helper T cells. The CD8+ subset presents antigens using the class I pathway. The peptide/MHC class I molecules are presented to CD8+ T cells which go on to become cytotoxic T lymphocytes (CTL). The CD8 cell surface protein in the mouse corresponds to the CD141 cell surface protein in the human. CD8/CD141-positive cells express TLR3 and are preferentially activated by TLR3 agonists.

Toll-Like Receptors (TLRs)

TLRs are a class of single transmembrane domain, non-catalytic, receptors that recognize structurally conserved molecules referred to as pathogen-associated molecular patterns (PAMPs). PAMPs are present on microbes and are distinguishable from host molecules. TLRs are present in all vertebrates. Thirteen TLRs (referred to as TLRs1-13, consecutively) have been identified in humans and mice. Humans comprise TLRs 1-10.

TLRs and interleukin-1 (IL-1) receptors comprise a receptor superfamily the members of which all share a TIR domain (Toll-IL-1 receptor). TIR domains exist in three varieties with three distinct functions. TIR domains of subgroup 1 are present in receptors for interleukins produced by macrophages, monocytes, and dendritic cells. TIR domains of subgroup 2 are present in classical TLRs which bind directly or indirectly to molecules of microbial origin. TIR domains of subgroup 3 are present in cytosolic adaptor proteins that mediate signaling between proteins comprising TIR domains of subgroups 1 and 2.

TLR ligands comprise molecules that are constantly associated with and highly specific for a threat to the host's survival such as a pathogen or cellular stress. TLR ligands are highly specific for pathogens and not the host. Exemplary pathogenic molecules include, but are not limited to, lipopolysaccharides (LPS), lipoproteins, lipoarabinomannan, flagellin, double-stranded RNA, and unmethylated CpG islands of DNA.

In one preferred embodiment of the present invention, the Toll-Like receptor 9 (TLR9) is activated by specific unmethylated CpG-containing sequences in bacterial DNA or synthetic oligonucleotides (ODNs) found in the endosomal compartment of dendritic cells. Methylation status of the CpG site is a crucial distinction between bacterial and mammalian DNA, as well as between normal and cancerous tissue. Unmethylated ODNs including one or more CpG motifs mimic the effects of bacterial DNA. Alternatively, or in addition, unmethylated ODNs including one or more CpG motifs occur within oncogenes present within malignant tumor cells.

One or more sequences of the TLR-9 receptor recognizes one or more CpG-ODN sequences of the present invention. TLR-9 receptors encompassed by the present invention are described by the following sequences.

Human TLR-9, isoform A, is encoded by the following mRNA sequence (NCBI Accession No. NM_017442 and SEQ ID NO: 1; the start codon for all mRNA sequences presented herein is bolded and capitalized):

```
   1 ggaggtcttg tttccggaag atgttgcaag gctgtggtga aggcaggtgc agcctagcct
  61 cctgctcaag ctacaccctg gccctccacg catgaggccc tgcagaactc tggagatggt
 121 gcctacaagg gcagaaaagg acaagtcggc agccgctgtc ctgagggcac cagctgtggt
 181 gcaggagcca agacctgagg gtggaagtgt cctcttagaa tggggagtgc ccagcaaggt
 241 gtacccgcta ctggtgctat ccagaattcc catctctccc tgctctctgc ctgagctctg
 301 ggccttagct cctccctggg cttggtagag gacaggtgtg aggccctcat gggatgtagg
 361 ctgtctgaga ggggagtgga aagaggaagg ggtgaaggag ctgtctgcca tttgactatg
 421 caaatggcct ttgactcatg ggaccctgtc ctcctcactg ggggcagggt ggagtggagg
 481 gggagctact aggctggtat aaaaatctta cttcctctat tctctgagcc gctgctgccc
 541 ctgtgggaag ggacctcgag tgtgaagcat ccttccctgt agctgctgtc cagtctgccc
 601 gccagaccct ctggagaagc ccctgcccce cagcATGggt ttctgccgca gcgccctgca
 661 cccgctgtct ctcctggtgc aggccatcat gctggccatg acccTggccc tgggtacctt
 721 gcctgccttc ctaccctgtg agctccagcc ccacgcctg gtgaactgca actggctgtt
 781 cctgaagtct gtgcccact tctccatggc agcacccgt ggcaatgtca ccagcctttc
 841 cttgtcctcc aaccgcatcc accacctcca tgattctgac tttgcccacc tgcccagcct
 901 gcggcatctc aacctcaagt ggaactgccc gccggttggc ctcagcccca tgcacttccc
 961 ctgccacatg accatcgagc ccagcacctt cttggctgtg cccacccctgg aagagctaaa
1021 cctgagctac aacaacatca tgactgtgcc tgcgctgccc aaatccctca tatccctgtc
1081 cctcagccat accaacatcc tgatgctaga tctgccagcc ctcgccggcc tgcatgccct
1141 gcgcttccta ttcatggacg gcaactgtta ttacaagaac ccctgcaggc aggcactgga
1201 ggtggcccg ggtgccctcc ttggcctggg caacctcacc cacctgtcac tcaagtacaa
1261 caacctcact gtggtgcccc gcaacctgcc ttccagcctg gagtatctgc tgttgtccta
1321 caaccgcatc gtcaaactgg cgcctgagga cctggccaat ctgaccgccc tgcgtgtgct
1381 cgatgtgggc ggaaattgcc gccgctgcga ccacgctccc aacccctgca tggagtgccc
```

-continued

```
1441 tcgtcacttc ccccagctac atcccgatac cttcagccac ctgagccgtc ttgaaggcct 1501 ggtgttgaag gacagttctc tctcctggct gaatgccagt tggttccgtg ggctgggaaa 1561 cctccgagtg ctggacctga gtgagaactt cctctacaaa tgcatcacta aaaccaaggc 1621 cttccagggc ctaacacagc tgcgcaagct taacctgtcc ttcaattacc aaaagagggt 1681 gtcctttgcc cacctgtctc tggccccttc cttcgggagc ctggtcgccc tgaaggagct 1741 ggacatgcac ggcatcttct tccgctcact cgatgagacc acgctccggc cactggcccg 1801 cctgcccatg ctccagactc tgcgtctgca gatgaacttc atcaaccagg cccagctcgg 1861 catcttcagg gccttccctg cctgcgcta cgtggacctg tcggacaacc gcatcagcgg 1921 agcttcggag ctgacagcca ccatggggga ggcagatgga ggggagaagg tctggctgca 1981 gcctggggac cttgctccgg ccccagtgga cactcccagc tctgaagact tcaggcccaa 2041 ctgcagcacc ctcaacttca ccttggatct gtcacggaac aacctggtga ccgtgcagcc 2101 ggagatgttt gcccagctct cgcacctgca gtgcctgcgc ctgagccaca actgcatctc 2161 gcaggcagtc aatggctccc agttcctgcc gctgaccggt ctgcaggtgc tagacctgtc 2221 ccacaataag ctggacctct accacgagca ctcattcacg gagctaccac gactggaggc 2281 cctggacctc agctacaaca gccagccctt tggcatgcag ggcgtgggcc acaacttcag 2341 cttcgtggct cacctgcgca ccctgcgcca cctcagcctg gcccacaaca acatccacag 2401 ccaagtgtcc cagcagctct gcagtacgtc gctgcgggcc ctggacttca gcggcaatgc 2461 actgggccat atgtgggccg agggagacct ctatctgcac ttcttccaag gcctgagcgg 2521 tttgatctgg ctggacttgt cccagaaccg cctgcacacc ctcctgcccc aaaccctgcg 2581 caacctcccc aagagcctac aggtgctgcg tctccgtgac aattacctgg ccttctttaa 2641 gtggtggagc ctccacttcc tgcccaaact ggaagtcctc gacctggcag aaaccagct 2701 gaaggccctg accaatggca gcctgcctgc tggcacccgg ctccggaggc tggatgtcag 2761 ctgcaacagc atcagcttcg tggccccgg cttcttttcc aaggccaagg agctgcgaga 2821 gctcaacctt agcgccaacg ccctcaagac agtggaccac tcctggtttg gcccctggc 2881 gagtgccctg caaatactag atgtaagcgc caaccctctg cactgcgcct gtggggcggc 2941 ctttatggac ttcctgctgg aggtgcaggc tgccgtgccc ggtctgccca gccgggtgaa 3001 gtgtggcagt ccgggccagc tccagggcct cagcatcttt gcacaggacc tgcgcctctg 3061 cctggatgag gccctctcct gggactgttt cgccctctcg ctgctggctg tggctctggg 3121 cctgggtgtg cccatgctgc atcacctctg tggctgggac ctctggtact gcttccacct 3181 gtgcctggcc tggcttccct ggcggggcg gcaaagtggg cgagatgagg atgccctgcc 3241 ctacgatgcc ttcgtggtct tcgacaaaac gcagagcgca gtggcagact gggtgtacaa 3301 cgagcttcgg gggcagctgg aggagtgccg tgggcgctgg gcactccgcc tgtgcctgga 3361 ggaacgcgac tggctgcctg caaaaccct ctttgagaac ctgtgggcct cggtctatgg 3421 cagccgcaag acgctgtttg tgctggccca cacggaccgg gtcagtggtc tcttgcgcgc 3481 cagcttcctg ctggcccagc agcgcctgct ggaggaccgc aaggacgtcg tggtgctggt 3541 gatcctgagc cctgacggcc gccgctcccg ctatgtgcgg ctgcgccagc gcctctgccg 3601 ccagagtgtc ctcctctggc cccaccagcc cagtggtcag cgcagcttct gggcccagct 3661 gggcatggcc ctgaccaggg acaaccacca cttctataac cggaacttct gccagggacc 3721 cacggccgaa tagccgtgag ccggaatcct gcacggtgcc acctccacac tcacctcacc 3781 tctgcctgcc tggtctgacc ctcccctgct cgcctccctc accccacacc tgacacagag 3841 caggcactca ataaatgcta ccgaaggc
```

Human TLR-9, isoform A, is encoded by the following amino acid sequence (NCBI Accession No. NP 059138 and SEQ ID NO: 2):

MGFCRSALHPLSLLVQAIMLAMTLALGTLPAFLPCELQPHGLVNCNWLFL
KSVPHFSMAAPRGNVTSLSLSSNRIHHLHDSDFAHLPSLRHLNLKWNCPP
VGLSPMHFPCHMTIEPSTFLAVPTLEELNLSYNNIMTVPALPKSLISLSL
SHTNILMLDSASLAGLHALRFLFMDGNCYYKNPCRQALEVAPGALLGLGN
LTHLSLKYNNLTVVPRNLPSSLEYLLLSYNRIVKLAPEDLANLTALRVLD
VGGNCRRCDHAPNPCMECPRHFPQLHPDTFSHLSRLEGLVLKDSSLSWLN
ASWFRGLGNLRVLDLSENFLYKCITKTKAFQGLTQLRKLNLSFNYQKRVS
FAHLSLAPSFGSLVALKELDMHGIFFRSLDETTLRPLARLPMLQTLRLQM
NFINQAQLGIFRAFPGLRYVDLSDNRISGASELTATMGEADGGEKVWLQP
GDLAPAPVDTPSSEDFRPNCSTLNFTLDLSRNNLVTVQPEMFAQLSHLQC
LRLSHNCISQAVNGSQFLPLTGLQVLDLSHNKLDLYHEHSFTELPRLEAL

DLSYNSQPFGMQGVGHNFSFVAHLRTLRHLSLAHNNIHSQVSQQLCSTSL
RALDFSGNALGHMWAEGDLYLHFFQGLSGLIWLDLSQNRLHTLLPQTLRN
LPKSLQVLRLRDNYLAFFKWWSLHFLPKLEVLDLAGNQLKALTNGSLPAG
TRLRRLDVSCNSISFVAPGFFSKAKELRELNLSANALKTVDHSWFGPLAS
ALQILDVSANPLHCACGAAFMDFLLEVQAAVPGLPSRVKCGSPGQLQGLS
IFAQDLRLCLDEALSWDCFALSLLAVALGLGVPMLHHLCGWDLWYCFHLC
LAWLPWRGRQSGRDEDALPYDAFVVFDKTQSAVADWVYNELRGQLEECRG
RWALRLCLEERDWLPGKTLFENLWASVYGSRKTLFVLAHTDRVSGLLRAS
FLLAQQRLLEDRKDVVVLVILSPDGRRSRYVRLRQRLCRQSVLLWPHQPS
GQRSFWAQLGMALTRDNHHFYNRNFCQGPTAE

Human TLR3 is encoded by the following mRNA sequence (GenBank Accession No. NM_003265.2 (GI: 19718735), incorporated herein by reference; SEQ ID NO: 5):

```
   1 cactttcgag agtgccgtct atttgccaca cacttccctg atgaaatgtc tggatttgga
  61 ctaaagaaaa aaggaaaggc tagcagtcat ccaacagaat cATGagacag actttgcctt
 121 gtatctactt ttggggggc cttttgccct ttgggatgct gtgtgcatcc tccaccacca
 181 agtgcactgt tagccatgaa gttgctgact gcagccacct gaagttgact caggtacccg
 241 atgatctacc cacaaacata acagtgttga accttaccca taatcaactc agaagattac
 301 cagccgccaa cttcacaagg tatagccagc taactagctt ggatgtagga tttaacacca
 361 tctcaaaact ggagccagaa ttgtgccaga aacttcccat gttaaaagtt ttgaacctcc
 421 agcacaatga gctatctcaa ctttctgata aacctttgc cttctgcacg aatttgactg
 481 aactccatct catgtccaac tcaatccaga aaattaaaaa taatcccttt gtcaagcaga
 541 agaatttaat cacattagat ctgtctcata tggcttgtc atctacaaaa ttaggaactc
 601 aggttcagct ggaaaatctc caagagcttc tattatcaaa caataaaatt caagcgctaa
 661 aaagtgaaga actggatatc tttgccaatt catctttaaa aaaattagag ttgtcatcga
 721 atcaaattaa agagttttct ccagggtgtt tcacgcaat tggaagatta tttggcctct
 781 ttctgaacaa tgtccagctg ggtcccagcc ttacagagaa gctatgtttg gaattagcaa
 841 acacaagcat tcggaatctg tctctgagta acagccagct gtccaccacc agcaatacaa
 901 ctttcttggg actaaagtgg acaaatctca ctatgctcga tctttcctac aacaacttaa
 961 atgtggttgg taacgattcc tttgcttggc ttccacaact agaatatttc ttcctagagt
1021 ataataatat acagcatttg ttttctcact ctttgcacgg gcttttcaat gtgaggtacc
1081 tgaatttgaa acggtctttt actaaacaaa gtatttccct tgcctcactc cccaagattg
1141 atgattttc ttttcagtgg ctaaaatgtt tggagcacct taacatggaa gataatgata
1201 ttccaggcat aaaaagcaat atgttcacag gattgataaa cctgaaatac ttaagtctat
1261 ccaactcctt tacaagtttg cgaactttga caaatgaaac atttgtatca cttgctcatt
1321 ctcccttaca catactcaac ctaaccaaga ataaaatctc aaaaatagag agtgatgctt
1381 tctcttggtt gggccaccta gaagtacttg acctgggcct taatgaaatt gggcaagaac
1441 tcacaggcca ggaatggaga ggtctagaaa atatttttcga aatctatctt tcctacaaca
1501 agtacctgca gctgactagg aactcctttg ccttggtccc aagccttcaa cgactgatgc
```

-continued

```
1561 tccgaagggt ggcccttaaa aatgtggata gctctccttc accattccag cctcttcgta 1621 acttgaccat tctggatcta agcaacaaca acatagccaa cataaatgat gacatgttgg 1681 agggtcttga gaaactagaa attctcgatt tgcagcataa caacttagca cggctctgga 1741 aacacgcaaa ccctggtggt cccatttatt tcctaaaggg tctgtctcac ctccacatcc 1801 ttaacttgga gtccaacggc tttgacgaga tcccagttga ggtcttcaag gatttatttg 1861 aactaaagat catcgattta ggattgaata atttaaacac acttccagca tctgtcttta 1921 ataatcaggt gtctctaaag tcattgaacc ttcagaagaa tctcataaca tccgttgaga 1981 agaaggtttt cgggccagct ttcaggaacc tgactgagtt agatatgcgc tttaatccct 2041 ttgattgcac gtgtgaaagt attgcctggt ttgttaattg gattaacgag acccatacca 2101 acatccctga gctgtcaagc cactacctt gcaacactcc acctcactat catgggttcc 2161 cagtgagact ttttgataca tcatcttgca aagacagtgc cccctttgaa ctcttttca 2221 tgatcaatac cagtatcctg ttgatttta tctttattgt acttctcatc cactttgagg 2281 gctggaggat atctttttat tggaatgttt cagtacatcg agttcttggt ttcaaagaaa 2341 tagacagaca gacagaacag tttgaatatg cagcatatat aattcatgcc tataaagata 2401 aggattgggt ctgggaacat ttctcttcaa tggaaaagga agaccaatct ctcaaatttt 2461 gtctggaaga aagggactt gaggcgggtg tttttgaact agaagcaatt gttaacagca 2521 tcaaagaag cagaaaaatt atttttgtta taacacacca tctattaaaa gacccattat 2581 gcaaaagatt caaggtacat catgcagttc aacaagctat tgaacaaaat ctggattcca 2641 ttatattggt tttccttgag gagattccag attataaact gaaccatgca ctctgtttgc 2701 gaagaggaat gtttaaatct cactgcatct tgaactggcc agttcagaaa gaacggatag 2761 gtgcctttcg tcataaattg caagtagcac ttggatccaa aaactctgta cattaaattt 2821 atttaaatat tcaattagca aaggagaaac tttctcaatt taaaaagttc tatggcaaat 2881 ttaagttttc cataaaggtg ttataatttg tttattcata tttgtaaatg attatattct 2941 atcacaatta catctcttct aggaaaatgt gtctccttat ttcaggccta ttttgacaa 3001 ttgacttaat tttacccaaa ataaaacata taagcacgta aaaaaaaaaa aaaaaaa
```

Human TLR3 is encoded by the following amino acid sequence (GenBank Accession No. ABC86910.1 (GI: 86161330), incorporated herein by reference; SEQ ID NO: 4):

```
  1 mrqtlpciyf wggllpfgml cassttkctv shevadcshl kltqvpddlp tnitvlnlth 61 nqlrrlpaan ftrysqltsl dvgfntiskl epelcqklpm lkvlnlqhne lsqlsdktfa 121 fctnltelhl msnsiqkikn npfvkqknli tldlshngls stklgtqvql enlqelllsn 181 nkiqalksee ldifansslk klelssnqik efspgcfhai grlfglflnn vqlgpsltek 241 lclelantsi rnlslsnsql sttsnttflg lkwtnltmld lsynnlnvvg ndsfawlpql 301 eyffleynni qhlfshslhg lfnvrylnlk rsftkqsisl aslpkiddfs fqwlkclehl 361 nmedndipgi ksnmftglin lkylslsnsf tslrtltnet fvslahsplh ilnltknkis 421 kiesdafswl ghlevldlgl neigqeltgq ewrglenife iylsynkylq ltrnsfalvp 481 slqrlmlrrv alknvdssps pfqplrnlti ldlsnnnian inddmlegle kleildlqhn 541 nlarlwkhan pggpiyflkg lshlhilnle sngfdeipve vfkdlfelki idlglnnlnt 601 lpasvfnnqv slkslnlqkn litsvekkvf gpafrnltel dmrfnpfdct cesiawfvnw 661 inethtnipe lsshylcntp phyhgfpvrl fdtssckdsa pfelffmint sillififiv
```

-continued

```
721 llihfegwri sfywnvsvhr vlgfkeidrq teqfeyaayi ihaykdkdwv wehfssmeke 781 dqslkfclee rdfeagvfel eaivnsikrs rkiifvithh llkdplckrf kvhhavqqai 841 eqnldsiilv fleeipdykl nhalclrrgm fkshcilnwp vqkerigafr hklqvalgsk 901 nsvh
```

The nucleic acid sequence of human TLR1 is provided in GenBank Accession No. NM_003263.3 (GI:41350336), incorporated herein by reference. The amino acid sequence of human TLR1 is provided in GenBank Accession No. NP 003254.2 (GI:41350337), incorporated herein by reference.

The nucleic acid sequence of human TLR2 is provided in GenBank Accession No. NM_003264.3 (GI:68160956), incorporated herein by reference. The amino acid sequence of human TLR2 is provided in GenBank Accession No. NP_003255.2 (GI:19718734), incorporated herein by reference.

The nucleic acid sequence of human TLR4 is provided in GenBank Accession No. NM_138554.4 (GI:373432600), incorporated herein by reference. The amino acid sequence of human TLR4 is provided in GenBank Accession No. NP_612564.1 (GI:19924149), incorporated herein by reference.

The nucleic acid sequence of human TLR5 is provided in GenBank Accession No. NM_003268.5 (GI:281427130), incorporated herein by reference. The amino acid sequence of human TLR5 is provided in GenBank Accession No. NP_003259.2 (GI:16751843), incorporated herein by reference.

The nucleic acid sequence of human TLR6 is provided in GenBank Accession No. NM_006068.4 (GI:318067953), incorporated herein by reference. The amino acid sequence of human TLR6 is provided in GenBank Accession No. NP_006059.2 (GI:20143971), incorporated herein by reference.

The nucleic acid sequence of human TLR7 is provided in GenBank Accession No. NM_016562.3 (GI:67944638), incorporated herein by reference. The amino acid sequence of human TLR7 is provided in GenBank Accession No. NP_057646.1 (GI:7706093), incorporated herein by reference.

The nucleic acid sequence of human TLR8 is provided in GenBank Accession No. NM_138636.4 (GI:257196253), incorporated herein by reference. The amino acid sequence of human TLR8 is provided in GenBank Accession No. NP_619542.1 (GI:20302168), incorporated herein by reference.

The nucleic acid sequence of human TLR10 is provided in GenBank Accession No. NM_030956.3 (GI:306140488), incorporated herein by reference. The amino acid sequence of human TLR10 is provided in GenBank Accession No. NP_112218.2 (GI:62865618), incorporated herein by reference.

The nucleic acid sequence of mouse TLR11 is provided in GenBank Accession No. NM_205819.3 (GI:408684412), incorporated herein by reference. The amino acid sequence of mouse TLR11 is provided in GenBank Accession No. NP_991388.2 (GI:408684413), incorporated herein by reference.

The nucleic acid sequence of mouse TLR12 is provided in GenBank Accession No. NM_205823.2 (GI:148539900), incorporated herein by reference. The amino acid sequence of mouse TLR12 is provided in GenBank Accession No. NP_991392.1 (GI:45430001), incorporated herein by reference.

The nucleic acid sequence of mouse TLR13 is provided in GenBank Accession No. NM_205820.1 (GI:45429998), incorporated herein by reference. The amino acid sequence of mouse TLR13 is provided in GenBank Accession No. NP_991389.1 (GI:45429999), incorporated herein by reference.

A representative list of TLR agonists (both synthetic and natural ligands), along with their corresponding receptor is provided in Table 2 below.

TABLE 2

| Receptor | Pathogen Associated Ligands (PAMPS) [1] | Ligand Natural host | Synthetic Ligands |
| --- | --- | --- | --- |
| TLR 1 | multiple triacyl lipopeptides | Bacteria | Pam3Cys-* |
| TLR 2 | multiple glycolipids | Bacteria | CFA |
|  | multiple lipopeptides | Bacteria | MALP2-** |
|  | multiple lipoproteins | Bacteria | Pam2Cys** |
|  | lipoteichoic acid | Gram Positive Bacteria | FSL-1 |
|  | HSP 70, or other heat shock proteins | Host cells | Hib-OMPC |
|  | zymosan (Beta- glucan) | Fungi |  |
|  | Numerous others |  |  |
| TLR 3 | Double stranded RNA | viruses | Poly (I:C); Low and High molecular weight Poly (A:U) |
| TLR 4 | lipopolysacharides (LPS); or LPS derivatives such as MPLA | Gram negative bacteria | AGP |
|  | several heat shock proteins | Bacteria and host cells | MPLA |
|  | fibrinogen | host cells | RC-529 |
|  | heparin sulfate fragments | host cells | MDF2β |
|  | hyaluronic acid fragments | host cells | CFA |
|  | nickel |  |  |
|  | Various opoid drugs |  |  |
| TLR 5 | Flagellin | Bacteria | Flagellin |
| TLR 6 | multiple diacyl lipopeptides | Mycoplasma | FSL1-** |
|  |  |  | Pam2Cys** |
|  |  |  | MALP2-** |

TABLE 2-continued

| Receptor | Pathogen Associated Ligands (PAMPS) [1] | Ligand Natural host | Synthetic Ligands |
|---|---|---|---|
| TLR 7 | Viral ssRNA (Influenza, VSV, HIV, HCV) | RNA viruses | Guanosine analogs; imidazoquinolines (e.g. Imiquimod, Aldara ® R848, Resiquimod ®), Loxoribine |
| TLR 8 | small synthetic compounds; single-stranded RNA | RNA, Human and viral | Imidazoquinoline; Loxoribine; ssPolyU, 3M-012 |
| TLR 9 | Unmethylated CpG Oligodeoxynucleotide DNA DNA; dsDNA viruses (HSV, MCMV); Hemozoin (Plasmodium) | Bacteria, DNA viruses | CpG-oligonucleotides, numerous sequences have been synthesized (e.g CpG-ODN 2006, 1826, 2395) |
| TLR 10 | unknown | | |
| TLR 11 | Profilin | Toxoplasma gondii | |
| TLR 12 | Profilin | Toxoplasma gondii | |
| TLR 13 [2][3] | bacterial ribosomal RNA sequence "CGGAAAGACC" (SEQ ID NO: 13) | Virus, bacteria | |

*Ligands recognized by TLR1 and TLR2
**Ligands recognized by TLR2 and TLR6
References
Meyer T, Stockfletch E. Clinical investigational of Toll-like receptor agonists. Expert opinion on investigational drugs. 2008; 17: 1051-1065. [PubMed]
van Duin D, Medzhitov R, Shaw A C. Triggering TLR signaling in vaccination. Trends in immunology. 2006; 27: 49-55
Kumar H, Kawai T, Akira Toll-like receptors and innate immunity. Biochemical and biophysical research communications. 2009; 388: 621-625.
Waltenbaugh C, Doan T, Melvoid R, Viselli S (2008). Immunology. Lippincott's Illustrated reviews. Philadelphia: Wolters Kluwer Health/Lippincott Williams & Wilkins. pp. 17.
Shi Z, Cai Z, Sanchez A, et al. (February 2011). A novel Toll-like receptor that recognizes vesicular stomatitis virus. 286. pp. 4517-24.
Oldenburg M. Kruger A, Ferstl R, et al. (August 2012). TLR1S recognizes bacterial 23S rRNA devoid of erthromycin resistance-forming modification. 337. pp. 1111-5
S. Gnjatic, N. B. Sawhney, N. Bhardwaj Toll-like receptor agonists: are they good adjuvants? Cancer J., 16 (4) (2010), pp. 382-391.

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

[01] GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO: 3):

```
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 7):

```
MAPTRSPITV TRPWKHVEAI KEALNLLDDM PVTLNEEVEV

VSNEFSFKKL TCVQTRLKIF EQGLRGNFTK LKGALNMTAS

YYQTYCPPTP ETDCETQVTT YADFIDSLKT FLTDIPFECK KPVQK
```

Human Endogenous GM-CSF is encoded by the following mRNA sequence (NCBI Accession No. NM_000758 and SEQ ID NO: 8):

```
  1 acacagagag aaaggctaaa gttctctgga ggatgtggct gcagagcctg ctgctcttgg 61 gcactgtggc ctgcagcatc tctgcacccg cccgctcgcc cagcccagc acgcagccct
```

-continued

```
121 gggagcatgt gaatgccatc caggaggccc ggcgtctcct gaacctgagt agagacactg 181 ctgctgagat gaatgaaaca gtagaagtca tctcagaaat gtttgacctc caggagccga 241 cctgcctaca gacccgcctg gagctgtaca agcagggcct gcggggcagc ctcaccaagc 301 tcaagggccc cttgaccatg atggccagcc actacaagca gcactgccct ccaaccccgg 361 aaacttcctg tgcaacccag attatcacct ttgaaagttt caaagagaac ctgaaggact 421 ttctgcttgt catcccttt gactgctggg agccagtcca ggagtgagac cggccagatg 481 aggctggcca agccggggag ctgctctctc atgaaacaag agctagaaac tcaggatggt 541 catcttggag ggaccaaggg gtgggccaca gccatggtgg gagtggcctg gacctgccct 601 gggccacact gaccctgata caggcatggc agaagaatgg gaatatttta tactgacaga 661 aatcagtaat atttatatat ttatattttt aaaatattta tttatttatt tatttaagtt 721 catattccat atttattcaa gatgttttac cgtaataatt attattaaaa atatgcttct 781 a
```

Human Endogenous GM-CSF is encoded by the following amino acid sequence (NCBI Accession No. NP_000749.2 and SEQ ID NO: 9):

MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silences while oncogenes, or cancer-inducing genes, are expressed. Importantly, CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

The present invention comprises CpG dinucleotides and oligonucleotides. Contemplated CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. In one embodiment, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell.

CpG oligonucleotides are condensed prior to cellular uptake. In one preferred embodiment, CpG oligonucleotides are condensed using polyethylimine (PEI), a cationic polymer that increases the efficiency of cellular uptake into dendritic cells.

CpG oligonucleotides of the present invention can be divided into multiple classes. For example, exemplary CpG-ODNs encompassed by compositions, methods and devices of the present invention are stimulatory, neutral, or suppressive. The term "stimulatory" used herein is meant to describe a class of CpG-ODN sequences that activate TLR9. The term "neutral" used herein is meant to describe a class of CpG-ODN sequences that do not activate TLR9. The term "suppressive" used herein is meant to describe a class of CpG-ODN sequences that inhibit TLR9. The term "activate TLR9" describes a process by which TLR9 initiates intracellular signaling.

Stimulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A Cpg-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Similar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 10).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Suppressive CpG ODNs that inhibit TLR9 are encompassed by the present invention. Exemplary potent inhibitory sequences are $(TTAGGG)_4$ (ODN TTAGGG, InvivoGen), found in mammalian telomeres and ODN 2088 (InvivoGen), derived from a murine stimulatory CpG ODN by replacement of 3 bases. Suppressive ODNs disrupt the colocalization of CpG ODNs with TLR9 in endosomal vesicles without affecting cellular binding and uptake. Suppressive CpG ODNs encompassed by the present invention are used to fine-tune, attenuate, reverse, or oppose the action of a stimulatory CpG-ODN. Alternatively, or in addition, compositions, methods, or devices of the present invention comprising suppressive CpG ODNs are used to treat autoimmune conditions or prevent immune responses following transplant procedures.

Cancer Antigens

Compositions, methods, and devices of the present invention comprise cancer antigens with means to vaccinate and/or provide protective immunity to a subject to whom such a device was administered. Cancer antigens are used alone or in combination with GM-CSF, CpG-ODN sequences, or immunomodulators. Moreover, cancer antigens are used simultaneously or sequentially with GM-CSF, CpG-ODN sequences, or immunomodulators.

Exemplary cancer antigens encompassed by the compositions, methods, and devices of the present invention include, but are not limited to, tumor lysates extracted from biopsies, irradiated tumor cells, MAGE series of antigens (MAGE-1 is an example), MART-1/melana, tyrosinase, ganglioside, gp100, GD-2, O-acetylated GD-3, GM-2, MUC-1, Sos1, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAM6), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA).

Immunomodulators

Compositions, methods, and devices of the present invention comprise immunomodulators including, but not limited to, TLR ligands, growth factors, and products of dying cells, e.g. heat shock proteins, with means to stimulate dendritic cell activation. Immunomodulators are used alone or in combination with GM-CSF, CpG-ODN sequences, or cancer antigens. Immunomodulators are used simultaneously or sequentially with GM-CSF, CpG-ODN sequences, or cancer antigens.

All known TLR ligands found either on a cell surface or an internal cellular compartment are encompassed by the compositions, methods, and devices of the present invention. Exemplary TLR ligands include, but are not limited to, triacyl lipoproteins (TLR1); lipoproteins, gram positive peptidoglycan, lipteichoic acids, fungi, and viral glycoproteins (TLR2); double-stranded RNA, poly I:C (TLR 3); lipopolysaccaride, viral glycoproteins (TLR 4); flagellin (TLR5); diacyl lipoproteins (TLR6); small synthetic compounds, single-stranded RNA (TLR7 and TLR 8); unmethylated CpG DNA (TLR9); Profilin (TLR11). Also included as TRL ligands are host molecules like fibronectin and heat shock proteins (HSPs). Host TLR ligands are also encompassed by the present invention. The role of TLRs in innate immunity and the signaling molecules used to activate and inhibit them are known in the art (for a review, see Holger K. Frank B., Hessel E., and Coffman R L. Therapeutic targeting of innate immunity with Toll-like receptor agonists and antagonists. Nature Medicine 13, 552-559 (2007), herein incorporated by reference).

All known growth factors are encompassed by the compositions, methods, and devices of the present invention. Exemplary growth factors include, but are not limited to, transforming growth factor beta (TGF-β), granulocyte-colony stimulating factor (G-CSF), granulocyte-macrophage colony stimulating factor (GM-CSF), nerve growth factor (NGF), neurotrophins, Platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), hepatocyte growth factor (HGF). The present invention encompasses cytokines as well as growth factors for stimulating dendritic cell activation. Exemplary cytokines include, but are not limited to, IL-1, IL-2, IL-3, IL-4, IL-5, IL-6, IL-8, IL-10, IL-12 1L-15, 1L-17, 1L-18, TNF-α, IFN-γ, and IFN-α.

Indications of cell death and products of dying cells stimulate dendritic cell activation. As such, all products of dying cells are encompassed by the compositions, methods, and devices of the present invention. Exemplary cell death products include, but are not limited to, any intracellular feature of a cell such as organelles, vesicles, cytoskeletal elements, proteins, DNA, and RNA. Of particular interest are heat shock proteins expressed when a cell is under stress and which are released upon cell death. Exemplary heat shock proteins include, but are not limited to, Hsp10, Hsp20, Hsp27, Hsp33, Hsp40, Hsp60, Hsp70, Hsp71, Hsp72, Grp78, Hsx70, Hsp84, Hsp90, Grp94, Hsp100, Hsp104, Hsp110.

Microenvironments and Vaccine Efficiency

The devices/scaffold described herein represent an infection-mimicking microenvironment. Each device constitutes a factory that attracts/accepts, educates/stimulates and sends forth to surrounding bodily tissues activated dendritic cells that are capable of stimulating/enhancing an immune response to a particular antigen. Specifically, the scaffold devices are implanted or coated with pathogenic molecules to mimic and infectious microenvironment to further activate the dendritic cell response.

Appropriately mimicking aspects of infection with material systems dramatically impacts tumor progression when applied as cancer vaccines by continuously recruiting, activating and homing DCs to LNs. The first PLG vaccine, using GM-CSF alone, led to a batch process where host DCs were recruited by GM-CSF to reside at a site of tumor antigen presentation, and were trapped until GM-CSF levels fell and the cells could become activated and disperse (see U.S. Ser. No. 11/638,796; herein incorporated by reference). Temporal variation of the local GM-CSF concentration allowed control over the number of recruited DCs, and the timing of their activation and dispersement. Although the best GM-CSF-based vaccine was able to confer protective immunity in nearly a quarter of the animals tested, approximately 26% of the recruited DCs were activated (~240,000 DCs) and approximately 6% of DCs dispersed to the LNs. High levels of GM-CSF recruited large numbers of DC, but also limited DC activation, leaving potentially therapeutic DCs entrapped within scaffolds. These results motivated the development of an improved system that mimicked bacterial infection by locally presenting CpG-ODNs as an overriding 'danger signal', that opposed GM-CSF inhibition of DC activation and dispersement. These devices described herein represent significant advances by mediating increased and continuous egress of DCs.

Figure 6B:
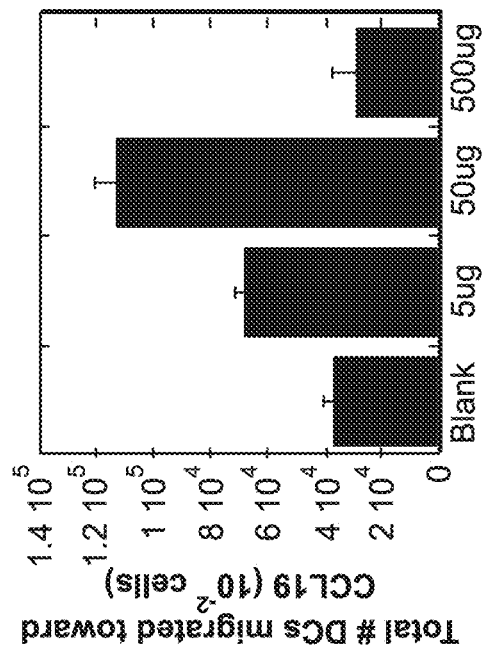
FIGS. 6A-C.
Figure 6A:
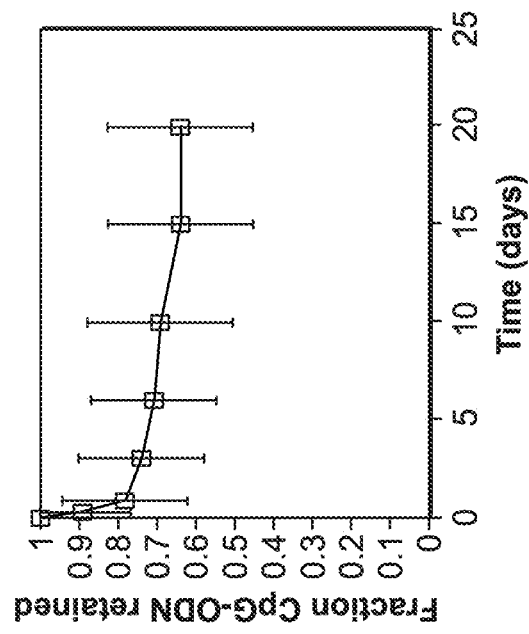
Figure 6C:
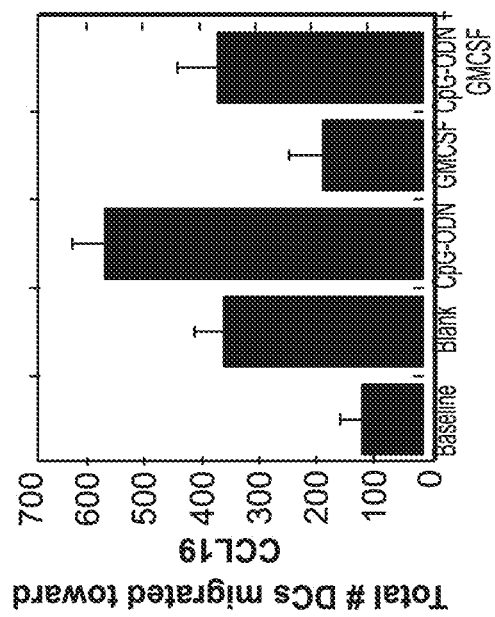

CpG-ODN molecules were condensed with PEI to not only promote ODN uptake into DCs and localization to its TLR-9 receptor (FIGS. 3A-D), but also to electrostatically immobilize it in PLG matrices to be presented simultaneously with tumor antigens (FIGS. 6A-C). In vitro results indicated that PEI-CpG-ODN condensates can decondense within DCs and stimulate TLR signaling that promoted DC activation and dispersion toward the lymph node derived chemokine, CCL19, in the presence of inhibitory levels of GM-CSF (500 ng/ml).

Figures 7A, 7B:
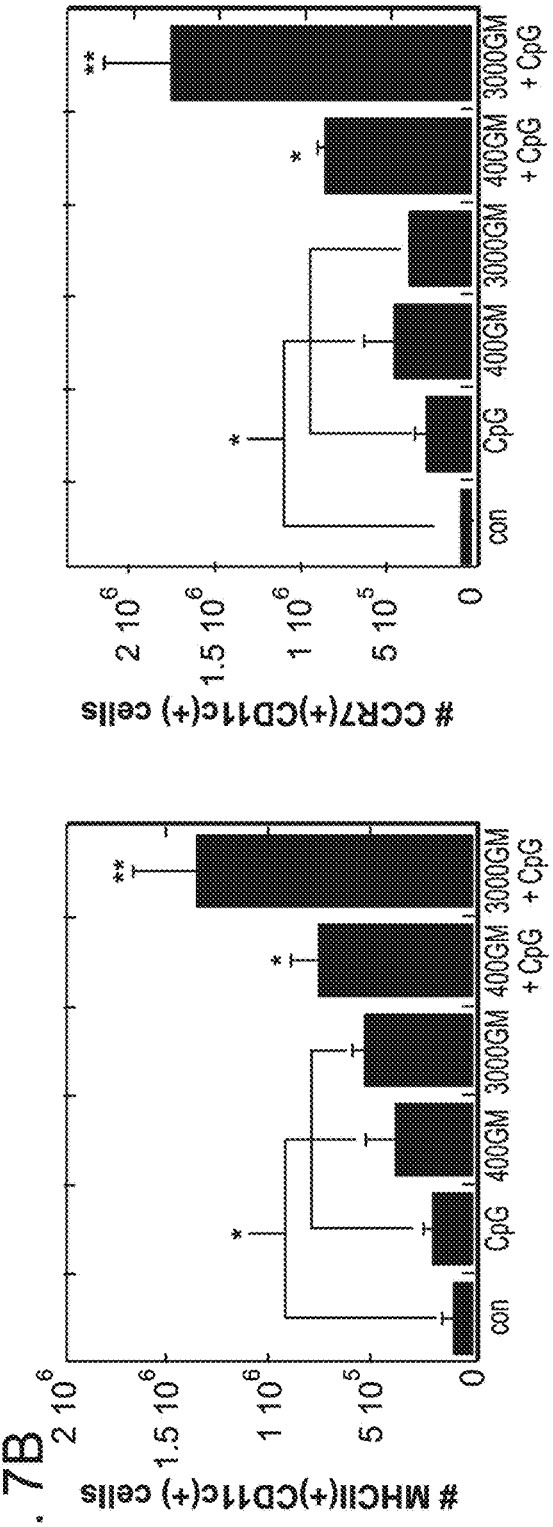
FIGS. 7A-B. PLG-based infection mimics continuously program DCs in situ.

In vivo, appropriately designed infection-mimics mediated a continuous process that shuttled DCs through an infectious-like microenvironment via recruitment with GM-CSF, followed by immediate activation of resident DCS via condensed CpG-ODN presentation, and subsequent release. An in vivo screen of the dose effects of combined CpG-ODN delivery revealed differential effects on DC activation, with an unusual decoupling of CCR7 and MHCII expression, at high CpG-ODN (>50 µg) and GM-CSF (>1 µg) doses, whereas optimal CpG-ODN doses (10-25 µg) induced significant DC activation (44%, and $1.5 \times 10^6$ cells) even when opposed by high GM-CSF levels (3 µg, in vivo). Therefore, optimal CpG-ODN presentation can activate large numbers of DCs recruited by strong GM-CSF pulses in situ, and these numbers exceed the numbers often programmed and transplanted in ex vivo protocols (FIGS. 7A-B).

This DC programming process proved to be continuous as DCs were shuttled through an infectious-like microenvironment via recruitment with intense pulses of GM-CSF, followed by the subsequent programming and release of resident DCS via condensed CpG-ODN stimulation. The percentage of DCs that homed to the LNs approximately doubled from 6% to 13% (U.S. Ser. No. 11/638,796 and FIGS. 8A-D), which corresponded to 180,000 programmed DCs (~4-fold enhancement compared to devices without CpG-ODN) being dispersed to the lymph nodes, with infection-mimics (FIGS. 7A-B and 8A-D). Strikingly, the lymph nodes in this condition were markedly enlarged (FIGS. 8A-D) and loaded with large numbers of DCs at sacrifice, supporting the conclusion that an infection-mimic was created in those animals.

The ability of these infectious-material systems to continuously control DC trafficking and activation translated to a regulation over the efficacy of the cancer vaccine. As the numbers of material-resident, activated DCs that were programmed and dispersed to the lymph nodes increased, the efficacy increased from 0 to 23 and finally 50%. Host T-cells mediated the immune protection, and a clear relation between the numbers of CD-4 and CD-8 lymphocytes (~50% increase due to infection mimicking) in the tumors that did form (FIGS. 10A-B) and vaccine efficacy was found. These results are qualitatively consistent with an ex vivo vaccine developed using irradiated tumor cells engineered to secrete GM-CSF, as that system was previously found to stimulate a potent, specific, and long-lasting anti-tumor immunity (Akira S, Takeda K, Kaisho T. Nature Immunol, 2, 675-80, 2001). In contrast, though, the infection-mimicking material system programmed DCs in situ, and bypassed all ex vivo cell manipulation and transplantation, and provided tight control over the number of DCs recruited, activated and dispersed to the lymph nodes (LNs).

These results indicate the value of finely controlling cell behavior and programming in situ. The mechanism behind vaccine efficacy in these studies was clearly the appropriate control over the number and timing of DC mobilization and programming. Infection-mimics are a useful tool for the development of vaccines with means to create immunity against otherwise lethal infection, cancers and autoimmunity.

Scaffold Compositions and Architecture

Components of the scaffolds are organized in a variety of geometric shapes (e.g., discs, beads, pellets), niches, planar layers (e.g., thin sheets). For example, discs of about 0.1-200 millimeters in diameter, e.g., 5, 10, 20, 40, 50 millimeters are implanted subcutaneously. The disc may have a thickness of 0.1 to 10 millimeters, e.g., 1, 2, 5 millimeters. The discs are readily compressed or lyophilized for administration to a patient. An exemplary disc for subcutaneous administration has the following dimensions: 8 millimeters in diameter and 1 millimeter in thickness. Multicomponent scaffolds are optionally constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration. Cells incubated in the scaffold are educated and induced to migrate out of the scaffold to directly affect a target tissue, e.g., and injured tissue site. For example, stromal vascular cells and smooth muscle cells are useful in sheet-like structures are used for repair of vessel-like structures such as blood vessels or layers of the body cavity. For example, such structures are used to repair abdominal wall injuries or defects such as gastroschisis. Similarly, sheet-like scaffolds seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by sequentially injecting or inserting matrix materials. Scaffold devices are optionally recharged with cells or with bioactive compounds, e.g., by sequential injection or spraying of substances such as growth factors or differentiation factors.

gradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA), poly lactic-coglycolic acid, or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogeneous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

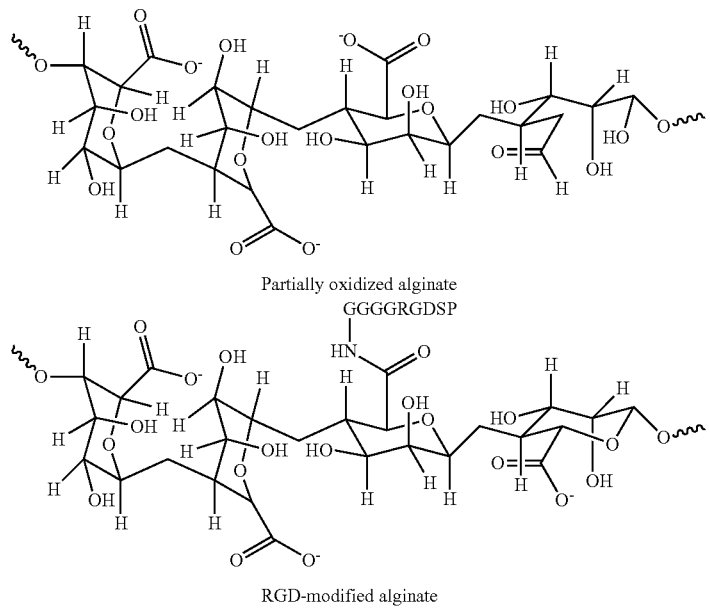

Partially oxidized alginate

RGD-modified alginate

A scaffold or scaffold device is the physical structure upon which or into which cells associate or attach, and a scaffold composition is the material from which the structure is made. For example, scaffold compositions include biode- The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysaccharides such as alginates or modified alginates that are particularly useful for cell transplantation and tissue engineering applications.

Useful polysaccharides other than alginates include agarose and microbial polysaccharides such as those listed in the table below.

Polysaccharide Scaffold Compositions

| Polymers[a] | Structure |
| --- | --- |
| Fungal | |
| Pullulan (N) | 1,4-; 1,6-α-D-Glucan |
| Scleroglucan (N) | 1,3; 1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-; 1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2; 1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N—neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 µm; or macroporous wherein the diameter of the pores are greater than about 20 µm, more preferably greater than about 100 µm and even more preferably greater than about 400 µm. In one example, the scaffold is macroporous with aligned pores of about 400-500 µm in diameter. The preparation of polymer matrices having the desired pore sizes and pore alignments are described in the Examples. Other methods of preparing porous hydrogel products are known in the art. (U.S. Pat. No. 6,511,650 incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. For example, the compositions include GM-CSF, CpG-ODN, and tumor antigens or other antigens. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Coupling of the polypeptides to the polymer matrix is accomplished using synthetic methods known to one of ordinary skill in the art. Approaches to coupling of peptides to polymers are discussed in Hirano and Mooney, Advanced Materials, p. 17-25 (2004). Other useful bonding chemistries include those discussed in Hermanson, Bioconjugate Techniques, p. 152-185 (1996), particularly by use of carbodiimide couplers, DCC and DIC (Woodward's Reagent K). Polypeptides contain a terminal amine group for such carbodiimide bonding. The amide bond formation is preferably catalyzed by 1-ethyl-3-(3-dimethylaminopropyl)carbodiimide (EDC), which is a water soluble enzyme commonly used in peptide synthesis.

Control of Release Kinetics of Bioactive Compositions

The release profile of bioactive compositions such as GM-CSF is controlled using a number of different techniques, e.g., encapsulation, nature of attachment/association with the scaffold, porosity of the scaffold, and particle size of the bioactive compositions.

For example, GM-CSF is encapsulated as one means by which to incorporate GM-CSF into the scaffolds. GM-CSF was first encapsulated into PLG microspheres, and then these GM-CSF loaded microspheres were then in a gas foaming process to develop macroporous PLG scaffolds. The incorporation of GM-CSF into the microspheres causes the GM-CSF to be more deeply embedded into the polymer, which causes the device to sustain the initial pulse of GM-CSF delivery over days 1-5. Other incorporation methods are optionally used to alter or fine tune the duration of the GM-CSF pulse as desired, which would in turn change the kinetics of DC recruitment. For example, foaming PLG particles mixed with lyophilized GM-CSF results in GM-CSF that is associated more with the surface of the polymer scaffold, and the protein diffuses more quickly.

Alternative methods for scaffold fabrication that modify release kinetics include modifying the physical structure of the scaffolds pores, thereby leading to different degradation times and release kinetics (change pore size or total porosity as a percentage of volume), e.g., as described in Riddle et al., Role of poly(lactide-co-glycolide) particle size on gas-foamed scaffolds. J Biomater Sci Polym Ed. 2004; 15(12): 1561-70. Another way to alter release kinetics is to modify the composition, i.e., the raw materials from which the scaffold is made, thereby altering the release properties. For example, different polymers, e.g. alginate, PLA, PGA, or using PLGA are used. Also, use of the polymers with different ratios of glycolic and lactic acid) leads to different release profiles. For example, a variety of PLGs, differing in composition (lactide to glycolide ratio) and molecular weight are used to prepare microspheres (5-50 µm) using known double emulsion (water/oil/water) process, followed by preparation of scaffolds using particulate PLG and PLG microspheres using gas foaming/particulate leaching techniques (Ennett et al., Temporally regulated delivery of VEGF in vitro and in vivo. J Biomed Mater Res A. 2006 October; 79(1). Another technique involves incorporating the protein into different compartments (e.g., encapsulating proteins PLG microspheres or simple mixing and lyophilizing with the polymer before foaming).

Charging and/or Recharging the Device

A bioactive composition such as GM-CSF is incorporated within different layers/compartments of the device, thereby allowing multiple pulses of GM-CSF to be delivered. Each pulse charges (or recharges) the device with an influx of DCs. Scaffolds are fabricated using a variety of methods to create multiple pulses of GM-CSF (or other bioactive agents). For example, such devices are made by incorporating the protein into different compartments (e.g encapsulating proteins PLG microspheres or simple mixing and lyophilizing with the polymer before foaming) thereby creating 2 or more distinct release profiles (i.e. pulses) of the protein (e.g., as described in Richardson et al., Polymeric system for dual growth factor delivery. Nat Biotechnol. 2001 November; 19(11)).

Alternatively, the protein is encapsulated in fast degrading PLG microspheres (e.g. low MW, 50:50 ratio) and slow degrading PLG microspheres (high MW, 85:15 ratio). Then these microspheres are mixed together to be used later to fabricate the scaffolds. Therefore, the protein is encapsulated in both fast a degrading polymer and a slow degrading polymer, thereby resulting in at least 2 distinct releases kinetics and pulses of delivery. This method is utilized to create 3, 4, 5, or more different kinds of microspheres, the ratiometric characteristics of which differ, thereby leading to 3, 4, 5 or more pulses of release of the bioactive composition such as GM-CSF.

Another approach to making a device that delivers more than one pulse is to fabricate a layered scaffold. Layered scaffolds are made by compression molding on different scaffold formulations with another. For example, the raw materials (sucrose+PLG1+Protein) is compressed in a mold and a slightly varied formulation (sucrose+PLG2+Protein) is also compressed in a mold. Then these two layers are compressed together and then foamed, resulting in a bilayered scaffold with distinct spatial control of the concentration of the protein, e.g., as described in Chen et al., Pharm Res. Spatio-temporal VEGF and PDGF delivery patterns blood vessel formation and maturation. 2007 February; 24(2):258-64).

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophillization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an ampliphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A 99:5133-5138. A method for reversible gellation following shear thinning is exemplified in Lee et al., 2003, Adv. Mat. 15:1828-1832.

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydrophilic/phobic characteristics or on secondary interactions within each compartment.

Compartmentalized Device

In certain situations, a device containing compartments with distinct chemical and/or physical properties is useful. A compartmentalized device is designed and fabricated using different compositions or concentrations of compositions for each compai iment.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly).

Alternatively, the compartmentalized device is formed using a printing technology. Successive layers of a scaffold precursor doped with bioactive substances is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (W T Brinkman et al., Photo-cross-linking of type 1 collagen gels in the presence of smooth muscle cells: mechanical properties, cell viability, and function. *Biomacromolecules,* 2003 July-August; 4(4): 890-895; W. Ryu et al., The construction of three-dimensional microfluidic scaffolds of biodegradable polymers by solvent vapor based bonding of micro-molded layers. *Biomaterials,* 2007 February; 28(6): 1174-1184; Wright, Paul K. (2001). *21st Century manufacturing.* New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 Apr. 2006 Issue 2547 p 19; Replacement organs, hot off the press, C. Choi, New Scientist, 25 Jan. 2003, v2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, long term presentation of a bioactive substance on the scaffold in a defined conformation. Exemplary reagents for covalent coupling of such substances are provided in the table below.

Methods to Covalently Couple Peptides/Proteins to Polymers

| Functional Group of Polymer | Coupling reagents and cross-linker | Reacting groups on proteins/peptides |
|---|---|---|
| —OH | Cyanogen bromide (CNBr) Cyanuric chloride 4-(4,6-Dimethoxy-1,3,5-triazin-2-yl)-4-methyl-morpholinium chloride (DMT-MM) | —$NH_2$ |
| —$NH_2$ | Diisocyanate compounds Diisothoncyanate compounds Glutaraldehyde Succinic anhydride | —$NH_2$ —OH |
| —$NH_2$ | Nitrous Acid Hydrazine + nitrous acid | —$NH_2$ —SH —Ph—OH |
| —$NH_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —$NH_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive substances suitable for use in the present invention include, but are not limited to: interferons, interleukins, chemokines, cytokines, colony stimulating factors, chemotactic factors, granulocyte/macrophage colony stimulating factor (GMCSF). Splice variants of any of the above mentioned proteins, and small molecule agonists or antagonists thereof that may be used advantageously to activate dendritic cells are also contemplated herein.

Examples of cytokines as mentioned above include, but are not limited to IL-1, IL-2, IL-3, IL-4, IL-5, IL-6, IL-7, IL-8, IL-10, IL-12, IL-15, IL-17, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Scaffolds of the invention optionally comprise at least one non-viral gene therapy vector such that either the transplanted cells or host cells in the vicinity of the implant would take up and express gene that lead to local availability of the desired factor for a desirable time frame. Such non-viral vectors include, but are not limited to, cationic lipids, polymers, targeting proteins, and calcium phosphate.

Scaffold Fabrication.

A 85:15, 120 kD copolymer of D,L-lactide and glycolide (PLG) (Alkermes, Cambridge, Mass.) was utilized in a gas-foaming process to form scaffolds with open, interconnected pores (Cohen S., Yoshioka T., Lucarelli, M., Hwang L. H., and Langer R. Pharm. Res, 8, 713-720 (1991); herein incorporated by reference). PLG microspheres encapsulating GM-CSF were made using standard double emulsion (Harris, L. D., Kim, B. S., and Mooney, D. J. J. Biomed. Mater. Res. 42, 396-402 (1998); herein incorporated by reference). 16 mg of PLG microspheres were then mixed with 150 mg of the porogens, NaCl or sucrose (sieved to a particle size between 250 µm and 425 µm), and compression molded. The resulting disc was allowed to equilibrate within a high-pressure $CO_2$ environment, and a rapid reduction in pressure causes the polymer particles to expand and fuse into an interconnected structure. The NaCl was leached from the scaffolds by immersion in water yielding scaffolds that were 90% porous. To incorporate tumor lysates into PLG scaffolds, biopsies of B16-F10 tumors, that had grown subcutaneously in the backs of C57BL/6J mice (Jackson Laboratory, Bar Harbor Me.), were digested in collagenase (250 U/ml) (Worthington, Lakewood, N.J.) and suspended at a concentration equivalent to $10^7$ cells per ml after filtration through 40 µm cell strainers. The tumor cell suspension was subjected to 4 cycles of rapid freeze in liquid nitrogen and thaw (37° C.) and then centrifuged at 400 rpm for 10 min. The supernatant (1 ml) containing tumor lysates was collected and lyophilized with the PLG microspheres and the resulting mixture was used to make PLG scaffold-based cancer vaccines. To incorporate CpG-ODNs into PLG scaffolds, PEI-CpG-ODN condensate solutions were vortexed with 60 µl of 50% (wt/vol) sucrose solution, lyophilized and mixed with dry sucrose to a final weight of 150 mg. The sucrose containing PEI-CpG-ODN condensate was then mixed with blank, GM-CSF and/or tumor lysate loaded PLG microspheres to make PLG cancer vaccines.

Scaffold compositions of the present invention comprise GM-CSF and CpG-ODN sequences. A range of concentrations of each element are contemplated. In a preferred embodiment, the scaffold composition comprises PLG. With respect to GM-CSF, per 40 mg polymeric scaffold composition, 0-100 µg of GM-CSF polypeptide is incorporated into or coated onto the scaffold composition. Alternatively, doses comprising 0-50 µg, 0-25 µg, 0-10 µg, 0-5 µg, and 0-3 µg of GM-CSF are incorporated into the scaffold composition. In a preferred embodiment, 0-3 µg of GM-CSF are incorporated into the scaffold composition. With respect to CpG-ODN sequences, or PEI-CpG-ODN condensates, per 40 mg polymeric scaffold composition, 0-1000 µg of PEI-CpG-ODN is incorporated into or coated onto the scaffold composition. Alternatively, doses comprising 0-500 µg, 0-250 µg, 0-100 µg, 0-50 µg, 0-25 µg, 0-10 µg, and 0-5 µg of PEI-CpG-ODN are incorporated into the scaffold composition. In a preferred embodiment, 0-50 µg of PEI-CpG-ODN are incorporated into the scaffold composition.

CpG-ODN Incorporation and In Vitro Release Studies

To determine the incorporation efficiency of CpG-ODN incorporation, PLG scaffolds were prepared with 50 ug of CpG-ODN and digested in 1 ml of chloroform (Sigma Aldrich, and washed with 2 mls of aqueous buffer. The aqueous phase was isolated and the amount of CpG-ODN incorporated was determined by absorbance readings (260/280 and 260/230 ratios calculated at 0.2 mm pathlength) using a Nanodrop instrument, ND1000 (Nanodrop technologies, Wilmington, Del.). Similarly, to determine CpG-ODN release kinetics CpG-ODN loaded scaffolds were placed in 1 ml of Phosphate Buffer Solution (PBS) in an incubator (37° C.). At various timepoints, the PBS release media was collected and replaced with fresh media. The total amount of CpG-ODN incorporated into PLG scaffolds and released into PBS over time was analyzed and recorded.

In Vitro DC Migration Assays and DC Activation

A DC line, JAWSII (ATCC, Manassas, Va.) was used for in vitro experiments and was maintained in α-MEM (Invitrogen, Carlsbad, Calif.) supplemented with 20% FBS (Invitrogen, Carlsbad, Calif.) and 5 ng/ml of GM-CSF. To determine the in vitro effects of CpG-rich oligonucleotides (CpG-ODN) on DC activation, JAWSII cells were cultured with 5 µg/ml of CpG-ODN 1826, 5'-tcc atg acg ttc ctg acg tt-3', (SEQ ID NO: 10; Invivogen, San Diego, Calif.) for 24 hours, and in the presence of 0, 50 or 500 ng/ml GM-CSF for 12 hours. To assess the effects of condensing CpG-ODN on DC activation, CpG ODN was condensed with PEI molecules by dropping ODN-1826 solutions into PEI solution, while vortexing the mixture (Huang Y C, Riddle F, Rice K G, and Mooney D J. Hum Gene Ther. 5, 609-17. (2005); herein incorporated by reference). The charge ratio between PEI and CpG-ODN ($NH_3+$:$PO_4-$) was kept constant at 7 during condensation. As a positive control for DC activation, DCs were also cultured with the stimulatory factors, TNF-α (10 ng/ml) (Peprotech, Rocky Hill, N.J.) and LPS (10 ng/ml) (Sigma-Aldrich, St. Louis, Mo.). The DCs were then harvested and stained with primary antibodies (BD Pharmingen, San Diego, Calif.): PE-conjugated CD86 (B7, costimulatory molecule), FITC-conjugated CCR7, and FITC-conjugated MHCII. Cells were analyzed by FACS and gated according to positive FITC, and PE using isotype controls, and the percentage of cells staining positive for each surface antigen was recorded.

Migration assays were performed with 6.5 mm transwell dishes (Costar, Cambridge, Mass.) with a pore size of 5 µm. To test whether CpG-ODN stimulation may affect DC chemotaxis towards CCL19 (Peprotech, Rocky Hill, N.J.) in the presence of GM-CSF, $5 \times 10^5$ DCs stimulated with either 5 µg/ml of CpG-ODN or PEI-CPG-ODN (Charge Ratio of 7), and 0, 50 and 500 ng/ml GM-CSF were placed in the top wells and 300 ng/ml of CCL19 was placed in the bottom well. After 12 hours the cells that migrated into the bottom wells of the chamber were harvested and counted using a coulter counter. Dispersement of DCs from PEI-CpG-ODN loaded PLG matrices toward CCL19 was assessed by incorporating 5, 50 and 500 µg of condensates into PLG scaffolds (13 mm diameter, 2 mm thick that were quartered) seeded with $1 \times 10^6$ DCs and fixed onto transwells using bovine collagen (BD Biosciences, San Jose, Calif.). To test the effects of CpG stimulation in the presence of GM-CSF, 500 ng/ml of GM-CSF was supplemented into the media of the top wells with scaffolds containing 25 µg of PEI-CpG-ODN. At various timepoints, the cells that migrated into the bottom wells of the chamber were harvested and counted using a coulter counter.

In Vivo DC Migration and Activation Assays

Blank scaffolds and scaffolds containing GM-CSF with or without 10 µg PEI-ODN control (5'-tcc atg agc ttc ctg agc tt-3') (SEQ ID NO: 6) or 10 µg PEI-CpG-ODN condensate loaded scaffolds were implanted into subcutaneous pockets on the back of 7-9 week old male C57BL/6J mice. For histological examination scaffolds were excised and fixed in Z-fix solution, embedded in paraffin, and stained with hematoxylin and eosin. To analyze DC recruitment, scaffolds were excised and the ingrown tissue was digested into single cell suspensions using a collagenase solution (Worthingtion, 250 U/ml) that was agitated at 37° C. for 45 minutes. The cell suspensions were then poured through a 40 μm cell strainer to isolate cells from scaffold particles and the cells were pelleted and washed with cold PBS and counted using a Z2 coulter counter (Beckman Coulter). The resultant cell populations were then stained with primary antibodies (BD Pharmingen, San Diego, Calif.) conjugated to fluorescent markers to allow for analysis by flow cytometry. APC-conjugated CD11c (dendritic cell marker) and PE-conjugated CD86 (B7, costimulatory molecule) stains were conducted for DC recruitment analysis, and APC-conjugated CD11c, FITC-conjugated CCR7, and PE-conjugated MHCII stains were conducted for DC programming analysis. Cells were gated according to positive FITC, APC and PE using isotype controls, and the percentage of cells staining positive for each surface antigen was recorded. To track in vivo DC emigration from scaffolds toward the inguinal lymph nodes, 250 μg of lyophilized fluoroscein isothiocyanate (FITC) (Molecular Probes, Carlsbad, Calif.) was incorporated into scaffolds by mixing with PLG microspheres before scaffold processing, and FITC was also applied by incubating scaffolds with 330 ul of 3% FITC solution for 30 min. FITC painted scaffolds were then implanted subcutaneously into the left flank of C57BL/6J mice and the inguinal lymph nodes (LNs) were harvested at various time-points after scaffold implantation. Cell suspensions from LNs were prepared by digestion in collagenase for 30 min and pressing of the tissue through 70 μm cell strainers, and examined for CD11c(+)FITC(+) cell numbers by flow cytometry.

Tumor Growth Assays

PLG scaffolds with melanoma tumor lysates and various dosages of GM-CSF and/or 10 μg PEI-CpG-ODN condensates were implanted subcutaneously into the lower left flank of C57BL/6J mice. Animals were challenged 14 days later with a subcutaneous injection of $10^5$ B16-F10 melanoma cells (ATCC, Manassas, N.J.) in the back of the neck. Animals were monitored for the onset of tumor growth (approximately 1 $mm^3$) and sacrificed for humane reasons when tumors grew to 20-25 mm (longest diameter). For histological examination, tumors were biopsied at days 20-25 after injection and fixed in Z-fix (Anatech, Battle Creek, Mich.) and stained for hematoxylin and eosin. To examine tumor tissue for T-cell infiltration, immunoperoxidase staining was performed using the avidin-biotin-peroxidase Vectastain Elite ABC kit (Vector Laboratories). The primary antibodies used were GK 1.5 (CD4), and 53-6.72 (CD8) and staining was developed using DAB+ substrate chromogen (DAKO, Carpinteria, Calif.). Sections from tumor samples (n=3 or 4) were visualized at 40× and 100× with a Nikon light microscope (Indianapolis, Ind.) and positively stained T-cells were counted manually. PLG cancer vaccines were also compared to a common cell-based vaccine using B16-F10 melanoma cells that were genetically modified to express GM-CSF, and subsequently irradiated (3500 rad) as described previously (Dranoff G., et al. Proc. Natl. Acad. Sci. USA. 90, 3539-3543(1993); herein incorporated by reference). The irradiated tumor cells ($5 \times 10^5$ cells) were then injected subcutaneously into C57BL/6J mice that were challenged 14 days later with $10^5$ B16-F10 melanoma cells.

Statistical Analysis

All values in the present study were expressed as mean±S.D. The significant differences between the groups were analyzed by a Student's t test and a P value of less than 0.05 was considered significant.

Vaccine Device

The biocompatible scaffolds are useful as delivery vehicles for cancer vaccines. The cancer vaccine stimulates an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. These treatments optionally involve cytokine exposure to activate the cells, genetic manipulation to overexpress cytokines from the cells, or priming with tumor specific antigens or cocktails of antigens, and expansion in culture. Dendritic cell vaccines activate antigen presenting cells directly, and their proliferation, activation and migration to lymph nodes is regulated by scaffold compositions to enhance their ability to elicit an immune response. Types of cancers to be treated include central nervous system (CNS) cancers, CNS Germ Cell tumor, lung cancer, Leukemia, Multiple Myeloma, Renal Cancer, Malignant Glioma, Medulloblastoma, and Melanoma.

For the purpose of eliciting an antigen-specific immune response, a scaffold device is implanted into a mammal. The device is tailored to activate immune cells and prime the cells with a specific antigen thereby enhancing immune defenses and destruction of undesired tissues and targeted microorganisms such as bacterial or viral pathogens. The device attracts appropriate immune cells, such as macrophages, T cells, B cells, NK cells, and dendritic cells, by containing and/or releasing signaling substances such as GM-CSF. These signaling substances are incorporated in the scaffold composition in such a way as to control their release spatially and temporally using the same techniques used to integrate other bioactive compounds in the scaffold composition.

Once the immune cells are inside the device, the device programs the immune cells to attack or cause other aspects of the immune system to attack undesired tissues (e.g., cancer, adipose deposits, or virus-infected or otherwise diseased cells) or microorganisms. Immune cell activation is accomplished by exposing the resident immune cells to preparations of target-specific compositions, e.g., ligands found on the surface of the undesired tissues or organisms, such as cancer cell surface markers, viral proteins, oligonucleotides, peptide sequences or other specific antigens. For example, useful cancer cell-specific antigens and other tissue or organism-specific proteins are listed in the table below.

The device optionally contains multiple ligands or antigens in order to create a multivalent vaccine. The compositions are embedded in or coated on the surface of one or more compartments of the scaffold composition such that immune cells migrating through the device are exposed to the compositions in their traverse through the device. Antigens or other immune stimulatory molecules are exposed or become exposed to the cells as the scaffold composition degrades. The device may also contain vaccine adjuvants that program the immune cells to recognize ligands and enhance antigen presentation. Exemplary vaccine adjuvants include chemokines/cytokines, CpG rich oligonucleotides. or antibodies that are exposed concurrently with target cell-specific antigens or ligands.

The device attracts immune cells to migrate into a scaffold where they are educated in an antigen-specific manner and activated. The programmed immune cells are then induced to egress towards lymph nodes in a number of ways. The recruitment composition and deployment signal/composition, e.g., a lymph node migration inducing substance, is released in one or more bursts, programmed by the method of incorporation and/or release from the scaffold material, or controlled by the sequential degradation of scaffold compartments which contain the attractant. When a burst dissipates, the cells migrate away. Compartments containing repulsive substances are designed to degrade and release the repulsive substance in one or more bursts or steadily over time. Relative concentration of the repulsive substances cause the immune cells to migrate out of the device. Alternatively, cells which have been placed in or have migrated into the device are programmed to release repulsive substances or to change their own behavior. For example, localized gene therapy is carried out by cell exposure to plasmid DNA attached to the scaffold. Useful repulsive substances include chemokines and cytokines. Alternatively, the device may cause immune cells to egress by degrading and releasing them.

Target disease states, stimulatory molecules and antigens useful in vaccine device construction are listed below.

Bioactive Factors to Promote Immune Responses
a. Interleukins: IL-1, IL-2, IL-3, IL-4, IL-5, IL-6, IL-8, IL-10, IL-12 1L-15, 1L-17, 1L-18 etc.
b. TNF-α
c. IFN-γ
d. IFN-α
e. GM-CSF
f G-CSF
g. Ftl-3 ligand
h. MIP-3 β (CCL19)
i. CCL21
j. M-CSF
k. MIF
l. CD40L
m. CD3
n. ICAM
o. Anti CTLA-4 antibodies
p. TGF-β
q. CPG rich DNA or oligonucleotides
r. Sugar moieties associated with Bacteria: Lipopolysacharides (LPS) is an example
s. Fas ligand
t. Trail
u. Lymphotactin
v. Mannan (M-FP)
w. Heat Shock Proteins (apg-2, Hsp70 and Hsp 90 are examples)

Diseases and Antigens—Vaccination Targets
a. Cancer: antigens and their sources
i. Tumor lysates extracted from biopsies
ii. Irradiated tumor cells
iii. Melanoma
1. MAGE series of antigens (MAGE-1 is an example)
2. MART-1/melana
3. Tyrosinase
4. ganglioside
5. gp100
6. GD-2
7. O-acetylated GD-3
8. GM-2
iv. Breast Cancer
1. MUC-1
2. Sos1
3. Protein kinase C-binding protein
4. Reverse trascriptase protein
5. AKAP protein
6. VRK1
7. KIAA1735
8. T7-1, T11-3, T11-9
v. Other General and Specific Cancer Antigens
1. *Homo Sapiens* telomerase ferment (hTRT)
2. Cytokeratin-19 (CYFRA21-1)
3. SQUAMOUS CELL CARCINOMA ANTIGEN 1 (SCCA-1), (PROTEIN T4-A)
4. SQUAMOUS CELL CARCINOMA ANTIGEN 2 (SCCA-2)
5. Ovarian carcinoma antigen CA125 (1A1-3B) (KIAA0049)
6. MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3)
7. CTCL tumor antigen se1-1
8. CTCL tumor antigen se14-3
9. CTCL tumor antigen se20-4
10. CTCL tumor antigen se20-9
11. CTCL tumor antigen se33-1
12. CTCL tumor antigen se37-2
13. CTCL tumor antigen se57-1
14. CTCL tumor antigen se89-1
15. Prostate-specific membrane antigen
16. 5T4 oncofetal trophoblast glycoprotein
17. Orf73 Kaposi's sarcoma-associated herpesvirus
18. MAGE-C1 (cancer/testis antigen CT7)
19. MAGE-B1 ANTIGEN (MAGE-XP ANTIGEN) (DAM10)
20. MAGE-B2 ANTIGEN (DAM6)
21. MAGE-2 ANTIGEN
22. MAGE-4a antigen
23. MAGE-4b antigen
24. Colon cancer antigen NY-CO-45
25. Lung cancer antigen NY-LU-12 variant A
26. Cancer associated surface antigen
27. Adenocarcinoma antigen ART1
28. Paraneoplastic associated brain-testis-cancer antigen (onconeuronal antigen MA2; paraneoplastic neuronal antigen)
29. Neuro-oncological ventral antigen 2 (NOVA2)
30. Hepatocellular carcinoma antigen gene 520
31. TUMOR-ASSOCIATED ANTIGEN CO-029
32. Tumor-associated antigen MAGE-X2
33. Synovial sarcoma, X breakpoint 2
34. Squamous cell carcinoma antigen recognized by T cell
35. Serologically defined colon cancer antigen 1
36. Serologically defined breast cancer antigen NY-BR-15
37. Serologically defined breast cancer antigen NY-BR-16
38. Chromogranin A; parathyroid secretory protein 1
39. DUPAN-2
40. CA 19-9
41. CA 72-4

42. CA 195
43. Carcinoembryonic antigen (CEA)
b. AIDS (HIV Associated Antigens)
i. Gp120
ii. SIV229
iii. SIVE660
iv. SHIV89.6P
v. E92
vi. HCl
vii. OKM5
viii. FVIIIRAg
ix. HLA-DR (Ia) antigens
x. OKM1
xi. LFA-3
c. General Infectious Diseases and Associated Antigens
i. Tuberculosis
1. *Mycobacterium tuberculosis* antigen 5
2. *Mycobacterium tuberculosis* antigen 85
3. ESAT-6
4. CFP-10
5. Rv3871
6. GLU-S
ii. Malaria
1. CRA
2. RAP-2
3. MSP-2
4. AMA-1
iii. Possible mutant influenza and meningitis strains
d. Neuro Protection—Protect Against Neurological Diseases (e.g., Alzheimer's, Parkinsons, Prion Disease)
1. Classes of self CNS antigens
2. human alpha-synuclein (Parkinson's)
3. beta amyloid plaques (Alzheimer's)
e. Autoimmune Diseases (multiple sclerosis, Rheumatoid arthritis etc)
i. Disease linked MHC antigens
ii. Different classes of Self antigens
iii. Insulin
iv. Insulin peptide B9-23
v. glutamic acid
vi. decarboxylase 65 (GAD 65)
vii. HSP 60
Disease linked T-cell receptor (TCR)

In Situ Regulation of DC Subsets and T Cells Mediates Tumor Regression in Mice

Prior vaccines have been largely ineffective for patients with established cancer, as advanced disease requires potent and sustained activation of $CD8^+$ cytotoxic T lymphocytes (CTLs) to kill tumor cells and clear the disease. Subsets of dendritic cells (DCs) specialize in antigen cross-presentation and in the production of cytokines, which regulate both CTLs and T regulatory (Treg) cells that shut down effector T cell responses. Coordinated regulation of a DC network, and plasmacytoid DCs (pDCs) and $CD8^+$ DCs in particular, enhances host immunity in mice. Functionalized biomaterials incorporating various combinations of an inflammatory cytokine, immune danger signal, and tumor lysates were used to control the activation and localization of host DC populations in situ. The numbers of pDCs and $CD8^+$ DCs, and the endogenous production of interleukin-12, all correlated strongly with the magnitude of protective antitumor immunity and the generation of potent $CD8^+$ CTLs. Vaccination by this method maintained local and systemic CTL responses for extended periods while inhibiting FoxP3 Treg activity during antigen clearance, resulting in complete regression of distant and established melanoma tumors. The efficacy of this vaccine as a monotherapy against large invasive tumors is a result of the local activity of pDCs and $CD8^+$ DCs induced by persistent danger and antigen signaling at the vaccine site. These results indicate that a critical pattern of DC subsets correlates with the evolution of therapeutic antitumor responses. Provision of secondary immunostimulatory site of tumor antigen presentation allows one to manipulate the in situ generation of a heterogeneous DC network capable of CTL induction, and activate robust CD8 T cell effector responses to established tumors.

Described herein is the in situ generation of a heterogeneous DC network capable of CTL induction to activate robust CD8+ T cell effector responses to established tumors, by providing a secondary immunostimulatory site of tumor antigen presentation. Inflammation or infection produces DC populations that are not found in the steady state (K. Shortman, S. H. Naik, Steady-state and inflammatory dendritic-cell development. *Nat. Rev. Immunol.* 7, 19-30 (2007)), suggesting that stimuli in tissue microenvironments provoke a response from the network of DCs. The cytokine granulocyte-macrophage colony-stimulating factor (GM-CSF) is present at increased concentrations during inflammation (J. A. Hamilton, GM-CSF in inflammation and autoimmunity. *Trends Immunol.* 23, 403-408 (2002); M. C. Dieu, B. Vanbervliet, A. Vicari, J. M. Bridon, E. Oldham, S. Aït-Yahia, F. Brière, A. Zlotnik, S. Lebecque, C. Caux, Selective recruitment of immature and mature dendritic cells by distinct chemokines expressed in different anatomic sites. *J. Exp. Med.* 188, 373-386 (1988)), which causes the recruitment of both monocytes and DCs while inducing local monocytes to differentiate into DCs (G. Dranoff, E. Jaffee, A. Lazenby, P. Golumbek, H. Levitsky, K. Brose, V. Jackson, H. Hamada, D. Pardoll, R. C. Mulligan, Vaccination with irradiated tumor cells engineered to secrete murine granulocyte-macrophage colony-stimulating factor stimulates potent, specific, and long-lasting anti-tumor immunity. *Proc. Natl. Acad. Sci. U.S.A.* 90, 3539-3543 (1993); B. Pulendran, J. Banchereau, S. Burkeholder, E. Kraus, E. Guinet, C. Chalouni, D. Caron, C. Maliszewski, J. Davoust, J. Fay, K. Palucka, Flt3-ligand and granulocyte colony-stimulating factor mobilize distinct human dendritic cell subsets in vivo. *J. Immunol.* 165, 566-572 (2000)).

Implantable synthetic polymer matrices (antigen-loaded acellular biomaterial device) that spatially and temporally control the in vivo presentation of cytokines, tumor antigens, and danger signals were utilized herein. GM-CSF is released from these polylactide-co-glycolide (PLG) [a Food and Drug Administration (FDA)-approved biomaterial] matrices into the surrounding tissue to recruit DC precursors and DCs. CpG-rich oligonucleotides are immobilized on the matrices as danger signals, and antigen (tumor lysates) is released to matrix-resident DCs to program DC development and maturation. These matrices quantitatively regulate DC activation and trafficking in situ and induce prophylactic immunity against inoculations of murine B16-F10 melanoma cells (P. Schnorrer, G. M. Behrens, N. S. Wilson, J. L. Pooley, C. M. Smith, D. El-Sukkari, G. Davey, F. Kupresanin, M. Li, E. Maraskovsky, G. T. Belz, F. R. Carbone, K. Shortman, W. R. Heath, J. A. Villadangos, The dominant role of $CD8^+$ dendritic cells in cross-presentation is not dictated by antigen capture. *Proc. Natl. Acad. Sci. U.S.A.* 103, 10729-10734 (2006)). As described herein, this system administered repeatedly over time to controls the recruitment and activation of multiple DC and T cell subsets and is effective as a therapeutic vaccine against established tumors.

The following materials and methods were used to generate the data described herein.

Matrix Fabrication

An 85:15, 120-kD copolymer of $_{D,L}$-lactide and glycolide (PLG) (Alkermes) was utilized in a gas-foaming process to form porous PLG matrices (L. D. Harris, B. S. Kim, D. J. Mooney, Open pore biodegradable matrices formed with gas foaming. *J. Biomed. Mater. Res.* 42, 396-402 (1998)). In brief, PLG microspheres encapsulating GM¬CSF were first made with standard double emulsion (S. Cohen, T. Yoshioka, M. Lucarelli, L. H. Hwang, R. Langer, Controlled delivery systems for proteins based on poly(lactic/glycolic acid) microspheres. *Pharm. Res.* 8, 713-720 (1991)). PLG micro-spheres were then mixed with 150 mg of the porogen, sucrose (sieved to a particle size between 250 and 425 mm), and compression molded. The resulting disc was allowed to equilibrate within a high-pressure $CO_2$ environment, and a rapid reduction in pressure causes the polymer particles to expand and fuse into an interconnected structure. The sucrose was leached from the scaffolds by immersion in water, yielding scaffolds that were 90% porous. To incorporate tumor lysates into PLG scaffolds, the biopsies of B16-F10 tumors that had grown subcutaneously in the backs of C57BL/6J mice (Jackson Laboratory) were digested in collagenase (250 U/ml) (Worthington) and suspended at a concentration equivalent to $10^7$ cells per milliliter after filtration through 40-μm cell strainers. The tumor cell suspension was subjected to four cycles of rapid freeze in liquid nitrogen and thaw (37° C.) and then centrifuged at 400 rpm for 10 min. The supernatant (1 ml) containing tumor lysates was collected, incubated with the PLG microspheres, and lyophilized, and the resulting mixture was utilized in the high-pressure $CO_2$ process to foam macroporous PLG matrices incorporating tumor lysates. To incorporate CpG-ODNs into PLG scaffolds, CpG-ODN 1826, 5'-tccatgacgttcct-gacgtt-3' (SEQ ID NO: 10) (Invivogen) was condensed with PEI ($M_n$~60,000) molecules by dropping ODN 1826 solutions into PEI solution while vortexing the mixture (L. D. Harris, B. S. Kim, D. J. Mooney, Open pore biodegradable matrices formed with gas foaming. J. Biomed. Mater. Res. 42, 396-402 (1998); S. Cohen, T. Yoshioka, M. Lucarelli, L. H. Hwang, R. Langer, Controlled delivery systems for proteins based on poly(lactic/glycolic acid) microspheres. Pharm. Res. 8, 713-720 (1991); Y. C. Huang, M. Connell, Y. Park, D. J. Mooney, K. G. Rice, Fabrication and in vitro testing of polymeric delivery system for condensed DNA. J. Biomed. Mater. Res. A 67, 1384-1392(2003)). The charge ratio between PEI and CpG-ODN ($NH3^+:PO4^-$) was kept constant at 7 during condensation. PEI-CpG-ODN condensate solutions were then vortexed with 60 μl of 50% (w/v) sucrose solution, lyophilized, and mixed with dry sucrose to a final weight of 150 mg. The sucrose containing PEI-CpG-ODN condensate was then mixed with blank, GM-CSF, and/or tumor lysate-loaded PLG microspheres to make PLG cancer vaccines.

In Situ Identification of DC Subsets and T Cells

Blank PLG matrices and matrices containing 3000 ng of GM-CSF alone or in combination with either 1, 10, 50, or 100 μg of CpG-ODN (studies were also performed with tumor lysates copresented with either 3000 ng of GM-CSF or 100 μg of CpG-ODN alone or in combination) were implanted into subcutaneous pockets on the back of 7- to 9-week-old male C57BL/6J mice. For histological examination, scaffolds were excised and fixed in Z-fix solution (Anatech), embedded in paraffin, and stained with hematoxylin and eosin (H&E). To analyze DC recruitment, scaffolds were excised at various time points and digested the ingrown tissue into single-cell suspensions with a collagenase solution (250 U/ml; Worthington) that was agitated at 37° C. for 45 min. The cell suspensions were then poured through a 40-μm cell strainer to isolate cells from scaffold particles, and the cells were pelleted and washed with cold PBS and counted with a Z2 coulter counter (Beckman Coulter). To assess DC infiltration and activation, subsets of the total cell population isolated from PLG matrices were stained with primary antibodies (BD Pharmingen) conjugated to fluorescent markers to allow for analysis by flow cytometry. Allophycocyanin (APC)-conjugated CD11c (DC marker) and phycoerythrin (PE)-conjugated CD86 (B7, costimulatory molecule) stains were conducted for DC recruitment analysis, and APC-conjugated CD11c, fluorescein isothiocyanate (FITC)-conjugated CCR7, and PE-conjugated MHCII stains were conducted for DC programming analysis. To further delineate the presence of specific DC subsets, cells were stained with APC-conjugated CD11c and PE-conjugated PDCA-1 (pDC marker), APC-conjugated CD11c and PE-conjugated CD8 (CD8 DCs), or APC-conjugated CD11c and FITC-conjugated CD11b (CD11b DCs). To assess T cell infiltration, PE-Cy7-conjugated CD3 stains were performed in conjunction with APC-conjugated CD8a (CD8 T cells), FITC-conjugated CD4 (CD4 T cells), and PE-conjugated FoxP3 (Treg) and analyzed with flow cytometry. Cells were gated according to positive FITC, APC, and PE with isotype controls, and the percentage of cells staining positive for each surface antigen was recorded.

Tumor Growth Assays, Protective Cytokines, and TRP2 Pentamer Analysis

PLG scaffolds with melanoma tumor lysates and various dosages of GM-CSF and/or various quantities of PEI-CpG-ODN condensates were implanted subcutaneously into the lower left flank of C57BL/6J mice. For prophylactic vaccinations, animals were challenged 14 days later with a subcutaneous injection of $10^5$ B16-F10 melanoma cells [American Type Culture Collection (ATCC)] in the back of the neck. Animals were monitored for the onset of tumor growth (~1 $mm^3$) and killed for humane reasons when tumors grew to 20 to 25 mm (longest diameter).

To assess PLG vaccine efficacy in the therapeutic setting, C57BL/6J mice were challenged with a subcutaneous injection of $5×10^5$ B16-F10 melanoma cells (ATCC) in the back of the neck. At either day 9 or day 13 after tumor challenge, PLG vaccines loaded with 3000 ng of GM-CSF, 100 μg of CpG-ODN, and tumor lysates were implanted subcutaneously into the lower left flank of C57BL/6J mice. A subset of mice was vaccinated again at 10 days after the initial vaccination (days 19 and 23).

To determine in vivo IL-12p70, IFN-α, IFN-γ, and TGF-β concentrations at the matrix implant site, the adjacent tissue was excised and digested with tissue protein extraction reagent (Pierce). After centrifugation, the concentrations of IL-12, IFN-α, IFN-γ, and TGF-β in the supernatant were then analyzed with enzyme-linked immunosorbent assay (R&D Systems) according to the manufacturer's instructions.

To determine the generation of TRP2-specific CTLs, single-cell suspensions were prepared from the spleens of mice immunized with PLG vaccines (lysate+3000 ng of GM-CSF+100 μg of CpG) at various time points. These cells were initially stained with APC-H-2Kb-TRP2 pentamers (Proimmune) and subsequently stained with PE-conjugated monoclonal antibody to CD8 (BD Pharmingen) before being analyzed by flow cytometry.

The data indicate that an implanted copolymer matrix (antigen-loaded acellular biomaterial device) that incorporates inflammatory cytokines, immune danger signal, and tumor antigens elicits an immune response network that eradicates established tumors in vivo.

Statistical Analysis

All values in the present study were expressed as mean±SD. The significant differences between the groups were analyzed by a Student's t test and a P value of <0.05 was considered significant.

Local GM-CSF Delivery Promotes Recruitment of CD11 b$^+$ DCs

Macroporous PLG matrices were fabricated for GM-CSF release to recruit DCs and with an interconnected porous structure facilitates cell infiltration. Matrices were loaded with 0, 3000, and 7000 ng of GM-CSF and implanted into the subcutaneous pockets of C57BL/6J mice. Histological analysis at day 14 after implantation of PLG matrices loaded with 3000 ng of GM-CSF revealed enhanced cellular infiltration when compared to blank controls. Fluorescence-activated cell sorting (FACS) analysis for CD11c DCs showed that GM-CSF delivery recruited significantly more DCs (a factor of ~8 increase) than blank PLG matrices. The matrix-resident DCs were almost exclusively CD11b$^+$ (~87%), in accordance with other studies of GM-CSF effects on DC recruitment in vivo (N. Mach, S. Gillessen, S. B. Wilson, C. Sheehan, M. Mihm, G. Dranoff, Differences in dendritic cells stimulated in vivo by tumors engineered to secrete granulocyte-macrophage colony stimulating factor or Flt3-ligand. Cancer Res. 60, 3239-3246 (2000); E. Daro, B. Pulendran, K. Brasel, M. Teepe, D. Pettit, D. H. Lynch, D. Vremec, L. Robb, K. Shortman, H. J. McKenna, C. R. Maliszewski, E. Maraskovsky, Polyethylene glycolmodified GM-CSF expands CD11bhighCD11chigh but not CD11blowCD11chigh murine dendritic cells in vivo: A comparative analysis with Flt3 ligand. J. Immunol. 165, 49-58 (2000)). The total number of DCs recruited and their expression of the costimulatory molecule CD86 increased with GM-CSF delivery in a dose-dependent manner. However, the highest dose (7000 ng) of GM-CSF reduced the number of activated DCs at the implant site, as indicated by diminished major histocompatibility complex class II (MHCII) and CCR7 expression at day 14 after implantation. Because total DC recruitment and activation both peaked at 3000 ng of GM-CSF, this dose was utilized to recruit and generate DCs. GM-CSF delivery promoted greater cellular penetration into and association with the PLG material, as indicated by histological analysis and measurement of DC numbers, allowing for the subsequent programming of resident DC precursors and DCs.

In Situ Delivery of CpG-Oligodeoxynucleotide Promotes pDC Recruitment and IFN Production The ability of local presentation of danger signals to regulate the ratio of distinct DC subtypes was next examined by immobilizing TLR-activating, polyethylenimine (PEI)-condensed CpG-oligodeoxynucleotide (ODN) molecules into the matrices. Condensation of oligonucleotides with the polycationic polymer PEI results in positively charged particles that bind electrostatically to the anionic PLG matrix. PLG matrices incorporating CpG-ODN alone recruited CD11c$^+$-PDCA-1$^+$-pDCs to the PLG matrix. This effect was enhanced with coadministration of GM-CSF. The dose of CpG-ODN presented in combination with 3000 ng of GM-CSF was altered to regulate the numbers of resident pDCs, resulting in 190,000, 520,000, and 1,200,000 cells at doses of 0, 10, and 100 µg of CpG-ODN, respectively. Copresentation of CpG-ODN had little effect on the ability of GM-CSF to enhance CD11c$^+$-CD11b$^+$ cDCs. High doses of CpG-ODN promoted the local production of IFN-α (~1010 µg/ml) and IFN-γ (~600 µg/ml) independently of the presence of GM-CSF. These results indicate that controlled GM-CSF and CpG-ODN danger signaling from synthetic extracellular matrices cooperates to regulate resident pDC and CD11c$^+$CD11b$^+$ cDC numbers, along with the production of protective cytokines commonly linked to TH1 and CTL immunity.

Tumor Lysate Co-Delivery with CpG-ODN and GM-CSF Stimulates CD8+ Generation and IL-12 Production Experiments were carried out to determine whether co-presenting cancer antigens with CpG-ODNs to matrix-resident DCs would promote further DC development, activation, and CTL antigen sensitization. In this context, necrotic tumor cells may be particularly immunostimulatory, as they release a variety of endogenous mediators (for example, heat shock proteins and damaged nucleic acids) that trigger innate immune recognition (C. Fonseca, G. Dranoff, Capitalizing on the immunogenicity of dying tumor cells. Clin. Cancer Res. 14, 1603-1608 (2008)). Thus, freeze-thaw lysates of B16 melanomas were prepared, and antigen-presenting matrices were fabricated by encapsulating these lysates into the PLG material, resulting in localized and sustained antigen presentation to the infiltrating cell population (O. A. Ali, N. Huebsch, L. Cao, G. Dranoff, D. J. Mooney, Infection-mimicking materials to program dendritic cells in situ. Nat. Mater. 8, 151-158 (2009)). These antigen-presenting matrices unexpectedly stimulated CD8$^+$ DC generation in situ). On viral invasion, CD8$^+$CD11c$^+$ cDCs are especially efficient at cross-presenting exogenous antigen on MHCII molecules (J. D. Farrar, H. Asnagli, K. M. Murphy, T helper subset development: Roles of instruction, selection, and transcription. J. Clin. Invest. 109, 431-435 (2002); D. Skokos, M. C. Nussenzweig, CD8 DCs induce IL-12-independent Th1 differentiation through Delta 4 Notch-like ligand in response to bacterial LPS. J. Exp. Med. 204, 1525-1531 (2007); J. M. den Haan, S. M. Lehar, M. J. Bevan, CD8$^+$ but not CD8$^-$ dendritic cells cross-prime cytotoxic T cells in vivo. J. Exp. Med. 192, 1685-1696 (2000)) and at producing the $T_H1$-promoting cytokine IL-12 (M. Moser, K. M. Murphy, Dendritic cell regulation of TH1-TH2 development. Nat. Immunol. 1, 199-205 (2000); D. Jankovic, M. C. Kullberg, S. Hieny, P. Caspar, C. M. Collazo, A. Sher, In the absence of IL-12, CD4+ T cell responses to intracellular pathogens fail to default to a Th2 pattern and are host protective in an IL-10$^{-/-}$ setting. Immunity 16, 429-439 (2002); V. E. Schijns, B. L. Haagmans, C. M. Wierda, B. Kruithof, I. A. Heijnen, G. Alber, M. C. Horzinek, Mice lacking IL-1 2 develop polarized Th1 cells during viral infection. J. Immunol. 160, 3958-3964 (1998); J. Magram, J. Sfarra, S. Connaughton, D. Faherty, R. Warner, D. Carvajal, C. Y. Wu, C. Stewart, U. Sarmiento, M. K. Gately, IL-12-deficient mice are defective but not devoid of type 1 cytokine responses. Ann. N.Y. Acad. Sci. 795, 60-70 (1996)), which are two mechanisms that aid in priming CTL immunity to viruses and tumors. This activity, however, is normally associated with lymphoid tissues. Co-presentation of tumor lysates with CpG-ODN led to the presence of 200,000 CD8$^+$ DCs, which increased to ~670,000 (a factor of 9 increase over blank matrices) when GM-CSF was added to stimulate recruitment. Additionally, tumor lysate in combination with GM-CSF and CpG enhanced the numbers of recruited pDCs at day 10 after implantation by a factor of 2 over matrices without lysate and by a factor of 10 over blank controls. No significant difference in pDC numbers was observed with tumor lysate in combination with only GM-CSF or CpG signaling. The CD11c$^+$CD11b$^+$ DC population at the vaccine site depended on GM-CSF alone, as tumor lysate or CpG signaling alone or in combination had no significant effect on the recruitment and expansion of these DCs.

In situ production of the T cell growth factor IL-12 at matrices that deliver both tumor lysate and CpG-ODN to cell populations recruited by GM-CSF was about four times at blank matrices and at least twice at all other matrix formulations. However, tumor lysates in the matrix did not increase the high concentrations of IFN-α and IFN-γ induced by CpG-ODN alone. These results indicate that the engineered matrices manipulated both the number and the function of specific DC subsets, as well as the accompanying CTL-polarizing activity.

PLG Matrices Co-Delivering GM-CSF, CpG-ODN, and Tumor Lysates Stimulate Potent Local and Systemic CD8+ Cytotoxic T Cells To elucidate the adaptive immune mechanisms induced by PLG vaccines that deliver tumor lysate, GM-CSF, and CpG-ODN, the activity of both local and systemic CTLs was examined. Flow cytometric analysis of cells infiltrating the vaccine site revealed a significant CD3$^+$CD8$^+$ T cell response by day 5 (representative sample: ~1.9×10$^5$ cells), which peaked at day 12 when a relatively large proportion of the matrix-resident cells were CTLs (representative sample: 8.5% of cells; ~8.5×10$^5$ cells). Local CD8$^+$ T cell numbers dropped sharply by day 16 and were negligible at day 21 likely because of antigen clearance. PLG vaccines containing tumor lysates, GM-CSF, and CpG-ODN preferentially tuned and promoted CD8$^+$ cytotoxic immune responses relative to other matrix formulations devoid of CpG. Further, the activation and persistence of systemic CTL responses was monitored by staining splenocytes with MHCII-tyrosinase-related protein 2 (TRP2) peptide pentamers to identify CTLs with specificity to TRP2, which is a major antigenic target of melanoma vaccines in mice and humans. A significant expansion of TRP2-specific CTLs was observed in the spleens of vaccinated mice by day5, which continued and peaked between days 7 and 16 before falling at days 21 to 28, indicating that systemic anti-melanoma responses were being generated and sustained for extended periods.

Tumor Protection Induced by PLG Matrices Correlated with DC Subsets and IL-12 Production This system is capable of generating prophylactic immunity against poorly immunogenic B16-F10 melanoma (O. A. Ali, N. Huebsch, L. Cao, G. Dranoff, D. J. Mooney, Infection-mimicking materials to program dendritic cells in situ. *Nat. Mater.* 8, 151-158 (2009)). The relation of this antitumor efficacy to the specific DC networks invoked by various vaccine formulations was investigated. C57BL/6J mice were vaccinated with PLG-based matrices incorporating B16 tumor lysates, GM-CSF, and CpG-ODN in varying combinations and then challenged with live B16-F10 melanoma tumor cells at day 14 after vaccination. PLG vaccines with both B16-F10 tumor lysates and either 1, 10, 50, or 100 mg doses of CpG-ODN danger signaling allowed 10 to 30% of the vaccinated mice to survive, tumor-free, after an otherwise lethal cell challenge, whereas 100% of unvaccinated mice were killed by day 23 due to tumor burden. When GM-CSF-mediated DC recruitment was combined with lysate and CpG-ODN delivery, the mice showed significant protection from tumor-induced lethality. CpG-ODN doses of 10, 50, and 100 μg resulted in 50%, 60%, and 90% survival rates, respectively.

The ability of vaccine systems to create a heterogeneous DC population correlated with the marked increase in antitumor efficacy. In comparison to antigen matrices delivering GM-CSF alone, the antigen-loaded matrices delivering CpG and GM-CSF together resulted in a higher proportion of pDCs (~31% versus 7%) and CD8$^+$ cDCs (~14% versus 5.5%), which correlated with a significant enhancement in mouse survival (90% versus 20%), although total DC numbers in situ were statistically similar (3.0±0.6 versus 4.2±0.9 million DCs; two-tailed Student's t test, n=5). Survival rates were proportional to the number of pDCs and CD8$^+$ cDCs, but not CD11b$^+$ DCs, generated at the PLG vaccine site at day 10. Additionally, the endogenous production of IL-12 was correlated with animal survival, indicating the importance of cross-presentation and T$_H$1-promoting cytokines to vaccine efficacy.

Engineered PLG Matrices Incorporating CpG-ODN Attenuate Immune Regulation by FoxP3 Treg Number and Immunosuppressive Cytokines Although several vaccines designed to program DCs either ex vivo or in situ have achieved significant and long-term prophylactic protection in mouse models of cancer, eradication of invasive and well-established tumors has not been achieved without adoptive T cell transfer or systemic therapies (W. W. Overwijk, M. R. Theoret, S. E. Finkelstein, D. R. Surman, L. A. de Jong, F. A. Vyth-Dreese, T. A. Dellemijn, P. A. Antony, P. J. Spiess, D. C. Palmer, D. M. Heimann, C. A. Klebanoff, Z. Yu, L. N. Hwang, L. Feigenbaum, A. M. Kruisbeek, S. A. Rosenberg, N. P. Restifo, Tumor regression and autoimmunity after reversal of a functionally tolerant state of self-reactive CD8$^+$ T cells. *J. Exp. Med.* 198, 569-580 (2003); Y. Tamura, P. Peng, K. Liu, M. Daou, P. K. Srivastava, Immunotherapy of tumors with autologous tumor-derived heat shock protein preparations. *Science* 278, 117-120 (1997)). This limitation might reflect, at least in part, the ability of DC-based vaccines to stimulate Treg cells (S. A. Quezada, K. S. Peggs, M. A. Curran, J. P. Allison, CTLA4 blockade and GM-CSF combination immunotherapy alters the intratumor balance of effector and regulatory T cells. *J. Clin. Invest.* 116, 1935-1945 (2006); M. Jinushi, Y. Nakazaki, M. Dougan, D. R. Carrasco, M. Mihm, G. Dranoff, MFG-E8-mediated uptake of apoptotic cells by APCs links the pro- and antiinflammatory activities of GM-CSF. *J. Clin. Invest.* 117, 1902-1 913 (2007)) that attenuate the cytotoxic activity of adaptive immune responses. Thus, the impact of the engineered matrices on the induction of immunosuppressive pathways was examined. Monitoring CD4$^+$ T cell responses to antigen-presenting matrices with GM-CSF and CpG revealed peak activity at days 5 and 7, which decreased to negligible concentrations by day 12 after implantation. By contrast, matrices containing GM-CSF and tumor lysate led to a significant enhancement of CD4 T cell infiltration at day 12, and these cells likely contribute to regulation of CTL responses. Incorporation of GM-CSF and tumor lysate into the vaccine matrix led to a factor of 10 increase in TGFβ concentrations and a significant increase in IL-10 at the vaccine site; these are cytokines commonly associated with Treg activity and immunosuppression. Further, as observed previously in GM-CSF-based vaccines, GM-CSF cosignaling with tumor antigens resulted in a significant CD3$^+$ FoxP3$^+$ response at the vaccine site when compared to all other matrix formulations, resulting in an almost even ratio of CD8$^+$ effectors and FoxP3 Treg cells. CpG-ODN presentation in concert with both tumor lysate and GM-CSF counteracted these immunosuppressive mechanisms, as TGFβ and IL-10 concentrations and Treg activity were not enhanced over the control matrices, and CD8 CTLs outnumbered FoxP3 T cells by a factor of ~25 at day 12 after implantation. These findings indicate that the vaccine system promotes and extends CTL responses through naïve T cell differentiation induced by pDCs and CD8+ DCs, the corresponding production of type 1 IFNs and IL-12, and inhibition of negative feedback mechanisms.

EXAMPLES

Example 1: PLG Devices Loaded with GM-CSF

Figure 11A:
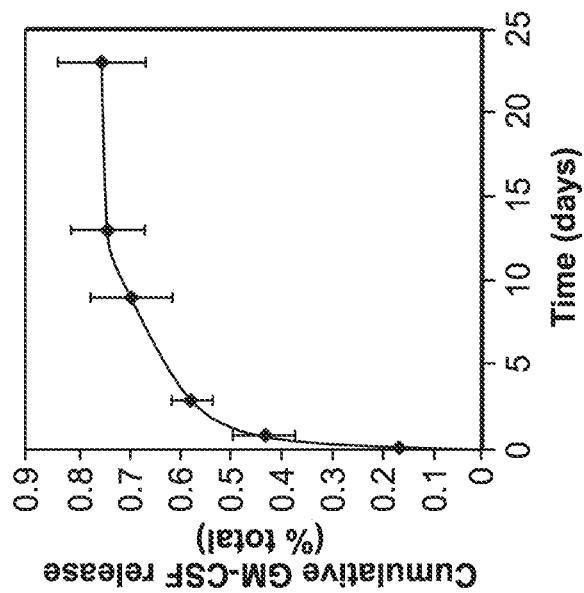
FIG. 11A is a line graph showing cumulative release of GM-CSF from PLG matrices over a period of 23 days.

PLG matrices loaded with 3 μg of GM-CSF were implanted into the subcutaneous pockets of C57BL/6J mice. The macroporous PLG matrix presents GM-CSF, danger signals, and cancer antigens in a defined spatiotemporal manner in vivo, and serves as a residence for recruited DCs as they are programmed. These matrices released approximately 60% of their bioactive GM-CSF load within the first 5 days, followed by slow and sustained release of bioactive GM-CSF over the next 10 days (FIG. 11A) to effectively recruit resident DCs.

The matrices were made as follows. A 85:15, 120 kD copolymer of D,L-lactide and glycolide (PLG) (Alkermes, Cambridge, Mass.) was utilized in a gas-foaming process to form macroporous PLG matrices (Harris, L. D., Kim, B. S., and Mooney, D. J. Open pore biodegradable matrices formed with gas foaming. J. Biomed. Mater. Res. 42, 396-402 (1998)). GM-CSF was encapsulated (54% efficiency) into PLG scaffolds using a high pressure $CO_2$ foaming process. PLG microspheres encapsulating GM-CSF were made using standard double emulsion (Cohen S., Yoshioka T., Lucarelli, M., Hwang L. H., and Langer R Controlled delivery systems for proteins based on poly(lactic/glycolic acid) microspheres. Pharm. Res. 8, 713-720 (1991)). To incorporate tumor lysates, biopsies of B16-F10 tumors that had grown subcutaneously in the backs of C57BL/6J mice (Jackson Laboratory, Bar Harbor Me.), were digested in collagenase (250 U/ml) (Worthington, Lakewood, N.J.), and subjected to 4 cycles of rapid freeze in liquid nitrogen and thaw (37° C.) and then centrifuged at 400 rpm for 10 min. The supernatant containing tumor lysates was collected and lyophilized with the PLG microspheres and the resulting mixture was used to make PLG scaffold-based cancer vaccines. To incorporate CpG-ODNs into PLG scaffolds, CpG-ODN 1826, 5'-tcc atg acg ttc ctg acg tt-3', (SEQ ID NO: 10; Invivogen, San Diego, Calif.) was first condensed with poly(ethylenimine) (PEI, Mw~25,000 g mol-1, Sigma Aldrich) molecules by dropping ODN-1826 solutions into PEI solution, while vortexing the mixture. The charge ratio between PEI and CpG-ODN (NH3+:PO4-) was kept constant at 7 during condensation. PEI-CpG-ODN condensate solutions were then vortexed with 60 μl of 50% (wt/vol) sucrose solution, lyophilized and mixed with dry sucrose to a final weight of 150 mg. The sucrose containing condensates was then mixed with blank, GM-CSF and/or tumor lysate loaded PLG microspheres to make PLG cancer vaccines.

Figure 11B:
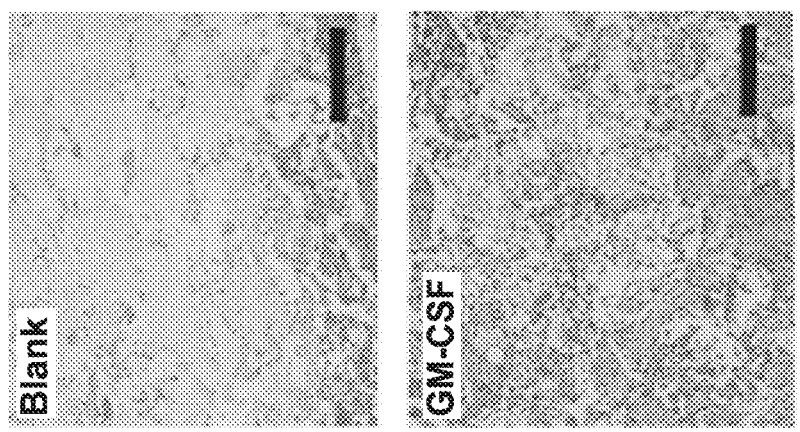
FIG. 11B is a photograph showing H&E staining of sectioned PLG scaffolds explanted from subcutaneous pockets in the backs of C57BL/6J mice after 14 days: Blank scaffolds, and GM-CSF (3000 ng) loaded scaffolds.
Figure 11C:
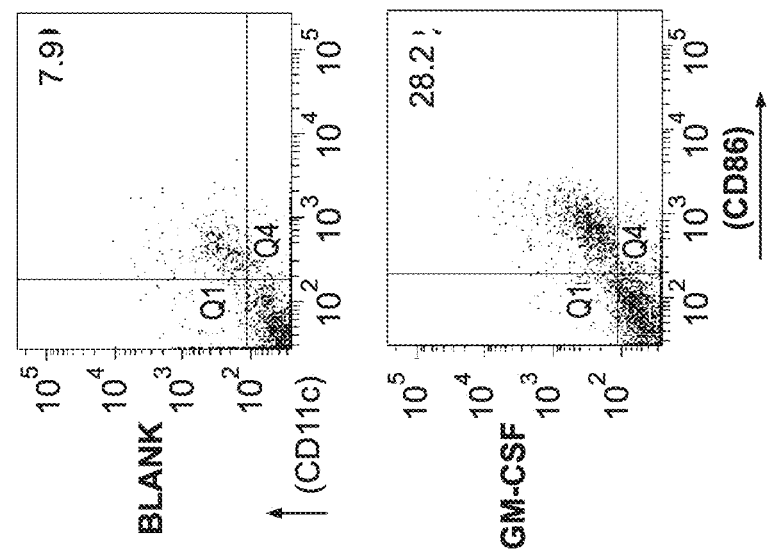
FIG. 11C is a series of FACS plots of cells isolated from explanted scaffolds and stained for the DC markers, CD11c and CD86. Cells were isolated from blank and GM-CSF (3000 ng) loaded scaffolds implanted for 28 days. Numbers in FACS plots indicate the percentage of the cell population positive for both markers.
Figure 11F:
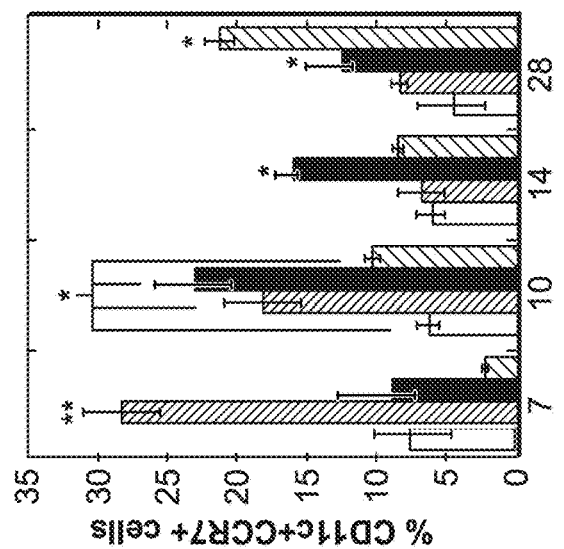
FIG. 11F is a bar graph showing the percentage of CD11c(+)CCR7(+) host DCs isolated from scaffolds loaded with 0 (□), 400 (■), 3000 ng (■), and 7000 ng of GM-CSF (☒) as a function of time after implantation into the backs of C57BL/6J mice. Scale bar in B—500 µm. Values in A, D, E, and F represent mean and standard deviation (n=4 or 5). * P<0.05 **P<0.01.

Following administration to the animals, histological analysis was carried out at day 14. The analysis revealed that the total cellular infiltration into scaffolds was significantly enhanced compared to control (no incorporated GM-CSF) (FIG. 11B). Analysis for DCs specifically (cells positive for cell surface antigens CD11c and CD86) showed that GM-CSF increased not just the total resident cell number, but also the percentage of cells that were DCs (FIG. 11C). The number of DCs residing in the material as a result of GM-CSF delivery was approximately the same or better than the number of DCs that are commonly programmed and administered by ex vivo protocols (~$10^6$ cells), and enhanced DC numbers were sustained in the material over time. The effects of GM-CSF on in vivo DC recruitment were time and dose-dependent (FIG. 11D).

Figure 11E:
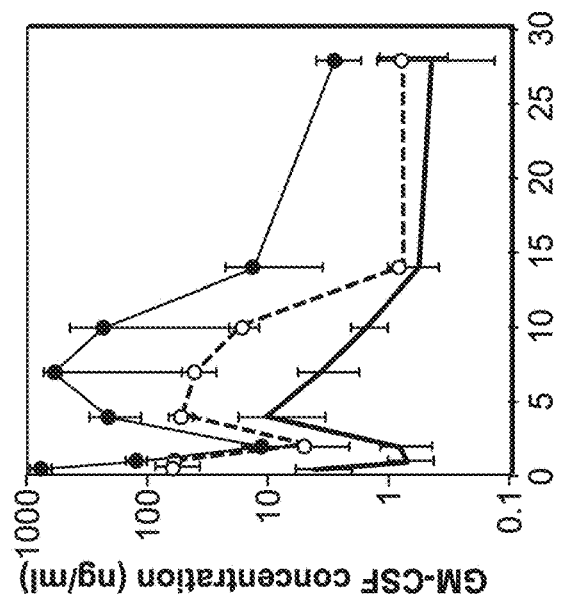
FIG. 11E is a line graph showing the in vivo concentration profiles of GM-CSF at the implant site of PLG scaffolds incorporating 0 (-), 3000 (-○-), and 7000 ng (-●-) of GM-CSF as a function of time post implantation.
Figure 11D:
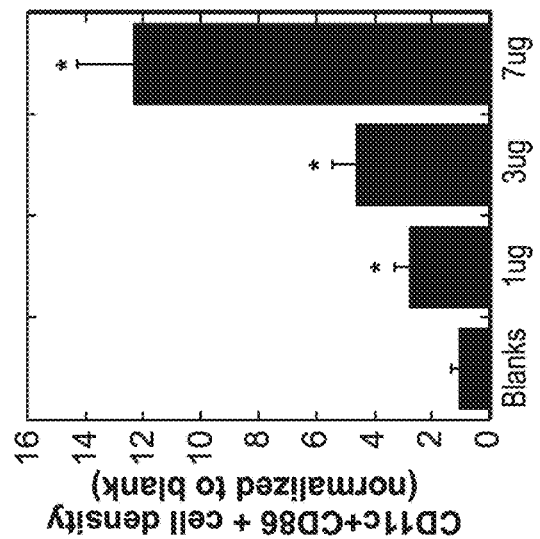
FIG. 11D is a bar graph showing the fractional increase in CD11c(+)CD86(+) DCs isolated from PLG scaffolds at day 14 after implantation in response to doses of 1000, 3000 and 7000 ng of GM-CSF, as normalized to the blank control (Blanks).

The dose of GM-CSF delivered from the PLG scaffolds was altered to provide distinct in vivo concentration profiles in the surrounding tissue, and regulate DC maturation and dispersion of resident DCs (FIG. 11E). Implantation of scaffolds with no GM-CSF led to moderate local levels immediately after implantation that subsequently fell to low levels by day 1-2, and then peaked again at day 5, likely due to the inflammatory response to the surgery and implanted PLG. Delivery of GM-CSF from the PLG scaffolds led to a similar GM-CSF concentration profile over time, but at much higher local concentrations. By approximately doubling the initial dose of GM-CSF, the system attained an order of magnitude difference in the peak levels of GM-CSF in vivo, likely due to endogenous GM-CSF production by resident DCs and leukocytes. The secondary peak for GM-CSF was found at day 5 for the 3000 ng dose, and at day 7 for the 7000 ng dose (FIG. 11E). Regardless of whether 3000 or 7000 ng doses of GM-CSF were utilized, the activation state of DCs peaked when GM-CSF levels began to subside (at days 10 and 28, respectively) and enter into the optimal concentration range for DC programming.

The ability of the pulse of GM-CSF to recruit and subsequently release a batch of activated DCs to home to the lymph nodes was then tested. Fluorescein isocyanate (FITC) was incorporated into and painted onto PLG scaffolds, as DCs recruited to the scaffold ingest this label. The label can be later used to identify these cells following their trafficking to the inguinal lymph nodes. At day 2, the 3000 ng dose of GM-CSF led to an inhibition of lymph node homing, likely due to the high initial levels of GM-CSF that entrap DCs at the scaffold site (FIG. 11F). However, as GM-CSF levels subsided, a batch of the recruited, FITC-positive DCs were released from the matrices, resulting in a superior and a sustained DC presence in the lymph nodes.

As temporally controlling the local GM-CSF concentration in turn controls recruitment, and dispersement of a batch of DCs, the utility of these cells as a cancer vaccine was evaluated by immobilizing melanoma tumor lysates into the matrices to load resident DCs with tumor antigens. These PLG cancer vaccines were implanted into C57BL/6J mice, and 14 days later these mice were injected with highly aggressive and metastatic B16-F10 melanoma cells. All mice implanted solely with blank PLG scaffolds had appreciable tumors within 18 days and had to be euthanized by day 23, due to the aggressiveness of these cells. Delivery of antigen alone from the PLG scaffolds slightly improved the fate of the mice, as some mice in this group survived until day 40. Surprisingly, co-delivery of GM-CSF with antigen dramatically decreased tumor formation, and the optimal GM-CSF dose delayed tumor formation by approximately 40 days in 50% of the animals, and cured 23% of animals. Moreover, localized tumor antigen presentation in combination with optimal GM-CSF exposure (400 ng) increased the average time before tumor formation by 3-fold as compared to antigen alone, and by nearly 2-fold over non-optimal GM-CSF exposure.

Analysis of T-cell infiltration into tumor tissue by immunohistochemistry was next performed to determine if programmed DCs were capable of inducing T-cell activation and homing to tumors. Vaccination with antigen alone resulted in CD4(+) T-cell infiltrates. Notably, recruiting and programming a batch of DCs in situ with appropriate GM-CSF presentation resulted in a 2-fold increase in CD8 (+) cytotoxic T-cell numbers over blank controls. The vaccine's efficacy was attenuated in CD8 and CD4 T-cell knock-out mice, attesting to the specific role of CD4 and CD8 T-cells in the immune protection.

A continuous process of in situ DC programming is achieved by presenting additional cues that released the DCs from GM-CSF inhibition once they reside in the matrices. In particular, the presentation of synthetic CpG-ODN with exogenous GM-CSF provides a mimic of bacterial infections, in which cells recruited by inflammatory cytokines are stimulated by local toll-like receptor activating "danger signals", such as CpG-ODN present in bacteria. CpG-ODN was immobilized to the PLG matrices by first condensing nucleotides with polyethylenimine (PEI) to form cationic nanoparticles. Following foaming of a combination of CpG-ODN and PLG particles, the CpG-ODN was largely retained in the matrices (>80% over 25 days) due to electrostatic interactions with the anionic PLG material. The CpG-ODN immobilization allows for host DCs, recruited by GM-CSF, to uptake these nucleotides locally as they reside in the matrices. Surprisingly, this approach resulted in approximately 2.5 and 4.5 fold increases in the numbers of activated DCs (positive for MHCII and CCR7) in the scaffolds, respectively, over GM-CSF or CpG-ODN delivery alone. CpG-ODN presentation enhanced DC activation in the presence of inhibitory GM-CSF levels (>40 ng/ml) in situ, indicating a more continuous process of DC recruitment and activation. This infection-mimicking system reliably generated activated DCs'. The magnitude of the immune response with this infection-mimic was confirmed grossly, as the lymph nodes of these animals were markedly enlarged. Most importantly, a 6-fold increase in the number of DCs that were first recruited to the matrices and subsequently dispersed to the lymph nodes was achieved with this system.

The ability of continuous DC recruitment, and programming to generate an immune response was next tested in the melanoma model. The vaccine provided significant protection, and the level of protection correlated with the CpG dose. Animal survival increased from 23% to 50% and finally 90% at CpG doses of 0 µg, 10 µg and 100 µg, respectively. This material infection-mimic induced equivalent or better immune protection than that obtained with existing cell-based therapy. Materials presenting CpG-ODN with lysates alone had only a 20% survival, indicating the benefit of recruiting DCs with GM-CSF. The benefit of providing a residence for recruited DCs while they are programmed was demonstrated by the failure of vaccine formulations consisting of bolus injections of tumor lysates, CpG-ODN, with and without 3000 ng of GM-CSF. Moreover, injecting GM-CSF loaded PLG microspheres to provide sustained GM-CSF delivery without providing a residence for recruited cells, with bolus CpG-ODN and tumor lysate delivery resulted in little immune protection and animals did not survive over 35 days.

To further examine the mechanism of immune protection with this material system, the subsets of DCs and the endogenous production of cytokines by these cells in materials presenting GM-CSF and CpG-ODN alone or together were analyzed, along with the specificity of the immune response. The delivery of GM-CSF alone enhanced the recruitment of CD11c(+)CD11b(+) myeloid DCs, whereas CpG-ODN delivery alone had little effect on the overall numbers of this subset. CpG-ODN delivery did, though, increase the number of plasmacytoid DCs at the site, which have been described to predominantly secrete Thelper(Th)-1 cytokines, especially type1 interferons and interleukin(IL)-12 that can promote CD8(+), cytotoxic T cell immunity in response to CpG-ODN presentation with antigen. Accordingly, CpG signaling not only upregulated the expression of activation markers on resident DCs, but also induced IFN-γ and IL-12 production at the vaccine site, as expected from the increased presence of plasmacytoid DCs. Moreover, analysis of T cell infiltrates into tumors that formed in the subset of animals that were not completely protected (infection mimics; 10 µg CpG-ODN dose) revealed that, even in these animals, DC programming with CpG-ODN resulted in an almost 3-fold increase in CD8(+) T-cell infiltration over controls. Further, tyrosinase-related protein (TRP)-2 is a main antigenic target of the immune response elicited by melanoma vaccines in both mice (including B16 whole cell vaccines) and humans, and staining cells isolated from spleens with MHC class I/TRP2 peptide pentamers revealed a dramatic expansion of TRP2-specific CD8 T cells in vaccinated mice. These antigen-specific T cells are involved in the killing of tumor cells, and facilitated immune protection after vaccination. Additionally, 33% of surviving mice developed patches of skin and hair depigmentation starting at the sites of tumor inoculation (back of neck). Depigmentation, which likely involves T cell responses to melanocyte antigens, has been correlated to improved clinical responses in human melanoma patients, and, in these studies, was only observed in mice treated with infection mimics.

These results indicate that mimicking aspects of infection with polymeric material systems dramatically impacts tumor progression by effectively recruiting, activating and homing DCs to lymph nodes. The first approach utilized a pulse of GM-CSF alone to recruit DCs to the tumor-antigen presenting material. The DCs subsequently resided within the material and were trapped until GM-CSF levels fell and cells could become activated and disperse. The specific concentration and duration of GM-CSF are critical to its effects. A continuous process was subsequently developed to shuttle DCs through an infectious-like microenvironment via recruitment with GM-CSF, followed by activation of resident DCs via CpG-ODN presentation, and subsequent release. The presentation of PEI condensed CpG-ODN from the material dramatically increased not only the numbers of activated, host DCs residing in the material, but also the percentage and total numbers of programmed DCs that emigrated to the lymph nodes. Further, CpG-ODN signaling selected for specific DC subsets and DC functions associated with protective immune responses.

The system's quantitative control over DC trafficking and activation translated to a regulation over the efficacy of the cancer vaccine. As the numbers of DCs that were programmed and dispersed to the lymph nodes increased, the survival increased from 0 to 25 and finally 90%. T-cells mediated immune protection, as a clear relation between the numbers of T cells in the tumors that did form and vaccine efficacy was found, and infection mimics induced the generation of melanoma-antigen specific T cells. The matrix structure was necessary to produce long-lasting immunity, as vaccines delivered in bolus form and sustained release without provision of a cell residence failed to produce significant protective immunity. Although reports concluded that either cell transplantation or multiple systemic injections are necessary to promote protective immunity in clinically relevant tumor models, the data indicate that devices comprising functional polymeric residence materials provide significant and specific immune protection that is equal to or superior to previous systems, even with single application at vastly reduced total drug doses (e.g., 3 µg in the scaffold system vs. 100's µg total dose in repeated, systemic injections).

These data have significant clinical relevance, as the material system programmed DCs in situ, and not only bypassed the complication and cost of ex vivo cell manipulation and transplantation, but also provided tight control over the number of DCs recruited, activated and dispersed to the lymph nodes. Patients are treated with and the devices provide an alternative to current cancer vaccines, or are used in concert with those and other approaches.

The system is applicable to other situations in which one desires to promote a destructive immune response (e.g., eradicate infectious diseases) or to promote tolerance (e.g., subvert autoimmune disease). The use of polymers as a temporary residence for in situ cell programming is a powerful alternative to current cell therapies that depend on ex vivo cell manipulation (e.g., stem cell therapies).

Example 2: Condensation of Synthetic CpG-ODN Molecules Increases Cellular Uptake Synthetic CpG-ODN molecules were condensed with PEI, which resulted in positively charged, small PEI-CpG-ODN condensates that facilitates cellular internalization via promoting association with the cell membrane and enhancing transmembrane transport (FIGS. 2A-C). ODN Condensation at charge ratios of 7 and 15, between the amine groups of PEI and the phosphate groups of ODNs, resulted in optimal particle sizes and positive charge (FIGS. 2B and C), but a charge ratio of 7 was utilized in experiments due to PEI toxicity at high doses.

Figure 3A:
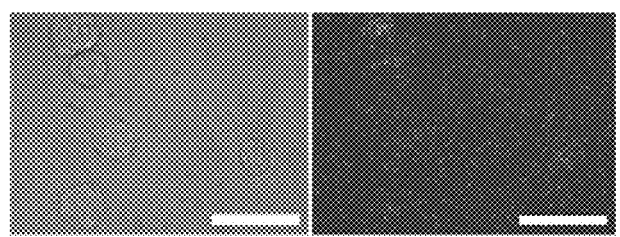
FIGS. 3A-D.
Figure 3B:
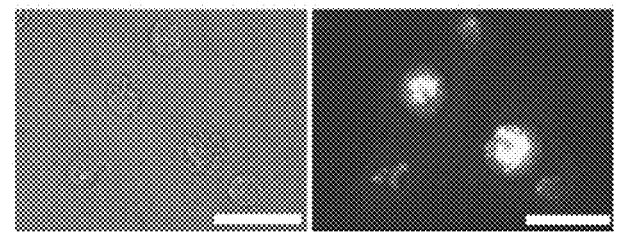
Figure 3C:
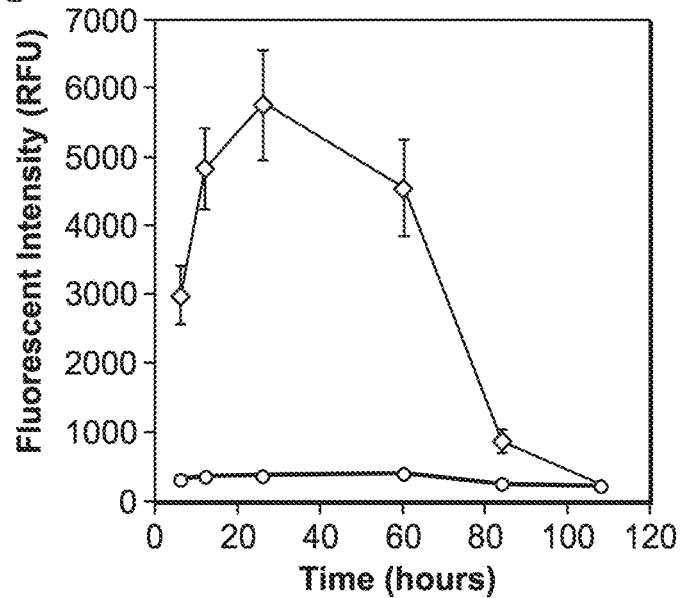
Figure 3D:
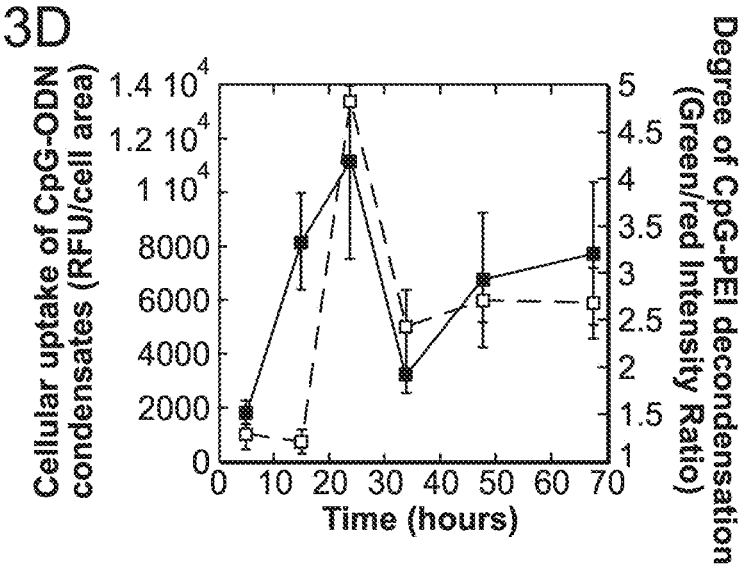

PEI condensation of CpG-ODN dramatically enhanced nucleotide uptake into DCs in vitro (FIGS. 3A-C). Quantification of CpG-ODN uptake into DCs revealed orders of magnitude differences (up to ~100-fold) between ODN condensates and naked ODN, which were maintained for extended time periods (>80 hrs) in vitro (FIG. 3C). The complexes subsequently decondense (FIG. 3D) allowing for CpG-ODN localization to its intercellular receptor, TLR-9, which has been previously demonstrated to be present in endosomes.

Example 3: CpG-ODN Induced DC Activation and DC Mobilization

Figure 4A:
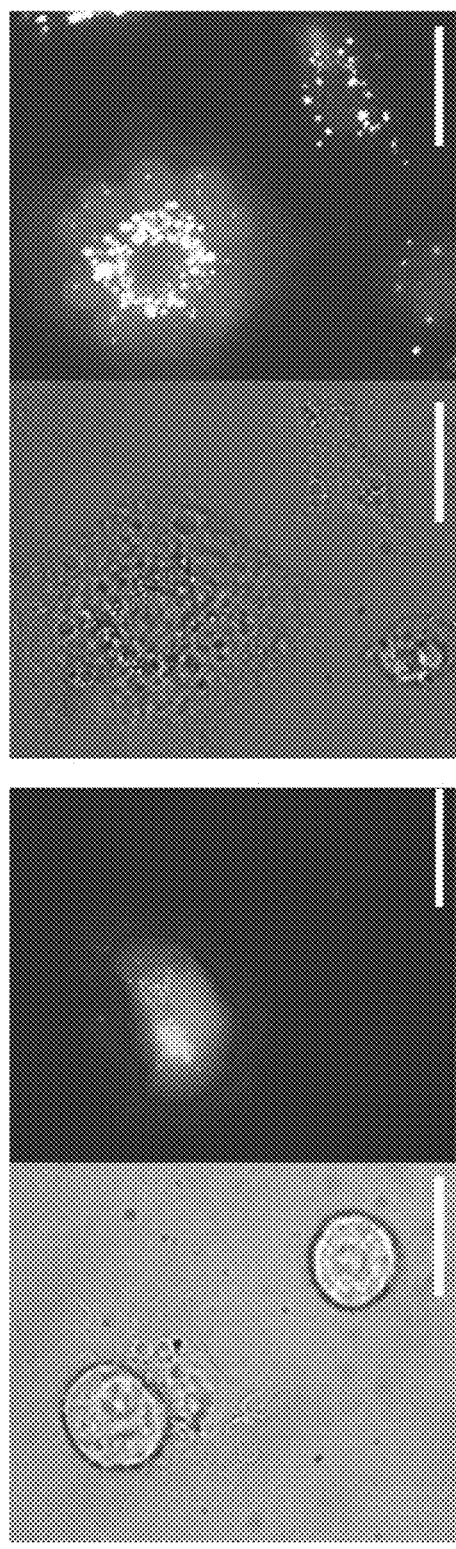
FIGS. 4A-D. (A) Imaging DC activation.
Figure 4B:
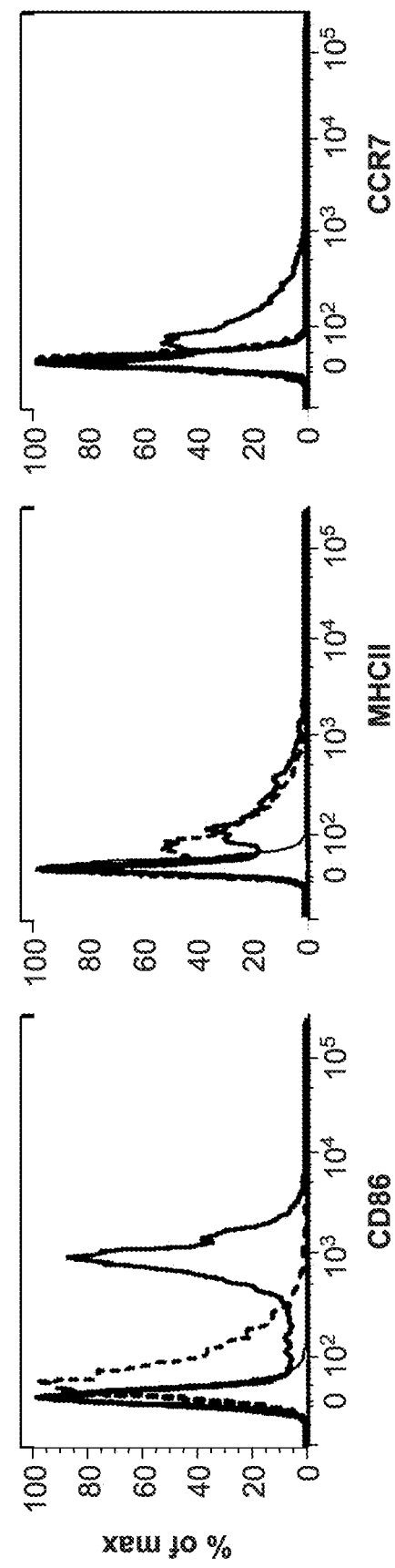
Figures 4C, 4D:
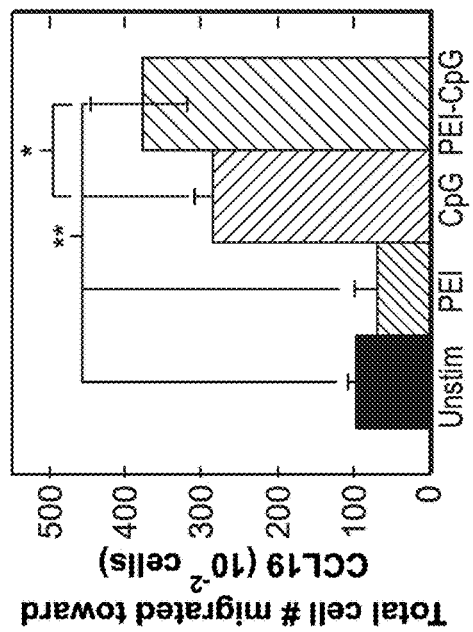

Because effective CpG stimulation of DCs requires intercellular localization, the effects of PEI-condensation were evaluated on DC activation. DCs stimulated with PEI-CpG-ODN in vitro exhibited enhanced levels of CD86, MHCII and CCR7 expression, in comparison to those stimulated with naked CpG-ODN, which correlated strongly with DC uptake of condensates (FIGS. 4A and B). DCs exhibited an activated morphology, upon cellular uptake of PEI-CpG-ODN including the development of fine needle-like dendrites and large membrane expansion, which allows mature DCs to "wrap-up" T-cells promoting strong cell-cell interactions. The activation states of PEI-CpG-ODN stimulated DCs mirrored or surpassed that of positive controls stimulated with TNF-α and LPS (FIG. 3C) and PEI-CpG-ODN condensates promoted a 3-fold increase in DC migration toward CCL19 in vitro, over unstimulated DCs (FIG. 4D).

Figure 5A:
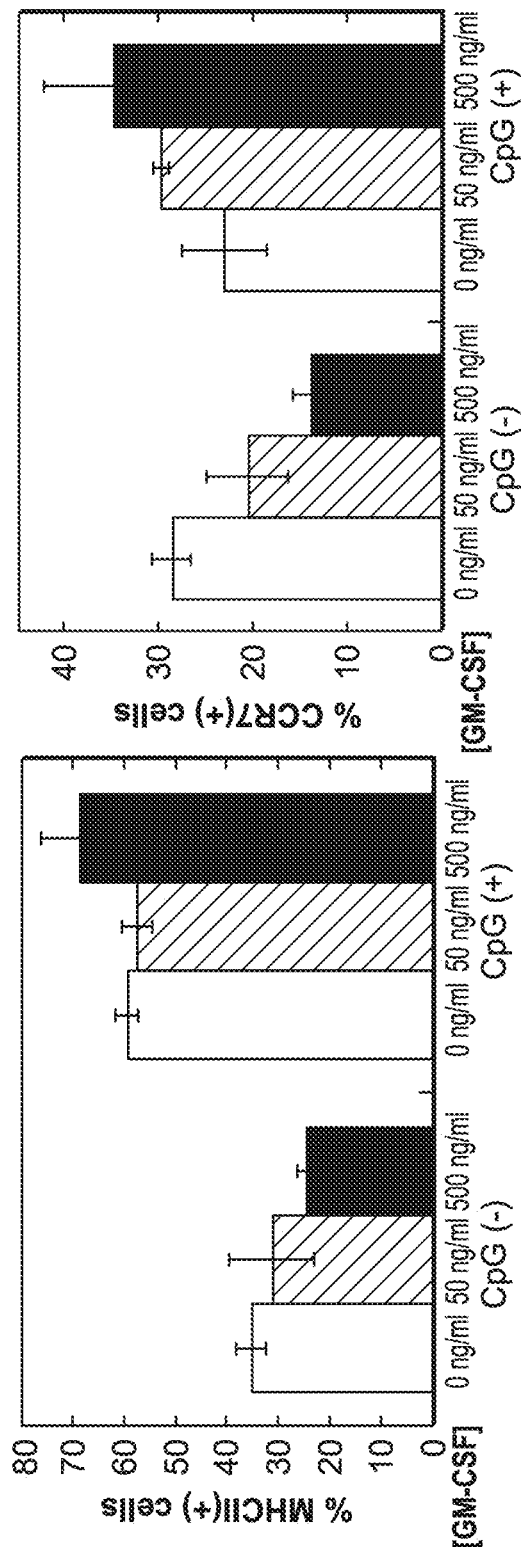
FIGS. 5A-B.
Figure 5B:
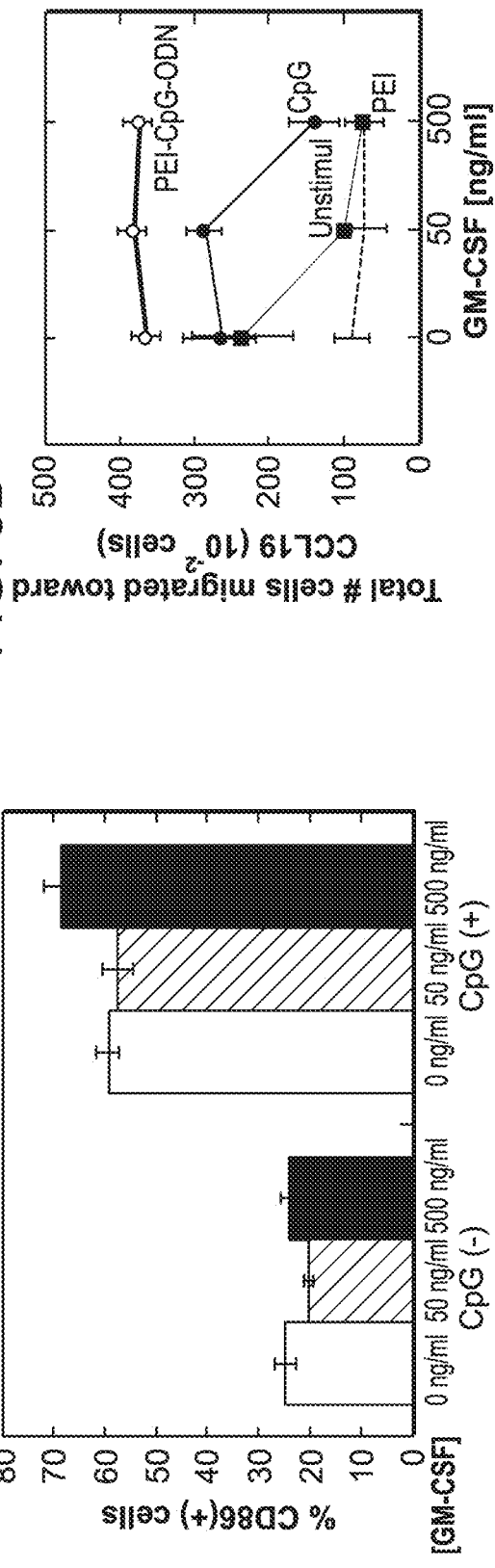

PEI-CpG-ODN condensates also released DCs from GM-CSF inhibition, as significant DC activation was noted in cells exposed to both condensed oligonucleotides and high levels of GM-CSF (FIG. 5A). Additionally, PEI-CpG-ODN stimulation also promoted DC migration away from high GM-CSF sources (500 ng/ml) toward CCL19 (FIG. 5B).

A PLG system was developed that effectively immobilized and presented PEI-CpG-ODN condensates (FIG. 6A) to resident DCs to stimulate DC activation and mobilization. Local PEI-CpG-ODN presentation promoted DC mobilization in vitro (FIGS. 6A-C). Interestingly, there is an optimal dose range, 5-50 μg, of PEI-CpG-ODN that enhanced DC emigration from PLG matrices toward CCL19, but high doses (500 μg) had no effect on DC migration (FIGS. 6B and C). A 25 μg of PEI-CpG-ODN also counteracted the suppressive effects that high GM-CSF levels had on DC migration, in this model (FIG. 6C). These results indicate that appropriate CpG-ODN presentation provides an avenue to continuously program and disperse host DCs that are recruited and otherwise trapped by high levels of GM-CSF in situ.

Example 4: Infection-Mimics Continuously Program and Disperse DCs In Vivo

An infection-mimicking system to continuously recruit and program DCs was created by simultaneous release of GM-CSF to attract host DCs to PLG matrices, while the PEI-CpG-ODN condensates were largely retained in the matrix (>80% over 25 days) (FIGS. 6A-C), likely via electrostatic interactions as has been shown for plasmid DNA, allowing for recruited DCs to uptake the complexes locally. Strikingly, when optimized, this approach resulted in approximately 2.5 and 4.5 fold increases in the numbers of MHCII and CCR7 expressing DCs resident in the matrices in situ, respectively (over GM-CSF or CpG-ODN delivery alone) (FIGS. 7A and B). Interestingly, high doses of PEI-CpG-ODN (>50 μg) resulted in relatively low MHCII expression and enhanced CCR7 expression, indicating differential regulation of DC function in comparison to low doses (FIG. 7A). Optimum CpG-ODN signaling (~10-25 μg) enhanced DC activation in the presence of inhibitory GM-CSF levels (>40 ng/ml) in situ, and this infection-mimicking system generated the numbers of activated DCs (>$10^6$) (FIGS. 7A and B) commonly administered in ex vivo protocols.

Most importantly, a 6-fold increase in the number of DCs that were first recruited to the matrices and subsequently dispersed to the lymph nodes was achieved with this system (FIG. 8 A). The magnitude of the immune response with infection-mimics could even be appreciated grossly, as the lymph nodes of these animals were markedly enlarged (FIGS. 8B and C). As characterized by infectious responses, these swollen lymph nodes contained greater numbers of immune cells including DCs (FIGS. 8C and D).

Figure 9:
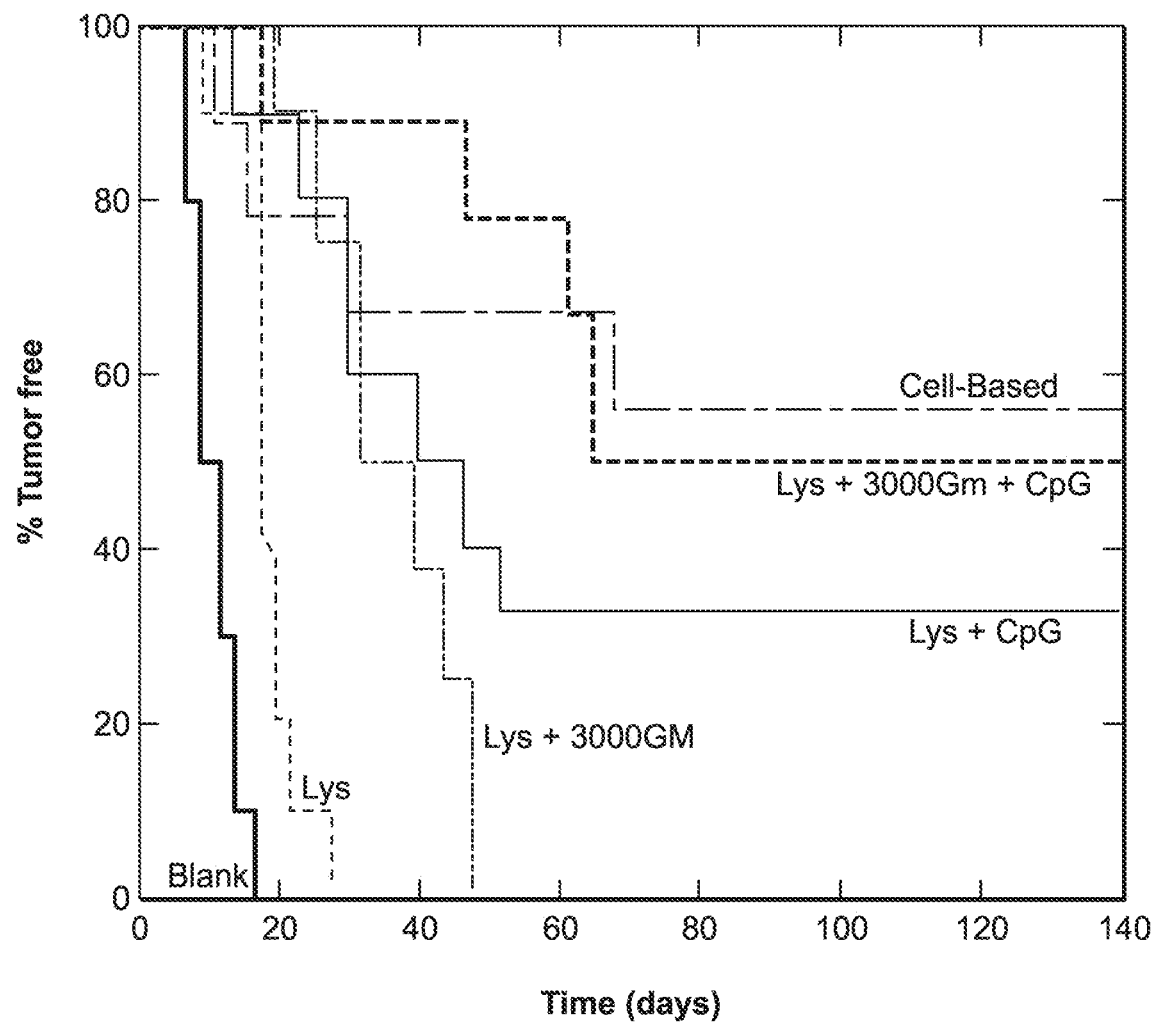
FIG. 9 is a bar graph showing infection-mimicking microenvironment confers potent anti-tumor immunity. The time to tumor occurrence after PLG cancer vaccines were implanted into mice. A comparison between blank PLG scaffolds (Blank), scaffolds loaded with antigen alone (Lys), antigen+3000 ng GM-CSF (Lys+3000 ng GMCSF), antigen+PEI-CpG-ODN condensate (Lys+CpG) and the combination of antigen, 3000 ng GM-CSF and PEI-CpG-ODN (Lys+3000 ng+ PEI-CpG-ODN). Animals were also immunized using a cell-based vaccine (cell-based) using irradiated B16-F10 melanoma cells that had been genetically modified to produce GM-CSF, for comparison. At Day 14 after vaccination, C57BL/6J mice were challenged with $10^5$ B16-F10 melanoma tumor cells and monitored for the onset of tumor occurrence (n=9 or 10).

Example 5: Infection-Mimicking Microenvironment Confers Potent Anti-Tumor Immunity The ability of continuous DC recruitment, and programming to generate an immune response was next tested in the melanoma model. This vaccine provided significant protection, as 50% of the animals did not form tumors over an 80 day time frame (FIG. 9), and this result was remarkably similar to that obtained with a widely investigated cell-based therapy (FIG. 9). Animals receiving lys+CpG were 37.5% tumor free 140 days after treatment and achieved protective immunity.

Figure 10A:
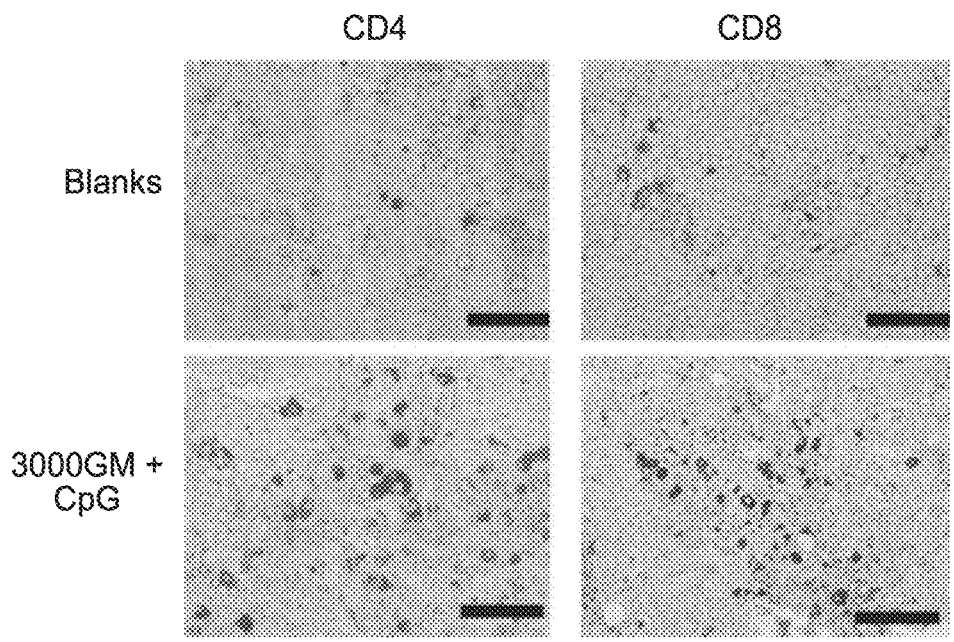
FIGS. 10A-B. Vaccination efficacy of Infection mimics dependent on T cell responses.
Figure 10B:
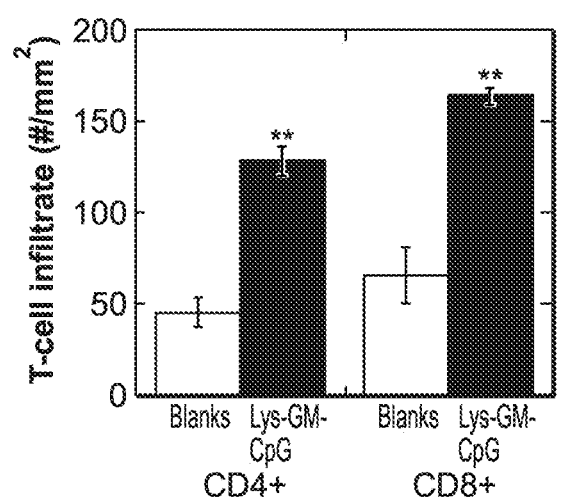

Furthermore, analysis of T-cell infiltrates into tissue of tumors that formed in the subset of animals that were not completely protected revealed that, even in these animals, DC programming with CpG-ODN resulted in an almost 3-fold increase in CD8(+) T-cell infiltration over controls (FIGS. 10A-B). Thus, all animals receiving the Lys-GM-CpG treatment demonstrated a therapeutic benefit.

Example 6: Tumor Protection is Regulated by CpG-ODN Presentation and Plasmacytoid DC (pDC) Enrichment Hematopoetic precursor cells of both the myeloid and lymphoid lineage have the capacity to differentiate into two main categories of DCs, plasmacytoid DCs (pDCs) and conventional DCs (cDCs), each of which are equipped with specific defense mechanisms capable of propagating specific responses to invading pathogens. This plasticity likely allows for the recruitment and generation of the DC subset (s) most proficient at eliciting the desired immune response. cDCs include $CD11c^+CD11b^+$ and $CD11c^+CD8\alpha^+$ cells exhibiting classical DC morphology with the long, protruding dendrites that make them especially adept at antigen processing and antigen presentation to T cells. pDCs are round non-dendritic cell capable of producing large amounts of type-1 interferons in response to 'danger signals', such as unmethylated CpG dinucleotide sequences in bacterial or viral DNA.

pDC derived type 1 interferons (IFN) link innate and adaptive immunity to viral infection by triggering antigen cross presentation to CD8+ T cells and interleukin production (e.g. IL-12) by cDCs that facilitate the clonal expansion of cytotoxic T cells. Type 1 IFNs also act to directly induce naïve T cell differentiation to T helper 1 cells. In addition to producing potent IFNs, pDCs stimulated by inflammatory stimuli and microbial infection differentiate into a dendritic form capable of processing and presenting antigen to prime T cell responses. pDCs and cDCs cooperate to perform specialized functions that initiate distinct cellular and molecular events leading to protective immunity.

Many cell-based vaccines for cancer fail to incorporate the different components of the DC network. Cancer vaccines are frequently developed using easily accessible, patient-derived blood monocytes that are transformed into DCs ex vivo using cytokine mixtures and pulsed with tumor antigens to promote antigen presentation. These antigen-loaded DCs are then injected back into cancer patients with the goal of inducing anti-tumor immune responses mediated primarily by Th1 cells and CTLs. While initial trials utilizing ex vivo DC vaccines in advanced cancer patients have resulted in antigen-specific T-cell expansion and the production of protective cytokines, many vaccines have failed to show survival advantage over traditional treatments (e.g., chemotherapy) and have failed to gain FDA approval. These cell-based vaccines provide no control over the in vivo function of the transplanted DCs and only incorporates one DC type into the vaccine, which may not be the most potent. Therefore, the rate-limiting step is likely the inability to fully recapitulate ex vivo the development of immunocompetent DCs, in particular the processes of DC activation and specialization during the generation of immune responses. The devices and methods described herein overcome the shortcomings of such earlier approaches, and therefore, have several advantages over earlier systems.

The devices comprise an implantable, synthetic extra-cellular matrix (ECM) that controls the in situ recruitment and generation of a heterogeneous DC network to produce protective immune responses to tumors. GM-CSF was incorporated into polylactide-co-glycolide (an FDA approved biomaterial) matrices to recruit DC precursors and DCs, as the cytokine is released from the material into the surrounding tissue. These macroporous matrices present immobilized tumor antigens and CpG-rich oligonucleotides as danger signals, capable of programming DC development and maturation as cells reside within the material. The distribution of the DC subsets generated at the vaccine site is regulated by modifying cancer-antigen presentation by the material and the dosages of danger signals, which significantly affected the magnitude of the protective immune response to tumors when tested in an art recognized B16-F10 tumor model.

Matrices were made to release a pulse of GM-CSF to recruit DCs, and were loaded with 0, 3000, and 7000 ng of GM-CSF, and implanted into the subcutaneous pockets of C57BL/6J mice. A GM-CSF gradient formed in the surrounding tissue, which peaked at 12 hours post-implantation as the GM-CSF concentration reached 100 μg/ml and 30 μg/ml (>30 fold difference over no incorporated GM-CSF) at distances of 1-3 mm and 3-5 mm, respectively, from the implant site. Elevated GM-CSF levels were maintained for extended periods (approximately 10 days) while the factor was released from the PLG to the neighboring tissue. Histological analysis at day 14 post-implantation of PLG matrices loaded with 3000 ng of GM-CSF revealed enhanced cellular infiltration over blank controls, and FACS analysis for the CD11c(+) DC population showed that GM-CSF delivery recruited significantly more DCs (~8 fold increase) than blank controls. The total number of DCs recruited and their expression of the co-stimulatory molecule CD86 increased with GM-CSF delivery in a dose dependent manner.

PLG matrices were then modified to immobilize TLR-activating, PEI-condensed CpG-ODN molecules and present them as danger signals to DC populations recruited by GM-CSF. Provision of condensed CpG-ODN signaling with GM-CSF dramatically enhanced cellular infiltration into PLG matrices, as revealed by histological analysis at Day 10 post-implantation. Importantly, CpG-ODN presentation from PLG matrices regulated the local presence of specific DC subsets and the resulting production of protective cytokines. Stimulation of the DC infiltrate recruited by GM-CSF with CpG-ODN enriched the PLG matrix with CD11c(+) PDCA-1(+) plasmacytoid DCs (pDCs), a DC subset exhibiting enhanced type 1 IFN production that are associated with t-helper 1 (Th1) immunity.

CpG-ODN leads to preferential recruitment and expansion of pDCs to the tumor site. The dose of CpG-ODN is controlled to regulate the numbers of resident pDCs, which increased from 190,000, to 520,000, to 1,100,000 cells at doses of 0, 10 and 100 μg of CpG-ODN, respectively. GM-CSF delivery alone significantly enhanced the numbers of CD11c(+)CD11b(+) cDCs recruited to the matrices, but co-presentation of CpG-ODN had little effect on either mDC populations or Cd11c(+)CD8(+) DCs. High doses of CpG-ODN promoted the local production of IFN-α (~1010 μg/ml), IFN-γ (~600 μg/ml) and, to a lesser degree, IL-12 (150 μg/ml) at the implant site, which correlated with the increased pDC numbers at this condition. The recruitment of DCs by GM-CSF was required for CpG-ODN signaling to have a significant effect, in terms of expansion of pDC populations and production of Th1 cytokines. These results indicate that controlled GM-CSF and CpG-ODN danger signaling from synthetic extra-cellular matrices can effectively regulate resident pDC and CD11c(+)CD11b(+) cDC numbers along with the production of Th1 cytokines.

Studies were carried out to determine whether co-presenting cancer antigens with CpG-ODNs to matrix-resident DCs would promote further DC development, activation and antigen sensitization, leading to protective tumor immunity and cytotoxic T cell responses. Antigen-presenting matrices were fabricated by encapsulating B16-F10 melanoma tumor lysates into the PLG matrices. Controlled antigen presentation in combination with GM-CSF and CpG signaling enhanced the numbers of resident pDCs at Day 10 post-implantation by 2-fold over matrices without antigen, and by 10-fold over blank controls (FIG. 12A). No significant difference in pDC numbers was observed with antigen presentation in combination with GM-CSF or CpG signaling alone, indicating the benefit of both GM-CSF-mediated recruitment and CpG-ODN activation of matrix-resident DCs. The CD11c(+)CD11b(+) DC population at the vaccine site depended on GM-CSF delivery alone (FIG. 12B), as antigen or CpG signaling alone or in combination had no significant effect on the recruitment and expansion of these cDCs (FIG. 12B). Antigen and CpG-ODN presenting matrices led to the presence of 200,000 CD11c(+)CD8(+) cDCs, which increased to approximately 670,000 (9-fold increase over blank matrices) with GM-CSF-mediated recruitment (FIG. 12C). Analysis of the endogenous production of IFNs and IL-12 revealed that antigen stimulation in combination with GM-CSF promoted endogenous IFN-α and IFN-γ production that was similar to CpG-ODN induction (FIGS. 12D-E). Additionally, the in situ production of the T-cell growth factor, IL-12, at matrices presenting both antigen and CpG-ODN to cell populations recruited by GM-CSF was approximately 4-fold higher than blank matrices at least 2-fold higher all other matrix formulations (FIG. 12F). Remarkably, a significant percentage (10.3%) of the total cells at the site of antigen presenting matrices were CD8(+) (cDC subset and cytotoxic T-cells) (FIG. 12G), which was in correlation with both the number of CD11c(+)CD8(+) cDCs and the concentration of IL-12 (FIGS. 12C, F,G). These results indicate that immune responses sensitive to cancer antigen presentation were generated by manipulating both the number and function of specific DC subsets in situ, including CD8(+)DCs, which was accompanied by CD8+ T cell activity.

C57BL/6J mice were vaccinated using melanoma antigens (e.g., B16-F10 tumor lysates) presented from PLG-based vaccines that differentially regulated the generation and function of specific DC subsets in situ (varying GM-CSF and CPG-ODN combinations), and challenged with B16-F10 melanoma tumor cells at D14 post-vaccination. PLG vaccines presenting both B16-F10 tumor lysates and either 1, 10, 50 or 100 µg doses of CpG-ODN danger signaling led to approximately 10-30% of the vaccinated mice surviving, tumor-free (FIG. 13A), after an otherwise lethal dose while 100% of unvaccinated mice were euthanized by day 23 due to tumor burden. Surprisingly, GM-CSF mediated DC recruitment combined with antigen and CpG-ODN presentation generated significant tumor protection. CpG-ODN doses of 10, 50, and 100 µg resulted in 50, 60 and 90% survival rates (FIG. 13B). Survival rates correlated strongly with the number of pDCs generated at the PLG vaccine site at day 10, but did not correlate with the total CD11c(+)CD11b(+) DC numbers recruited. Additionally, high survival rates (60% and 90%) were attained with PLG systems that generated relatively high numbers of CD11c (+)CD8(+) DCs (~2×10$^5$ cells) (FIG. 13E) and increased IFN-α, IFN-γ, and IL-12 production in situ.

The ability of vaccine systems to recruit a heterogeneous DC network also had a profound effect on vaccine efficacy, as the DC population generated by CpG and GM-CSF loaded scaffolds compared to GM-CSF loaded scaffolds resulted in a higher proportion of pDCs (~38% vs. 7%) and CD8+ cDCs (~9.4% vs. 5.5%) (FIG. 13F), leading to a significant enhancement in mouse survival (90% vs. 20%), even though total DC numbers in situ, were statistically similar (3.05±0.55 vs. 2.67±0.64 million DCs). Moreover, tyrosinase-related protein (TRP)-2 is a main antigenic target of the immune response elicited by melanoma vaccines in both mice (including B16 whole cell vaccines) and humans, and staining splenocytes with MHC class I/TRP2 peptide pentamers revealed a significant expansion of TRP2-specific CD8 T cells in mice vaccinated with GM-CSF, antigen and 100 µg of CpG-ODN (0.55% splenocytes, 1.80×10$^5$±0.6× 10$^4$ cells) in comparison to matrices presenting lower CpG doses, either 0 or 50 µg (0.2% and 0.3% splenocytes). The development and expansion of these antigen-specific T cells were induced by the promotion of pDC activation and their corresponding production of type 1 IFNs. These cytotoxic T cells were in turn involved in the killing of tumor cells, which facilitated immune protection after vaccination. These results indicate that devices (PLG matrices) described herein precisely regulate the in situ recruitment and expansion of specialized DC subsets. This preferential recruitment and expansion of pDCs dramatically improves immune responses to cancer antigens, reduces tumor progression, and improves survival of cancer patients compared to previous vaccine approaches.

Figure 14A:
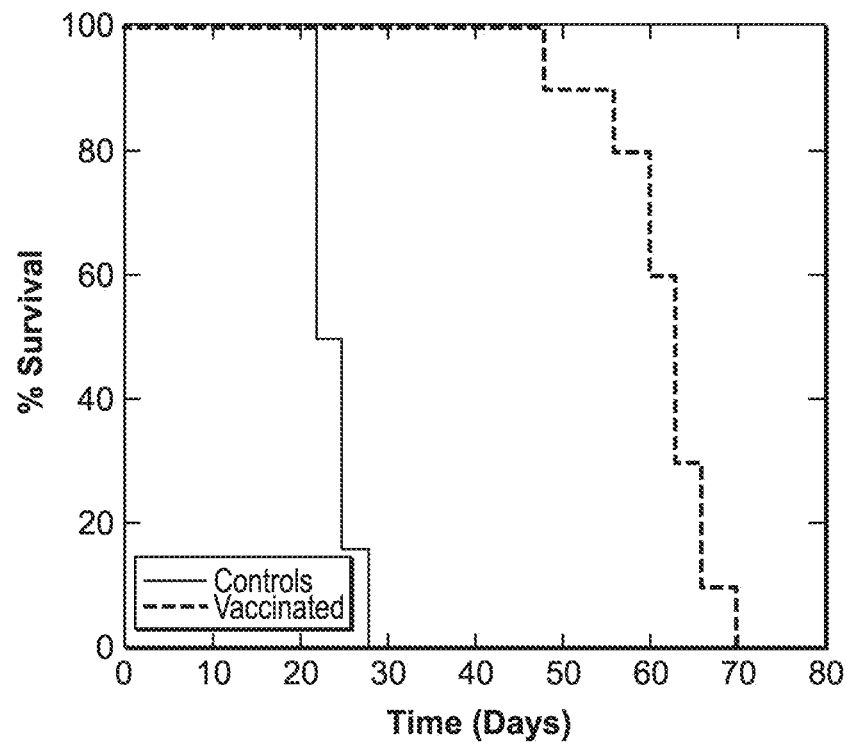
FIGS. 14A-B are line graphs showing PLG vaccine efficacy against established tumors.
Figure 14B:
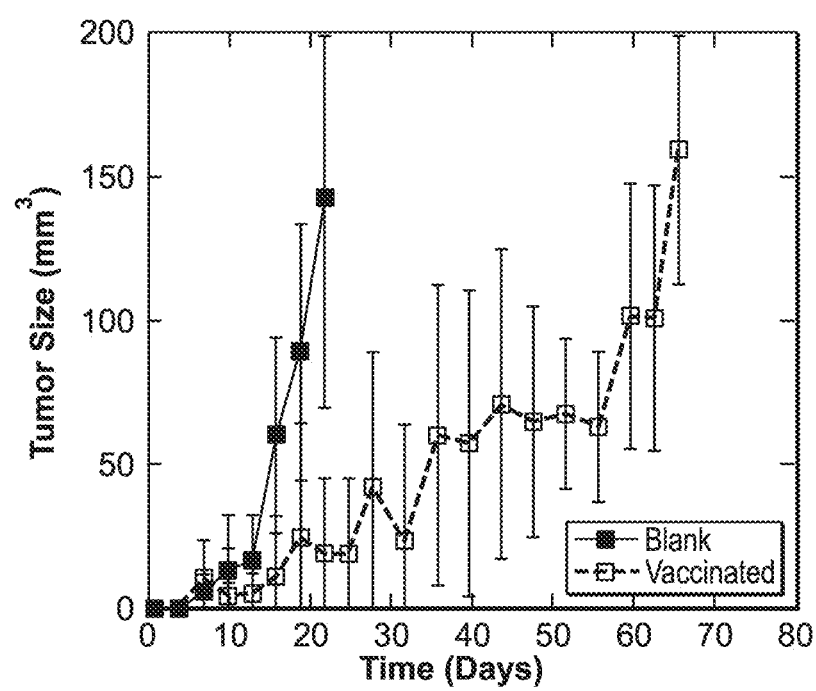

FIGS. 14A-B show survival of mice vaccinated with PLG vaccines versus controls in a therapeutic model. Mice were innoculated with 5×10$^5$ tumor cells and tumors were allowed to grow for 7 days in mice until palpable (1-3 mm$^3$). Mice were vaccinated (at Day 7) with PLG scaffolds containing 3 µg GM-CSF, tumor lysates and 100 µg CpG-ODN. Survival data was obtained using mice (n=10) with established tumors (7 days after tumor inoculation). PLG vaccines containing GM-CSF, lysates and CpG-ODN were using for the vaccination.

[02] The macroporous, synthetic ECMs described herein provided control over the presentation of inflammatory and infectious signaling agents creating microenvironments capable of generating distinct DC networks in situ. The total cell number and heterogeneity of these DC networks correlated with the magnitude of immune responses to cancer antigens in B16 melanoma models. GM-CSF was released quickly from PLG-based ECMs to recruit and house host DC precursors and DCs in its macroporous structure. CpG-ODNs were then immobilized within the GM-CSF-secreting matrices to direct pDC development in situ, and, indeed, the CpG signaling not only enhanced CD11c(+)PDCA-1(+) pDC numbers at the implant site, but also enriched the site with pDCs in a dose dependent manner. When tumor antigen was incorporated into PLG matrices, enhancement of activity and enrichment of CD11c+CD8+ cDCs at the vaccine site was observed. The provision of cancer antigens resulted in an enhancement of the total CD8+ cell population, indicating that Cd8+ DCs and Cd8+ T cells responded in situ to the antigen-presenting material and that the immune response had cytotoxic components. Cytokine analysis at the vaccine implant site indicated that DC subsets act in a cooperative fashion to generate an effective immune response. pDC numbers correlated strongly with the presence of type-1 IFNs, which aided the activation of and antigen cross-presentation by CD11c(+)CD11b(+) cDCs to enhance CTL priming by these cells. Additionally, pDCs and CD8+ cDC numbers correlated with IL-12 production, which promotes antigen expression and cross-presentation by matrix resident DCs and the development and growth of CTLs.

Tumor growth and T-cell analysis indicated that as the heterogeneity of the DC network increased in situ, so did vaccine efficacy. Although total DC numbers remained statistically similar with GM-CSF signaling, provision of CpG-ODN danger signaling increased pDC numbers in a dose dependent manner, which strongly correlated to animal survival after a B16-F10 tumor challenge. CpG-ODN doses of 10, 50 and 100 µg (in GM-CSF secreting matrices) along with melanoma antigen presentation from PLG vaccines resulted in 45%, 60% and 90% survival in mice. Removal of GM-CSF signaling from PLG vaccines sharply reduced the total numbers of DCs generated in situ, which resulted in survival dropping to 10%, whereas removal of CpG-ODN signaling reduce pDC numbers in situ, as a majority of the DCs (87.4%) were CD11b+ CDCs. The minimum number of DCs required to induce protective immunity was determined for each DC subset, as approximately 600,000 pDCs and 200,000 CD8+ cDCs (~30% of total DCs) were required to cooperate with approximately 2,000,0000 CD11b+ cDCs to achieve greater than 50% survival after tumor challenge.

The results are clinically significant as the devices and methods demonstrated the ability to quantitatively target and employ DC subsets in vivo for the generation of immunity, resulting in distinct and protective immune responses.

Example 7: Presentation of TLR Agonists in Structural Polymeric Devices

Materials & Methods
Mice

C57BL/6 mice and Batf3−/− knockout mice (6-8-week-old female; Jackson Laboratories) were used in the studies described in Example 7.

Matrix Fabrication

A 85:15, 120 kD copolymer of D,L-lactide and glycolide (PLG) (Alkermes, Cambridge, Mass.) was utilized in a gas-foaming process to form porous PLG matrices (Harris et al., 1998 J. Biomed. Mater. Res., 42: 396-402). PLG microspheres encapsulating GM-CSF were first made using standard double emulsion (Cohen et al., 1991 Pharm. Res., 8: 713-720). The double emulsion process was also utilized to fabricate PLG microspheres containing MPLA (Avanti Polar Lipids, Alabaster, Ala.) as an adjuvant. PLG microspheres were then mixed with 150 mg of the porogen, sucrose (sieved to a particle size between 250 µm and 425 µm), and compression molded, thereby yielding a disc device with open, interconnected pores that are generally of the size range of the porogen. The resulting disc was allowed to equilibrate within a high-pressure $CO_2$ environment, and a rapid reduction in pressure causes the polymer particles to expand and fuse into an interconnected structure (Harris et al., 1998 J. Biomed. Mater. Res., 42: 396-402). The sucrose was leached from the scaffolds by immersion in water yielding scaffolds that were 90% porous.

To incorporate tumor lysates into PLG scaffolds, biopsies of B16-F10 tumors that had grown subcutaneously in the backs of C57BL/6J mice (Jackson Laboratory, Bar Harbor Me.), were digested in collagenase (250 U/ml) (Worthington, Lakewood, N.J.) and suspended at a concentration equivalent to $10^7$ cells per ml after filtration through 40 µm cell strainers. The tumor cell suspension was subjected to 4 cycles of rapid freeze in liquid nitrogen and thaw (37° C.) and then centrifuged at 400 rpm for 10 min. The supernatant (1 ml) containing tumor lysates was collected, incubated with the PLG microspheres and lyophilized and the resulting mixture was used to make PLG scaffold-based cancer vaccines.

To incorporate CpG-ODNs and P(I:C) into PLG scaffolds, CpG-ODN 1826, 5'-tcc atg acg ttc ctg acg tt-3', (SEQ ID NO: 10; Invivogen, San Diego, Calif.) or P(I:C) (high molecular weight; Invivogen, Sand Diego, Calif.) was first condensed with poly(ethylenimine) (PEI, Mn~60,000, Sigma Aldrich) molecules by dropping ODN-1826 solutions into a PEI solution, while vortexing the mixture (Huang, et al., 2003 J. Biomed. Mater. Res., A 67: 1384-1392). The charge ratio between PEI and CpG-ODN (NH3+:PO4-) was kept constant at 7 during condensation. The charge ratio between PEI and P(I:C) (NH3+:PO4-) was kept constant at 3 during condensation. The condensate solutions were then vortexed with 60 µl of 50% (wt/vol) sucrose solution, lyophilized and mixed with dry sucrose to a final weight of 150 mg. The sucrose containing PEI-CpG-ODN condensate was then mixed with blank, GM-CSF and/or tumor lysate loaded PLG microspheres to make PLG cancer vaccines.

In Situ Identification of DCs and T Cells

GM-CSF loaded PLG matrices and matrices containing GM-CSF in combination with either 100 µg of CpG-ODN, MPLA, or P(I:C) were implanted into subcutaneous pockets on the back of 7-9 week old male C57BL/6J mice. To analyze DC recruitment, scaffolds were excised at various time-points and the ingrown tissue was digested into single cell suspensions using a collagenase solution (Worthingtion, 250 U/ml) that was agitated at 37° C. for 45 minutes. The cell suspensions were then poured through a 40 µm cell strainer to isolate cells from scaffold particles and the cells were pelleted and washed with cold PBS and counted using a Z2 coulter counter (Beckman Coulter). To assess, DC infiltration and activation, subsets of the total cell population isolated from PLG matrices were then stained with primary antibodies (BD Pharmingen, San Diego, Calif.) conjugated to fluorescent markers to allow for analysis by flow cytometry. APC-conjugated CD11c (dendritic cell marker), FITC-conjugated MHCII and PE-conjugated CD86 (B7, costimulatory molecule) stains were conducted for DC recruitment and activation analysis. To further delineate the presence of specific DC subsets, cells were also stained with APC-conjugated CD11c and PE-conjugated PDCA-1 (plasmacytoid DC marker) or APC-conjugated CD11c and PE-conjugated CD8 (CD8 DCs). To assess T-cell infiltration PE-Cy7 conjugated CD3 stains were performed in conjunction with APC-conjugated CD8a (CD8 T cells), and PE-conjugated FoxP3 (Treg) and analyzed with flow cytometry. Cells were gated according to single positive FITC, APC and PE stainings and using isotype controls. The percentage of cells staining positive for each surface antigen was recorded.

Tumor Growth Assays, Protective Cytokines and Trp2 Pentamer Analysis

PLG scaffolds with melanoma tumor lysates and GM-CSF in combination with CpG-ODN, MPLA, or P(I:C) were implanted subcutaneously into the lower left flank of C57BL/6J mice. For prophylactic vaccinations, animals were challenged 14 days later with a subcutaneous injection of $10^5$ B16-F10 melanoma cells (ATCC, Manassas, N.J.) in the back of the neck. Animals were monitored for the onset of tumor growth (approximately 1 $mm^3$) and sacrificed for humane reasons when tumors grew to 20-25 mm (longest diameter).

To assess PLG vaccine efficacy in the therapeutic setting, C57/BL6J mice were challenged with a subcutaneous injection of $5\times10^5$ B16-F10 melanoma cells (ATCC, Manassas, N.J.) in the back of the neck. At day 9 after tumor challenge PLG vaccines loaded with 3000 ng GM-CSF in combination with 100 µg of CpG-ODN, MPLA or P(I:C), and tumor lysates were implanted subcutaneously into the lower left flank of C57BL/6J mice. A subset of mice were vaccinated again 10 days after the initial vaccination (Days 19 and 23).

To determine in vivo IL-12p70 concentration at the matrix implant site, adjacent tissue was excised and digested with tissue protein extraction reagent. After centrifugation, the concentrations of IL-12, in the supernatant were then analyzed with ELISA (R&D systems), according to the manufacturer's instructions.

To determine the generation of TRP-2-specific cytotoxic T lymphocytes, single cell suspensions were prepared from the spleens of mice immunized with PLG vaccines [Antigen +3000 ng GM-CSF+100 μg (CpG or MPLA or P(I:C)] at various timepoints. These cells were initially stained with PE-H-2Kb/TRP2 pentamers (Sigma Aldrich), and subsequently stained with FITC-anti-CD8 and PE-CY7 CD3 mAb (mAb (BD Pharmingen, San Diego) before being analyzed using flow cytommetry.

Tumor Infiltrating Leukocyte (TIL) Characterization

On the indicated days, B16-F10 tumors were removed from mice, and digested in 1 mg/mL collagenase II (250 U/ml) (Worthington, Lakewood, N.J.) and 0.1 mg/mL DNase for 1 hour at 37° C. Dissociated cells were filtered through a 40-μm filter, and directly stained with antibodies for phenotype characterization by fluorescence-activated cell sorting (FACS) analysis. APC-anti-CD8 and PE-Cy7-anti CD3 were used to identify T cells isolated from the B16F10 tumors. These TILs were also costained with FITC-anti-IFNγ, and PE-anti-CD107a. All antibodies were obtained from eBioscience, San Diego, Calif.

Statistical Analysis

All values in the present study were expressed as mean±S.D. The significant differences between the groups were analyzed by a Student's t test and a P value of less than 0.05 was considered significant.

Controlled GM-CSF and TLR Agonist Presentation

Figure 15A:
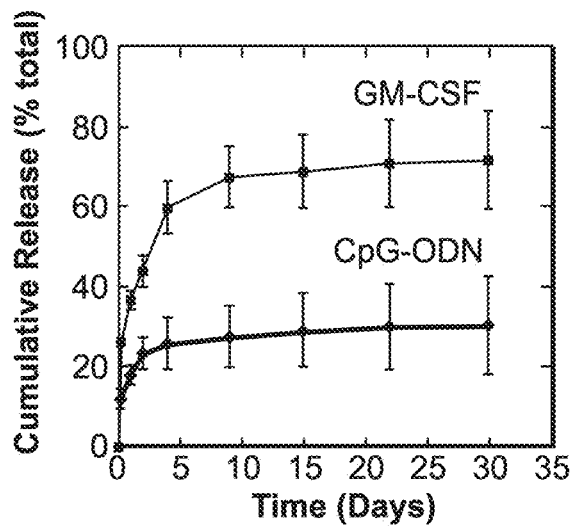
FIGS. 15A-B are line graphs showing cumulative release of (A) CpG-rich oligonucleotides (CpG 1826) or (B) P(I:C) in combination with the cumulative release of GM-CSF from PLG scaffolds.
Figure 15B:
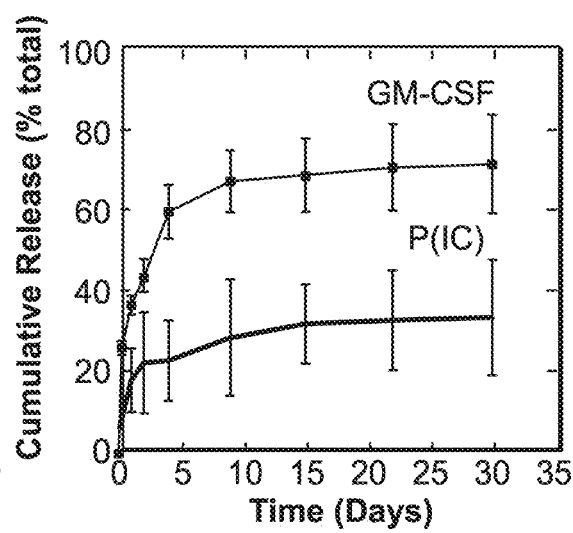
Figure 15C:
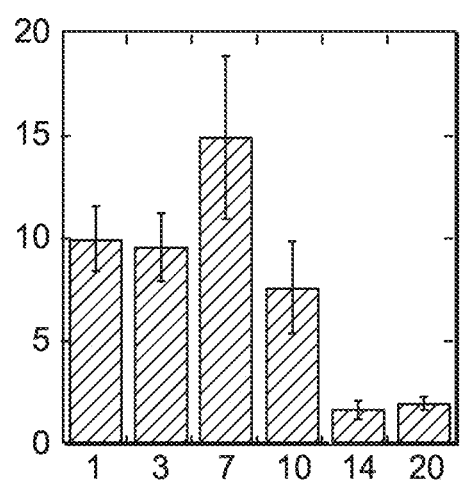
FIGS. 15C-D are bar graphs showing bioactivity of P(I:C) and MPLA, respectively, released from PLG scaffolds presented as fold-increase over controls. Bioactivity measured by the ability of the Poly(I:C) and MPLA released from PLG scaffolds to stimulate HEK293 cells expressing TLR3 and TLR4, respectively, and stably transfected with NF-κB-dependent alkaline phosphatase reporter. Bioactivity was measured over time and compared to controls of unstimulated cells.
Figure 15D:
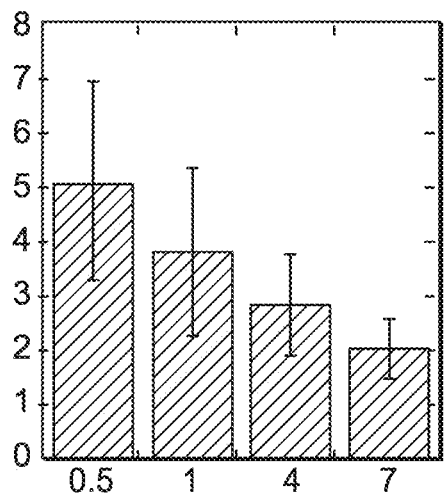
Figure 15E:
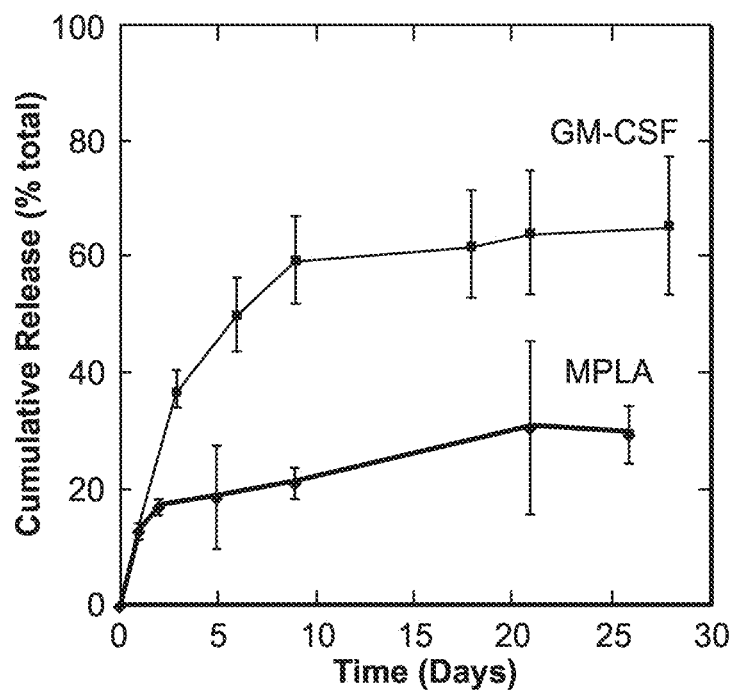
FIG. 15E is a line graph showing MPLA in combination with the cumulative release of GM-CSF from PLG scaffolds. Values represent mean and standard deviation (n=5 or 6). These data show in vitro release kinetics and bioactivity of various TLR agonists from GM-CSF loaded PLG scaffolds.
Figure 15F:
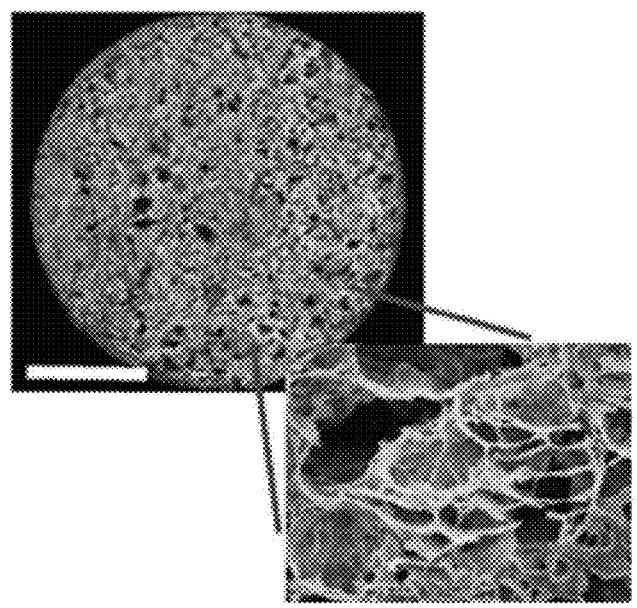
FIG. 15F is a photomicrograph showing the top surface of a macroporous PLG scaffold (scale bar—3 mm), and SEM micrograph of a scaffold cross section (scale bar—50 μm).

Macroporous, poly-lactide-co-glycolide (PLG) matrices (FIG. 15F) were designed to quickly release GM-CSF (Ali et al., 2009 Nat Mater, 2: 151-8), approximately 60% of the protein was released by day 10 (FIGS. 15A, 15B, and 15E), to induce the recruitment of DCs or their precursors. GM-CSF loaded PLG scaffolds were also modified to present TLR-activating, CpG-ODN, MPLA and P(I:C) molecules, as danger signals. The in vitro release kinetics of GM-CSF were similar in all conditions (FIGS. 15A, 15B, and 15E). TLR agonists were more stably associated with scaffolds, as approximately 20-30% of incorporated CpG-ODN, P(I:C) and MPLA was released over the first 10 days in vitro, followed by slow and sustained release of danger signals over the next 14 days. Presentation of the TLR agonists was designed to provide a long-term, local signal to activate DCs. Importantly, the relatively high molecular weight and composition of the particular PLG chosen to fabricate scaffolds results in slow scaffold degradation, allowing for long-term analysis of the vaccine site and its regulation over DC activation and T cell immunity.

Controlled DC Generation and Activation In Vivo

Figure 16A:
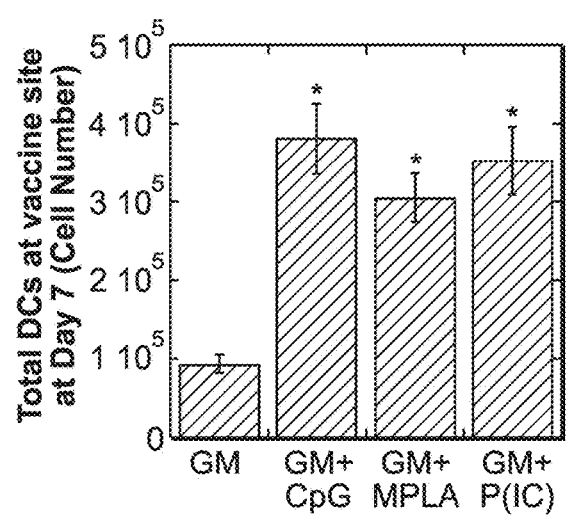
FIGS. 16A-D are bar graphs showing DC recruitment and Activation at Vaccine Site is regulated by TLR agonist presentation. The total numbers of (A) CD11c(+) DCs, (B) activated CD11c(+) DCs positive for MHCII and CD86 expression, (C) PDCA-1(+) plasmacytoid DCs, and (D) CD11c(+)CD8(+) DCs recruited to scaffold site at day 7 after implantation of GM-CSF loaded matrices (GM) and matrices loaded with GM-CSF in combination with CpG-ODN (CpG), MPLA (MPLA), and P(I:C) (P(IC)).
Figure 16B:
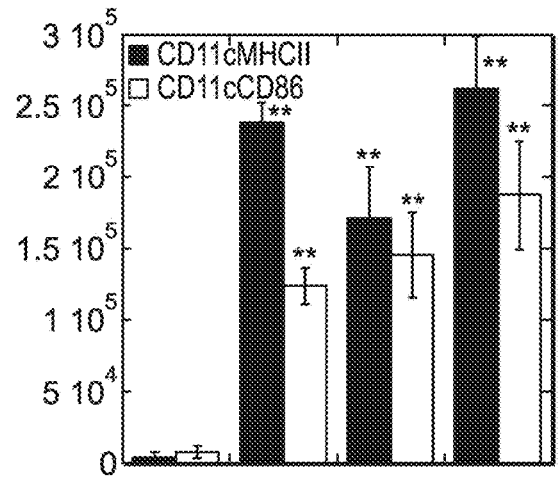
Figure 16C:
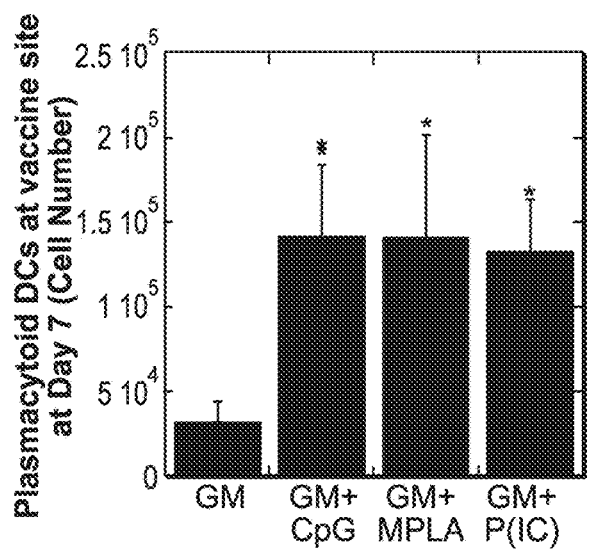
Figure 16D:
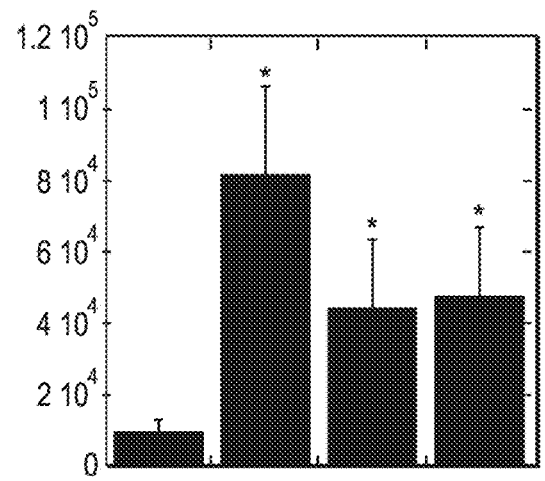
Figure 16E:
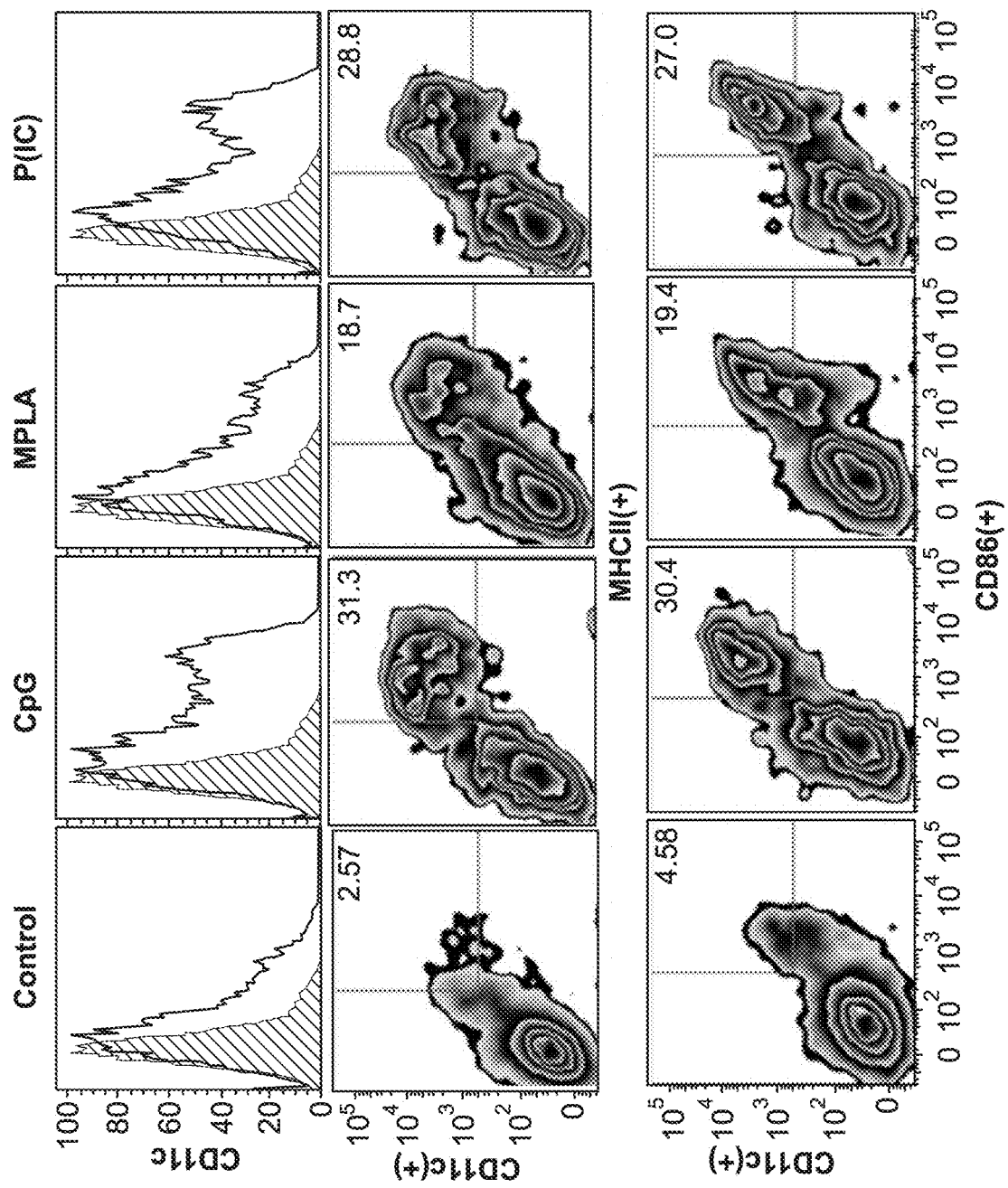
FIG. 16E shows FACS histograms and plots representing scaffold infiltrating dendritic cells in GM-CSF loaded scaffolds (Con) or scaffolds loaded with GM-CSF in combination with CpG-ODN (CpG), MPLA (MPLA), and P(I:C) (P(IC)) at day 7 postimplantation in mice. Histograms indicate the relative frequency of CD11c(+) dendritic cells infiltrating the indicated scaffold formulation. Density plots indicate cells stained for CD11c(+) in combination with activated, DC markers, CD86(+) and MHCII(+). Numbers in the upper right quadrant of FACS plots indicate the percentage of CD11c(+) dendritic cells positive for activation markers.
Figure 16F:
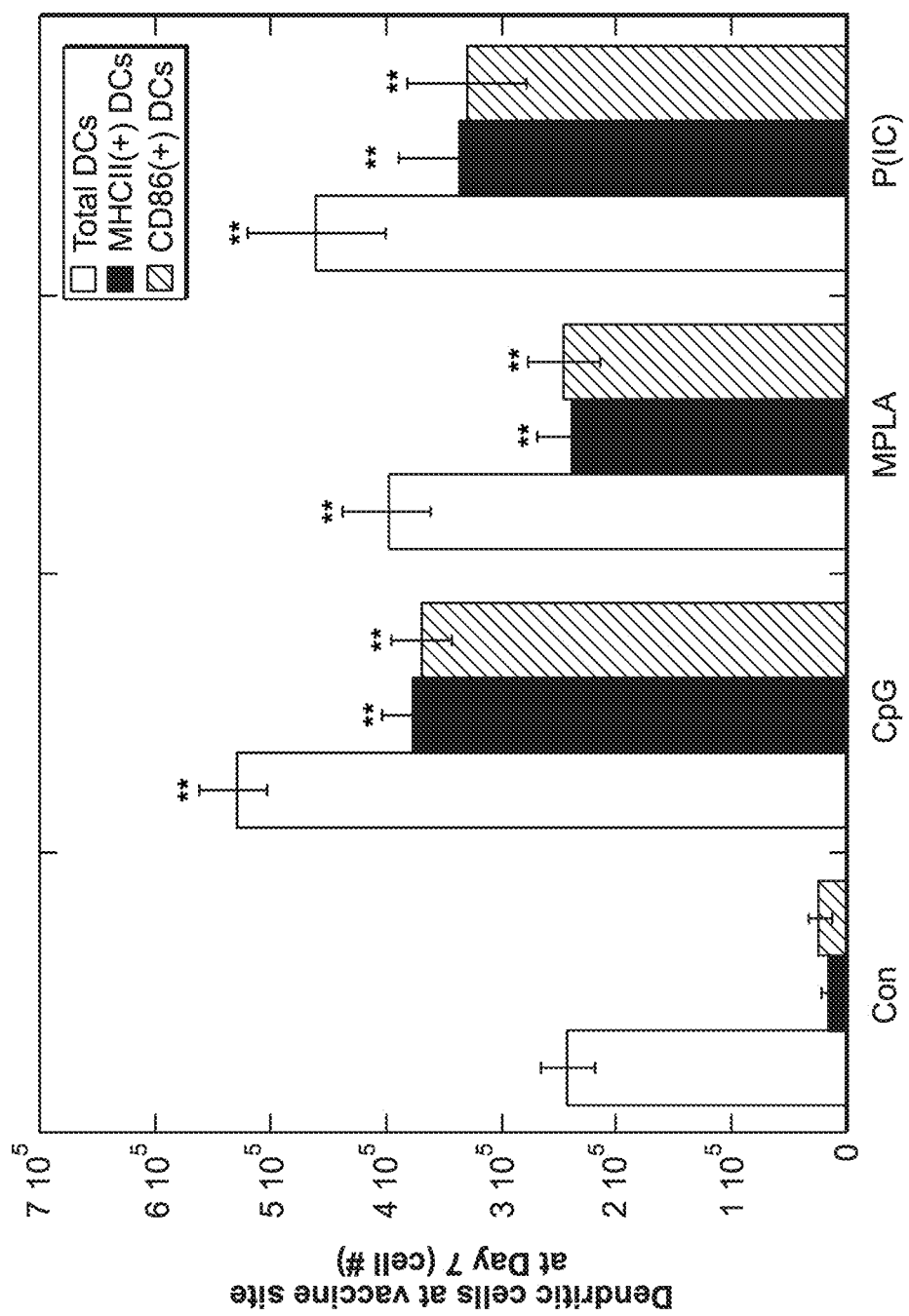
FIG. 16F is a bar graph showing the total numbers of CD11c(+) DCs, and activated CD11c(+) DCs positive for MHCII and CD86 expression, at the scaffold site at day 7 after implantation of GM-CSF loaded matrices (Con) and matrices loaded with GM-CSF in combination with CpG-ODN (CpG), MPLA (MPLA), and P(I:C) (P(IC)). Values represent mean and standard deviations (n=6). * P<0.05  P<0.01, as compared to GM-CSF loaded matrices.  P<0.01, as compared to GM-CSF loaded matrices (Con).

To examine the ability of PLG matrices to recruit and activate dendritic cells in vivo, matrices delivering GM-CSF in combination with danger signals were implanted subcutaneously into the backs of C57BL/6J mice. The magnitude of DC infiltration and activation into the matrices was determined by FACS analysis of cell populations isolated from the polymeric material after 7 days. Control matrices delivering GM-CSF alone contained $2.41 \pm 0.24 \times 10^5$ CD11c (+) (FIGS. 16E and 16F) cells, with relatively low expression levels of the activation markers, MHCII (2.57% of total CD11c(+) cells) and CD86 (4.58% of CD11c(+) cells). Inclusion of TLR-activating danger signals into PLG matrices dramatically enhanced dendritic cell generation and activation in situ. Presentation of CpG-ODN, MPLA and P(I:C) enhanced the total number of recruited DCs by 2.5, 1.9, and 2.2 fold, respectively (FIG. 16F), as compared to GM-CSF delivery alone. Analysis of the activation state of matrix-resident DCs revealed that local TLR induction produces significant percentages of activated DCs, as CD11c(+) cells positive for MHCII(+) and CD86(+), comprised approximately 30%, 19%, and 28% of the total cells recruited to CpG, MPLA and P(I:C) loaded matrices, respectively. Matrices presenting TLR agonists mediated approximately 15 (MPLA) to 20 (P(I:C)) to 23-fold (CpG-ODN) increases in the total number of activated DCs at the implant site relative to control matrices devoid of this signaling (FIG. 16F).

Figure 16G:
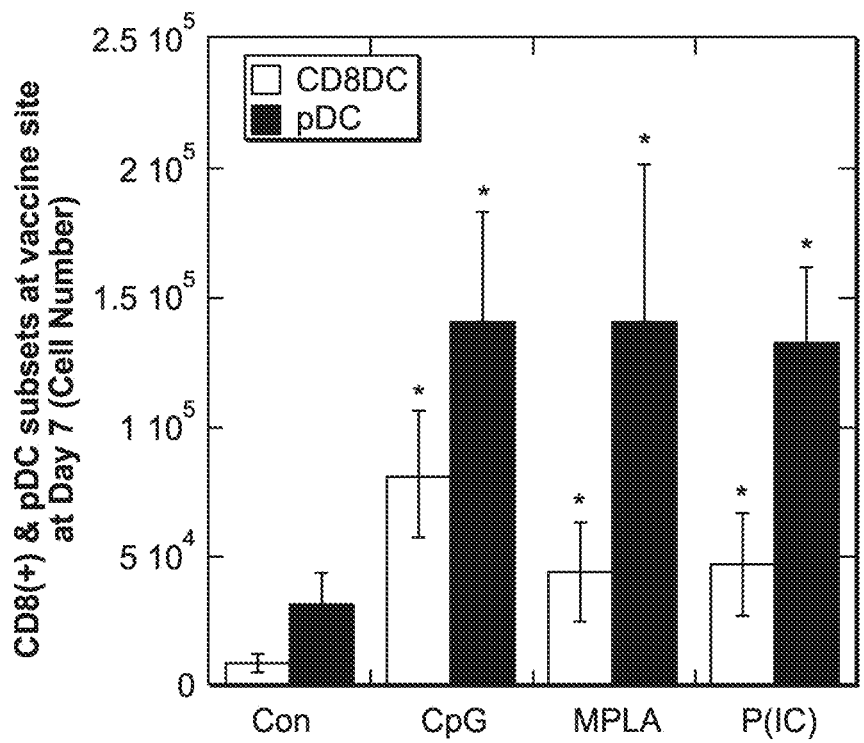
FIGS. 16G and 16H are bar charts showing that CD8(+) DC, and pDC subsets and IL-12 concentrations at vaccine site.
Figure 16H:
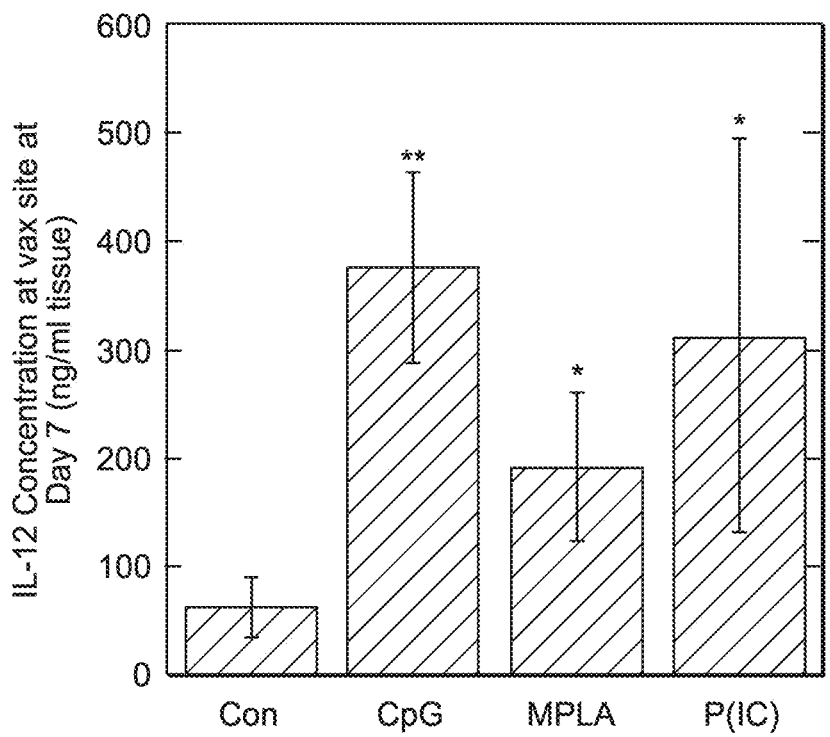
Figure 21A:
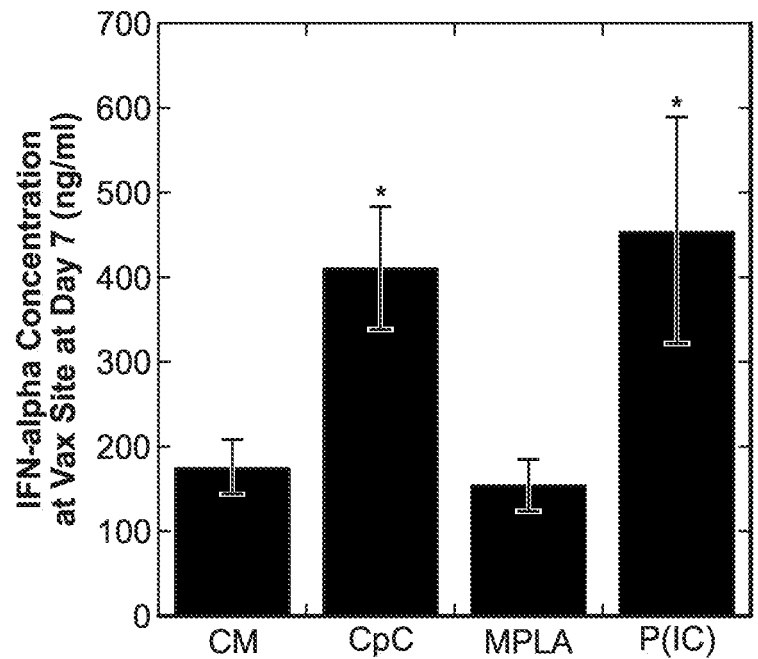
FIGS. 21A-D are a series of bar charts.
Figure 21B:
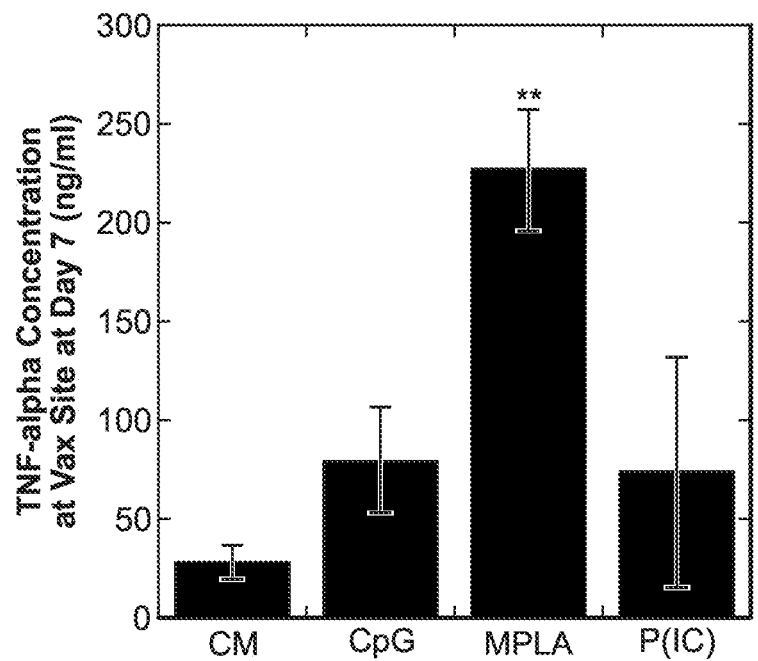

Stimulation of the cells which infiltrated PLG matrices with CpG-ODN, MPLA or P(I:C) enriched the numbers of CD11c(+)PDCA-1(+) pDCs and CD11c(+)CD8(+) cDCs (FIG. 16G) relative to controls. The danger signals increased the numbers of pDCs at the implant site by approximately 4-fold relative to control matrices, with an average pDC number of 140,000 cells residing in the scaffolds presenting any of the TLR agonists (FIG. 16G). CD8(+) DCs were also present at the implant site at approximately 5-fold higher levels with MPLA and P(I:C) presentation and at a 9-fold higher number when utilizing CpG-ODN as a stimulant. Strikingly, the local delivery of TLR-activating agents promoted the local production of IL-12 (200-400 ng/ml) at the implant site (FIG. 16H), with CpG and P(I:C) inducing the highest levels. The IL-12 concentration correlated with the increased numbers of activated DCs and DC subsets in these conditions (FIG. 16H). Additionally, the concentrations of a panel of candidate inflammatory cytokines were assayed at the vaccine site. Similar elevated levels of IFN-α (FIG. 21A) resulted from CpG-ODN and P(I:C) induction while MPLA had no effect on IFN-α concentration. However, MPLA led to 4-fold higher levels of TNF-α (FIG. 21B). IL-12 concentrations at MPLA loaded matrices were 2-fold lower than CpG-ODN and P(I:C). TNF-α inhibits monocyte and DC derived IFN-γ, IL-12, and T cell priming (Hodge-Dufour et al., 1998 Proc. Natl. Acad. Sci. USA, 95: 13806-13811) and the aforementioned cytokine profiles, suggesting that MPLA loaded matrices are less efficient at stimulating anti-tumor T cell responses compared to matrices incorporating CpG-ODN and P(I:C) signaling.

Prophylactic Vaccination and Correlates to its Efficacy

Figure 17A:
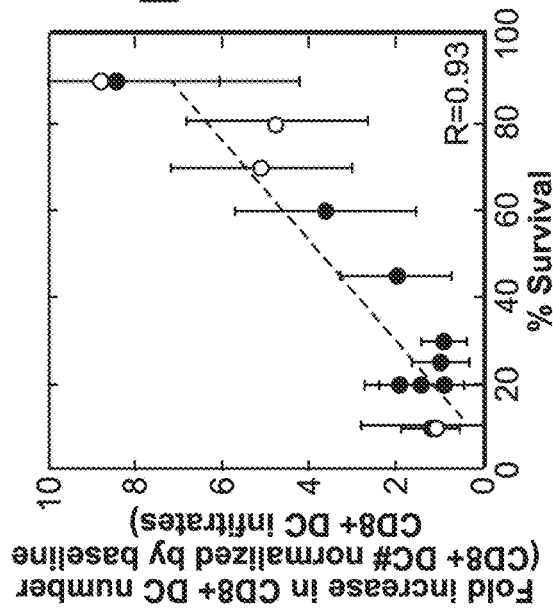
FIGS. 17A-D are graphs showing prophylactic vaccination and correlation to CD8(+)DC, and pDC subsets and IL-12 concentrations at vaccine site. Survival times of mice vaccinated with PLG vaccines 14 days prior to B16-F10 melanoma tumor challenge ($10^5$ cells).
Figure 17B:
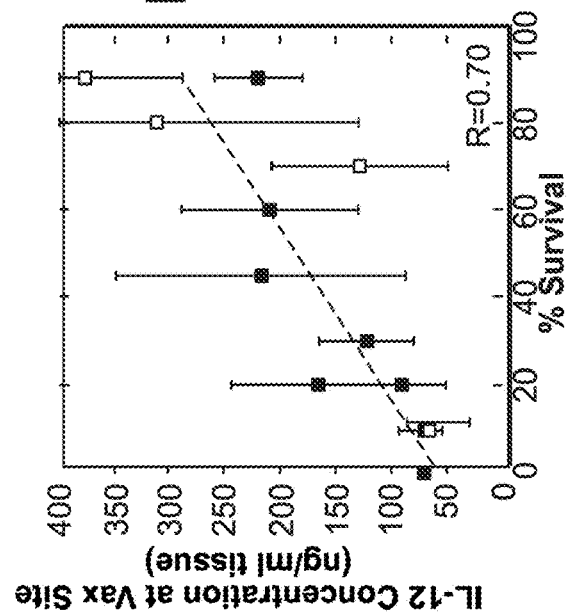
Figure 17C:
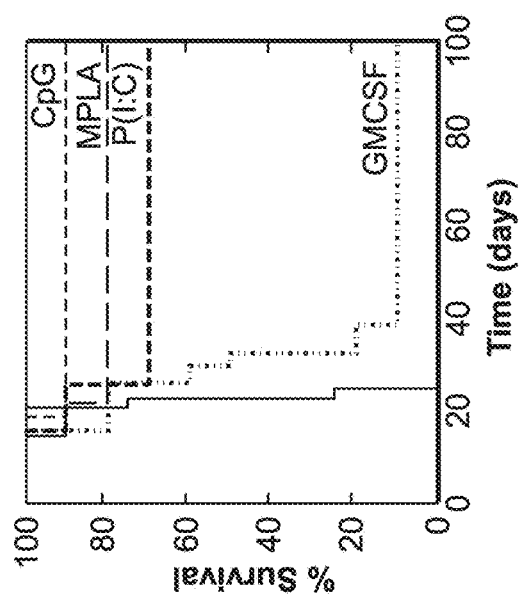
Figure 17D:
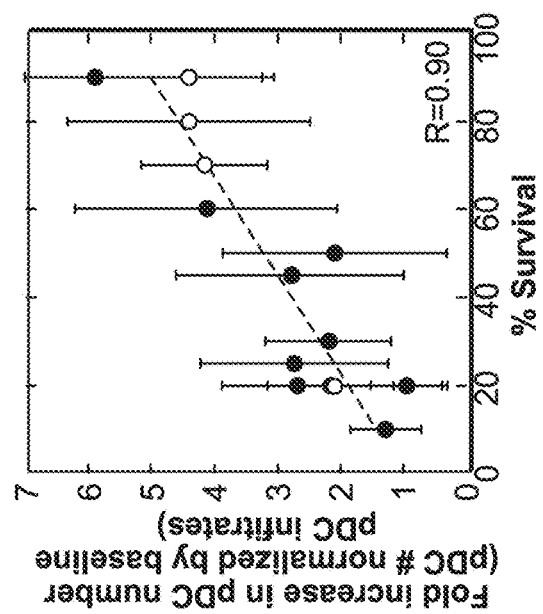
Figure 18A:
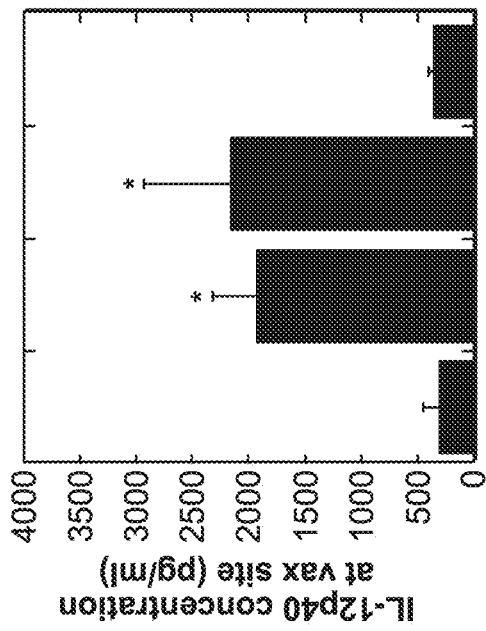
FIGS. 18A-D are bar graphs showing T cell Activity and cytokine production at vaccine site at Day 14 of scaffold implantation. (A) The number of CD3(+)CD8(+) cytotoxic T cells at day 14 after implantation of GM-CSF loaded matrices (GM) and matrices loaded with GM-CSF in combination with CpG-ODN (CpG), MPLA (MPLA), and P(I:C) (P(IC)). The in vivo concentration of (B) IL-12, (C) Rantes, and (D) IFN-g at day 14 after implantation of GM-CSF loaded matrices (GM) and matrices loaded with GM-CSF in combination with CpG-ODN (CpG), MPLA (MPLA), and P(I:C) (P(IC)). Values represent mean and standard deviations (n=5). * P<0.05 ** P<0.01, as compared to control matrices (loaded with GM-CSF).
Figure 18B:
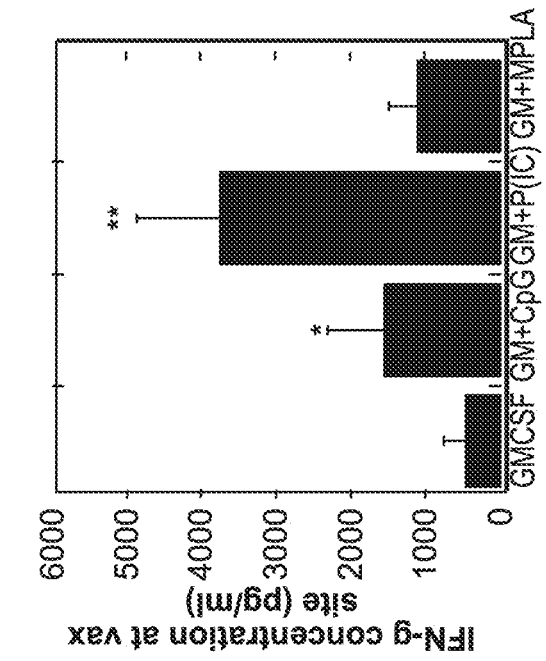
Figure 18C:
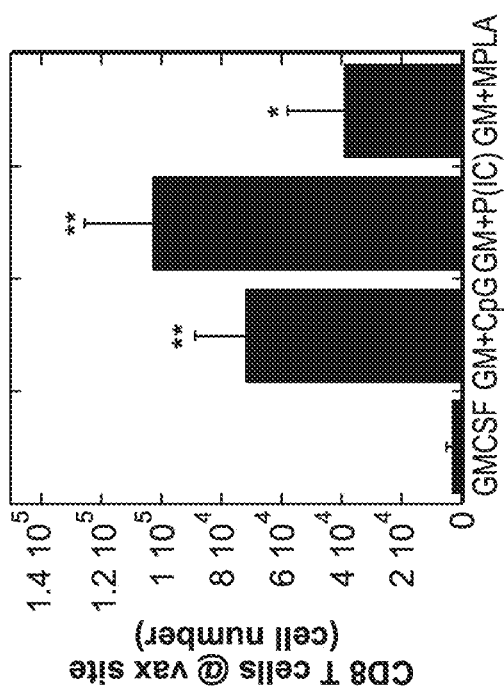
Figure 18D:
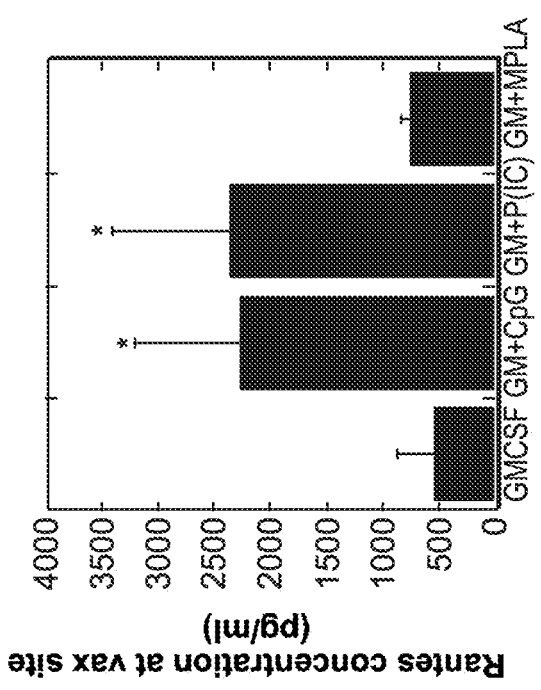

Since PLG matrices presenting TLR agonists generate distinct and activated DC populations in situ and potent cytokine production, the anti-tumor efficacy of these systems were tested in the poorly immunogenic, B16-F10 melanoma model. B16 tumor lysates were used to act as a source of tumor antigen in vaccine formulations. Prophylactic PLG-based vaccines presenting both B16-F10 tumor lysates and GM-CSF resulted in 10% of the vaccinated mice surviving, tumor-free (FIG. 17A), after an otherwise lethal cell challenge at day 14 post-vaccination. Importantly, antigen loaded matrices with GM-CSF in combination with TLR agonists produced significant, and long-term tumor protection. CpG-ODN, MPLA and P(I:C) presentation from PLG vaccines resulted in 90, 80 and 70% survival rates (FIG. 19B). Regression analysis was subsequently performed to determine whether induction of long-term survival was related to pDC, CD8(+), and IL-12 levels at the vaccine site: previously published data using various doses of CpG-ODN were included in the analysis. Strikingly, animal survival rates were strongly correlated with the numbers of pDCs, CD8(+) DCs and with endogenous IL-12 generated by PLG vaccines (FIGS. 17A-C). These findings demonstrate the importance of antigen cross-presentation by CD8(+) DCs and the Th1-promoting cytokine, IL-12 to vaccine efficacy.

Therapeutic Vaccination and Anti-Tumor T Cell Activity

As specific vaccine formulations containing various TLR agonists produced significant numbers of activated DCs and conferred prophylactic immunity, studies were carried out to determine whether the vaccines would lead to superior therapeutic responses and cytotoxic T-cell responses. Mice challenged with $5 \times 10^5$ B16-F10 melanoma cells were subsequently vaccinated at days 9 and 19, after tumors were established. All tumor-bearing mice implanted with control PLG matrices demonstrated rapid tumor growth and required euthanasia by Day 24, as expected (FIGS. 19A and B) PLG vaccines presenting MPLA as an adjuvant decreased the rate of tumor progression (FIG. 19A), and a slight increase in mean survival time (~1.5 fold increase) over controls was found (FIGS. 19A and B). Complete tumor regression (Tumors <36 mm$^2$) and long term survival of mice (33% survival) was achieved in the subset of mice vaccinated with PLG vaccines exploiting P(I:C) and CpG-ODN as an adjuvant.

FACs analysis was used to characterize the numbers of B16-F10 tumor-infiltrating leukocytes (TILs) induced by the various vaccines. Significantly greater numbers of CD8(+) CTLs per $1 \times 10^6$ tumor cells were present in animals treated with TLR-agonist-loaded vaccines, as compared with control animals (FIGS. 19C-D). CD8(+) T cell infiltrates were further characterized for IFNγ expression and expression of CD107a, a marker for cytotoxic-associated cell degranulation. These cell populations were markedly enhanced in vaccine treated animals (FIGS. 19C-D). Vaccines featuring CpG-ODN, P(I:C) and MPLA signaling resulted in approximately 6.1, 3.1 and 1.4 fold increases in IFNγ(+), CD107a (+) TILs in comparison to controls. Moreover, CpG loaded vaccines resulted in significantly higher numbers of activated TILs in comparison to their P(I:C) and MPLA counterparts (FIG. 19D).

The activation of systemic CTL responses was also monitored by staining splenocytes with MHC class I/TRP2 peptide pentamers to identify CTLs with specificity to tyrosinase-related protein (TRP)-2. This is a main antigenic target of melanoma vaccines in mice and humans. A significant expansion of TRP2 specific CTLs was observed in the spleens of mice vaccinated with CpG-ODN, MPLA and P(I:C) loaded vaccines, in comparison to controls devoid of TLR agonists (FIG. 19E). Taken together, these data indicate that vaccine formulations containing various TLR agonists produce significant and systemic anti-melanoma CTLs in correlation with the activation of specific DC subsets and reduce tumor burden.

Vaccine Efficacy is Impaired in Mice Lacking CD8(+) DCs

Figure 20B:
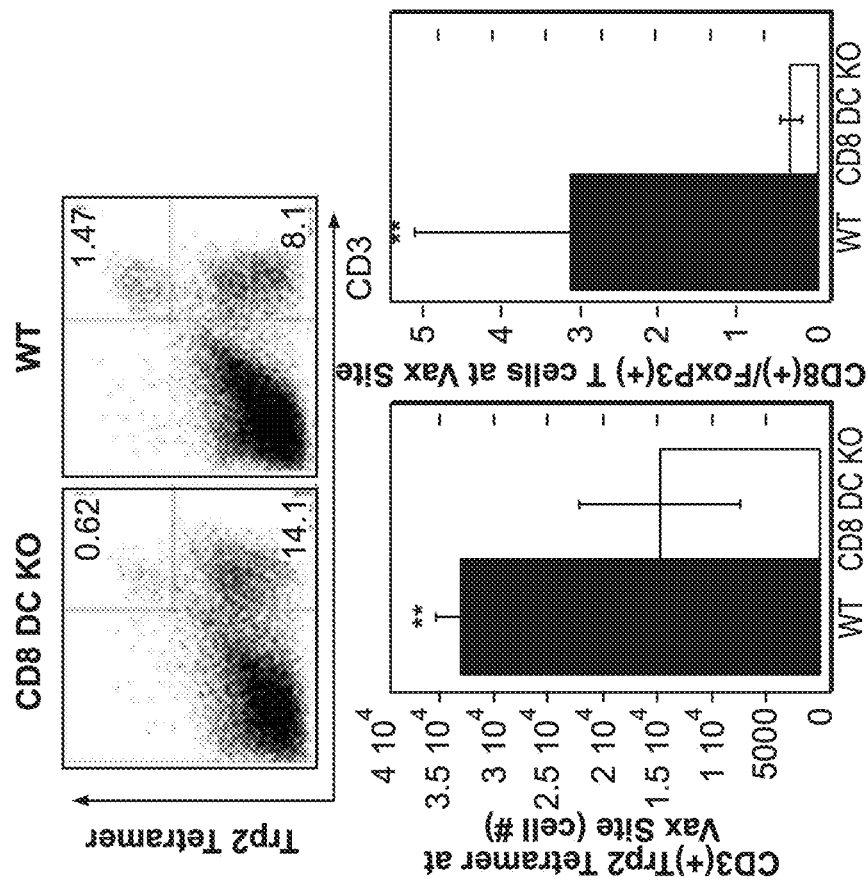
FIGS. 20A-D are a series of bar charts, line graphs and dot plots showing that vaccine efficacy is impaired in mice lacking CD8(+) DC. (A) Survival times of untreated mice (control), wildtype C57BL/6J mice (WT) and Batf3−/− mice (CD8 DC KO), vaccinated with PLG vaccines 14 days prior to B16-F10 melanoma tumor challenge (105 cells). (B) Analysis of cytotoxic and regulatory T cells at PLG vaccine site of wildtype C57BL/6J mice (WT) and Batf3−/− mice (CD8 DC KO) at day 10 post implantation. FACS dot plots indicate scaffold-infiltrating cells stained for CD3(+) and Trp2(+) tetramer. Numbers in the upper right quadrant of FACS plots indicate the percentage Trp2 specific cytotoxic T cell, and numbers in lower right quadrant represent the rest of the T cell population at the vaccine site. Graphs indicate the total numbers of Trp2-specific cytotoxic T cells at implant site and the ratio of CD8(+) cytotoxic T cells to regulatory T cells. (C) Fold increase in IL-12 concentration at vaccine site and (D) Trp(2)-specific cytotoxic T cells in spleens of vaccinated, wildtype C57BL/6J mice (WT) and Batf3−/− mice (CD8 DC KO). CpG-ODN was the adjuvant utilized in vaccines. Data represent mean and standard deviation, (n=5)* P<0.05 ** P<0.01.
Figure 20A:
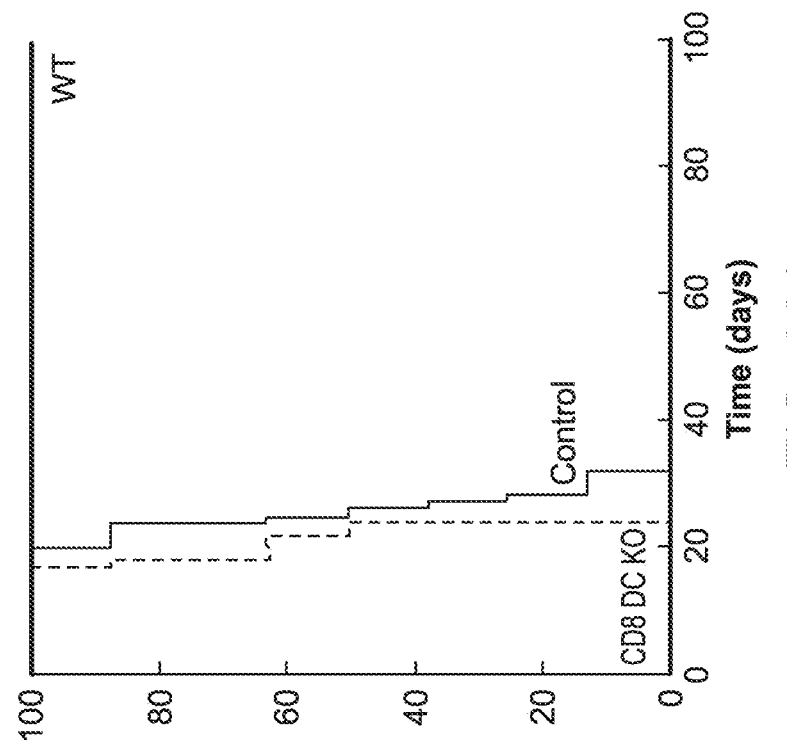

Since PLG vaccines incorporating TLR agonists were capable of generating CD8(+) DC populations in situ, which correlated to potent anti-tumor CTL responses and survival (FIGS. 17A-D and 19A-F), studies were carried out to examine whether these cells were required to confer anti-tumor immunity in vivo. Batf3-/- transgenic mice were used in these experiments, as lack CD8(+) DCs, without exhibiting abnormalities in other hematopoietic cell types or tissue architecture (Hildner et al., 2008 Science, 322: 1097-1100). Wild-type and Batf3-/- mice were vaccinated with CpG-ODN loaded PLG vaccines and challenged with B16-F10 cells 14 days later. Vaccination of wildtype mice promoted complete protection against tumor growth and long-term survival (100% survival), as expected, but vaccinated Batf3-/- were not protected and tumor growth rates were similar to untreated, wild-type animals (FIG. 20A). Moreover, vaccinated Batf3-/- failed to produce the local CTL responses observed in wild-type mice, and a 3-fold decrease in TRP2 specific cytotoxic T cells coincided with higher ratios of FoxP3(+) T regulatory (Tregs) cells at the vaccine site in this condition (FIG. 20B). These results indicated that a lack of CD8(+) DCs resulted in limited cytotoxicity and allowed regulatory pathways mediated by Tregs to potentially extinguish the vaccine mediated, immune response.

Figure 20D:
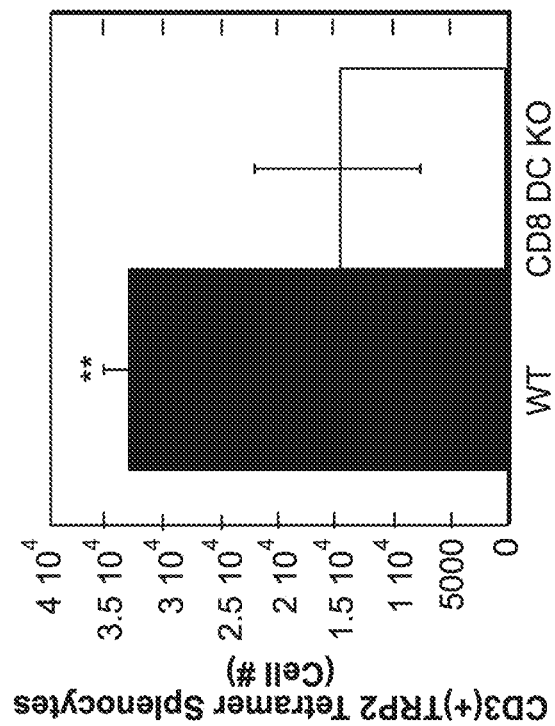
Figure 20C:
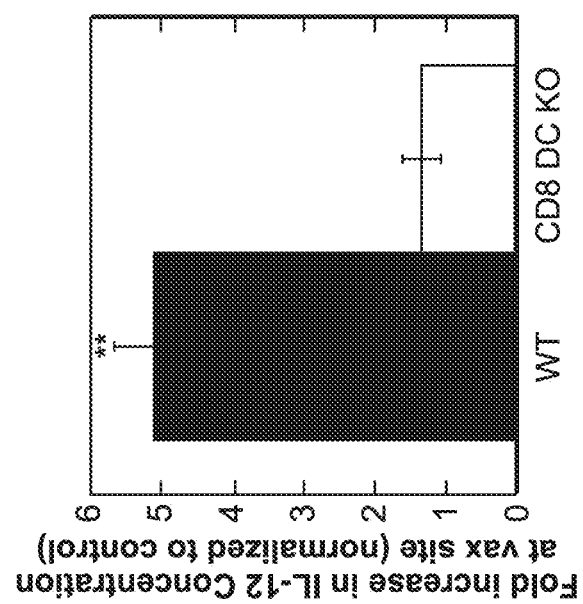
Figure 21C:
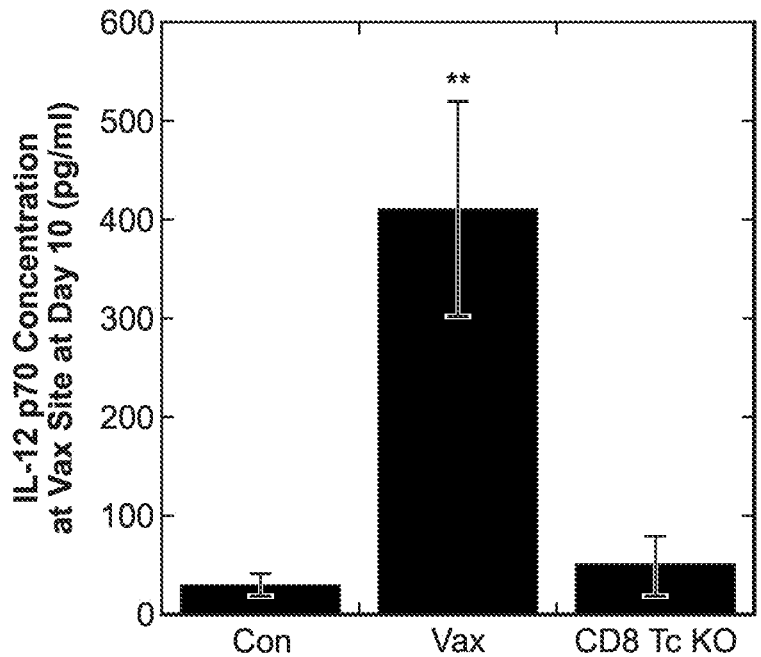
Figure 21D:
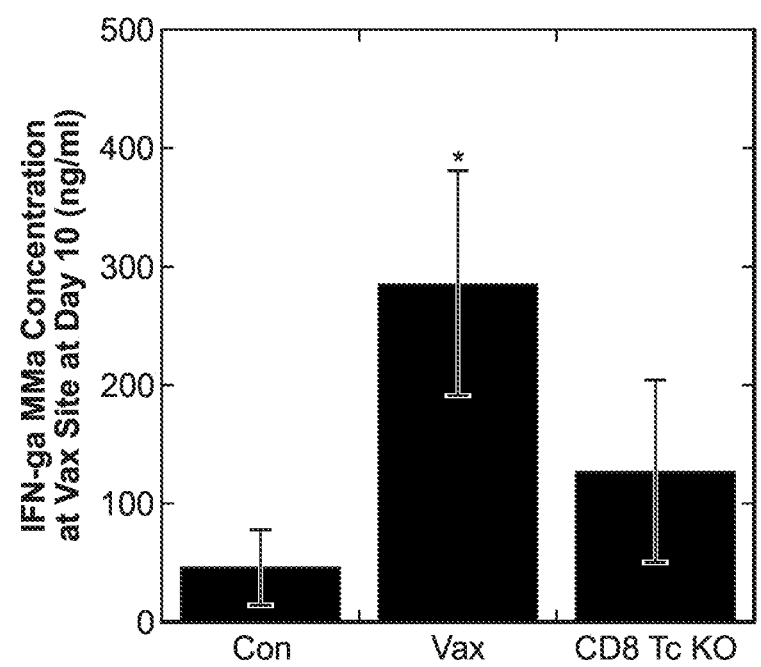

Wild type mice were also able to induce the production of the T cell growth factor, IL-12, at the vaccine site at 5-fold higher levels than found in vaccinated Batf3-/- mice (FIG. 20C). The partial loss of IL-12 production in CD8(+) DC knock-out mice indicates that these cells are important producers or mediators of this Th1-polarizing cytokine. The vaccine sites of CD8(+) T cell knock out mice also showed decreased levels of IL-12 and IFN-γ (FIGS. 21C and D). The IL-12-IFNγ pathway is a positive feedback mechanism with each cytokine augmenting production of its counterpart. The data with Batf3-/- mice and CD8(+) T cell knock-out mice indicate that the immune response resulting from vaccination in normal mice may be amplified by cytokine mediated cross talk between DCs and CTLs. Finally, the systemic production of anti-tumor CTLs was also impaired in Batf3-/-, as a 3 fold reduction in Trp2 specific CTLs was measured in the spleens of these mice in comparison to wild-type controls (FIG. 20D). These results indicate that vaccine efficacy in this system is critically regulated by CD8 DCs, via their ability to cross present tumor antigens, to produce Th-1 induction factors such as IL-12, and to generate and interact with CTLs.

To address the limitations of earlier cancer vaccines, a PLG matrix was utilized that controls the presentation of tumor lysate, GM-CSF and TLR agonists to create a vaccine node that recruits and activates multiple DC subsets in situ. The contribution of DC subsets to vaccine efficacy was analyzed and it was demonstrated that effective tumor cell killing required the participation of CD8(+) DCs, with strong correlations to pDCs and IL-12. These components were critical to the vaccine results regardless of the type or dose of stimulant incorporated within the scaffolds.

Inclusion of TLR agonists was required to activate DCs, in general, increasing their surface expression of MHCII and the costimulatory molecule, CD86 (FIGS. 16A-H) indicating an enhanced capacity to present antigen and activate T cell populations. In particular, appropriate TLR signaling enhanced the generation of CD8(+) and pDC subsets at the vaccine site and stimulated the production of IFNs and the potent T cell growth factor, IL-12. Moreover, removal of TLR agonists from the system resulted in decreased numbers of Trp2 specific, cytotoxic CD8(+) T cells locally at the vaccine site and systemically in spleens and tumors and this coincided with reduced survival in vaccine studies. PLG vaccines presenting P(I:C) or CpG-ODN induced potent tumor rejection in therapeutic models of B16-F10 melanoma, causing complete tumor regression in over a third of vaccinated animals and eradicating tumors reaching 35 mm$^2$ in size. Analysis of the tumor sites in vaccinated animals demonstrated intense and activated CD8(+), cytotoxic T cell infiltrates likely effecting tumor-cell killing. These systems outperformed the preclinical results of current vaccine modalities extensively studied in the clinic, including irradiated tumor cell vaccines and DC based vaccines (Gilboa E, 2007 J Clin Invest, 117: 1195-1203; Banchereau J. and Steinman R. M. 2007 Nature, 49: 419-426; Ali et al., 2009 Sci Transl Med, 1: 8-19; Rosenberg et al., 2004 Nat Med, 10: 909-915; Klebanoff et al., 2006 Immunol Rev, 211: 214-

224). Vaccines presenting MPLA signaling also slowed tumor growth rates, but did not cause tumors to completely regress. This may be explained by the fact that, CpG-ODN and P(I:C) signaling outperformed MPLA in terms of promoting higher average levels of cell surface activation markers on DCs and cytokine profiles that promote Th-1 polarization and CTL responses. Additionally, MPLA was a strong inducer of TNF-α, in comparison to CPG-ODN and P(I: C), which can inhibit IL-12, and IFN pathways priming CTL responses (Hodge-Dufour et al., 1998 Proc. Natl. Acad. Sci. USA, 95: 13806-13811). Thus, the differential effects of TLR agonists on survival rates are consistent with the numbers and subsets of activated DCs produced at the vaccine site and cytotoxic T-cell activity. Combinations of TLR agonists, e.g., poly (I:C) and CpG or poly (I:C) and MPLA, lead to a synergistic anti-tumor effect.

All vaccinated mice without the CD8(+) DC compartment, Batf3-/- mice, generated tumors in prophylactic models that produced 90% tumor-free survival rates in wild-type mice. Cytokine analysis of the vaccine site of these animals revealed that local IL-12 levels, and CTL responses were markedly reduced indicating that CD8(+) DCs are an important source of IL-12, and Th-1 polarization. Without CD8(+) DC participation, vaccination not only resulted in reduced cytotoxic, CD8(+) T cell activity (at tumor site and spleen) it also allowed the progression of Treg activity. High FoxP3(+) Treg to CD8(+) T-cell ratios indicates unbalanced immunosuppression that extinguishes vaccine efficacy and promotes tumor growth (Quezada et al., 2006 J. Clin. Invest., 116: 1935-1945; Hodi et al., 2008 Proc. Natl. Acad. Sci. U.S.A., 105: 3005-3010). CD8(+) DCs and IL-12 can cause Tregs inhibition or their conversion to IFNγ-producing, effector T cells (Wei et al., 2009 Immunity, 30: 155-167; Zhou et al., 2009 Nat Immunol., 10: 1000-1007; Oldenhove et al., 2009 Immunity, 31: 772-786), and these mechanisms are potentially critical to the efficacy of material-based cancer vaccines.

An interesting aspect of these systems is CTL homing to the vaccine site due to long term antigen presentation, and knocking out CD8(+) T cells resulted in a significant reduction of local levels of IFNγ and IL-12 (S3 &S4). T cell derived IFNγ enhances DC expression of IL-12 and costimulatory molecules creating a feedback loop that amplifies CTL-mediated responses to infection. In this setting, after vaccine priming, T cells that home back to the antigen-presenting vaccine site may be important vaccine components themselves as they may sustain and amplify CTL responses via IFNγ-mediated DC activation and IL-12 production. These findings provide evidence that CD8(+) DCs, pDCs and IL-12, or their equivalent functionally (i.e., appropriate antigen presentation, and Th1 polarization) lead to improved material-based cancer vaccines. The methods and devices described herein are also useful for other clinical indications, such as infectious and autoimmune disease.

As described above, three different types of pathogen associated molecular patterns (PAMPs) were incorporated into or onto structural polymeric devices such as PLG disc structures/scaffolds to act as adjuvants in vaccines (3 types; a short oligonucleotide (CpG-ODN); a synthetic RNA-(Poly (I:C); P(I:C)), a synthetic lipid (monophosphoryl lipid A; MPLA) (FIGS. 15A-D). Such vaccine formulations recruit and activate dendritic cells in situ, which was quantitatively assessed (FIGS. 16A-D).

Vaccine-dependent survival in an aggressive melanoma cancer model correlates strongly with the ability of the vaccine to specifically activate 2 subsets of dendritic cells—CD8(+) DCs and plasmacytoid DCs—regardless of the adjuvant utilized in the vaccine system (FIGS. 17A-C). This correlation has been confirmed utilizing 4 different vaccine adjuvants in the PLG vaccine. These vaccines induce potent tumor rejection in a therapeutic model of melanoma, by activating specific T cell responses that have been detected at the vaccine site and at tumors (FIGS. 18A-D and 19A-D). These findings demonstrate the PLG vaccine system's versatility in incorporating different types of agonists that stimulate different pathways in innate and adaptive immune responses (FIGS. 15A-D).

DC subsets that are critical for anti-tumor immune responses were identified. Subsets of DCs include myeloid dendritic cell (mDC), plasmacytoid DCs, and CD8+ DCs. mDCs are most similar to monocytes. mDC are made up of at least two subsets: (1) the more common mDC-1, which is a major stimulator of T cells; and (2) the extremely rare mDC-2, which may have a function in fighting wound infection. mDCs secrete IL-12 and are characterized by TLR 2 and TLR4. Plasmacytoid DCs look like plasma cells, but have certain characteristics similar to myeloid dendritic cells, can produce high amounts of interferon-alpha, and are characterized by TLR7 and TLR9. The TLR agonist, CpG, binds to TLR9. CD8+ DCs in mice are equivalent to CD141+ dendritic cells.

CD141+ DCs are found in human lymph nodes, bone marrow, tonsil, and blood. They are characterized by high expression of toll-like receptor 3 (TLR3), production of IL-12p70 and IFN-β, and superior capacity to induce T helper 1 cell responses, when compared with the more commonly studied CD1c+DC subset. Polyinosine-polycytidylic acid (poly I:C)-activated CD141+ DCs have a superior capacity to cross-present antigens to CD8+ cytotoxic T lymphocytes than poly I:C-activated CD1c+ DCs. Thus CD141+DC subset represents an important functionally distinct human DC subtype with characteristics similar to those of the mouse CD8α+ DC subset. CD141+ DCs play a role in the induction of cytotoxic T lymphocyte responses and their activation is important for vaccination against cancers, viruses, and other pathogens.

CD141+ DCs and plasmacytoid DCs are critical for successful cancer vaccination (prophylactic and therapeutic). The results described herein indicate that p(I:C) in vaccine device stimulates CD141+ DCs in humans (CD8+ DCs in mice) and CpG stimulates plasmacytoid DCs. Devices with one or both of these TLR agonists lead to potent DC activation and the generation of significant prophylactic and therapeutic anti-tumor immune responses. A combination of different TLR agonists, e.g., a combination of p(I:C) and CpG, in a device leads to a synergistic effect in the activation of a DC immune response against tumors. CD141+ DCs and plasmacytoid DCs have not been specifically utilized or targeted in current clinical trials. The data obtained from these experiments was used to design cancer vaccine systems and provide a more informed translation of immune response data from mouse to humans.

Synergistic Effect of P(I:C)+CpG ODN on Tumor Inhibition

Figure 22:
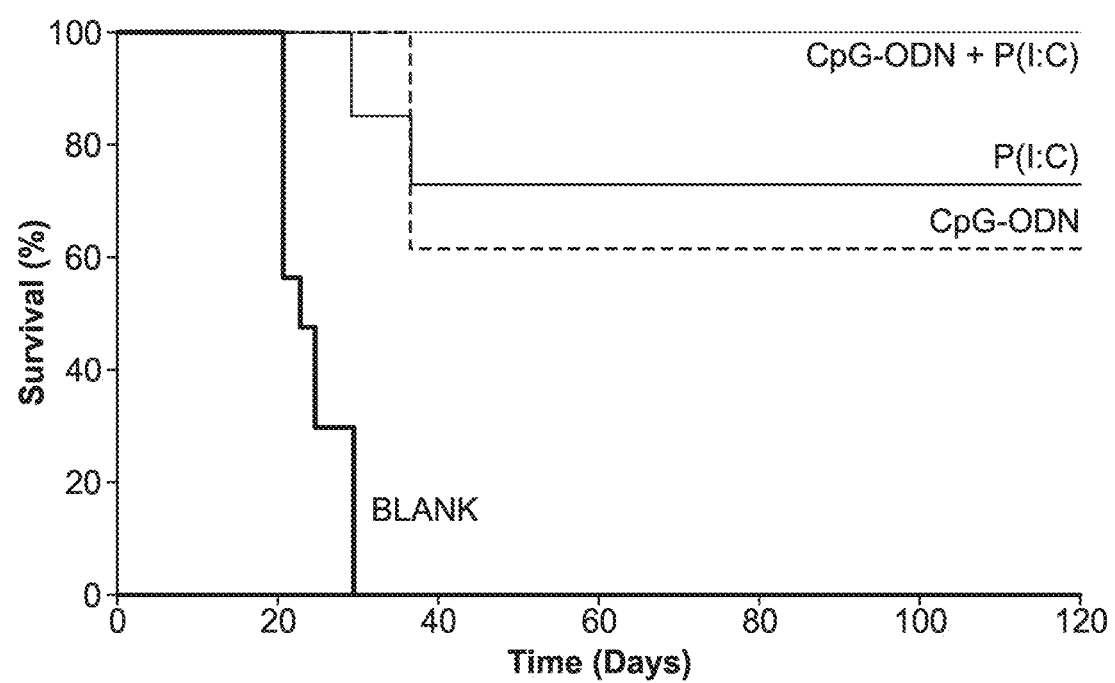
FIG. 22 is a line graph showing that PLG vaccines incorporating CpG-ODN and/or P(I:C) generate significant tumor protection. The overall survival of mice bearing melanoma tumors, and treated with either blank matrices [Blank] or matrices loaded with CpG-ODN or P(I:C) alone or in combination [CpG-ODN+P(I:C)] (n=8). Mice were challenged with 5×10$^5$ B16-F10 cells and vaccinated 3 days later with PLG vaccines. Total dose of TLR agonist was approximately 100 μg in all vaccines.

FIG. 22 shows the results of a vaccine experiment where P(I:C) and CpG-ODN in combination were examined versus the CpG-ODN and P(I:C) alone. As shown in FIG. 22, the combination of the TLR agonists P(I:C) and CpG-ODN outperformed the vaccines incorporating CpG-ODN or P(I:C) alone. Specifically, PLG vaccines incorporating CpG-ODN and P(I:C) act synergistically to generate significant tumor inhibition, reduced tumor burden, and to generate improved anti-tumor immune responses.

FIG. 22 shows the overall survival of mice bearing melanoma tumors, and treated with either blank matrices

[Blank] or matrices loaded with CpG-ODN or P(I:C) alone or in combination [CpG-ODN+P(I:C)] (n=8). Mice were challenged with $5 \times 10^5$ B16-F10 cells and vaccinated 3 days later with PLG vaccines. Total dose of TLR agonist was approximately 100 µg in all vaccines.

Example 8: Inflammatory Cytokines Presented from Polymer Matrices Differentially Generate and Activate DCs In Situ During infection, inflammatory cytokines mobilize and activate dendritic cells (DCs), which are essential for efficacious T cell priming and immune responses that clear the infection. Described herein is the design of macroporous poly(lactide-co-glycolide) (PLG) matrices that release the inflammatory cytokines GM-CSF, Flt3L and CCL20, in order to mimic infection-induced DC recruitment. The ability of these infection mimics to function as cancer vaccines was examined via induction of specific, anti-tumor T cell responses. As described in detail below, all vaccine systems tested were able to confer specific anti-tumor T cell responses and long-term survival in a therapeutic, B16-F10 melanoma model. However, GM-CSF and Flt3L vaccines resulted in similar survival rates, and outperformed CCL20 loaded scaffolds, even though they had differential effects on DC recruitment and generation. GM-CSF signaling was identified as the most potent chemotactic factor for conventional DCs and significantly enhanced surface expression of MHC(II) and CD86(+), which are utilized for priming T cell immunity. In contrast, Flt3L vaccines led to greater numbers of plasmacytoid DCs (pDCs), correlating with increased levels of T cell priming cytokines that amplify T cell responses. These results demonstrate that 3D polymer matrices modified to present inflammatory cytokines are utilized to effectively mobilize and activate different DC subsets in vivo for immunotherapy.

An exemplary amino acid sequence of human Flt3 is provided below (GenBank Accession No.: P49771.1 (GI: 1706818), incorporated herein by reference; SEQ ID NO: 12):

```
  1 mtvlapawsp ttyllllll ssglsgtqdc sfqhspissd favkirelsd yllqdypvtv 61 asnlqdeelc gglwrlvlaq rwmerlktva gskmqgller vnteihfvtk cafqpppscl 121 rfvqtnisrl lqetseqlva lkpwitrqnf srclelqcqp dsstlpppws prpleatapt 181 apqppllll  llpvgllla  aawclhwqrt rrrtprpgeq vppvpspqdl llveh
```

An exemplary amino acid sequence of human CCL20 is provided below (GenBank Accession No.: AAH20698.1 (GI:18088857), incorporated herein by reference; SEQ ID NO: 11):

```
  1 mcctkslla  almsvlllhl cgeseasnfd cclgytdril hpkfivgftr glanegcdin 61 aiifhtkkkl svcanpkqtw vkyivrllsk kvknm
```

Materials & Methods
Mice
C57BL/6 mice (6-8-week-old female; Jackson Laboratories) were used in the experiments described in Example 8.
Primary Cells (DCs) Isolation and Culture
Primary bone-marrow-derived dendritic cells (BMDCs) were flushed from the femurs of C57BL/6 mice and cultured in 100-mm bacteriological petri dishes (Falcon number 1029/Becton Dickinson). Cell culture medium RPMI-1640 (R10) (Sigma) was supplemented with 1% Penicillin-Streptomycin (Invitrogen), 2 mM 1-Glutamine (Invitrogen), 50 µM 2-mercaptoethanol (Sigma) and 10% heat-inactivated fetal bovine serum (FBS, Invitrogen). At day 0, bone marrow leukocytes were seeded at $2 \times 10^6$ cells per 100-mm dish in 10 ml R10 medium containing 20 ng/nil granulocyte-macrophage colony-stimulating factor (GM-CSF) (Peprotech). At day 3, another 10 ml R10 medium containing 20 ng/mL GM-CSF was added. to the plates. At days 6 and 8, half of the culture supernatant was collected and centrifuged, the cell pellet was resuspended in 10 ml fresh R10 containing 20 ng/mL GM-CSF, and placed back into the original plate. The non-adherent cell population in the culture supernatant was used between days 8 and 12 for all the experiments.
Transwell Migration Studies for Chemotaxis and Chemokinesis
Transwell migration studies were performed by plating bone marrow derived dendritic cells in the top well of 6.5 mm transwell dishes (Costar, Cambridge, Mass.) with a pore size of 5 µm. The chemotactic effects of GM-CSF, FL (Flt3), and CCL20 on the migration of BMDCs was assessed by placing 500 ng/ml of recombinant murine GM-CSF, FL or CCL20 (Peprotech, Rocky Hill, N.J.) in the bottom wells and $3 \times 10^5$ DCs in the top wells. For chemokinesis studies, the concentration of cytokine in each compartment was equal at 500 ng/ml and $3 \times 10^5$ DCs were added to the top wells. The number of cells that migrated from the top well to the bottom well through the porous membrane was counted at the end of 12 h to quantify migration. Cells that had migrated to the bottom well were collected by treatment with 0.25% trypsin-0.03% ethylenediaminetetraacetic acid (EDTA, Invitrogen) and counted with a Z2 coulter counter (Beckman Coulter, Inc).
Matrix Fabrication
A 85:15, 120 kD copolymer of D,L-lactide and glycolide (PLG) (Alkermes, Cambridge, Mass.) was utilized in a gas-foaming process to form porous PLG matrices. PLG microspheres encapsulating GM-CSF, FLt3L, or CCL20 were first made using standard double emulsion, incorporating approximately 170 ng/mg of protein PLG microspheres. PLG microspheres were then mixed with 150 mg of the porogen, sucrose (sieved to a particle size between 250 µm and 425 µm), and compression molded. The resulting disc was allowed to equilibrate within a high-pressure $CO_2$ environment, and a rapid reduction in pressure causes the polymer particles to expand and fuse into an interconnected structure. The sucrose was leached from the scaffolds by immersion in water yielding scaffolds that were 90% porous.
To incorporate tumor lysates into PLG scaffolds, biopsies of B16-F10 tumors that had grown subcutaneously in the backs of C57BL/6J mice (Jackson Laboratory, Bar Harbor Me.), were digested in collagenase (250 U/ml) (Worthington, Lakewood, N.J.) and suspended at a concentration equivalent to $10^7$ cells per ml after filtration through 40 μm cell strainers. The tumor cell suspension was subjected to 4 cycles of rapid freeze in liquid nitrogen and thaw (37° C.) and then centrifuged at 400 rpm for 10 min. The supernatant (1 ml) containing tumor lysates was collected, incubated with the PLG microspheres and lyophilized and the resulting mixture was used to make PLG scaffold-based cancer vaccines.

To incorporate CpG-ODNs into PLG scaffolds, CpG-ODN 1826, 5'-tcc atg acg ttc ctg acg tt-3', (Invivogen, San Diego, Calif.; SEQ ID NO: 10) was first condensed with poly(ethylenimine) (PEI, Mn~60,000, Sigma Aldrich) molecules by dropping ODN-1826 solutions into PEI solution, while vortexing the mixture. The charge ratio between PEI and CpG-ODN (NH3+:PO4-) was kept constant at 7 during condensation. The condensate solutions were then vortexed with 60 μl of 50% (wt/vol) sucrose solution, lyophilized and mixed with dry sucrose to a final weight of 150 mg. The sucrose containing PEI-CpG-ODN condensate was then mixed with blank, GM-CSF and/or tumor lysate loaded PLG microspheres to make PLG cancer vaccines.

In Situ Identification of DCs and T Cells

GM-CSF loaded PLG matrices containing approximately 3 μg of GM-CSF, Flt3L, or CCL20 in combination with 100 μg of CpG-ODN were implanted into subcutaneous pockets on the back of 7-9 week old male C57BL/6J mice. To analyze DC recruitment by FACS analysis, scaffolds were excised and the ingrown tissue was digested into single cell suspensions using a collagenase solution (Worthingtion, 250 U/ml) that was agitated at 37° C. for 45 minutes. The cell suspensions were then poured through a 40 μm cell strainer to isolate cells from scaffold particles and the cells were pelleted and washed with cold PBS and counted using a Z2 coulter counter (Beckman Coulter). To assess, DC infiltration and activation, subsets of the total cell population isolated from PLG matrices were then stained with primary antibodies (BD Pharmingen, San Diego, Calif.) conjugated to fluorescent markers to allow for analysis by flow cytometry. APC-conjugated CD11c (dendritic cell marker), FITC-conjugated MHCII and PE-conjugated CD86 (B7, costimulatory molecule) stains were conducted for DC recruitment and activation analysis. To delineate the presence of the plasmacytoid DC subset, cells were also stained with APC-conjugated CD11c and PE-conjugated PDCA-1 (plasmacytoid DC marker). Cells were gated according to single positive FITC, APC and PE stainings using isotype controls. The percentage of cells staining positive for each surface antigen was recorded.

For the immunostaining of DC infiltrates in paraffin sections of scaffolds, samples were prepared and re-hydrated according to standard procedures. Antigen retrieval was performed with citrate buffer in a pressurized cooker (10 mM Sodium Citrate, 0.05% Tween 20, pH 6.0, for 5 min in 950 C). After brief washes with PBST buffer (0.01% Tween-20), samples were blocked with 5% goat serum in staining buffer (5% BSA, 2% Fetal Bovine Serum in PBST, pH 7.4) for 1 hour in ambient temperature. Anti-CD11c Armenian Hamster IgG (20 mg/ml, Abcam, Cambridge, Mass.) was diluted in staining buffer and allowed to bind overnight at 40 C in a humidified chamber. After washing 3 times with PBST, Alexa®594 Goat anti-Hamster (5 mg/ml, Life Technologies, Grand Island, N.Y.) secondary IgG was diluted in staining buffer and applied for 1 h at RT. After three washes with PBS, samples were air-dried and mounted with Pro-Long Gold Antifade reagent with DAPI for nuclear staining (Life Technologies, Grand Island, N.Y.). Confocal tile scans were obtained and processed with Zeiss LSM 710 laser-scanning microscope and bundled software (Zeiss, Thornwood, N.Y.).

Tumor Growth Assays, Protective Cytokines and Trp2 Pentamer Analysis

PLG scaffolds containing B16-F10 melanoma tumor lysates, 100 μg CpG-ODN in combination with 3 μg GM-CSF, Flt3L or CCL20 were implanted subcutaneously into the lower left flank of C57BL/6J mice to act as cancer vaccines. To assess PLG vaccine efficacy in the therapeutic setting, C57/BL6J mice were challenged with a subcutaneous injection of $5 \times 10^5$ B16-F10 melanoma cells (ATCC, Manassas, N.J.) in the back of the neck, and 3 days after tumor challenge PLG vaccines were implanted subcutaneously into the lower left flank. Animals were monitored for the onset of tumor growth (approximately 1 mm$^3$) and sacrificed for humane reasons when tumors grew to 20-25 mm (longest diameter).

To determine the in vivo IL-12p70 and IFN-γ concentration at the matrix implant site, adjacent tissue was excised and digested with tissue protein extraction reagent at Day 10 after implantation (Pierce). After centrifugation, the concentrations of IL-12 and IFN-γ, in the supernatant were then analyzed with ELISA (R&D systems), according to the manufacturer's instructions. To determine the generation of TRP-2-specific cytotoxic T lymphocytes, single cell suspensions were prepared at Day 10 from the spleens of mice immunized with PLG vaccines. These cells were initially stained with PE-H-2Kb/TRP2 pentamers (Sigma Aldrich), and subsequently stained with FITC-anti-CD8 and PE-CY7 CD3 mAb (mAb (BD Pharmingen, San Diego) before being analyzed using flow cytometry.

The Role of Dendritic Cells in the Immune Response

Dendritic cells (DCs) orchestrate immune responses to infection and tumors by priming and propagating specific, cytotoxic T lymphocyte (CTL) responses. Immature DCs residing in peripheral tissue detect foreign substances (i.e. antigens) unique to invading pathogens, and are activated by stimuli, such as pathogen associated molecular patterns (PAMPs) or products of dying cells (i.e. "danger signals"), originating during pathogen induced inflammatory responses. Maturing DCs mature both process and present antigens on major histocompatibility complexes (MHC) receptors, and express the costimulatory molecules CD80 and CD86, both of which are required for effector T-cell stimulation. Another important result of DC maturation by 'danger signaling', is that DCs acquire the ability to home to the lymph nodes to engage and activate naive T-cells, enabling the T cells to recognize the antigens DCs are presenting.

The ability of particular DCs to initiate and control immune responses is a consequence of both their localization within tissues and their specialized capacity for mobilization. DCs originate from pluripotent stem cells in the bone marrow, enter the blood stream and localize into almost all organs. Based on the relative expression of a series of surface markers, different subsets of DCs or DC precursors can be identified in peripheral blood, including plasmacytoid DCs (pDCs) and conventional DCs (cDCs)2. pDCs are major type I interferon (IFN) producers, and specialize in activating adaptive immune responses to virus challenge via cytokine signaling. CD11c(+) cDCs, such as epidermal DCs, are especially adept at antigen presentation and co-stimulation of T cells.

Upon microbial invasion and inflammation, DCs rapidly migrate into the draining lymph nodes and primary sites of infection at rates that vastly outnumber other APCs, such as macrophages. The production of most DC subsets, including (pDCs) is controlled in the steady state by the cytokine Fms-related tyrosine kinase 3 ligand (FL). Other cytokines, such as GM-CSF and CCL20, released by damaged or infected cells, actively recruit and localize cDCs to the sites of inflammation. In inflammatory models, both in vivo and in vitro, these inflammatory cytokines have been shown to also enhance DC migration and proliferation and may regulate DC activation state. The quantity of DCs activated during infection or within tumors is correlated with the strength of the subsequent immune response and disease prognosis.

To generate sufficient numbers of dendritic cells (DCs) for immunotherapy, laboratory-based culture of DC precursors with inflammatory cytokines, such as granulocyte macrophage-colony stimulating factor (GM-CSF) and FL (Flt3) has often been used. DCs modified in vitro to present tumor antigens are capable of eliciting antitumor effects in murine models upon transplantation. Initial clinical testing of ex vivo DC-based vaccines has revealed the induction of tumor regression in a subset of cancer patients, but little survival benefit. Protocols involving the ex vivo manipulation of DCs are limited by the quantities and types of DCs that can be produced, poor engraftment efficiency and LN homing, and loss of DC activation upon injection in the in vivo environment.

To address these limitations, infection-mimicking materials were developed to present inflammatory cytokines in combination with a danger signal to recruit and activate DCs in vivo. As described below, the abilities of multiple inflammatory cytokines, GM-CSF, FL (Flt3), and CCL20 to recruit and activate DCs when delivered from macroporous, implantable polymer scaffolds was examined. Also, nanoparticles containing cytosine-guanosine (CpG) rich oligo-nucleotide (CpG-ODN) sequences were immobilized onto scaffolds, as CpG-ODN are expressed in bacterial DNA, and are potent danger signals that can stimulate activation of matrix resident DCs. Finally, the ability of these systems to prime anti-tumor T cell responses and confer tumor protection via presentation of cancer antigens was examined.

In Vitro Chemotaxis and Chemokinesis of Cytokines

Figure 23A:
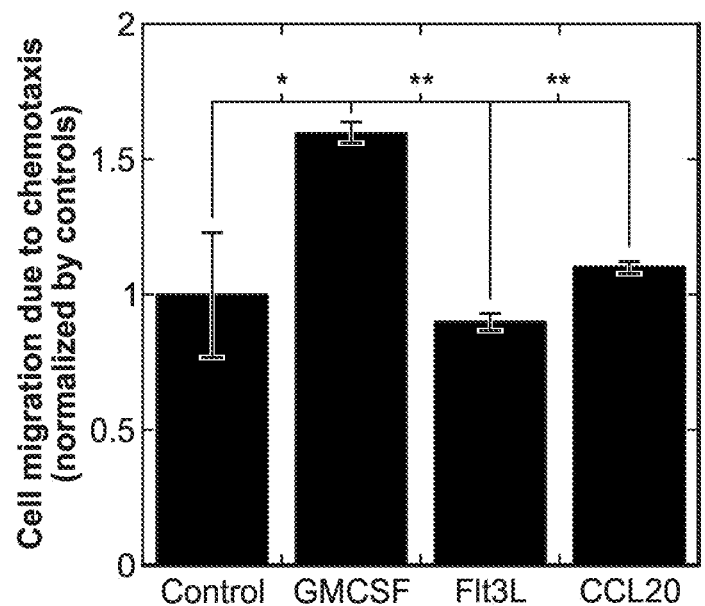
FIGS. 23A-B are bar charts demonstrating in vitro chemotaxis and chemokinesis of DCs. The in vitro (FIG. 23A) chemotaxis and (FIG. 23B) chemokinesis of bone marrow derived DCs in response to control media and media supplemented with GMCSF, Flt3L, and CCL20. * P<0.05 ** P<0.01, as compared to GM-CSF loaded matrices. Values represent mean and standard deviation. (n=4).
Figure 23B:
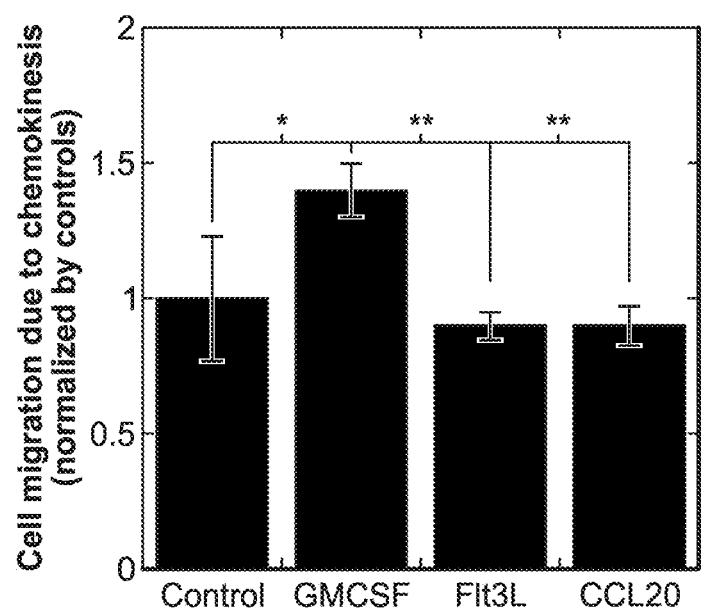

In vitro transwell studies were conducted to investigate the chemotaxis and chemokinesis effects of bone-marrow derived DCs in response to GM-CSF, FL and CCL20. GM-CSF gradients promoted significant DC chemotaxis, as DC migration in this condition was approximately 50% higher than the control condition (FIG. 23A). Similar effects on chemokinesis were observed, as GMCSF exposure promoted a similar 50% increase in the number of migrated cells in response to homogenous levels of the cytokine (FIG. 23B). In contrast, FL and CCL20 had no effect on the chemotaxis or chemokineses of DCs in these assays (FIGS. 23A-B). These results indicate that GM-CSF has a superior effect on DC mobilization and recruitment in comparison to FL and CCL20.

Controlled Release of Cytokines and In Vivo DC Recruitment

Figure 24A:
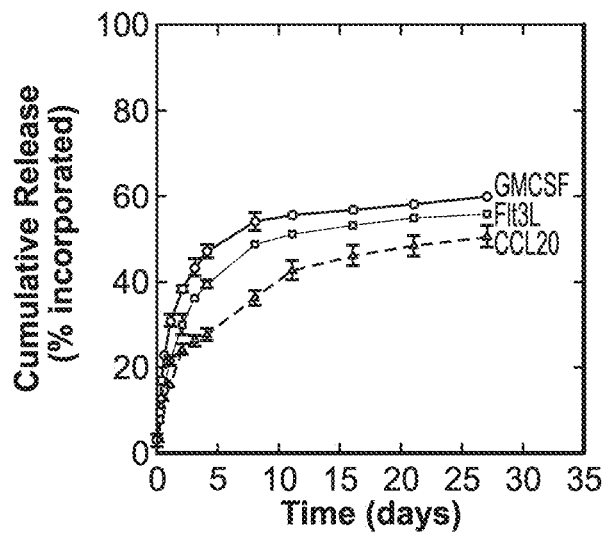
FIGS. 24A-C are a series of line graphs, bar charts, and photomicrographs demonstrating PLG scaffolds that release cytokines for DC recruitment.

Macroporous, poly-lactide-co-glycolide (PLG) matrices were designed to provide long-term and sustained release of GM-CSF, FL, and CCL20 (FIG. 23A) and to house DCs for activation. These PLG scaffolds were 80-90% porous with an average pore size between 125-200 μm to facilitate dendritic cell infiltration. The in vitro release kinetics for the three cytokines were similar, as the matrices quickly released protein with a burst over the first 5 days followed by sustained release over the next several weeks (FIG. 24A). The scaffolds released approximately 43, 36, and 26% of the incorporated GMCSF, FL and CCL20, respectively, by day 4 followed by approximately 0.9% daily release of protein over the next 23 days (FIG. 24A).

Figure 24B:
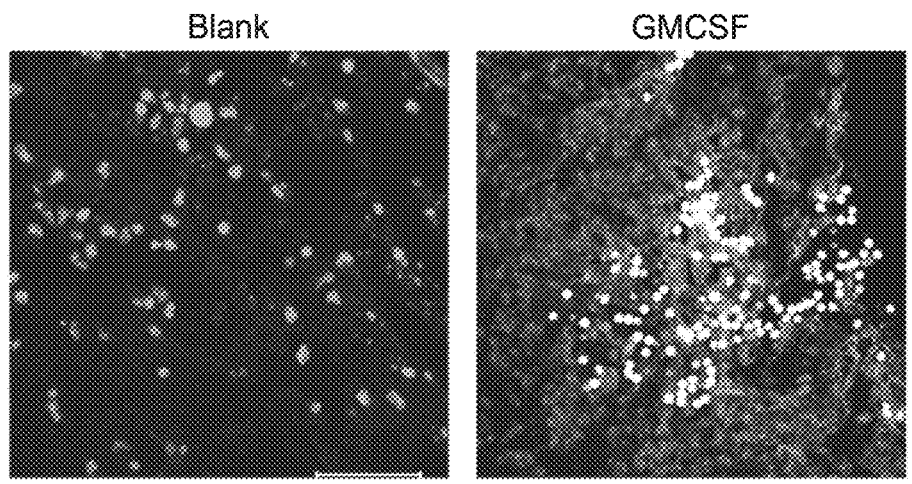
Figure 24C:
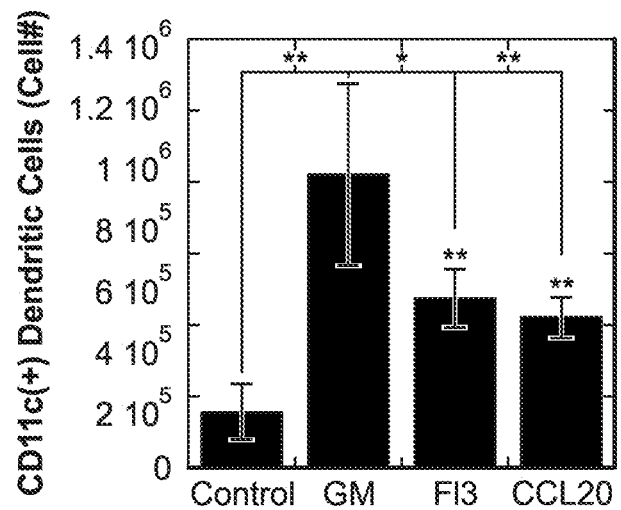

To examine the ability of PLG matrices loaded with inflammatory cytokines to recruit and activate dendritic cells in vivo, PLG matrices delivering GM-CSF, FL and CCL20 were implanted subcutaneously into the backs of C57BL/6J mice and removed at day 7 after implantation. Immunohistochemical analysis revealed intense CD11c(+) DC infiltrates penetrating the porous network of all the scaffolds releasing cytokines, and GM-CSF mediated the most dense DC clustering (FIG. 24B). The magnitude of DC infiltration and activation into the matrices was quantified by FACS analysis of cell populations isolated from the polymeric material. Blank PLG matrices recruited approximately 190,000 CD11c(+) DCs, whereas scaffolds delivering GM-CSF recruited approximately 960,000 DCs, equating to over a 5-fold difference in cell recruitment (FIG. 24C). Scaffolds presenting FL and CCL20 recruited 2.5 fold more DCs than control conditions, but significantly less than GM-CSF presenting scaffolds (FIG. 24C). These results are consistent with the in vitro results that identified GM-CSF as the most potent mobilizing and chemotactic factor for DCs, in comparison to FL and CCL20.

In Vivo DC Activation

Figure 25A:
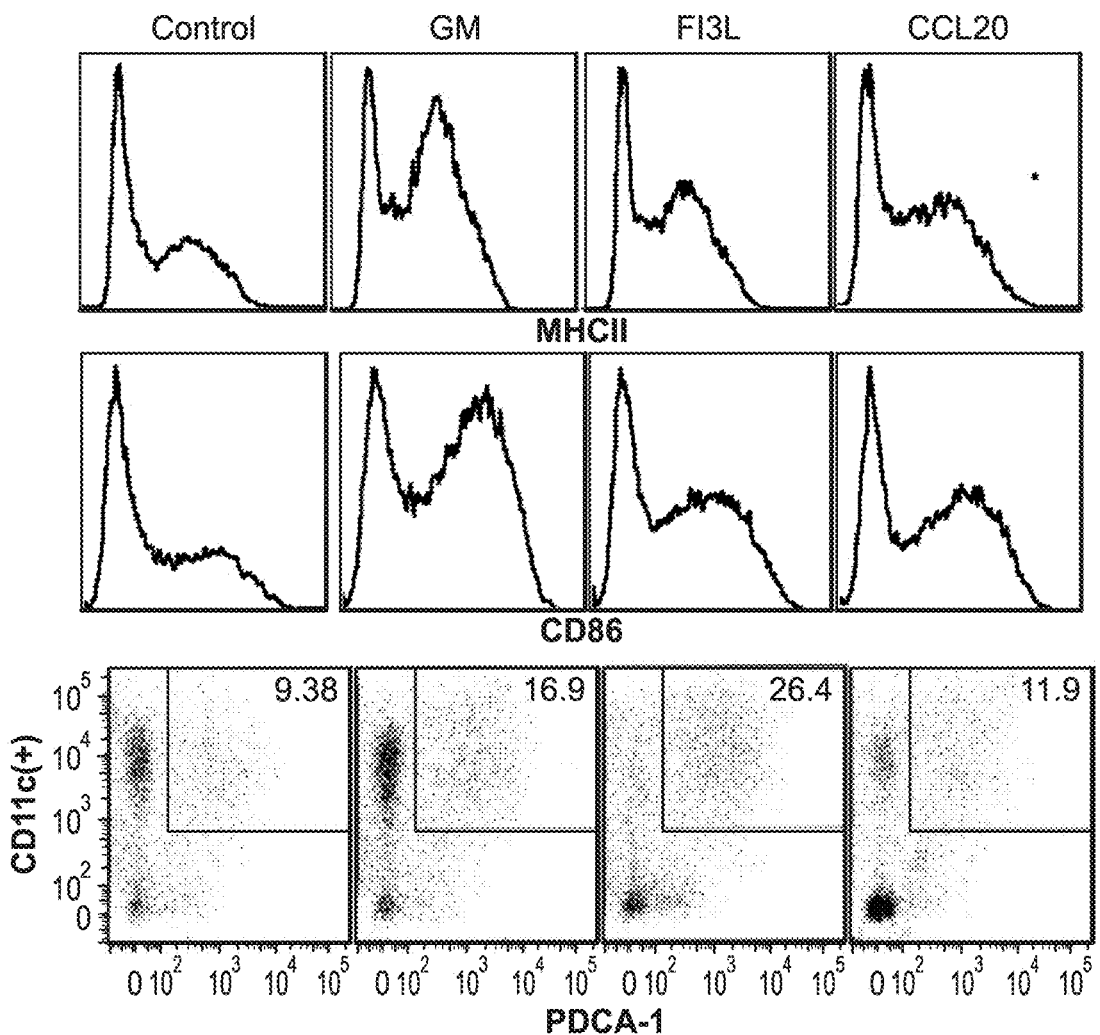
FIGS. 25A-C are a series of line graphs, dot plots, and bar charts demonstrating DC recruitment and activation mediated by PLG matrices loaded with Cytokines and CpG-ODN.
Figure 25B:
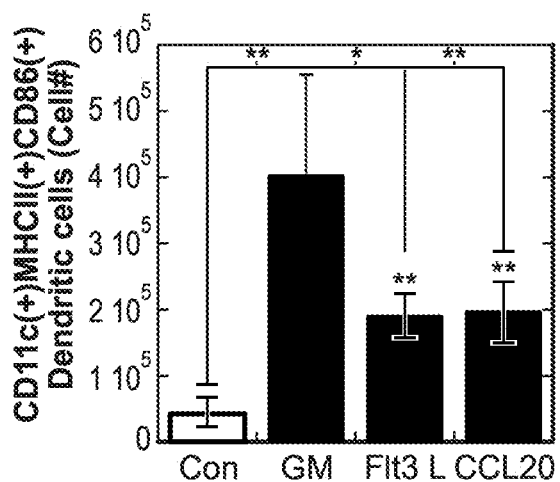
Figure 25C:
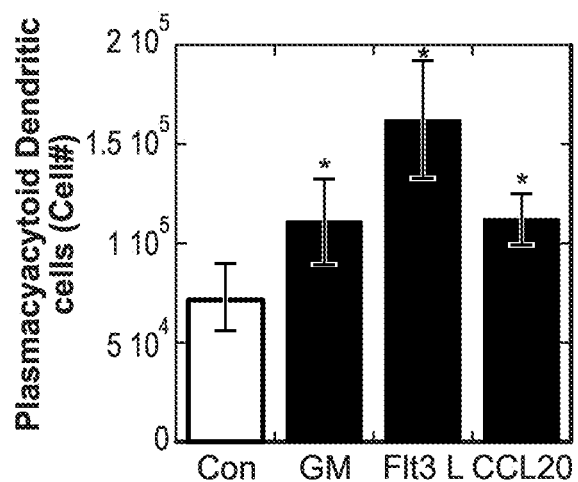

PLG scaffolds were modified to present nanoparticles containing TLR-activating, CpG-ODN, as an infection-mimicking danger signal in concert with delivery with inflammatory cytokines. This dramatically enhanced DC activation in situ over control conditions lacking cytokine signaling (FIG. 25A). Analysis of the activation state of matrix-resident DCs revealed that GM-CSF induced recruitment in combination with CpG-ODN produced significant percentages of activated DCs, as MHCII(+) and CD86(+) DCs comprised approximately 54-66% of the total DCs recruited to scaffolds. Approximately 8-fold, 4-fold, and 4-fold increases in the total number of activated DCs were found with GM-CSF, at the implant site relative to control matrices devoid of cytokines (FIG. 25B).

FL presentation in combination with CpG-ODN enriched the PLG matrix with the highest average number of CD11c(+)PDCA-1(+) pDCs (FIG. 1C), generating over 160,000 resident pDCs. Strikingly, approximately 22% of the total cells resident in these scaffolds consisted of this DC subset (FIG. 25A). This indicates that FL is a strong mobilizing agent for pDCs. Scaffolds presenting GM-CSF and CCL20 also significantly enhanced pDC generation, leading to approximately 110,000 resident pDCs. The pDC subset has been associated with the induction of t-helper 1 (Th1) immunity via its capacity to induce IL-12 and type-1 interferons (IFNs), which are critical to propagating CTL responses to infections and tumors. These data indicate that while the three cytokines tested all enhanced DC recruitment and activation, GM-CSF signaling in combination with CpG-ODN produced the highest numbers of activated cDCs, while FL led to the greatest number of resident pDCs.

Induction of T Cell Immunity and Therapeutic Vaccination

Figure 26A:
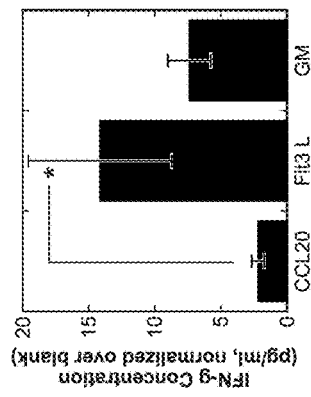
FIGS. 26A-D are a series of bar charts and a line graph demonstrating PLG vaccines generate immunoprotective cytokines, antigen-specific T cells, and cancer protection. Fold difference in local (FIG. 26A) IL-12 and (FIG. 26B) IFN-γ concentration after implantation of scaffolds loaded with B16-F10 tumor lysate, CpG-ODN in combination with GM-CSF (GM), Flt3L(F13L) or CCL20(CCL20). Concentrations were normalized to the value found with control (matrices delivering lysate and CpG-ODN, no cytokines) (FIG. 26C). The total numbers of Trp2-specific CD8(+) T cells in spleens of vaccinated animals at Day 10 post-implantation.
Figure 26B:
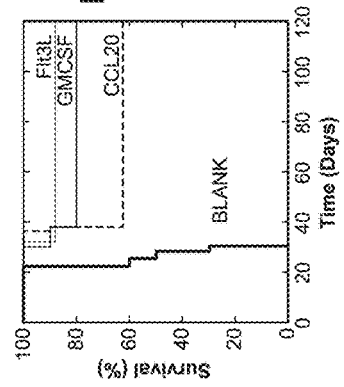

B16-F10 tumor lysates were incorporated into PLG matrices as tumor antigens. IL-12 and IFN-γ secretion by activated DCs can prime CTL-mediated immune responses and tumor cell death. Thus, the presence of these Th-1 inducers at the scaffold implant site was quantified. PLG vaccines presenting FL in combination with CpG-ODN enhanced the local concentration of IL-12 and IFN-γ by 8 and 13-fold, respectively, over control scaffolds (FIGS. 26A and 26B). GM-CSF release resulted in approximately 3 and 6-fold increases in the local concentration of IL-12 and IFN-γ (FIGS. 26A and 26B). CCL20 release from PLG vaccines led to a 2-fold increase in IL-12 concentration, and no effect on IFN-γ levels at the vaccine site (FIGS. 26A and 26B).

Figure 26C:
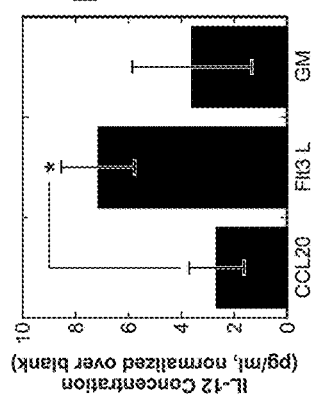

The activation of systemic CTL responses was monitored by staining isolated splenocytes with MHC class I/TRP2 peptide pentamers. This allows one to identify CTLs with specificity to tyrosinase-related protein (TRP)-2, which is a main antigenic target of melanoma vaccines in mice and humans. A significant expansion of TRP2 specific CTLs was observed in the spleens of mice vaccinated with scaffolds incorporating all three cytokines (FIG. 26C). Vaccines incorporating FL and GMCSF led to approximately 5 and 4-fold higher numbers of Trp2 specific CTLs than control vaccines, which was a significantly greater effect than found with CCL20 vaccines (FIG. 26C). Taken together, these data indicate that vaccine formulations containing various inflammatory agents are capable of producing significant and systemic anti-melanoma CTLs and the local production of Th1 cytokines.

Figure 26D:
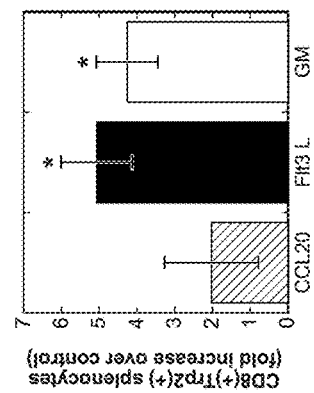

The anti-tumor efficacy of these vaccines were then tested in the poorly immunogenic, B16-F10 melanoma, model. C57BL/6J mice were challenged with $10^5$ tumor cells, and then vaccinated with PLG vaccines three days later. Animals treated with control scaffolds required euthanization after 30 days due to progressive disease. PLG vaccines loaded with cytokines induced long-term tumor protection in a significant subset of animals (FIG. 26D). GMCSF, FL and CCL20 presentation from PLG vaccines resulted in 88, 75 and 62% long-term survival rates (FIG. 26D).

Controlled mobilization and activation of DCs and DC precursors is of particular interest in the development of ex vivo DC based vaccines, and more generally the design of material systems that activate the immune system in vivo. As described herein, polymers which mimic key aspects of microbial infection effectively recruit DCs for cancer vaccination. PLG scaffolds engineered to release GM-CSF, FL, and CCL20 led to significant numbers of resident DCs, and the co-presentation of danger signals led to DC maturation. Even though all vaccine formulations were capable of inducing tumor protection in a therapeutic model of B16-F10 melanoma, GM-CSF and FL vaccines produced more antigen specific CTLs, higher levels of Th1 priming cytokines, and greater survival rates when compared to CCL20 (FIG. 26D).

While GM and FL releasing PLG vaccines resulted in statistically similar T cell and anti-tumor responses, they had differential effects on DC recruitment and activation. In vitro tests indicated that GM-CSF was the most potent chemotactic factor for cDCs (FIGS. 23A-B). This finding was consistent with the ability of GM-CSF releasing matrices to recruit significantly more total DCs (~$10^6$, on par with ex vivo DC based protocols) and activated DCs, in comparison to FL scaffolds (FIGS. 24A-C and 25A-C). In contrast, and in agreement with other reports, FL vaccines led to more matrix-resident pDCs when combined with CpG-ODN danger signaling. pDCs are an important source of Th1 priming cytokines that amplify CTL responses, and increased pDCs numbers likely contributed to the enhanced local production of IL-12 and IFNγ at the vaccine site. As described herein, GM and FL are combined in material systems to exploit GMCSF mediated activation of cDCs and FL mediated generation of pDCs. This creates a superior DC network that is employed for cancer vaccination and immunotherapy.

The results presented herein indicate that pDCs, and their cDC counterparts are targeted to exploit their specialized abilities to mediate anti-tumor T cell responses. In contrast to nanoparticle targeting systems, the polymer systems described herein not only serve as an antigen delivery devices to recruit and activate DCs, but also serve as a physical structure where DCs temporarily reside while they are activated.

The systems described herein demonstrated significant anti-tumor activity. In addition to the polymers, e.g., PLG, described herein, matrices are optionally fabricated from other more inflammatory polymers to boost immune responses and DC mobilization. Another important aspect of subsequent T cell priming by these cells is LN homing. The exit or dispersion of DCs after antigen exposure is optimized by incorporating different adjuvants into the material to activate migratory function. Alternatively, other matrix properties, including degradation kinetics and porosity are altered to promote further control over DC trafficking.

Altogether, these findings provide evidence that FL, CCL20 and GM-CSF are utilized in biomaterial systems to mimic infection-induced recruitment of DCs in situ. As described herein, infection-mimicking porous devices are effective as therapeutic cancer vaccines.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A device comprising a porous polymeric structure composition, and a toll-like receptor 3 (TLR3) agonist, wherein said TLR3 is in an amount effective to activate an antigen presenting cell.

2. The device of claim 1, further comprising a tumor antigen.

3. The device of claim 1, wherein said polymeric structure composition comprises poly-lactide-co-glycolide (PLG).

4. The device of claim 1, wherein said TLR3 agonist comprises polyinosine-polycytidylic acid (poly I:C) or PEI-poly (I:C).

5. The device of claim 1, further comprising pathogen associated molecular patterns (PAMPs).

6. The device of claim 1, wherein said TLR3 agonist comprises a nucleic acid.

7. The device of claim 1, further comprising a TLR9 agonist.

8. The device of claim 7, wherein said TLR9 agonist comprises a cytosine-guanosine oligonucleotide (CpG-ODN) or a PEI-CpG-ODN.

9. The device of claim 1, wherein said device further comprises a cytokine capable of recruiting an antigen presenting cell into the porous polymeric structure composition.

10. The device of claim 9, wherein said cytokine comprises granulocyte macrophage colony stimulating factor (GM-CSF), Flt3L, or CCL20.

11. The device of claim 9, wherein said cytokine comprises encapsulated GM-CSF.

12. The device of claim 2, wherein said tumor antigen comprises a tumor lysate, purified protein tumor antigen, or synthesized tumor antigen.

13. The device of claim 5, wherein said PAMPs comprises a monophosphoryl lipid A (MPLA).

14. The device of claim 7, wherein said TLR3 agonist comprises poly (I:C) and said TLR9 agonist comprises CpG-ODN.

15. The device of claim 1, further comprising a TLR4 agonist.

16. The device of claim 15, wherein said TLR3 agonist comprises poly (I:C) and said TLR4 agonist comprises MPLA.

17. The device of claim 1, wherein said TLR3 agonist is present in an amount to preferentially stimulate CD8+ dendritic cells or CD141+ dendritic cells.

18. A device comprising a polymeric structure composition, a toll-like receptor 3 (TLR3) agonist, and a second toll-like receptor (TLR) agonist selected from the group consisting of TLR1, TLR2, TLR4, TLR5, TLR6, TLR7, TLR8, TLR9, TLR10, TLR11, TLR12, and TLR13.

19. A method for eliciting an anti-tumor immune response, comprising contacting or implanting into a subject a device comprising a polymeric structure composition, and a toll-like receptor 3 (TLR3) agonist, wherein said TLR3 agonist is in an amount effective to activate an antigen presenting cell.

20. The method of claim 19, wherein said device further comprises a tumor antigen.

21. The method of claim 19, wherein said device further comprises a TLR9 agonist.

22. The method of claim 19, wherein said anti-tumor immune response comprises activation of a CD8+ dendritic cell or a CD141+ dendritic cell.

23. The method of claim 21, wherein said anti-tumor immune response comprises activation of a plasmacytoid dendritic cell or a CD141+ dendritic cell.

24. The method of claim 20, wherein said anti-tumor immune response comprises a reduction in tumor burden.

25. The method of claim 19, wherein said TLR3 agonist is present at a concentration effective to induce production of interleukin-12 (IL-12) by dendritic cells.

26. The device of claim 1, wherein said antigen presenting cell is a dendritic cell.

27. The method of claim 19, wherein said antigen presenting cell is a dendritic cell.

* * * * *